US012528797B2

(12) United States Patent
Nasveschuk et al.

(10) Patent No.: US 12,528,797 B2
(45) Date of Patent: Jan. 20, 2026

(54) HETEROCYCLIC COMPOUNDS FOR MEDICAL TREATMENT

(71) Applicant: C4 Therapeutics, Inc., Watertown, MA (US)

(72) Inventors: Christopher G. Nasveschuk, Stoneham, MA (US); Roger Norcross, Basel (CH); Fabian Dey, Basel (CH); Annick Goergler, Colmar (FR); Eric Andre Kusznir, Basel (CH)

(73) Assignee: C4 Therapeutics, Inc.

( * ) Notice: Subject to any disclaimer, the term of this patent is extended or adjusted under 35 U.S.C. 154(b) by 1120 days.

(21) Appl. No.: 17/465,583

(22) Filed: Sep. 2, 2021

(65) Prior Publication Data

US 2023/0019060 A1 Jan. 19, 2023

Related U.S. Application Data

(63) Continuation of application No. PCT/US2020/021491, filed on Mar. 6, 2020.

(60) Provisional application No. 62/814,706, filed on Mar. 6, 2019.

(51) Int. Cl.

*C07D 413/04* (2006.01)
*C07D 403/04* (2006.01)
*C07D 417/04* (2006.01)
*C07D 471/04* (2006.01)

(52) U.S. Cl.

CPC ......... *C07D 413/04* (2013.01); *C07D 403/04* (2013.01); *C07D 417/04* (2013.01); *C07D 471/04* (2013.01)

(58) Field of Classification Search

None
See application file for complete search history.

(56) References Cited

U.S. PATENT DOCUMENTS

| | | | |
|---|---|---|---|
| 5,635,517 | A | 6/1997 | Muller et al. |
| 6,306,663 | B1 | 10/2001 | Kenten et al. |
| 7,041,298 | B2 | 5/2006 | Deshaies et al. |
| 7,208,157 | B2 | 4/2007 | Deshaies et al. |
| 9,125,915 | B2 | 9/2015 | Miyoshi et al. |
| 9,249,161 | B2 | 2/2016 | Albrecht et al. |
| 11,254,672 | B2 | 2/2022 | Norcross et al. |
| 11,787,802 | B2 | 10/2023 | Norcross et al. |
| 2003/0092749 | A1 | 5/2003 | Dombroski et al. |
| 2010/0081643 | A1 | 4/2010 | Bookser et al. |
| 2011/0245257 | A1 | 10/2011 | Cushing et al. |
| 2013/0190340 | A1 | 7/2013 | Hedstrom et al. |
| 2014/0302523 | A1 | 10/2014 | Crews et al. |
| 2014/0356322 | A1 | 12/2014 | Crews et al. |
| 2015/0119435 | A1 | 4/2015 | Crews et al. |
| 2015/0232462 | A1 | 8/2015 | Jones et al. |
| 2015/0274738 | A1 | 10/2015 | Gray et al. |
| 2015/0291562 | A1 | 10/2015 | Crew et al. |
| 2016/0008356 | A1 | 1/2016 | Hege |
| 2016/0016966 | A1 | 1/2016 | Amans et al. |
| 2016/0022642 | A1 | 1/2016 | Crews et al. |
| 2016/0045607 | A1 | 2/2016 | Crew et al. |
| 2016/0046661 | A1 | 2/2016 | Gray et al. |
| 2016/0058872 | A1 | 3/2016 | Crew et al. |
| 2016/0176916 | A1 | 6/2016 | Bradner et al. |
| 2016/0214972 | A1 | 7/2016 | Jin et al. |
| 2016/0272639 | A1 | 9/2016 | Crew et al. |
| 2017/0008904 | A1 | 1/2017 | Crew et al. |
| 2017/0037004 | A1 | 2/2017 | Crew et al. |
| 2017/0065719 | A1 | 3/2017 | Qian et al. |
| 2017/0101401 | A1 | 4/2017 | Hong-Yu et al. |
| 2018/0015087 | A1 | 1/2018 | Liu et al. |
| 2018/0085465 | A1 | 3/2018 | Bradner et al. |

FOREIGN PATENT DOCUMENTS

| | | | |
|---|---|---|---|
| BR | PI1100318 | A2 | 5/2013 |
| CN | 103421061 | A | 12/2013 |
| EP | 385850 | A2 | 3/1993 |
| EP | 1256578 | A1 | 1/2009 |
| WO | WO 1998/011111 | A1 | 3/1998 |
| WO | WO 2001/092239 | A1 | 12/2001 |
| WO | WO 2002/059106 | A1 | 8/2002 |
| WO | WO 2002/072576 | A1 | 9/2002 |
| WO | WO 2004/108133 | A2 | 12/2004 |
| WO | WO 2005/060967 | A1 | 7/2005 |
| WO | WO 2005/113489 | A1 | 12/2005 |
| WO | WO 2006/058338 | A2 | 6/2006 |
| WO | WO 2006/102557 | A2 | 9/2006 |
| WO | WO 2007/041598 | A1 | 4/2007 |
| WO | WO 2007/065518 | A1 | 6/2007 |
| WO | WO 2007/143434 | A2 | 12/2007 |

(Continued)

OTHER PUBLICATIONS

Agafonov, Roman et al., Poster Presentation titled "Quantitative and high throughput method for measuring complex formation between target proteins and E3 ubiquitin ligase", EMBO, Sep. 16, 2017.
Bartlett et al., "The evolution of thalidomide and its IMiD derivatives as anticancer agents." Nat Rev Cancer, 4(4):312-322, 2004. Published: Apr. 1, 2004.
Berndsen et al., "New insights into ubiquitin E3 ligase mechanism" Nat. Struct. Mol. Biol., 21:301-307, 2014. Published: Apr. 4, 2014.
Bondeson et al., "Catalytic in vivo protein knockdown by small-molecule PROTACs" Nature Chemical Biology, 11:611-617, 2015. Published: Jun. 10, 2015.
Buckley et al., "HaloPROTACS: use of small molecule protacs to induce degradation of HaloTag fusion proteins" ACS Chemical Biology, 10:1831-1837, 2015. Published: Jun. 23, 2015.
Buckley et al., "Small-molecule control of intracellular protein levels through modulation of the ubiquitin proteasome system" Angewandte Reviews, 53:2312-2330, 2014. Published: Jan. 23, 2014.

(Continued)

*Primary Examiner* — Po-Chih Chen
(74) *Attorney, Agent, or Firm* — Knowles Intellectual Property Strategies, LLC

(57) ABSTRACT

The present invention provides heterocyclic compounds that bind to the ubiquitously expressed E3 ligase protein cereblon (CRBN) and their use for the treatment of abnormal cellular proliferation in a human or other host. The present invention also provides compounds that can be used as synthetic intermediates in the synthesis of bifunctional compounds used for targeted protein degradation.

20 Claims, No Drawings

(56) References Cited

FOREIGN PATENT DOCUMENTS

WO WO 2008/027542 A2 3/2008
WO WO 2008/033567 A1 3/2008
WO WO 2008/039489 A2 4/2008
WO WO 2008/115516 A2 9/2008
WO WO 2008/122038 A1 10/2008
WO WO 2009/042177 A1 4/2009
WO WO 2009/050232 A1 4/2009
WO WO 2009/135651 A1 11/2009
WO WO 2009/139880 A1 11/2009
WO WO 2009/145899 A1 12/2009
WO WO 2010/023161 A1 3/2010
WO WO 2010/036613 A1 4/2010
WO WO 2010/053732 A1 5/2010
WO WO 2010/085684 A1 7/2010
WO WO 2010/107485 A1 9/2010
WO WO 2010/108187 A2 9/2010
WO WO 2010/130794 A1 11/2010
WO WO 2011/035124 A1 3/2011
WO WO 2011/097218 A1 8/2011
WO WO 2011/130628 A1 10/2011
WO WO 2011/143669 A2 11/2011
WO WO 2011/156245 A2 12/2011
WO WO 2012/021382 A1 2/2012
WO WO 2012/044537 A1 4/2012
WO WO 2012/061708 A1 5/2012
WO WO 2012/079022 A1 6/2012
WO WO 2012/174199 A1 6/2012
WO WO 2012/178208 A2 12/2012
WO WO 2013/020557 A1 2/2013
WO WO 2013/059215 A1 4/2013
WO WO 2013/063560 A2 5/2013
WO WO 2013/106643 A2 7/2013
WO WO 2013/106646 A2 7/2013
WO WO 2013/170147 A1 11/2013
WO WO 2014/134240 A1 9/2014
WO WO 2014/145887 A1 9/2014
WO WO 2016/011906 A1 1/2016
WO WO 2016/040508 A1 3/2016
WO WO 2016/065139 A1 4/2016
WO WO 2016/105518 A1 6/2016
WO WO 2016/146985 A1 9/2016
WO WO 2016/169989 A1 10/2016
WO WO 2016/176449 A1 11/2016
WO WO 2016/176460 A1 11/2016
WO WO 2016/191178 A1 12/2016
WO WO 2016/197032 A1 12/2016
WO WO 2016/197114 A1 12/2016
WO WO 2017/007612 A1 1/2017
WO WO 2017/024317 A2 2/2017
WO WO 2017/024318 A1 2/2017
WO WO 2017/024319 A1 2/2017
WO WO 2017/046318 A1 3/2017
WO WO 2017/079267 A1 5/2017
WO WO 2017/117473 A1 7/2017
WO WO 2017/161119 A1 9/2017
WO WO 2017/176708 A1 10/2017
WO WO 2017/176957 A1 10/2017
WO WO 2017/176958 A1 10/2017
WO WO 2017/180417 A1 10/2017
WO WO 2017/197051 A1 11/2017
WO WO 2017/197055 A1 11/2017
WO WO 2017/197240 A1 11/2017
WO WO 2017/201069 A1 11/2017
WO WO 2017/201449 A1 11/2017
WO WO 2018/023029 A1 2/2018
WO WO 2018/051107 A1 3/2018
WO WO 2018/052945 A1 3/2018
WO WO 2018/052949 A1 3/2018
WO WO 2018/053354 A1 3/2018
WO WO 2018/071606 A1 4/2018
WO WO 2018/085247 A1 5/2018
WO WO 2018/102067 A2 6/2018
WO WO 2018/102725 A1 6/2018
WO WO 2018/118598 A1 6/2018
WO WO 2018/118947 A1 6/2018
WO WO 2018/119357 A1 6/2018
WO WO 2018/119441 A1 6/2018
WO WO 2018/119448 A1 6/2018
WO WO 2018/140809 A1 8/2018
WO WO 2018/144649 A1 8/2018
WO WO 2018/169777 A1 9/2018
WO WO 2018/183411 A1 10/2018
WO WO 2018/189554 A1 10/2018
WO WO 2018/191199 A1 10/2018
WO WO 2018/208123 A1 11/2018
WO WO 2019/043217 A1 3/2019

OTHER PUBLICATIONS

Buckley et al., "Targeting the Von Hippel-Lindau E3 ubiquitin ligase using small molecules to disrupt the Vhl/Hif-1alpha interaction" J. Am. Chem. Soc., 134:4465-4468, 2012. Published: Feb. 27, 2012.

Burkhard et al., "Synthesis and stability of oxetane analogs of thalidomide and lenalidomide" Organic Letters, 15(7):4312-4315, 2013. Published: Aug. 12, 2013.

Cancer [online], Medline Plus Trusted Health Information for you, [retrieved on Jul. 6, 2007] Retrieved from the Internet, URL: http://www.nlm.nih.gov/medlineplus/cancer.html (Year: 2007).

Chamberlain et al., "Structure of the human cereblon-DDB1-lenalidomide complex reveals basis for responsiveness to thalidomide analogs" Nature Structural and Molecule Biology, 21(9):803-809, 2014. Published: Aug. 10, 2014.

Chang, X. and Stewart, K. A. "What is the functional role of the thalidomide binding protein cereblon?" Int J Biochem Mol Bio., 2(3):287-294, 2011. Published: Sep. 10, 2011.

Chen et al; "Synthesis of structurally diverse benzimidazolyl benzimidazolones by application of soluble polymer support," Tetrahedron, Elsevier Science Publishers, Amsterdam, NL, vol. 64, No. 27, pp. 6387-6394, 2008. Published: Jun. 30, 2008.

Choi et al., "The impact of an indeno[1,2-b ]thiophene spacer on dye-sensitized solar cell performances of cyclic thiourea functionalized organic sensitizers", Journal of Materials Chemistry, 32, 12931-12939, 2014. Published: Jun. 10, 2014.

Choi et al., "Structure guided development of novel thymidine mimetics targeting pseudomonas aeruginosa thymidylate kinase: From hit to lead generation", Journal of Medicinal Chemistry, 55(13), 852-870, 2012. Published: Jan. 13, 2012.

Collins et al., "Chemical approaches to targeted protein degradation through modulation of the ubiquitin-protease pathway", Biochem. J. 474(7), 1127-1147, 2017. Published: Mar. 15, 2017.

Contino-Pepin et al., "Preliminary biological evaluations of new thalidomide analogues for multiple sclerosis application", Bioorganic & Medicinal Chemistry Letters, 19(3), 878-881, 2009. Published: Dec. 7, 2008.

Corson et al., "Design and applications of bifunctional small molecules: Why two heads are better than one" ACS Chemical Biology, 3(11): 677-692, 2008. Published: Oct. 24, 2008.

Crews, C. M., "Targeting the undruggable proteome: the small molecules of my dreams" Chemistry and Biology, 17(6):551-555, 2010. Published: Jun. 24, 2010.

Deshaies et al., "Ring domain E3 ubiquitin ligases." Ann. Rev. Biochem., 78:399-434, 2009. Published: Jul. 2009.

Elam W.A. et al., Poster Presentation titled "Application of biophysical techniques to the targeted protein degradation therapeutic strategy", Sep. 24, 2017.

Faden et al., "Generic tools for conditionally altering protein abundance and phenotypes on demand" Biol. Chem., 395(7-8):737-762, 2014. Published: Jul. 8, 2014.

Fischer et al., "Structure of the DDB1-CRBN E3 ubiquitin ligase in complex with thalidomide" Nature 2014, 512:49-53, 2014. Published: Jul. 16, 2014.

Fischer et al., "The molecular basis of CRL4DDB2/CSA ubiquitin ligase architecture, targeting, and activation" Cell, 147:1024-1039, 2011. Published: Nov. 23, 2011.

(56) References Cited

OTHER PUBLICATIONS

Fisher et al., "Targeted protein degradation and the enzymology of degraders", Current Opinion of Chemical Biology, 44, 47-55, 2018. Published: Jun. 7, 2018.
Golub et al., "Molecular Classification of Cancer: Class Discovery and Class Prediction by Gene Expression Monitoring", Science, 286, 531-537, 1999. Published: Oct. 15, 1999.
Gosink et al., "Redirecting the specificity of ubiquitination by modifying ubiquitin-conjugating enzymes" Proc. Natl. Acad. Sci. USA, 92:9117-9121, 1995. Published: Sep. 26, 1995.
Gustafson et al., "Small-molecule-mediated degradation of the androgen receptor through hydrophobic tagging" Angewandte Chemie, 54:9659-9662, 2015. Published: Jun. 17, 2015.
Hines et al., "Posttranslational protein knockdown couple to receptor tyrosine kinase activation with phosphor PROTACs" PNAS, 110(22):8942-8947, 2013. Published: May 14, 2013.
International search report and Written Opinion for PCT/EP2018/073584 mailed on Jan. 28, 2019.
Invitation to pay additional fees for PCT/EP2018/073584 mailed on Dec. 5, 2018.
International Search Report and Written Opinion for PCT/US2020/021491 mailed on Jun. 19, 2020.
Ito et al., "Identification of a Primary Target of thalidomide teratogenicity", Science, 327(5971), 1345-1350, 2010. Published: Mar. 12, 2010.
Itoh et al., "Protein knockdown using methyl bestatin-ligand hybrid molecules: design and synthesis of inducers of ubiquitination-mediated degradation of cellular retinoic acid-binding proteins" Journal of the American Chemical Society, 132(16), 5820-5826, 2010. Published Apr. 6, 2010.
Jacques et al., "Differentiation of anti-inflammatory and antitumorigenic properties of stabilized enantiomers of thalidomide analogs" PNAS, 112(12): E1471-E1479, 2015. Published: Mar. 9, 2015.
Krönke et al., "Lenalidomide causes selective degradation of IKZF1 and IKZF3 in Multiple Myeloma Cells" Science, 343(6168):301-305, 2014. Published: Nov. 28, 2013.
Krönke et al., "Lenalidomide induces ubiquitination and degradation of CDK1α in del(5q) MDS" Nature, 523(7559):183-188, 2015. Published: Jul. 1, 2015.
Lai et al., "Modular PROTAC design for the degradation of oncogenic BCR-ABL" Angewandte Chemie International Edition, 55:807-810, 2016. Published: Nov. 23, 2015.
Lala et al., "Role of nitric oxide in tumor progression: Lessons from experimental tumors" Cancer and Metastasis Reviews 17, 91-106, 1998. Published: Mar. 1998.
Lee et al., "Targeted degradation of the aryl hydrocarbon receptor by the PROTAC approach: a useful chemical genetic tool" ChemBioChem, 8:2058-2062, 2007. Published: Nov. 23, 2007.
Li et al., "Genome-wide and functional annotation of human E3 ubiquitin ligases identifies MULAN, a mitochondrial E3 that regulates the organelle's dynamics and signaling" PLOS One, 3:1487, 2008. Published: Jan. 23, 2008.
Liu et al., "Design and biological characterization of hybrid compounds of curcumin and thalidomide for multiple myeloma" Organic and Biomolecular Chemistry, 11:4757, 2013. Published: Jun. 11, 2013.
Lu et al., "Hijacking the E3 Ubiquitin ligase cereblon to efficiently target BRD4" Chemistry and Biology, 22(6):755-763, 2015. Published: Jun. 18, 2015.
Lu et al., "The Myeloma Drug Lenalidomide Promotes the Cereblon-Dependent Destruction of Ikaros Proteins", Science, 343, 305-309, 2014. Published: Nov. 28, 2013.
Nasveschuk C., Presentation titled "Advances in the medicinal chemistry of targeted protein degradation", Aug. 7, 2018.
Nawaz et al., "Proteasome-Dependent Degradation of the Human Estrogen Receptor" Proc. Natl. Acad. Sci. USA, 96:1858-1862, 1999. Published: Mar. 2, 1999.
Neklesa et al., "Small-molecule hydrophobic tagging-induced degradation of HaloTag fusion proteins" Nat Chem Biol, 7(8):538-543, 2011. Published: Jul. 3, 2011.
Ohta et al., "Novel 5-hydroxytryptamine (5-HT3) receptor antagonists. IV. Synthesis and pharmacological evaluation of the oxidation products of (−)-(R)-5-[(1-methyl-1H-indol-3-yl)carbonyl]-4,5,6,7-tetrahydro-1H-benzimidazole hydrochloride (YM060: Ramosetron)", Chem. Phann. Bull. 44(9), 1717-22, 1996. Published: Sep. 15, 1996.
Patel, J., Poster Presentation titled "Diverse Utility of Targeted Protein Degradation at C4 Therapeutics", Sep. 17, 2017.
Paul et al., "HZSM-5 catalysed regiospecific benzoylation of activated aromatic compounds", Tetrahedron Lett. 35(16), 2601-2602, 1994. Published: Apr. 18, 1994.
Phillips A., Presentation titled "Targeted Protein Degradation", Applied Pharmaceutical Chemistry, Cambridge, MA, Apr. 5, 2018.
Raina et al., "Chemical Inducers of Targeted Protein Degradation" Journal of Biological Chemistry, 285:11057-11060, 2010. Published: Feb. 10, 2010.
Rangarajan et al. "Topoisomerase I inhibition and cytotoxicity of 5-bromo- and 5-phenylterbenzimidazoles" Bioorganic & Medicinal Chemistry, vol. 8, 2591-2600, 2000. Published: Oct. 17, 2000.
Rodriguez-Gonzalez et al., "Targeting steroid hormone receptors for ubiquitination and degradation in breast and prostate cancer" Oncogene, 27:7201-7211, 2008. Published: Sep. 15, 2008.
Rozin et al., "Synthesis and properties of aroyl derivatives of 2-imidazolone and 2-benzimidazolone", Chemistry of Heterocyclic Compounds, 4(4), 698-701, 1968.
Ruchelman et al., "Isosteric analogs of lenalidomide and pomalidomide: Synthesis and biological activity" Bioorganic and Medicinal Chemistry Letters, 23:360-365, 2013. Published: Oct. 27, 2012.
Sakamoto et al., "Development of Protacs to Target Cancer-Promoting Proteins for Ubiquitination and Degradation" Molecular and Cellular Proteomics, 2(12):1350-1357, 2003. Published: Oct. 2, 2003.
Sakamoto et al., "Protacs: chimeric molecules that target proteins to the Skp1-Cullin-F box complex for ubiquitination and degradation" PNAS, 98(15):8554-8559, 2001. Published: Jul. 3, 2001.
Schneekloth et al., "Chemical approaches to controlling intracellular protein degradation" Chembiochem, 6(1):40-46, 2005. Published: Jan. 7, 2005.
Schneekloth et al., "Chemical genetic control of protein levels: selective in vivo targeted degradation" Journal of the American Chemical Society, 126(12):3748-3754, 2004. Published: Mar. 6, 2004.
Schneekloth et al., "Targeted intracellular protein degradation induced by a small molecule: En route to chemical proteomics" Bioorganic and Medicinal Chemistry Letters, 18:5904-5908, 2008. Published: Jul. 31, 2008.
Shoji, et al., "Modified DNA aptamer that binds the (R)-isomer of a thalidomide derivative with high enantioselectivity", J. Am. Chem. Soc., 129, 1456-1464, 2007. Published: Jan. 11, 2007.
Smith et al., "Targeted intracellular protein degradation induced by a small molecule: En route to chemical proteomics" Bioorganic and Medicinal Chemistry Letters, 18:5904-5908, 2008. Published: Jul. 31, 2008.
Smolyar et al., "Synthesis of 1,3-dialkyl-5-(hetaryl-1-yl)-1,3-dihydrobenzimidazol-2-ones", Russian Journal of Organic Chemistry, 47(8), 1190-1193, 2011. Published: Sep. 11, 2011.
Spratt et al., "RBR E3 ubiquitin ligases: new structures, new insights, new questions." Biochem. J., 458:421-437, 2014. Published: Feb. 28, 2014.
Terefenko et al., "SAR studies of 6-aryl-1,3-dihydrobenzimidazol-2-ones as progesterone receptor antagonists" Bioorganic & Med Chem Lett., 15(15), 3600-3603, 2005. Published: Jun. 22, 2005.
Toure et al., "Small-Molecule PROTACs: New Approaches to Protein Degradation" Angewandte Chemie International Edition, 55:1966-1973, 2016. Published: Jan. 12, 2016.
Vassilev et al., "In Vivo Activation of the P53 pathway by small-molecule antagonists of MDM2" Science, 303:844-848, 2004. Published: Feb. 6, 2004.
Vieux, Ellen et al., Poster Presentation titled "Measuring Small Molecule Induced Ubiquitination of Proteins", EMBO, Sep. 18, 2017.
Wang et al. "Roles of F-box proteins in cancer" Nat. Rev. Cancer, 14:233-347, 2014. Published: Mar. 24, 2014.

(56) References Cited

OTHER PUBLICATIONS

Winter et al., "Phthalimide conjugation as a strategy for in vivo target protein degradation", Science, 348(6241):1376-1381, 2015. Published: May 21, 2015.
Zeid, Rhamy, Presentation titled "Targeted protein degradation as a novel therapeutic approach", Gordon Research Conference, Jun. 26, 2017.
Zengerle et al., "Selective small molecule induced degradation of the bet bromodomain protein BRD4" Acs Chem. Biol., 10:1770-1777, 2015. Published: Jun. 16, 2015.
Zhou et al., "Harnessing the ubiquitination machinery to target the degradation of specific cellular proteins" Molecular Cell, 6:751-756, 2000. Published: Sep. 2000.
U.S. Pat. No. 11,802,131 B2, U.S. Appl. No. 16/809,336, Norcross et al., Mar. 4, 2020.
U.S. Pat. No. 10,646,575 B2, U.S. Appl. No. 16/186,339, Phillips et al., May 12, 2020.
U.S. Pat. No. 10,660,968 B2, U.S. Appl. No. 16/186,334, Phillips et al., May 26, 2020.
U.S. Pat. No. 10,849,982 B2, U.S. Appl. No. 16/186,341, Phillips et al., Dec. 1, 2020.
U.S. Pat. No. 10,905,768 B1, U.S. Appl. No. 16/872,225, Phillips et al., Feb. 2, 2021.
U.S. Pat. No. 11,185,592 B2, U.S. Appl. No. 16/882,236, Phillips et al., Nov. 30, 2021.
U.S. Pat. No. 11,254,672 B2, U.S. Appl. No. 16/809,325, Norcross et al., Feb. 22, 2022.
U.S. Pat. No. 11,401,256 B2, U.S. Appl. No. 16/809,345, Norcross et al., Jul. 13, 2022.
U.S. Pat. No. 11,407,732 B1, U.S. Appl. No. 17/498,617, Henderson et al., Aug. 9, 2022.
U.S. Pat. No. 11,459,335 B2, U.S. Appl. No. 16/721,650, Phillips et al., Sep. 14, 2022.
U.S. Pat. No. 11,524,949 B2, U.S. Appl. No. 16/874,475, Phillips et al., Dec. 13, 2022.
U.S. Pat. No. 11,584,748 B2, U.S. Appl. No. 17/072,896, Nasveschuk et al., Dec. 1, 2023.
U.S. Pat. No. 11,623,929 B2, U.S. Appl. No. 17/103,621, Nasveschuk et al., Mar. 22, 2023.
U.S. Pat. No. 11,673,902 B2, U.S. Appl. No. 17/843,769, Nasveschuk et al., Jun. 13, 2023.
U.S. Pat. No. 11,691,972 B2, U.S. Appl. No. 17/541,035, Nasveschuk et al., Jul. 4, 2023.
U.S. Pat. No. 11,787,802 B2, U.S. Appl. No. 17/576,582, Norcross et al., Oct. 17, 2023.
U.S. Pat. No. 11,753,397 B2, U.S. Appl. No. 17/031,550, Henderson et al., Aug. 23, 2023.
U.S. Pat. No. 11,992,531 B2, U.S. Appl. No. 17/107,781, Phillips et al., May 28, 2024.
U.S. Pat. No. 12,048,747 B2, U.S. Appl. No. 17/121,389, Phillips et al., Jul. 30, 2024.
U.S. Pat. No. 12,048,748 B2, U.S. Appl. No. 17/524,558, Phillips et al., Jul. 30, 2024.
U.S. Pat. No. 12,049,464 B2, U.S. Appl. No. 17/901,775, Nasveschuk et al., Jul. 30, 2024.
U.S. Pat. No. 12,076,405 B2, U.S. Appl. No. 17/164,446, Phillips et al., Sep. 3, 2024.
U.S. Pat. No. 12,091,397 B2, U.S. Appl. No. 17/878,753, Norcross et al., Sep. 17, 2024.
U.S. Publication No. 2022/0372016 A1, U.S. Appl. No 17/351,935, Phillips et al., Nov. 24, 2022.
U.S. Publication No. 2023/0082430 A1, U.S. Appl. No 17/723,199, Henderson et al., Mar. 16, 2023.
U.S. Publication No. 2023/0145336 A1, U.S. Appl. No 18/084,380, Nasveschuk et al., May 11, 2023.
U.S. Publication No. 2023/0190760 A1, U.S. Appl. No. 18/106,893, Proia et al., Jun. 22, 2023.
U.S. Publication No. 2023/0233692 A1, U.S. Appl. No. 18/105,735, Henderson et al., Jul. 27, 2023.
U.S. Publication No. 2023/0279023 A1, U.S. Appl. No. 17/959,144, Phillips et al., Sep. 7, 2023.
U.S. Publication No. 2023/0339902 A1, U.S. Appl. No. 18/134,985, Nasveschuk et al., Oct. 26, 2023.
U.S. Publication No. 2023/0357180 A1, U.S. Appl. No. 18/079,815, Phillips et al., Nov. 9, 2023.
U.S. Publication No. 2023/0372496 A1, U.S. Appl. No. 18/134,971, Nasveschuk et al., Nov. 23, 2023.
U.S. Publication No. 2023/0416251 A1, U.S. Appl. No. 18/100,992, Nasveschuk et al., Dec. 28, 2023.
U.S. Publication No. 2024/0018118 A1, U.S. Appl. No. 18/134,990, Nasveschuk et al., Jan. 18, 2024.
U.S. Publication No. 2024/0018156 A1, U.S. Appl. No. 18/117,978, Nasveschuk et al., Jan. 18, 2024.
U.S. Publication No. 2024/0051953 A1, U.S. Appl. No. 17/965,569, Nasveschuk et al., Feb. 15, 2024.
U.S. Publication No. 2024/0076300 A1, U.S. Appl. No. 18/144,800, Nasveschuk et al., Mar. 7, 2024.
U.S. Publication No. 2024/0109889 A1, U.S. Appl. No. 18/370,186, Norcross et al., Apr. 4, 2024.
U.S. Publication No. 2024/0158418 A1, U.S. Appl. No. 18/516,589, Nasveschuk et al., May 16, 2024.
U.S. Publication No. 2024/0199581 A1, U.S. Appl. No. 18/534,395, Nasveschuk et al., Jun. 20, 2024.
U.S. Publication No. 2024/0199638 A1, U.S. Appl. No. 18/385,277, Norcross et al., Jun. 20, 2024.
U.S. Publication No. 2024/0245677 A1, U.S. Appl. No. 18/600,097, Jackson et al., Jul. 25, 2024.
U.S. Appl. No. 18/240,231, Henderson et al., filed Aug. 30, 2023.
U.S. Appl. No. 18/642,602, Phillips et al., filed Apr. 22, 2023.
U.S. Appl. No. 18/774,794, Phillips et al., filed Jul. 16, 2024.
U.S. Appl. No. 18/774,801, Phillips et al., filed Jul. 16, 2024.
U.S. Appl. No. 18/775,662, Phillips et al., filed Jul. 17, 2024.
U.S. Appl. No. 18/797,261, Henderson et al., filed Aug. 7, 2024.
U.S. Appl. No. 18/806,363, Norcross et al., filed Aug. 15, 2024.
Database Registry [Online] American Chemical Society; Chemical Library: "3-Benzofurancarboxamide, N-(2,3-dihydro-2-oxo-5-benzoxazolyl)-5-methoxy-2-methyl—", XP093241532, Database accession No. 1252412-69-3; Compound 3-Benzofurancarboxamide, N-(2,3-dihydro-2-oxo-5-benzoxazolyl)-5-methoxy-2-methyl—, Nov. 10, 2010.
Database Registry [Online] American Chemical Society; Aurora Fine Chemicals: "1-Naphthalenecarboxamide, N-(2,3-dihydro-2-oxo-1H-benzimidazol-5-yl)-1,2,3,4-tetrahydro", XP093241541, Database accession No. 219654-37-5; Compound 1-Naphthalenecarboxamide, N-(2,3-dihydro-2-oxo-1H-benzimidazol-5-yl)-1,2,3,4-tetrahydro—, Mar. 22, 2018.
Database Registry [Online] American Chemical Society; Aurora Fine Chemicals: "1-Naphthalenecarboxamide, N-(2,3-dihydro-2-oxo-5-benzoxazolyl)-1,2,3,4-tetrahydro-", XP093241564, Database accession No. 2196039-34-4; Compound 1-Naphthalenecarboxamide, N-(2,3-dihydro-2-oxo-5-benzoxazolyl)-1,2,3,4-tetrahydro—, Mar. 21, 2018.
U.S. Pat. No. 12,157,735 B2, U.S. Appl. No. 17/965,569, Nasveschuk et al., Dec. 3, 2024.
U.S. Pat. No. 12,180,225 B2, U.S. Appl. No. 17/959,144, Phillips et al., Dec. 31, 2024.
U.S. Pat. No. 12,227,504 B2, U.S. Appl. No. 18/100,992, Nasveschuk et al., Feb. 18, 2025.
U.S. Publication No. 2023/0024096 A1, U.S. Appl. No. 17/771,204, Duplessis et al., Jan. 26, 2023.
U.S. Publication No. 2024/0391912 A1, U.S. Appl. No. 18/797,261, Henderson et al., Nov. 28, 2024.
U.S. Publication No. 2024/0398959 A1, U.S. Appl. No. 18/642,602, Phillips et al., Dec. 5, 2024.
U.S. Publication No. 2025/0057957 A1, U.S. Appl. No. 18/774,801, Phillips et al., Feb. 20, 2025.
U.S. Publication No. 2025/0084055 A1, U.S. Appl. No. 18/806,363, Norcross et al., Mar. 13, 2025.
U.S. Publication No. 2025/0084081 A1, U.S. Appl. No. 18/945,284, Nasveschuk et al., Mar. 13, 2025.
U.S. Publication No. 2025/0101037 A1, U.S. Appl. No. 18/973,867, Phillips et al., Mar. 27, 2025.

(56) References Cited

OTHER PUBLICATIONS

U.S. Publication No. 2025/0115580 A1, U.S. Appl. No. 18/980,700, Nasveschuk et al., Apr. 10, 2025.
U.S. Publication No. 2025/0121069 A1, U.S. Appl. No. 18/775,662, Phillips et al., Apr. 17, 2025.
U.S. Publication No. 2025/0121070 A1, U.S. Appl. No. 18/979,247, Nasveschuk et al., Apr. 17, 2025.
U.S. Publication No. 2025/0122179 A1, U.S. Appl. No. 18/972,557, Nasveschuk et al., Apr. 17, 2025.
U.S. Publication No. 2025/0127903 A1, U.S. Appl. No. 18/774,794, Phillips et al., Feb. 24, 2025.
U.S. Appl. No. 19/053,297, Nasveschuk et al., filed Feb. 13, 2025.
U.S. Appl. No. 19/205,510, Nasveschuk et al., filed May 12, 2025.
U.S. Appl. No. 19/224,081, Yu et al., filed May 30, 2025.

HETEROCYCLIC COMPOUNDS FOR MEDICAL TREATMENT

CROSS-REFERENCE TO RELATED APPLICATION

This application is a continuation of International Patent Application No. PCT/US2020/021491, filed in the U.S. Receiving Office on Mar. 6, 2020, which claims the benefit of provisional U.S. Application No. 62/814,706, filed Mar. 6, 2019. The entirety of each of these applications is incorporated herein for all purposes.

FIELD OF THE INVENTION

The present invention provides compounds which bind to the ubiquitously expressed E3 ligase protein cereblon (CRBN), which can alter the substrate specificity of the CRBNE3 ubiquitin ligase complex, resulting in breakdown of intrinsic downstream proteins that mediate disease. The present invention also provides compounds that can be used as synthetic intermediates in the preparation of bifunctional compounds for use in targeted protein degradation. The present compounds are thus useful for the treatment or prophylaxis of abnormal cellular proliferation, including tumors and cancer.

BACKGROUND OF THE INVENTION

Protein degradation is a highly regulated and essential process that maintains cellular homeostasis. The selective identification and removal of damaged, misfolded, or excess proteins is achieved via the ubiquitin-proteasome pathway (UPP). The UPP is central to the regulation of almost all cellular processes, including antigen processing, apoptosis, biogenesis of organelles, cell cycling, DNA transcription and repair, differentiation and development, immune response and inflammation, neural and muscular degeneration, morphogenesis of neural networks, modulation of cell surface receptors, ion channels and the secretory pathway, the response to stress and extracellular modulators, ribosome biogenesis and viral infection.

Covalent attachment of multiple ubiquitin molecules by an E3 ubiquitin ligase to a terminal lysine residue marks the protein for proteasome degradation, where the protein is digested into small peptides and eventually into its constituent amino acids that serve as building blocks for new proteins. Defective proteasomal degradation has been linked to a variety of clinical disorders including Alzheimer's disease, Parkinson's disease, Huntington's disease, muscular dystrophies, cardiovascular disease, and cancer among others.

Cereblon is a protein that in humans is encoded by the CRBN gene. CRBN orthologs are highly conserved from plants to humans, which underscores its physiological importance. Cereblon forms part of an E3 ubiquitin ligase protein complex which interacts with damaged DNA binding protein 1 (DDB1), forming an E3 ubiquitin ligase complex with Cullin 4 (CUL4A) and the E2-binding protein ROC1 (also known as RBX1) where it functions as a substrate receptor to select proteins for ubiquitination. Through a mechanism that has not been completely elucidated, cereblon ubiquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this E3 ubiquitin ligase complex is important for limb outgrowth in embryos. In the absence of cereblon, DDB1 forms a complex with DDB2 that functions as a DNA damage-binding protein.

In unrelated parallel research, Ito et al. (*Science* 2010, 327, 1345-1350) titled "Identification of a Primary Target of Thalidomide Teratogenicity", described that cereblon is a thalidomide binding protein. The study revealed that thalidomide-cereblon binding in vivo may be responsible for thalidomide teratogenicity. After the discovery that thalidomide causes teratogenicity in the mid-1960's, the compound and certain related structures were notwithstanding found to be useful as anti-inflammatory, anti-angiogenic and anticancer agents (see Bartlett et al. (*Nat. Rev. Cancer* 2004, 4, 314-322) titled "The Evolution of Thalidomide and Its Imid Derivatives as Anticancer Agents"). Thalidomide has been approved for the treatment of certain neoplastic diseases, including multiple myeloma, and is currently under investigation for use in treating a variety of other types of cancer along with the structural derivatives lenalidomide and pomalidomide (see Martiniani, R. et al. "Biological activity of lenalidomide and its underlying therapeutic effects in multiple myeloma" Adv Hematol, 2012, 2012:842945; and Terpos, E. et al. "Pomalidomide: a novel drug to treat relapsed and refractory multiple myeloma" Oncotargets and Therapy, 2013, 6:531).

The disclosure that thalidomide binds to the cereblon E3 ubiquitin ligase led to research to investigate incorporating thalidomide and certain derivatives into compounds for the targeted destruction of proteins. Celgene has disclosed imids for similar uses, including those in U.S. Pat. Nos. 6,045,501; 6,315,720; 6,395,754; 6,561,976; 6,561,977; 6,755,784; 6,869,399; 6,908,432; 7,141,018; 7,230,012; 7,820,697; 7,874,984; 7,959,566; 8,204,763; 8,315,886; 8,589,188; 8,626,531; 8,673,939; 8,735,428; 8,741,929; 8,828,427; 9,056,120; 9,101,621; and 9,101,622.

Patent applications filed by C4 Therapeutics, Inc., that describe compounds capable of binding to an E3 ubiquitin ligase include: WO 2019/236483 titled "Spirocyclic Compounds"; WO 2019/191112 titled "Cereblon Binders for the Degradation of Ikaros"; WO 2019/099868 titled "Degraders and Degrons for Targeted Protein Degradation"; WO 2018/237026 titled "N/O-Linked Degrons and Degronimers for Protein Degradation"; WO 2017/197051 titled "Amine-Linked C3-Glutarimide Degronimers for Target Protein Degradation"; WO 2017/197055 titled "Heterocyclic Degronimers for Target Protein Degradation"; WO 2017/197036 titled "Spirocyclic Degronimers for Target Protein Degradation"; WO 2017/197046 20 titled "C3-Carbon Linked Glutarimide Degronimers for Target Protein Degradation"; and WO 2017/197056 titled "Bromodomain Targeting Degronimers for Target Protein Degradation."

Patent applications filed by C4 Therapeutics, Inc. and Hoffmann-La Roche that describe compounds capable of binding to an E3 ubiquitin ligase include WO 2019/121562 titled "Bifunctional Inhibitors with EGFR having a E3 Ubiquitin Ligase Moiety"; WO 2019/149922 titled "Compounds Which Cause Degradation of EGFR, for use Against Cancer"; WO 2018/220149 titled "Compounds"; and WO 2018/115218 titled "2-Benzopyrazinyl-N-Heteroaryl-2-Phenyl-Acetamide Compounds."

Additional compound publications include: WO 2011/035124; WO 02/072576; WO 2010/085684; WO 2014/134240; WO 2011/130628; WO 2007/065518; WO 2016/176640; WO 2009/135651; WO 2011/156245; WO 2017/046318; WO 2010/130794; WO 2012/021382; WO 2005/060967; WO 2012/174199; EP385850; WO 2016/176449;

WO 2016/040508; WO 00/20358; EP125678; WO 2006/058338; WO 2004/108133; WO 2010/108817; WO 2005/113489; WO 2012/061708; WO 2010/023161; WO 2007/041598; WO 2009/050232; WO 2018/93569; Terefenk et al. *Bioorg. Med Chem. Lett.* 2005, 15(15):3600-03; Smolyar et al. *Russian Journal of Organic Chemistry* 2011, 47(8): 119-3; Jun Yon Choi et al. *J. Med Chem.* 2012, 55(13):852-70.

There is a need for new compounds, compositions, and uses thereof that bind to the E3 ligase protein cereblon to treat various medical conditions, notably abnormal cellular proliferation. There is also a need for new compounds that may be used in the preparation of bifunctional molecules that are used in the degradation of proteins that are involved in disease processes.

SUMMARY OF THE INVENTION

In a first aspect, compounds and their uses and manufacture are provided that bind to cereblon and modify the ubiquitination of proteins by a cereblon-containing E3 ubiquitin ligase. In a second aspect, compounds are provided that contain a chemical moiety capable of binding to cereblon, which can be used as synthetic intermediates in the preparation of bifunctional compounds that cause degradation of a selected protein via the ubiquitin proteosome pathway (UPP).

The compounds described herein can be administered to a host, for example, a human, in need thereof, in an effective amount, optionally as a pharmaceutically acceptable salt, and optionally in a pharmaceutically acceptable composition. The compounds can be administered for any therapeutic indication which can be treated by modulating the function or activity of the cereblon-containing E3 Ubiquitin Ligase Protein Complex, including but not limited to the treatment of abnormal cell proliferation, such as cancer or a tumor, or other uses known for the cereblon binders thalidomide, pomalidomide, and lenalidomide. In certain embodiments, the compounds as described herein can modulate the natural activity of cereblon.

The invention includes new compounds of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, and Formulas XIII-a to XIII-I. In addition, the invention includes the use of compounds generally in Formula XIV for the treatment of a therapeutic condition that can be treated by modulating the function or activity of the cereblon-containing E3 Ubiquitin Ligase Protein Complex. The invention also includes the use of compounds generally in Formula XIV(1) in the preparation of bifunctional compounds that degrade a target protein by the ubiquitin proteasome pathway (UPP). The invention also includes compounds of Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), and Formulas XIII(1)-a to XIII(1)-i.

In one aspect, a compound is provided of Formula I:

(I)

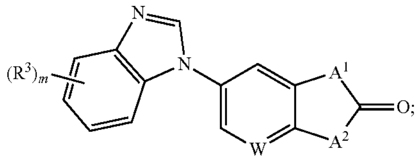

or a pharmaceutically acceptable salt thereof;

wherein:

$A^1$ is selected from the group consisting of —O—, —S—, —$CH_2$—, —$CF_2$— and —NH—, and $A^2$ is —$CH_2$—; or $A^1$ is selected from the group consisting of —O—, —S—, —$CH_2$—, and —$CF_2$—, and $A^2$ is —NH—;

W is CH or N;

$R^3$ is independently selected at each occurrence from: —$(CH_2)_{0-1}$—($C_{3-7}$cycloalkyl)-aryl substituted by $R^{10}$; —$(CH_2)_{0-1}$—($C_{3-7}$cycloalkyl)-aryl; —$(CH_2)_{0-1}$-aryl substituted by $R^{10}$; —$(CH_2)_{0-1}$-aryl; —$(CH_2)_{0-1}$—$C_{3-7}$cycloalkyl substituted by $R^{10}$; —$(CH_2)_{0-1}$—$C_{3-7}$cycloalkyl; —$(CH_2)_{0-1}$-heteroaryl substituted by $R^9$; —$(CH_2)_{0-1}$-heteroaryl; —$(CH_2)_{0-1}$-heterocycloalkyl; —C(=O)$C_{1-6}$alkyl; —$(CH_2)_{0-2}$—C(=O)—N($R^7$, $R^8$); —C(=O)O$C_{1-6}$alkyl; —$C_{1-6}$alkoxy; —$C_{1-6}$alkyl; —OH; —$NO_2$; —$C_{1-6}$alkyl-N($R^{11}$)—C(=O)—$R^{12}$; —$CH_2$—O—$(CH_2)_{0-1}$-aryl substituted by $R^{10}$; —$CH_2$—O—$(CH_2)_{0-1}$-aryl; —O—$(CH_2)_{0-1}$-aryl; -halogen; -halogen-$C_{1-6}$alkyl; -hydroxy-$C_{1-6}$alkyl; -hydroxy-$C_{1-6}$alkyl-aryl; —N($R^5$,$R^6$); —NH—C(=O)$C_{1-6}$alkyl; —NH—C(=O)O$C_{1-6}$alkyl; and =O as allowed by valence;

m is 0, 1, or 2;

$R^5$ and $R^6$ are independently selected at each occurrence from H, $C_{1-6}$alkyl and phenyl;

or $R^5$ and $R^6$, taken together with the nitrogen to which they are attached, form a heterocycloalkyl ring;

$R^7$ and $R^8$ are independently selected at each occurrence from H and $C_{1-6}$alkyl;

or $R^7$ and $R^8$, taken together with the nitrogen to which they are attached, form a heterocycloalkyl ring;

$R^9$ is independently selected at each occurrence from $C_{1-6}$alkoxy, $C_{1-6}$alkyl, halogen, halogen-$C_{1-6}$alkyl, heteroaryl, and heteroaryl substituted by $C_{1-6}$alkyl or $C_{1-6}$alkoxy;

$R^{10}$ is independently selected at each occurrence from $C_{1-6}$alkoxy, $C_{1-6}$alkyl, $C_{1-6}$alkyl-$C_{1-6}$alkoxy, halogen, and halogen-$C_{1-6}$alkyl;

$R^{11}$ is independently selected at each occurrence from H and $C_{1-6}$alkyl; and $R^{12}$ is independently selected at each occurrence from H, $C_{1-6}$alkyl and $C_{3-7}$cycloalkyl.

In another aspect, a compound is provided of one of the following formulas:
(II-a)
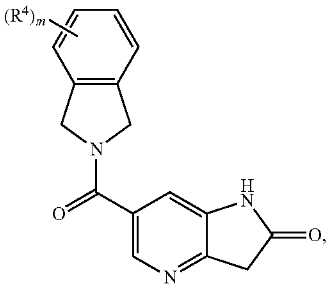
(II-b)
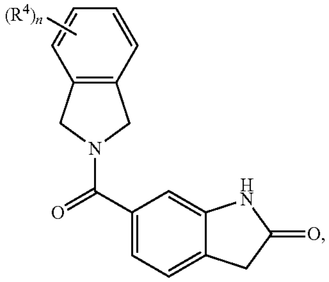
(II-c)
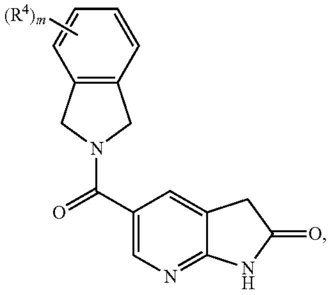
(II-d)
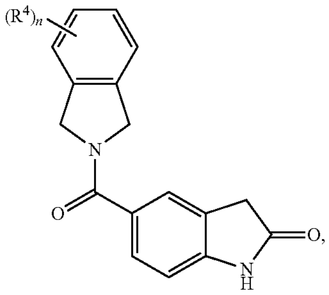
(II-e)
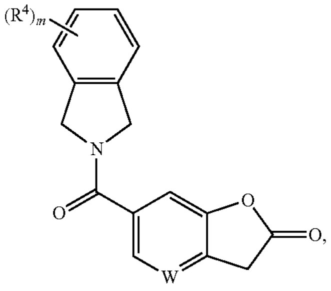
-continued
(II-f)
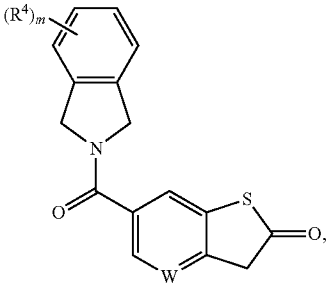
(II-g)
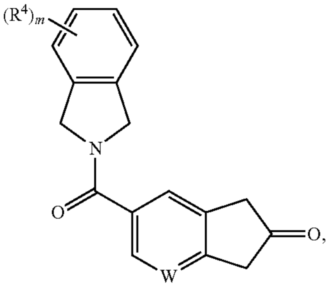
(II-h)
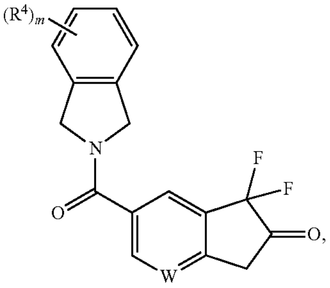
(II-i)
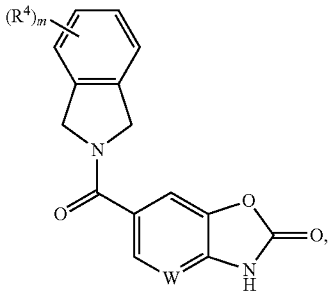
(II-j)
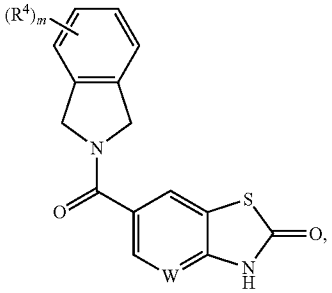
and -continued (II-k)

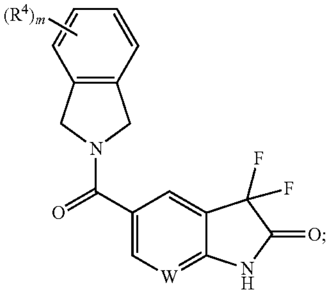

or a pharmaceutically acceptable salt thereof;

wherein:

n is 1 or 2; and all other variables are as defined herein.

In another aspect, a compound is provided of Formula III:

(III)

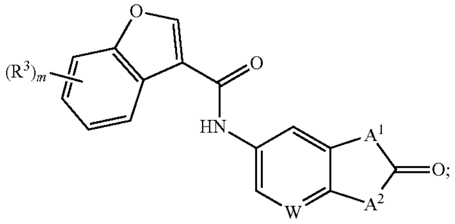

or a pharmaceutically acceptable salt thereof;

wherein all variables are as defined herein.

In another aspect a compound is provided of one of the following formulas:

(IV-a)

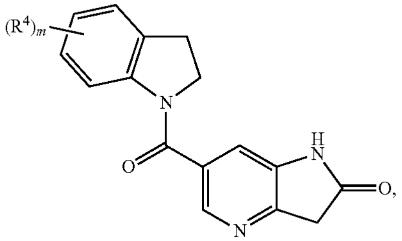

(IV-b)

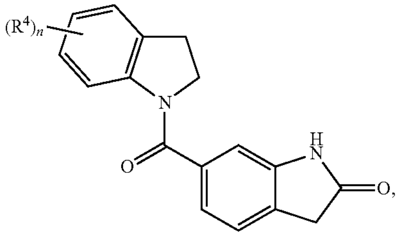

-continued (IV-c)

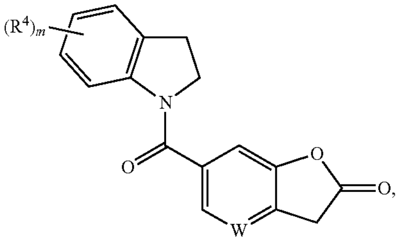

(IV-d)

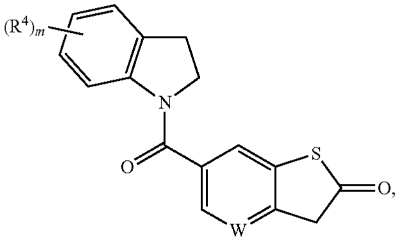

(IV-e)

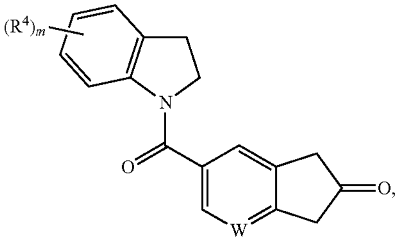

(IV-f)

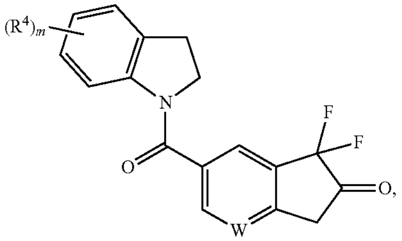

(IV-g)

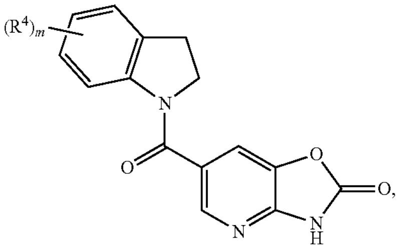

(IV-h)

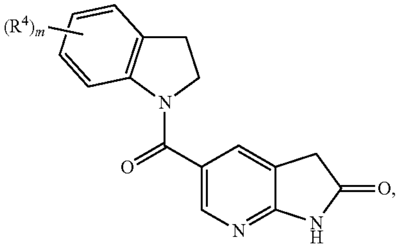

-continued (IV-i)

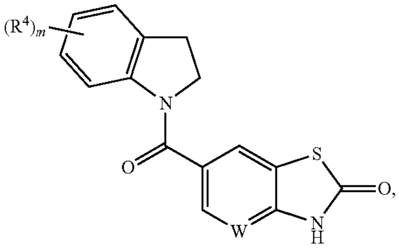

and (IV-j)

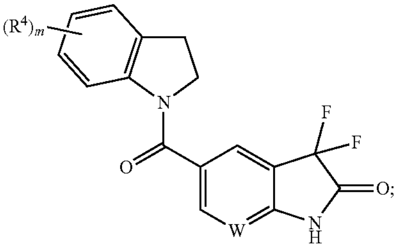

or a pharmaceutically acceptable salt thereof; wherein all variables are as defined herein.

In another aspect, a compound is provided of Formula V:

(V)

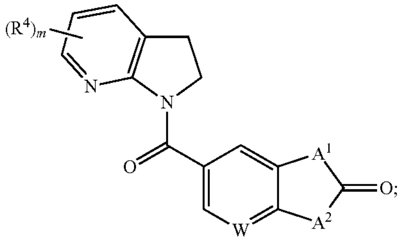

or a pharmaceutically acceptable salt thereof; wherein all variables are as defined herein.

In another aspect, a compound is provided of Formula VI:

(VI)

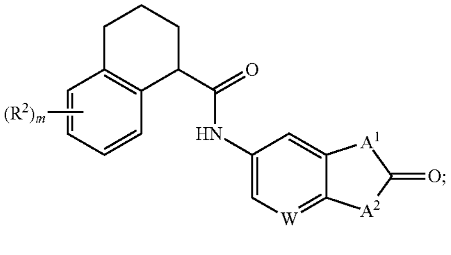

or a pharmaceutically acceptable salt thereof; wherein:

$R^2$ is independently selected at each occurrence from: —$(CH_2)_{0-1}$—($C_{3-7}$cycloalkyl)-aryl substituted by $R^{10}$; —$(CH_2)_{0-1}$—($C_{3-7}$cycloalkyl)-aryl; —$(CH_2)_{0-1}$-aryl substituted by $R^{10}$; —$(CH_2)_{0-1}$-aryl; —$(CH_2)_{0-1}$—$C_{3-7}$cycloalkyl substituted by $R^{10}$; —$(CH_2)_{0-1}$—$C_{3-7}$cycloalkyl; —$(CH_2)_{0-1}$-heteroaryl substituted by $R^9$; —$(CH_2)_{0-1}$-heteroaryl; —C(═O)$C_{1-6}$alkyl; —C(═O)—N($R^7$,$R^8$); —C(═O)O$C_{1-6}$alkyl; —$C_{1-6}$ alkoxy; —$C_{1-6}$alkyl; —$CH_2$—O—$(CH_2)_{0-1}$-aryl substituted by $R^{10}$; —$CH_2$—O—$(CH_2)_{0-1}$-aryl; —O—

$(CH_2)_{0-1}$-aryl; -halogen; -halogen-$C_{1-6}$alkyl; -hydroxy-$C_{1-6}$alkyl; —N($R^5$,$R^6$); —$NO_2$; —NH—C(═O)$C_{1-6}$ alkyl; and —$SO_2$—N($R^5$,$R^6$); and all other variables are as defined herein.

In another aspect, a compound is provided of one of the following formulas:

(VII-a)

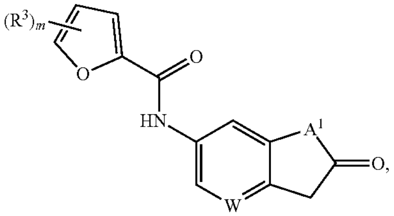

(VII-b)

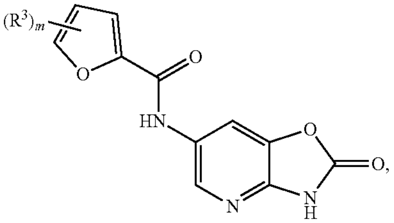

(VII-c)

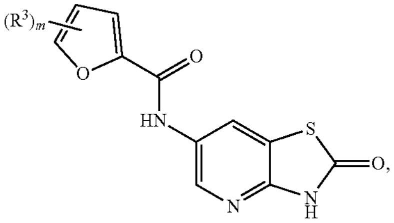

(VII-d)

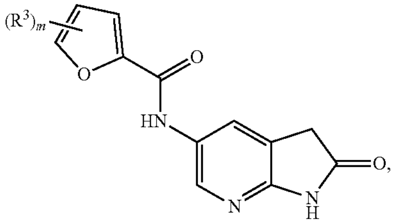

and (VII-e)

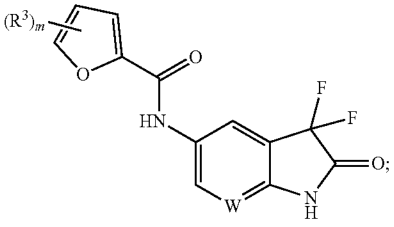

or a pharmaceutically acceptable salt thereof; wherein all variables are as defined herein.

In another aspect, a compound is provided of one of the following formulas:
(VIII-a)
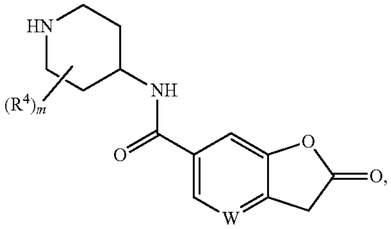
(VIII-b)
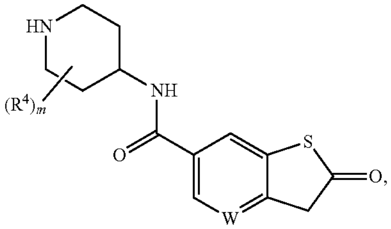
(VIII-c)
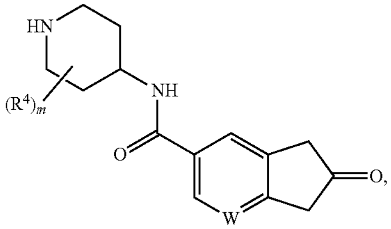
(VIII-d)
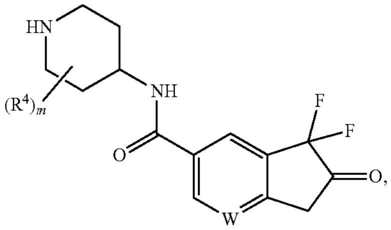
(VIII-e)
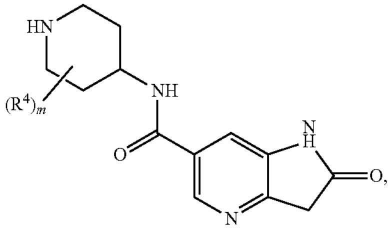
(VIII-f)
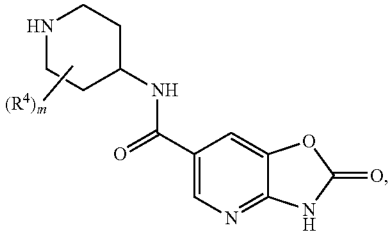
-continued
(VIII-g)
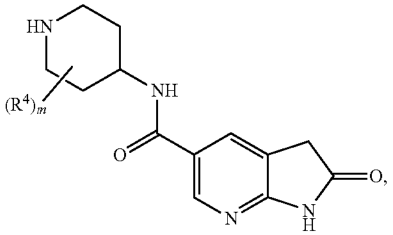
(VIII-h)
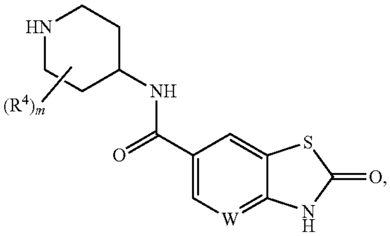
and
(VIII-i)
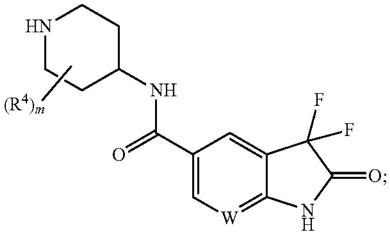
or a pharmaceutically acceptable salt thereof;
wherein all variables are as defined herein.
In another aspect, a compound is provided of one of the following formulas:
(IX-a)
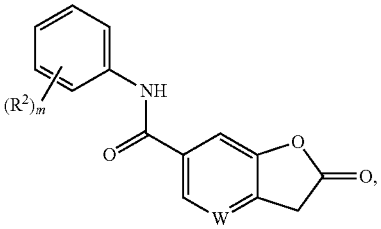
(IX-b)
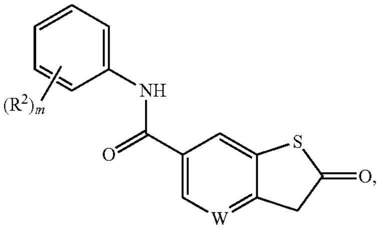
(IX-c)
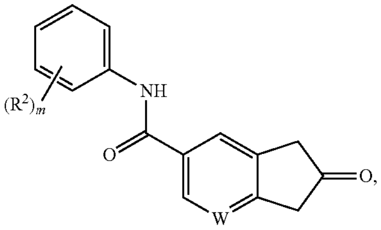

-continued
(IX-d)
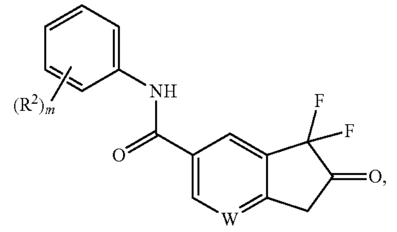
(IX-e)
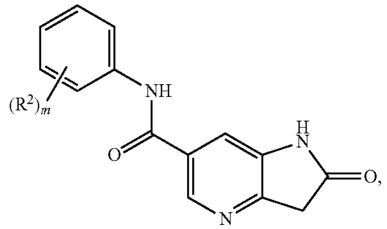
(IX-f)
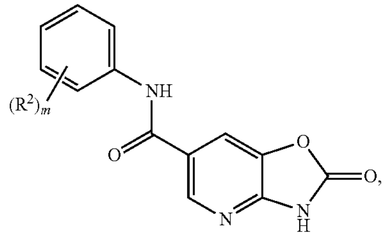
(IX-g)
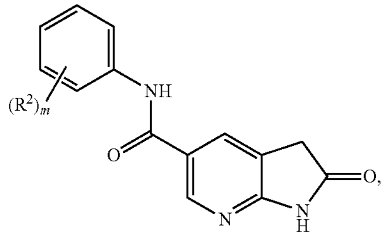
(IX-h)
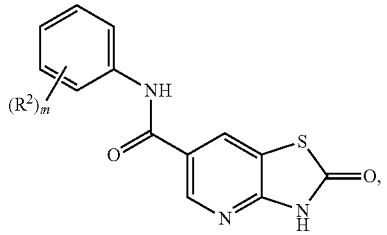
(IX-i)
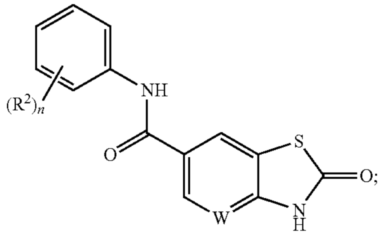
and
-continued
(IX-j)
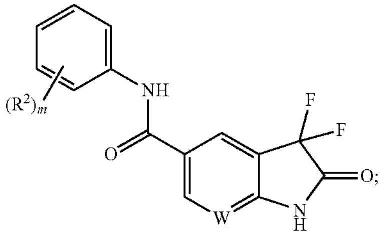
or a pharmaceutically acceptable salt thereof; wherein all variables are as defined herein.
In another aspect, a compound is provided of one of the following formulas:
(X-a)
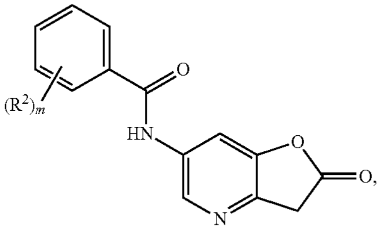
(X-b)
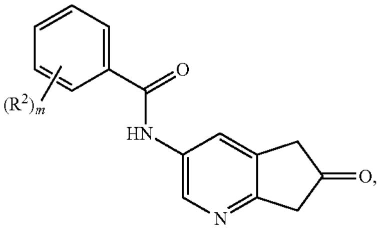
(X-c)
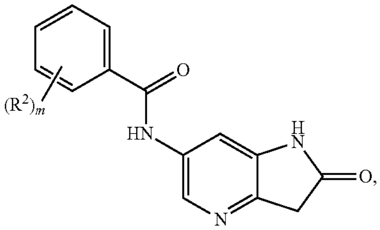
(X-d)
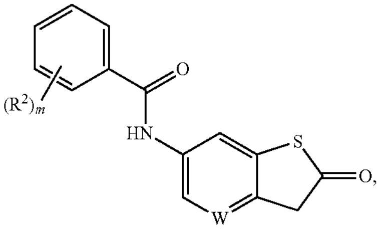
(X-e)
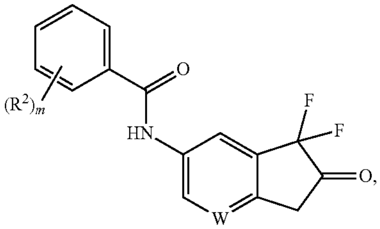

-continued
(X-f)
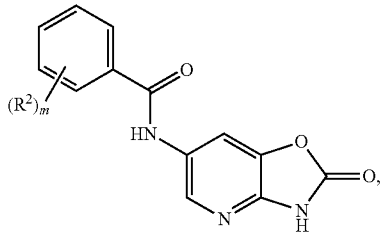
(X-g)
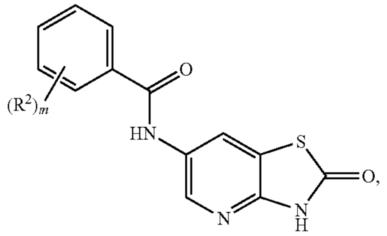
(X-h)
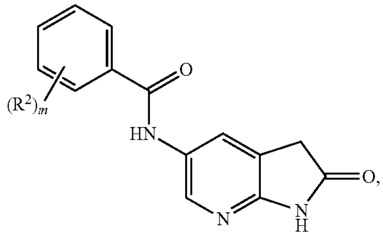
and
(X-i)
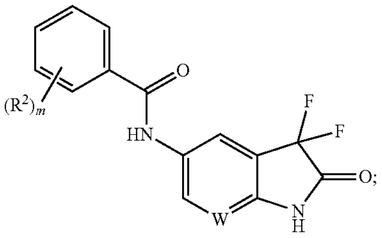
or a pharmaceutically acceptable salt thereof;
wherein all variables are as defined herein.
In another aspect, a compound is provided of one of the following formulas:
(XI-a)
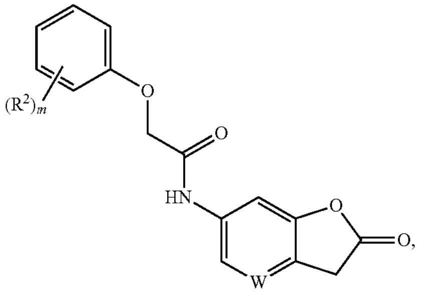
-continued
(XI-b)
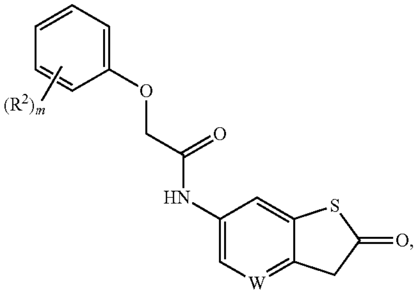
(XI-c)
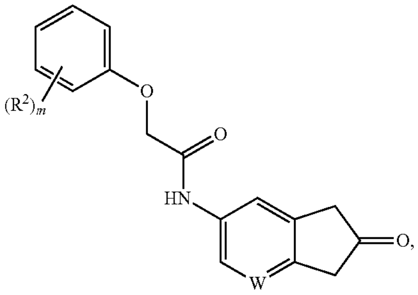
(XI-d)
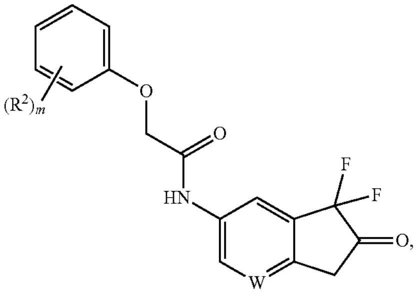
(XI-e)
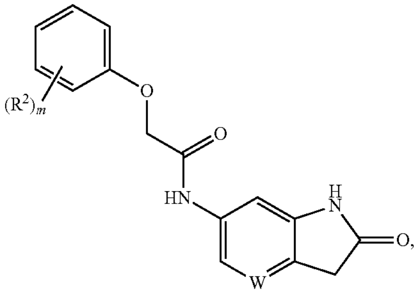
(XI-f)
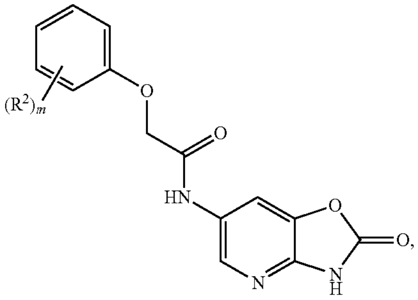

-continued (XI-g)

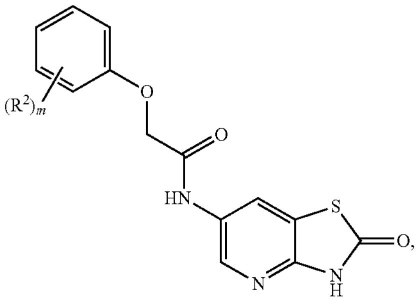

(XI-h)

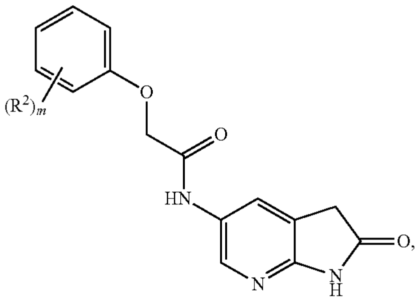

and (XI-i)

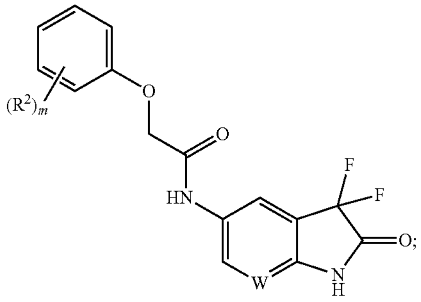

or a pharmaceutically acceptable salt thereof;

wherein all variables are as defined herein.

In another aspect, a compound is provided of Formula XII:

(XII)

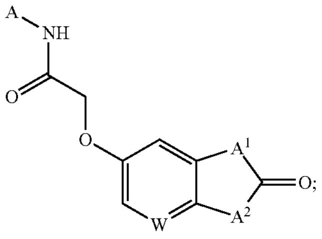

or a pharmaceutically acceptable salt thereof;

wherein:

A is selected from: aryl optionally substituted with one or two $R^2$ groups; heteroaryl optionally substituted with one or two $R^3$ groups; heterocycloalkyl optionally substituted with one or two $R^4$ groups; —NH—C(═O)—$C_{1-6}$alkyl; and cycloalkyl; and all other variables are as defined herein.

In another aspect, a compound is provided of one of the following formulas:

(XIII-a)

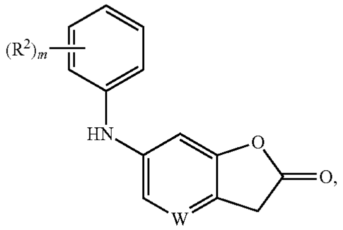

(XIII-b)

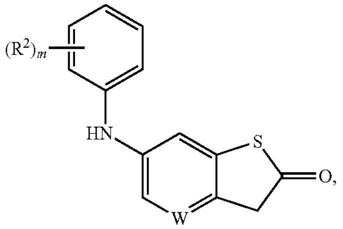

(XIII-c)

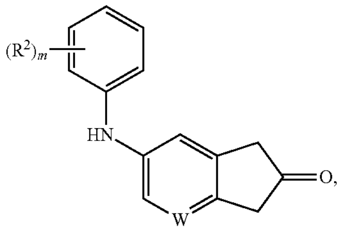

(XIII-d)

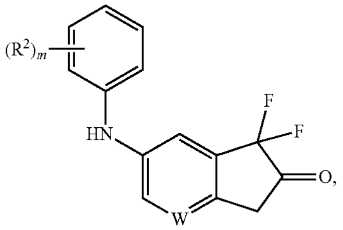

(XIII-e)

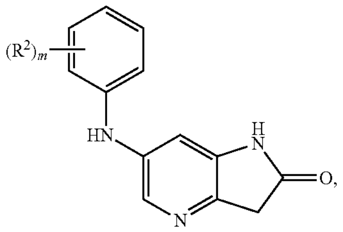

(XIII-f)

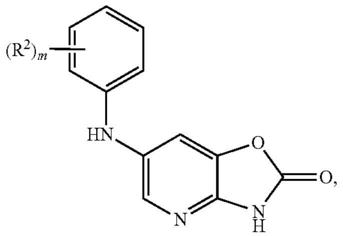

-continued (XIII-g)

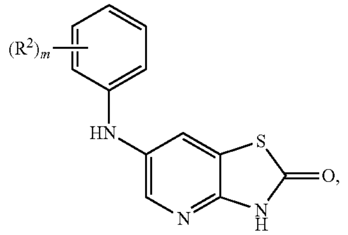

(XIII-h)

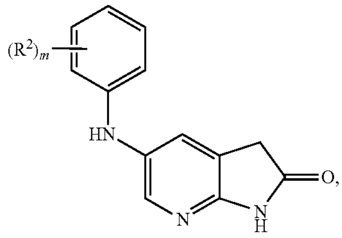

and (XIII-i)

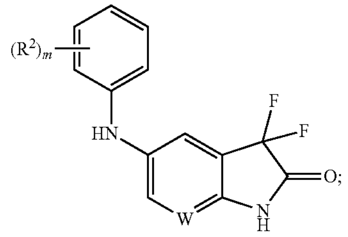

or a pharmaceutically acceptable salt thereof;

wherein all variables are as defined herein.

In another aspect, the use of a compound for the treatment of a therapeutic condition which can be treated by modulating the function or activity of the cereblon-containing E3 Ubiquitin Ligase Protein Complex is provided of Formula XIV:

(XIV)

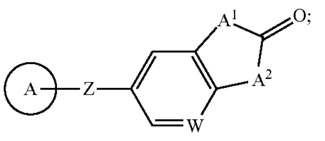

or a pharmaceutically acceptable salt thereof;

wherein Z is selected from: a covalent bond; carbonyl; $-(CH_2)_{0-2}-NR^1-(CH_2)_{0-2}-$; $-(NR^1)_{0-1}-C(=O)-(NR^1)_{0-1}-$; $-(NR^1)_{0-1}-C(=O)-(CH_2)_{1-3}-$; $-O-(CH_2)_{0-2}-C(=O)-NR^1-$; $-(CH_2)_{1-3}-$; $-(CH_2)_{1-3}-$; $-(CH_2)_{0-2}-O-(CH_2)_{0-2}$; and $-(NR^1)_{0-1}-SO_{0-2}-(NR^1)_{0-1}-$; or in an alternative embodiment, Z is selected from alkylene, alkenylene, alkynylene, arylene, heteroarylene, heterocyclyl, or carbocyclyl;

each occurrence of $R^1$ is independently selected from H or $C_{1-6}$alkyl; and all other variables are as defined herein.

The compounds of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, and Formula IV can activate, decrease, or change the natural activity of cereblon. These compounds of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, and Formula XIV are useful as therapeutic agents when administered in an effective amount to a host, typically a human, for the treatment of a medical disorder including, but not limited to, abnormal cellular proliferation, including a tumor or cancer, or a myelo- or lymphoproliferative disorder such as B- or T-cell lymphomas, multiple myeloma, Waldenstrom's macroglobulinemia, Wiskott-Aldrich syndrome, or a post-transplant lymphoproliferative disorder; an immune disorder, including autoimmune disorder such as Addison disease, Celiac disease, Dermatomyositis, Graves disease, thyroiditis, multiple sclerosis, pernicious anemia, reactive arthritis, lupus, or type I diabetes; a disease of cardiologic malfunction including hypercholesterolemia; an infectious disease including viral or bacterial infections; inflammatory conditions including asthma, chronic peptic ulcers, tuberculosis, rheumatoid arthritis, periodontitis, ulcerative colitis, Crohn's disease, or hepatitis; or any disorder than can be treated with thalidomide, pomalidomide, or lenalidomide.

In certain embodiments, the present invention provides the administration of an effective amount of a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, or Formula XIV to treat a patient, for example a human, having an infectious disease, wherein the therapy acts via binding to cereblon or its E3 Ubiquitin Ligase or acts through an independent mechanism, optionally in combination with another bioactive agent. The disease state or condition may be caused by a microbial agent or other exogenous agent such as a virus (as non-limiting examples, HIV, HBV, HCV, HSV, HPV, RSV, CMV, Ebola, Flavivirus, Pestivirus, Rotavirus, Influenza, Coronavirus, EBV, viral pneumonia, drug-resistant viruses, Bird Flu, RNA virus, DNA virus, adenovirus, poxvirus, Picomavirus, Togavirus, Orthomyxovirus, Retrovirus, or Hepadovirus), bacterial (including but not limited to Gram-negative, Gram-positive, Atypical, *Staphylococcus, Streptococcus, E. Coli, Salmonella, Helicobacter pylori*, meningitis, gonorrhea, Chlamydiaceae, Mycoplasmataceae, etc.), fungus, protozoa, helminth, worm, prion, parasite, or other microbe.

In another aspect, the compounds disclosed can be used as synthetic intermediates in the preparation of bifunctional compounds that cause degradation of a selected protein via the ubiquitin proteosome pathway (UPP) is provided. These compounds contain a functional group that can react with a second compound, wherein the second compound is capable of binding to a selected protein of interest, to create a bifunctional compound as described above that can cause the degradation of the selected protein via the UPP.

Thus, compounds of Formula XIV(1), or a pharmaceutically acceptable salt thereof, which can be used in the preparation of bifunctional compounds that cause degradation of a selected protein via the UPP are provided:

[XIV(1)]

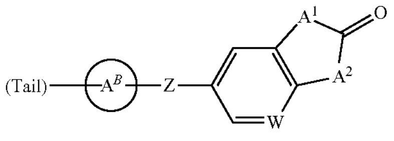

wherein:

$A^B$ is selected from arylene optionally substituted with one or two $R^2$ groups, heteroarylene optionally substituted with one or two $R^3$ groups; heterocycloalkylene optionally substituted with one or two $R^4$ groups, —NH—C(═O)—$C_{1-6}$alkylene-, and cycloalkylene;

"Tail" is a chemical moiety that contains a reactive functional group that can covalently bind to a protein binding moiety to produce a targeted protein degrader, or "Tail" is a chemical moiety that can be used to modify the properties of the compound such as hydrophobicity, hydrophilicity, solubility, drug delivery, pharmacokinetics, or other properties such as charge, polarity, or fit within the active pocket;

in one embodiment, "Tail" is

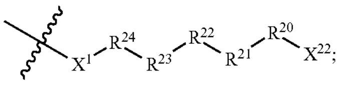

$X^1$ is selected from bond, $NR^{34}$, $CH_2$, $CHR^{34}$, $C(R^{34})_2$, O, and S;

$X^{22}$ is a functional group that can be used as a linking group to a protein binding moiety; or $X^{22}$ is a group that caps the valence and is not typically a linking group; representative examples of $X^{22}$ include, but are not limited to, halo, —$NH_2$, —$NHR^{34}$, —$N(R^{34})_2$, hydroxyl, thiol, —$B(OH)_2$, —$Sn(R^{36})_3$, —$Si(R^{36})_3$, —$OS(O)_2$alkyl, —$OS(O)_2$haloalkyl, alkenyl, alkynyl, ethynyl, ethenyl, —C(O)H, —$NR^{34}$C(O)alkene, —$NR^{34}$C(O)alkyne, cyano, —SC(O)alkyl, OC(O)alkyl, heterocycle, —C(O)OH, hydrogen, alkyl, aryl, heteroaryl, aliphatic, heteroaliphatic, and carbocyclic;

$R^{34}$ and $R^{34'}$ are independently selected at each occurrence from hydrogen, $C_1$-$C_6$alkyl (for example methyl, ethyl, cyclopropyl, or $C_1$-$C_3$alkyl), $C_1$-$C_6$haloalkyl, $C_2$-$C_6$alkenyl, $C_2$-$C_6$alkynyl, $C_3$-$C_6$cycloalkyl, $C_3$-$C_6$heterocycle, aryl, heteroaryl, —$(CO)R^{36}$, —$(CS)R^{36}$, —$(C{=}NH)R^{36}$, —$(SO)R^{36}$, and —$(SO_2)R^{36}$;

$R^{36}$ is independently selected at each occurrence from hydrogen, $C_1$-$C_6$alkyl, $C_1$-$C_6$haloalkyl, $C_2$-$C_6$alkenyl, $C_2$-$C_6$alkynyl, $C_3$-$C_6$cycloalkyl, $C_3$-$C_6$heterocycle, aryl, heteroaryl, hydroxyl, $C_1$-$C_6$alkoxy, thio, $C_1$-$C_6$thioalkyl, —$NH_2$, —NH($C_1$-$C_6$alkyl, $C_3$-$C_7$cycloalkyl, $C_3$-$C_7$heterocycle, aryl, or heteroaryl), and —N(independently $C_1$-$C_6$alkyl, $C_3$-$C_7$cycloalkyl, $C_3$-$C_7$heterocycle, aryl, or heteroaryl)$_2$;

$R^{20}$, $R^{21}$, $R^{22}$, $R^{23}$, and $R^{24}$ are independently a divalent or multivalent linking group, including but not limited to a covalent bond, alkyl, —C(O)—, —C(O)O—, —OC(O)—, —C(O)alkyl, —C(O)Oalkyl, —C(S)—, —$SO_2$—, —S(O)—, —C(S)—, —C(O)NH—, —NHC(O)—, —N(alkyl)C(O)—, —C(O)N(alkyl)-, —O—, —S—, —NH—, —N(alkyl)-, —CH(—O—$R^{26}$)—, —CH(—$NR^{34}R^{34'}$)—, —C(—O—$R^{26}$)alkyl-, —C(—$NR^{34}R^{34'}$)alkyl-, —$C(R^{40}R^{40})$—, -alkyl($R^{27}$)-alkyl($R^{28}$)—, —$C(R^{27}R^{28})$—, —P(O)($OR^{26}$)O—, —P(O)($OR^{26}$)—, —$NR^{34}C(O)NR^{34}$—, alkene, haloalkyl, alkoxy, alkyneheteroarylalkyl, aryl, arylalkyl, heterocycle, aliphatic, heteroaliphatic, heteroaryl, lactic acid, glycolic acid, carbocycle, -(ethylene glycol)$_{1-6}$-, -(lactic-co-glycolic acid)$_{1-6}$-, -(propylene glycol)$_{1-6}$-, —O—$(CH_2)_{1-12}$—O—, —NH—$(CH_2)_{1-12}$—NH—, —NH—$(CH_2)_{1-12}$—O—, —O—$(CH_2)_{1-12}$—NH—, —S—$(CH_2)_{1-12}$—O—, —O—$(CH_2)_{1-12}$—S—, —S—$(CH_2)_{1-12}$—S—, —S—$(CH_2)_{1-12}$—NH—, and —NH—$(CH_2)_{1-12}$—S—, wherein the 1-6 can be independently 1, 2, 3, 4, 5, or 6, wherein the 1-12 can be independently 1, 2, 3, 4, 5, 6, 7, 8, 9, 10, 11 or 12, and wherein one or more of the $CH_2$ or NH groups can be modified by substitution of a H for a methyl, ethyl, cyclopropyl, F (if on carbon), etc, as described herein, and optionally, a heteroatom, heteroalkyl, aryl, heteroaryl or cycloaliphatic group is interspersed in the chain. Certain non-limiting examples include —O—CH($CH_3$)—CH($CH_3$)CH—O—, —O—$CH_2$—CH($CH_3$)CH—O—, —O—CH($CH_3$)—$CH_2$CH—O—, etc.

each of which $R^{20}$, $R^{21}$, $R^{22}$, $R^{23}$, and $R^{24}$ is optionally substituted with one or more substituents selected from $R^{101}$ or alternatively as described in the Definitions section; wherein at least one of $R^{20}$, $R^{21}$, $R^{22}$, $R^{23}$, and $R^{24}$ is not a bond;

$R^{101}$ is independently selected at each occurrence from hydrogen, alkyl, alkene, alkyne, haloalkyl, alkoxy, hydroxyl, aryl, heteroaryl, heterocycle, arylalkyl, heteroaryl alkyl, heterocycloalkyl, aryloxy, heteroaryloxy, CN, —COOalkyl, COOH, $NO_2$, F, Cl, Br, I, $CF_3$, $NH_2$, NHalkyl, N(alkyl)$_2$, aliphatic, and heteroaliphatic;

$R^{26}$ is selected from hydrogen, alkyl, silane, arylalkyl, heteroaryl alkyl, alkene, alkyne, aryl, heteroaryl, heterocyclic, aliphatic and heteroaliphatic;

$R^{27}$ and $R^{28}$ are independently selected from hydrogen, alkyl, amine, or together with the carbon atom to which they are attached, form C(O), C(S), C═$CH_2$, a $C_3$-$C_6$ spirocarbocycle, or a 4-, 5-, or 6-membered spiroheterocycle comprising 1 or 2 heteroatoms selected from N and O, or form a 1 or 2 carbon bridged ring;

$R^{40}$ is selected at each instance from: hydrogen, alkyl, alkene, alkyne, halogen, hydroxyl, alkoxy, azide, amino, cyano, —NH(aliphatic, including alkyl), —N(aliphatic, including alkyl)$_2$, —$NHSO_2$(aliphatic, including alkyl), —N(aliphatic, including alkyl)$SO_2$alkyl, —$NHSO_2$(aryl, heteroaryl or heterocyclic), —N(alkyl)$SO_2$(aryl, heteroaryl or heterocyclic) —$NHSO_2$alkenyl, —N(alkyl)$SO_2$alkenyl, —$NHSO_2$alkynyl, —N(alkyl)$SO_2$alkynyl, haloalkyl, aliphatic, heteroaliphatic, aryl, heteroaryl, heteroalkyl, heterocyclic, and carbocyclic; and all other variables are as defined herein.

In another aspect, new compounds are provided comprising the compounds of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, and Formulas XIII-a to XIII-I, wherein one of the free hydrogens on the molecule has been replaced by a "Tail" group as defined herein. Thus, new compounds are also provided of Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), and Formulas XIII(1)-a to XIII(1)-i.

In one aspect, a compound is provided of Formula I(1)
[I(1)]
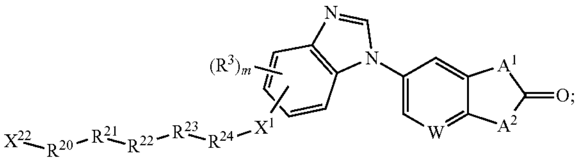
wherein all variables are as defined herein.
In one aspect, a compound is provided of one of the following formulas:
[II(1)-a]
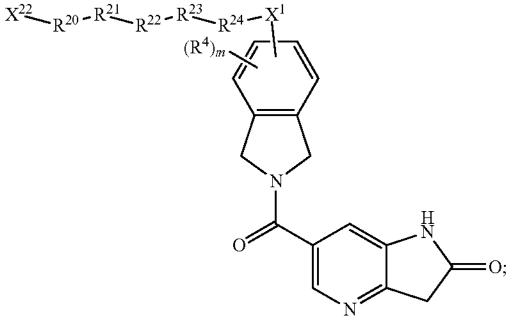
[II(1)-b]
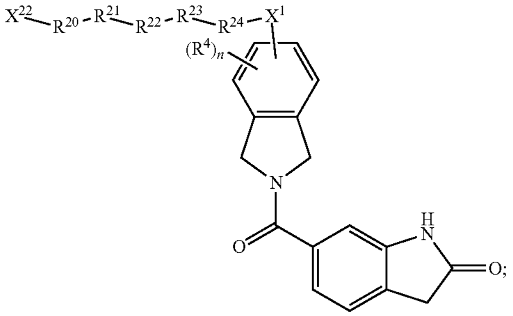
[II(1)-c]
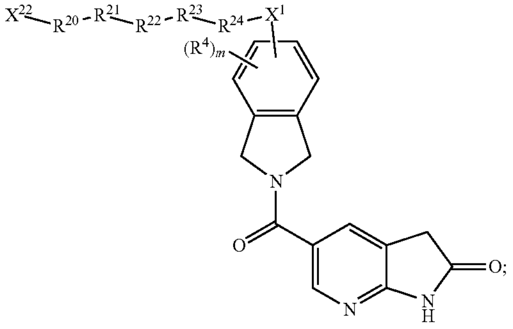
-continued
[II(1)-d]
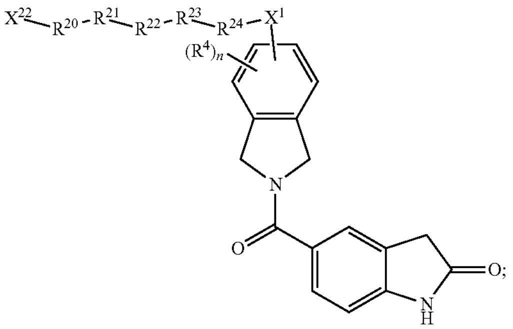
[II(1)-e]
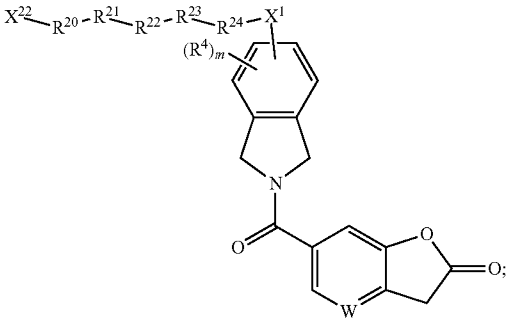
[II(1)-f]
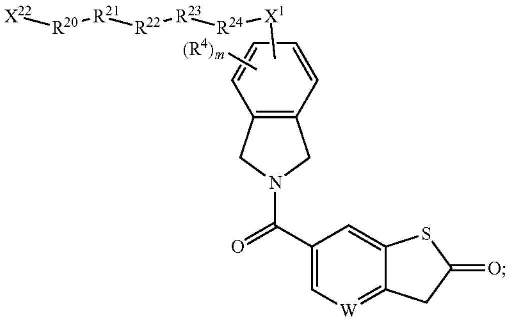
[II(1)-g]
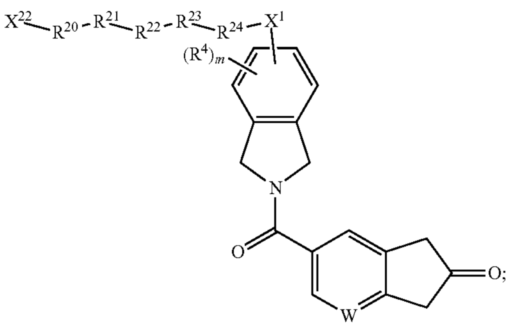

-continued
[II(1)-h]
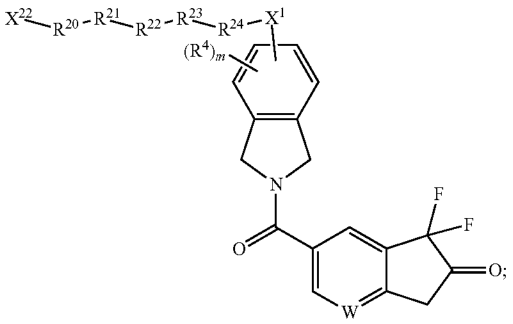
[II(1)-i]
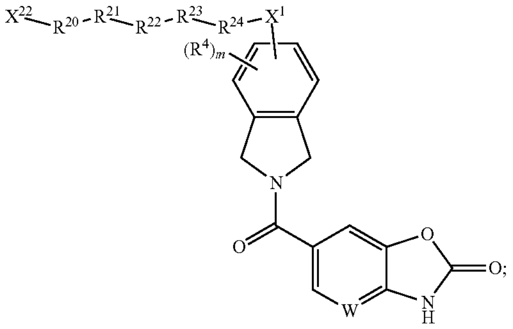
[II(1)-j]
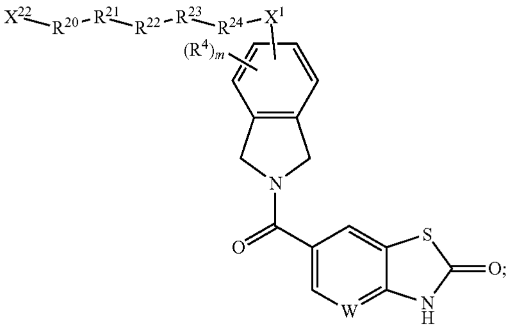
and
[II(1)-k]
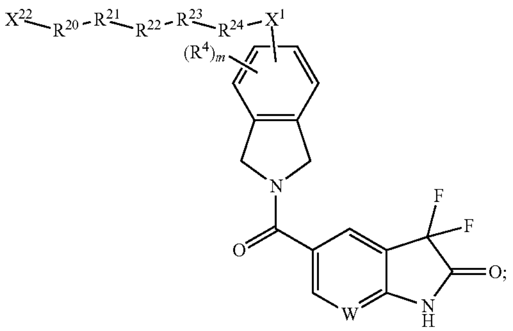
wherein all variables are as defined herein.
In one aspect, a compound is provided of Formula III(1):
[III(1)]
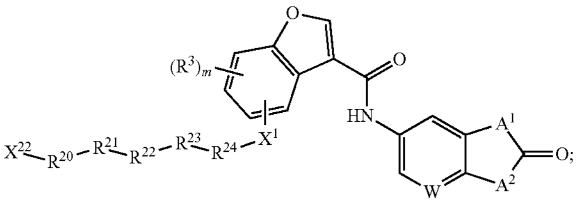
wherein all variables are as defined herein.
In one aspect, a compound is provided of one of the following formulas:
[IV(1)-a]
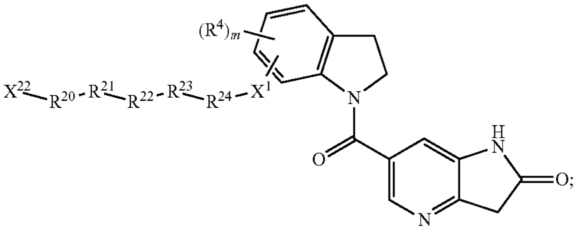
[IV(1)-b]
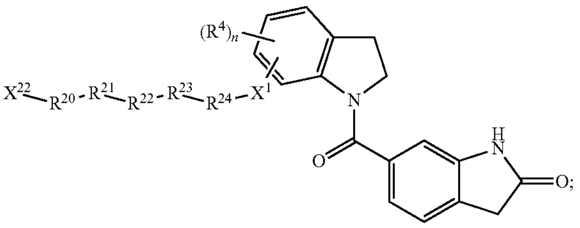
[IV(1)-c]
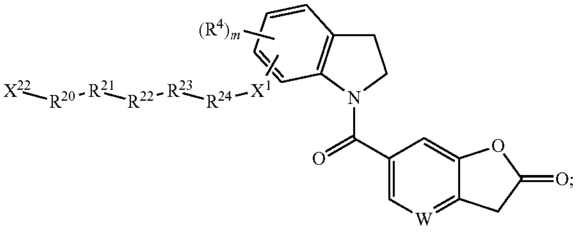
[IV(1)-d]
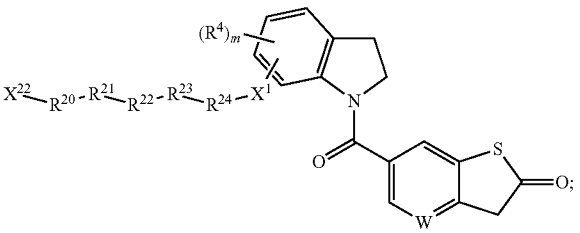

-continued
[IV(1)-e]
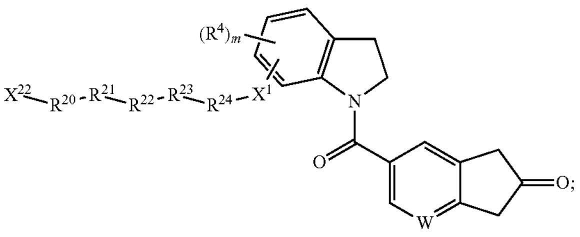
[IV(1)-f]
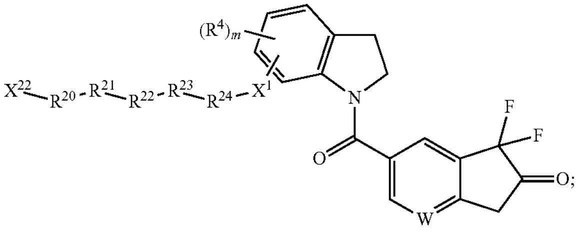
[IV(1)-g)]
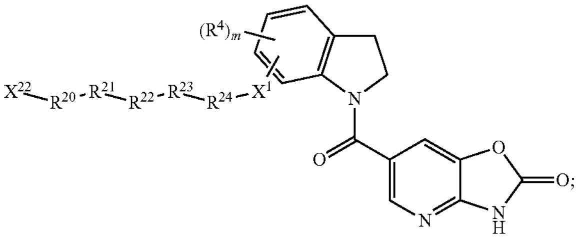
[IV(1)-h)]
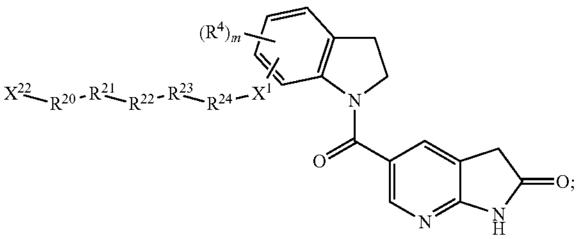
[IV(1)-i]
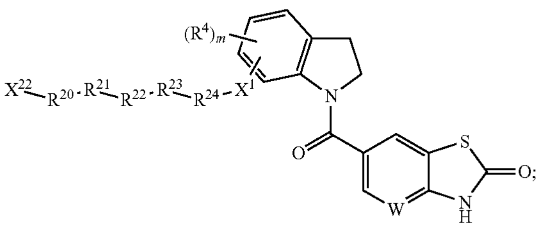
and
[IV(1)-j]
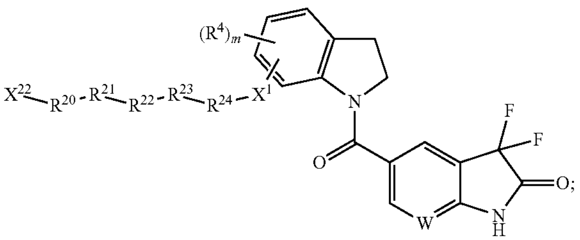
wherein all variables are as defined herein.
In one aspect, a compound is provided of Formula V(1):
[V(1)]
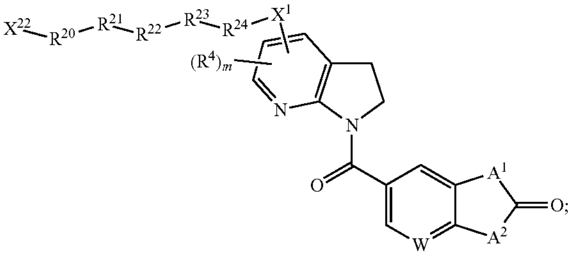
wherein all variables are as defined herein.
In one aspect, a compound is provided of Formula VI(1):
[VI(1)]
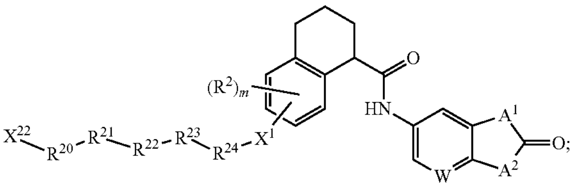
wherein all variables are as defined herein.
In one aspect, a compound is provided of one of the following formulas:
[VII(1)-a]
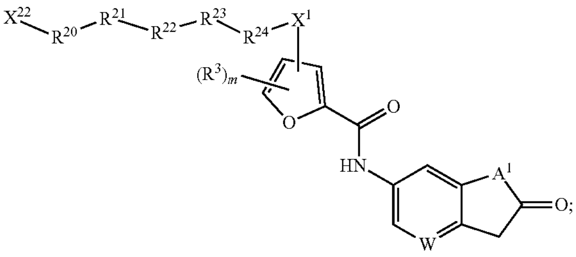
[VII(1)-b]
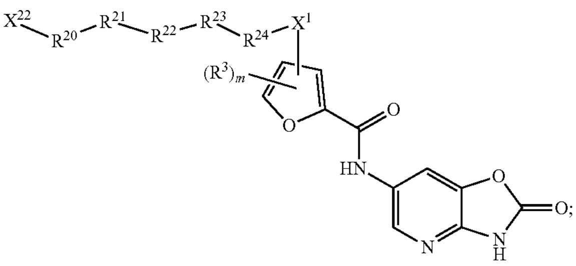

-continued
[VII(1)-c]
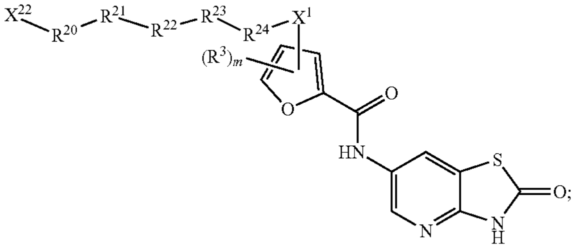
[VII(1)-d]
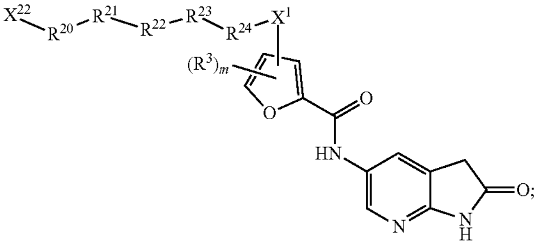
and
[VII(1)-e]
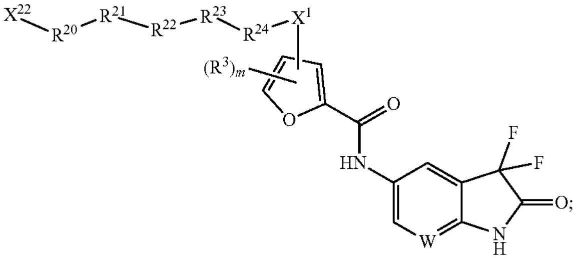
wherein all variables are as defined herein.
In one aspect, a compound is provided of one of the following formulas:
[VIII(1)-a]
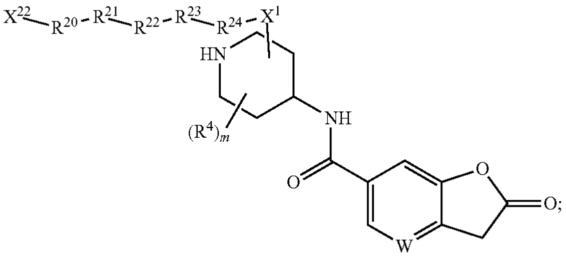
[VIII(1)-b]
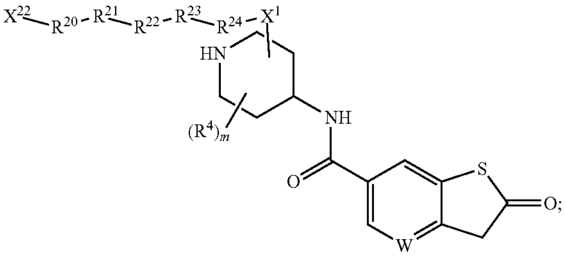
-continued
[VIII(1)-c]
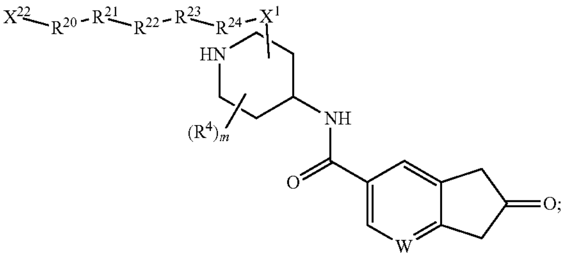
[VIII(1)-d]
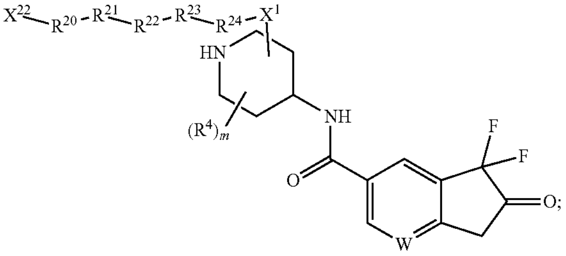
[VIII(1)-e]
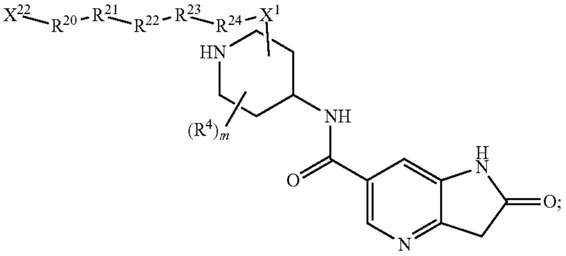
[VIII(1)-f]
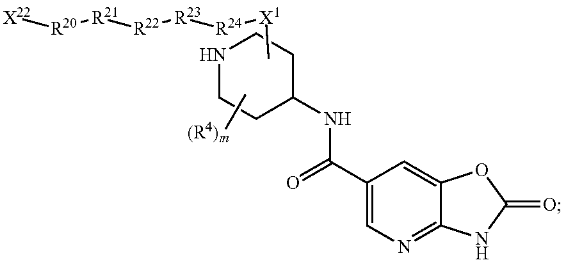
[VIII(1)-g]
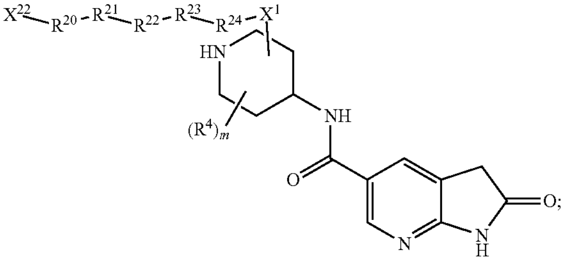

-continued
[VIII(1)-h]
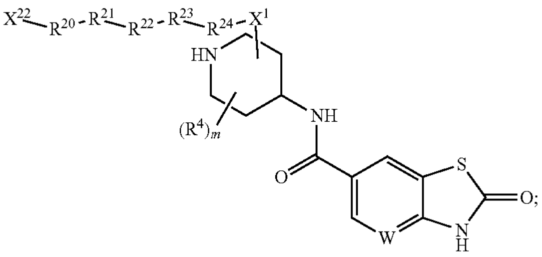
and
[VIII(1)-i]
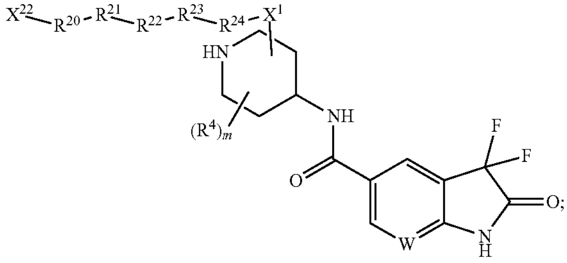
wherein all variables are as defined herein.
In one aspect, a compound is provided of one of the following formulas:
[IX(1)-a]
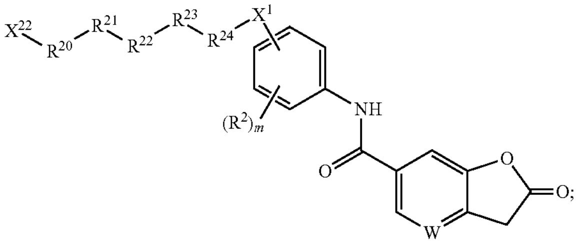
[IX(1)-b]
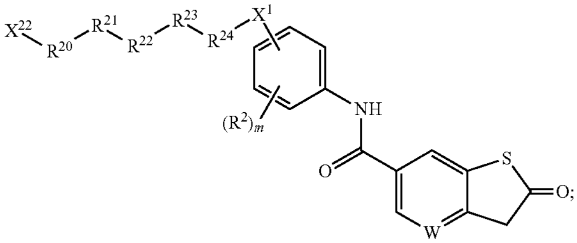
[IX(1)-c]
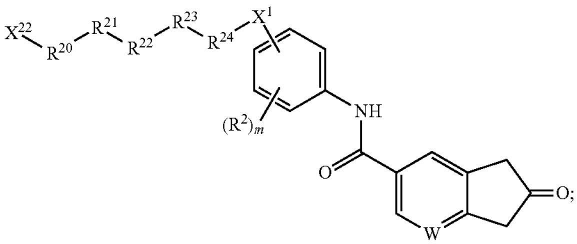
-continued
[IX(1)-d]
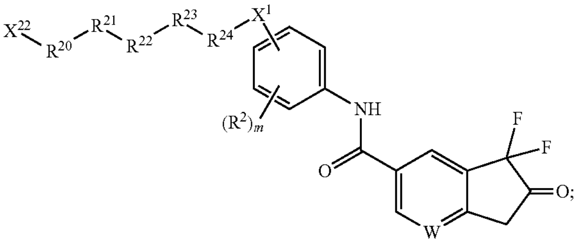
[IX(1)-e]
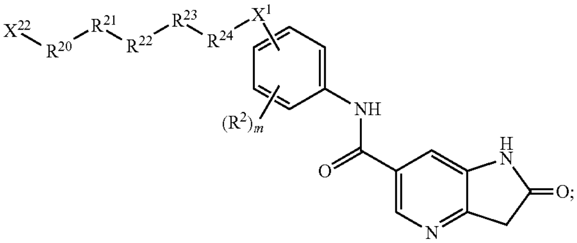
[IX(1)-f]
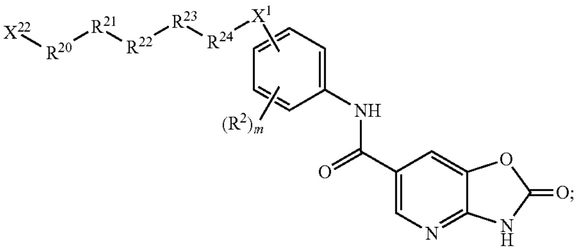
[IX(1)-g]
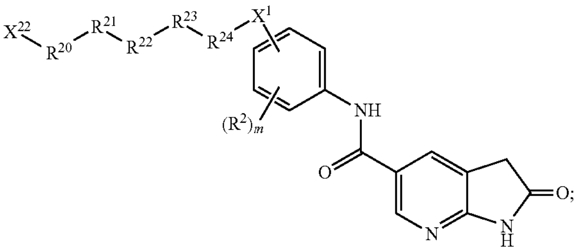
[IX(1)-h]
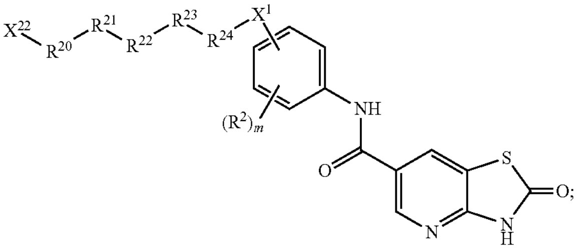
[IX(1)-i]
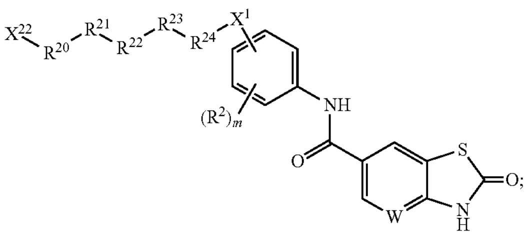
and -continued
[IX(1)-j]
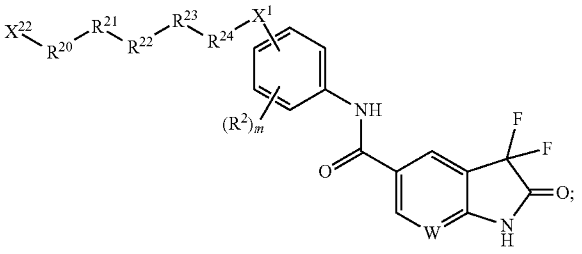
wherein all variables are as defined herein.
In one aspect, a compound is provided of one of the following formulas:
[X(1)-a]
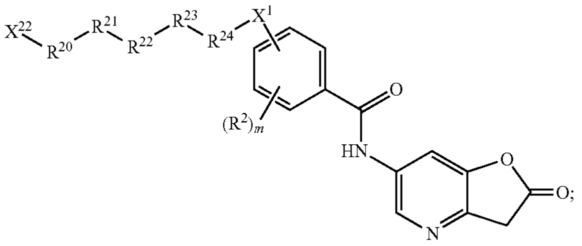
[X(1)-b]
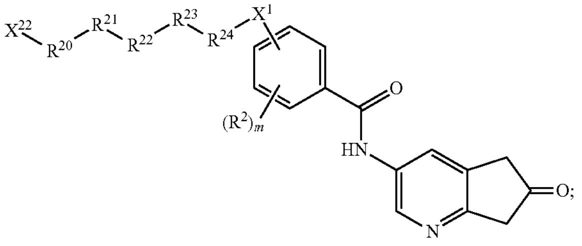
[X(1)-c]
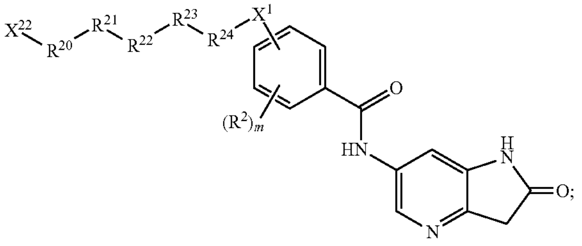
[X(1)-d]
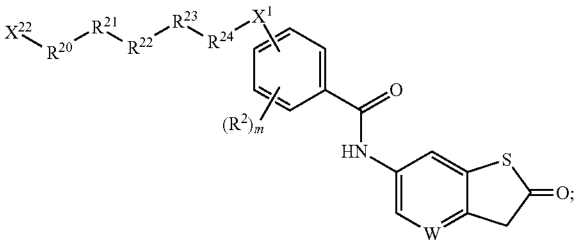
-continued
[X(1)-e]
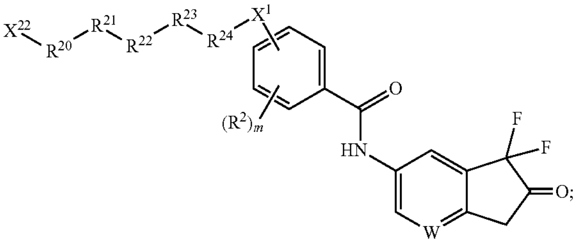
[X(1)-f]
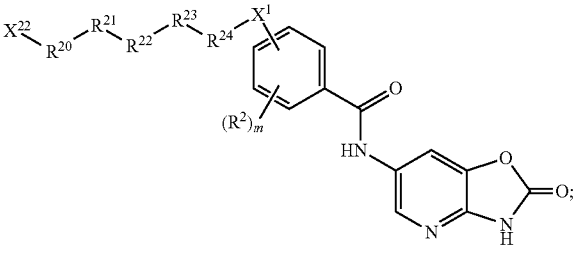
[X(1)-g]
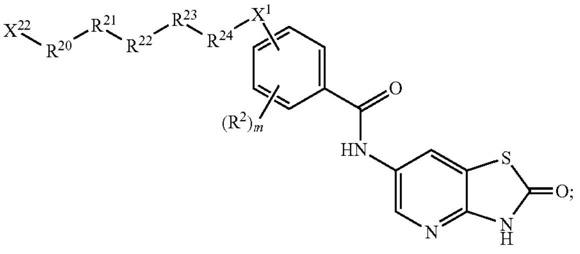
[X(1)-h]
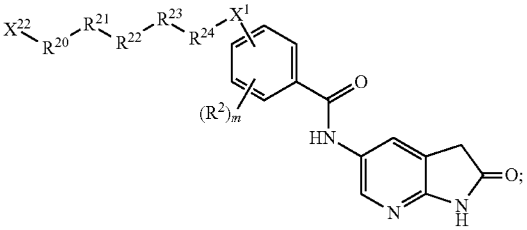
and
[X(1)-i]
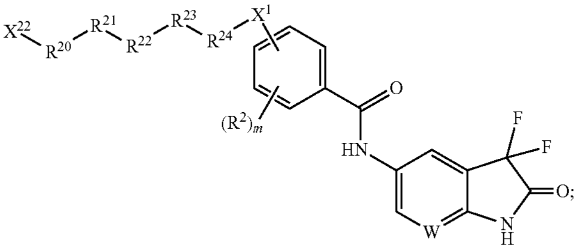
wherein all variables are as defined herein.

In one aspect a compound is provided of one of the following formulas:
[XI(1)-a]
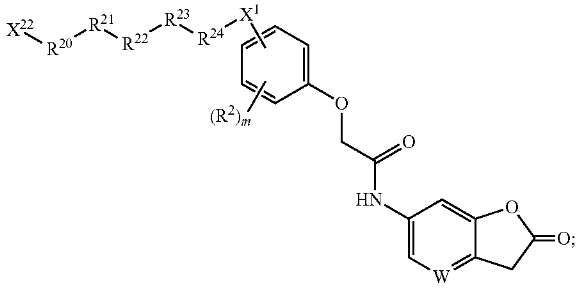
[XI(1)-b]
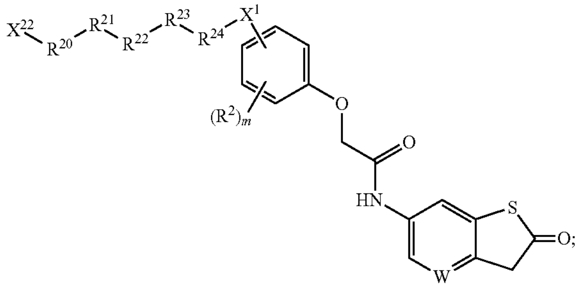
[XI(1)-c]
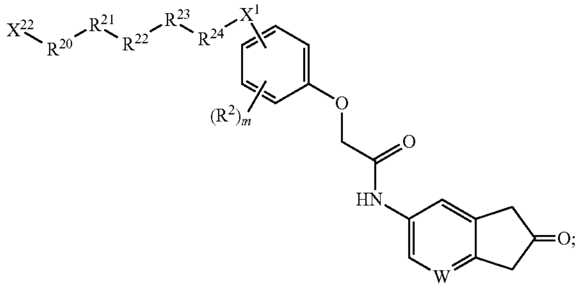
[XI(1)-d]
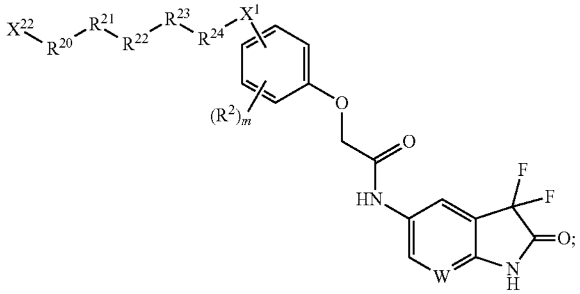
[XI(1)-e]
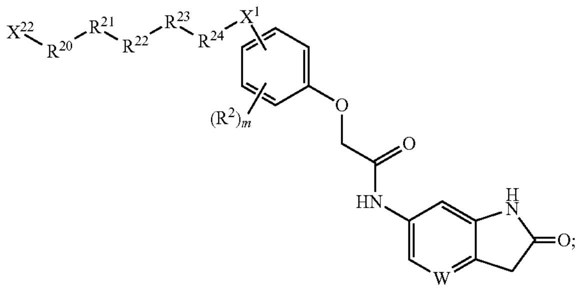
-continued
[XI(1)-f]
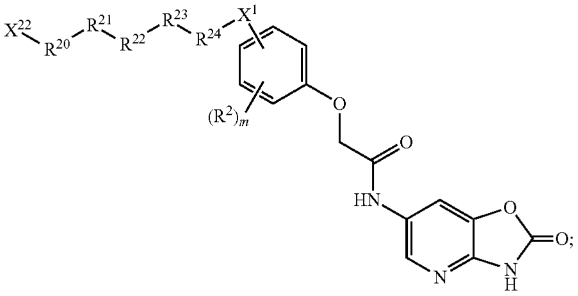
[XI(1)-g]
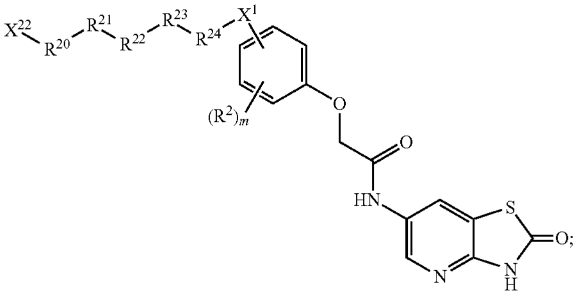
[XI(1)-h]
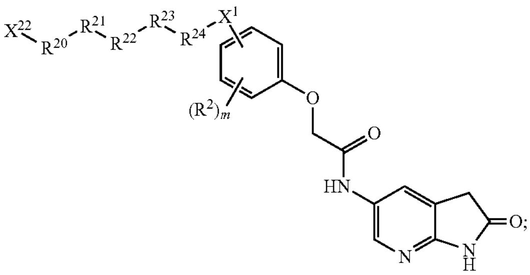
and
[XI(1)-i]
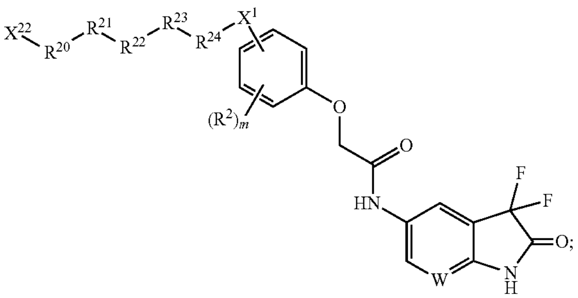
wherein all variables are as defined herein.

In one aspect, a compound is provided of Formula XII(1):

[XII(1)]

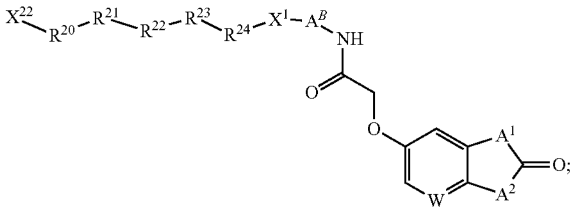

wherein all variables are as defined herein.

In one aspect a compound is provided of one of the following formulas:

[XIII(1)-a]

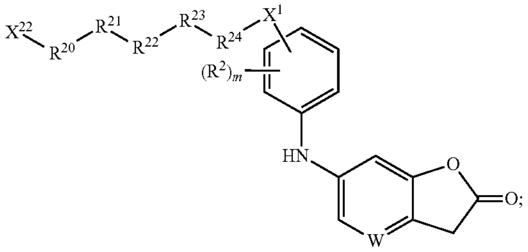

[XIII(1)-b]

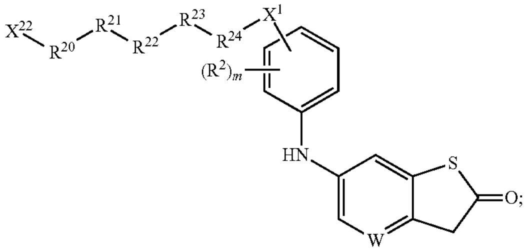

[XIII(1)-c]

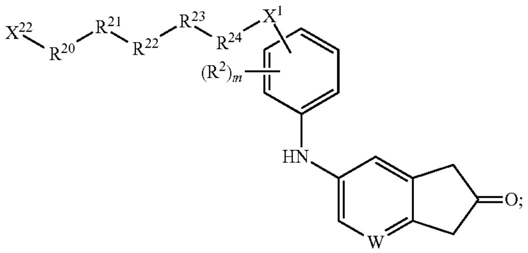

[XIII(1)-d]

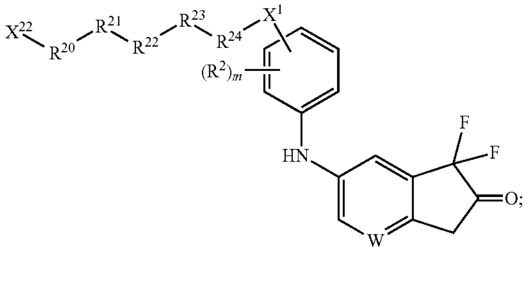

-continued

[XIII(1)-e]

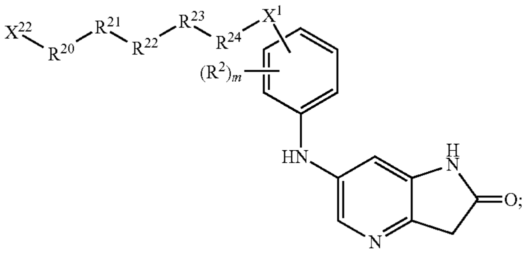

[XIII(1)-f]

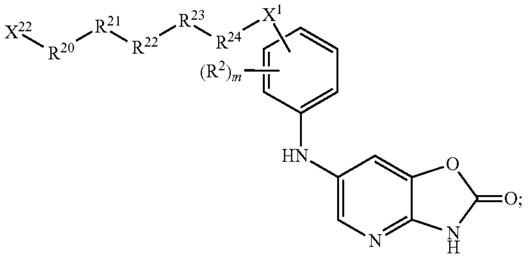

[XIII(1)-g]

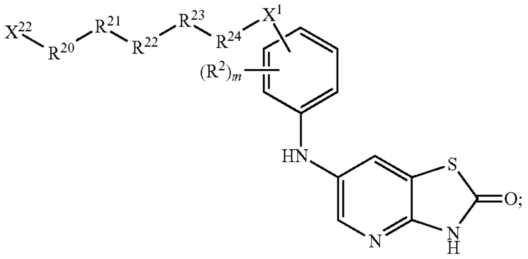

[XIII(1)-h]

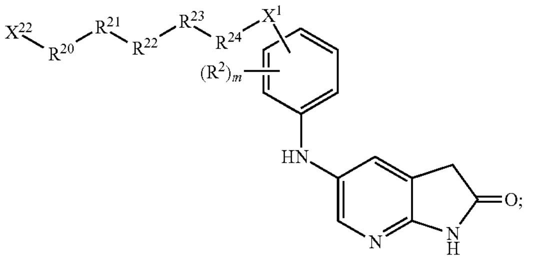

and

[XIII(1)-i]

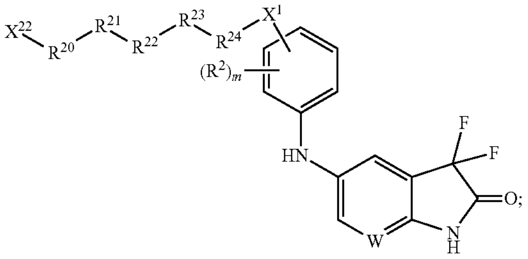

wherein all variables are as defined herein.

In a first aspect, the present invention provides compounds of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) as defined herein for use as a therapeutically active substance.

In a further aspect, the present invention provides pharmaceutical compositions comprising a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) as defined herein and a therapeutically inert carrier.

In certain embodiments, the compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) has at least one desired isotopic substitution of an atom, at an amount above the natural abundance of the isotope, i.e., enriched. In one embodiment, the compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) includes a deuterium or multiple deuterium atoms.

Other features and advantages of the present application will be apparent from the following detailed description and claims.

The present invention therefore includes at least the following features:

a) a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or a pharmaceutically acceptable salt thereof;

b) use of a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1), or a pharmaceutically acceptable salt thereof, in an effective amount in the treatment of a patient, typically a human, with a disorder that responds to such treatment, including by modulating the cereblon-based ubiquitination of a protein, such as for example, abnormal cellular proliferation such as a tumor or cancer, an immune or autoimmune or inflammatory disorder, a cardiologic disorder, an infectious disease, or other disorder that responds to such treatment;

c) use of a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1), or a pharmaceutically acceptable salt thereof, in the manufacture of a medicament for the treatment of a medical disorder, as further described herein;

d) a method for manufacturing a medicament intended for the therapeutic treatment of a disorder in a host, characterized in that a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) is used in the manufacture;

e) a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1), or a pharmaceutically acceptable salt thereof, that is useful in the treatment of an abnormal cellular proliferation such as cancer in a host, including any of the cancers described herein;

f) use of a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1), or a pharmaceutically acceptable salt thereof, in the manufacture of a medicament for the treatment of an abnormal cellular proliferation such as cancer, including any of the cancers described herein;

g) a method for manufacturing a medicament intended for the therapeutic use to treat an abnormal cellular proliferation such as cancer in a host, including any of the cancers described herein, characterized in that a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) is used in the manufacture;

h) a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1), or a pharmaceutically acceptable salt thereof, that is useful in the treatment of a tumor in a host, including any of the tumors described herein;

i) use of a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1), or a pharmaceutically acceptable salt thereof, in the manufacture of a medicament for the treatment of a tumor in a host, including any of the tumors described herein;

j) a method for manufacturing a medicament intended for the therapeutic use to treat a tumor in a host, including any of the tumors described herein, characterized in that a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) is used in the manufacture;

k) a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1), or a pharmaceutically acceptable salt thereof, that is useful in the treatment of an immune, autoimmune, or inflammatory disorder in a host;

l) use of a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1), or a pharmaceutically acceptable salt thereof, in the manufacture of a medicament for the treatment of an immune, autoimmune, or inflammatory disorder in a host;

m) a method for manufacturing a medicament intended for the therapeutic use to treat an immune, autoimmune, or inflammatory disorder in a host, characterized in that a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) is used in the manufacture;

n) a pharmaceutical formulation comprising an effective host-treating amount of a compound of a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1), or a pharmaceutically acceptable salt thereof, with a pharmaceutically acceptable carrier or diluent;

o) a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) as described herein in enantiomerically or diastereomerically (as relevant) enriched form, including an isolated enantiomer or diastereomer (i.e., greater than 85, 90, 95, 97, or 99% pure);

p) a process for the preparation of therapeutic products that contain an effective amount of a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1), or a pharmaceutically acceptable salt thereof; and q) a process for the preparation of a bifunctional compound that causes degradation of a selected protein via the ubiquitin proteasome pathway, characterized in that a compound of Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) is used in the preparation of the bifunctional compound.

DETAILED DESCRIPTION OF THE INVENTION

I. Definitions

Unless otherwise defined, all technical and scientific terms used herein have the same meaning as commonly understood by one of ordinary skill in the art to which this application belongs. In the specification, singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the claimed application. In the case of conflict, the present specification, including definitions, will control. In addition, the materials, methods, and examples are illustrative only and are not intended to be limiting.

Compounds are described using standard nomenclature. Unless defined otherwise, all technical and scientific terms used herein have the same meaning as is commonly understood by one of skill in the art to which this invention belongs.

The compounds in any of the Formulas described herein may be in the form of a racemate, enantiomer, mixture of enantiomers, diastereomer, mixture of diastereomers, tautomer, N-oxide, isomer, such as rotamer, as if each is specifically described unless specifically excluded by context.

The terms "a" and "an" do not denote a limitation of quantity, but rather denote the presence of at least one of the reference item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and are independently combinable. All methods described herein can be performed in a suitable order unless otherwise indicated herein or otherwise clearly contradicted by context. The use of example, or exemplary language (e.g., "such as"), is intended merely to better illustrate the invention and does not pose a limitation on the scope of the invention unless otherwise claimed.

The compounds of the present invention may form a solvate with a solvent (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, isopropanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

A dash ("—") that is not between two letters or symbols is used to indicate a point of attachment for a substituent. For example, —(C═O)$NH_2$ is attached through the carbon of the carbonyl (C═O) group.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl (2-methyl-propyl), 1,2-dimethyl-propyl and the like. A specific group is methyl.

The term "halogen-$C_{1-6}$-alkyl", alone or in combination with other groups, refers to Cue-alkyl as defined herein, which is substituted by one or multiple halogen, particularly 1-5 halogen, more particularly 1-3 halogen. Particular halogen is fluoro. Particular "halogen-$C_{1-6}$-alkyl" is fluoro-$C_{1-6}$-alkyl and a particular "halogen-$C_{1-3}$-alkyl" is fluoro-$C_{1-3}$-alkyl. Examples are trifluoromethyl, difluoromethyl, fluoromethyl and the like.

In one embodiment "halogen-$C_{1-6}$-alkyl" has one carbon.

In one embodiment "halogen-$C_{1-6}$-alkyl" has one carbon and one halogen.

In one embodiment "halogen-$C_{1-6}$-alkyl" has one carbon and two halogens.

In one embodiment "halogen-$C_{1-6}$-alkyl" has one carbon and three halogens.

In one embodiment "halogen-$C_{1-6}$-alkyl" has two carbons.

In one embodiment "halogen-$C_{1-6}$-alkyl" has three carbons.

In one embodiment "halogen-$C_{1-6}$-alkyl" has four carbons.

In one embodiment "halogen-$C_{1-6}$-alkyl" has five carbons.

In one embodiment "halogen-$C_{1-6}$-alkyl" has six carbons.

Non-limiting examples of "halogen-$C_{1-6}$-alkyl" include:

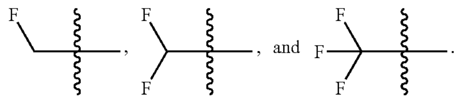

, , and .

Additional non-limiting examples of "halogen-$C_{1-6}$-alkyl" include:

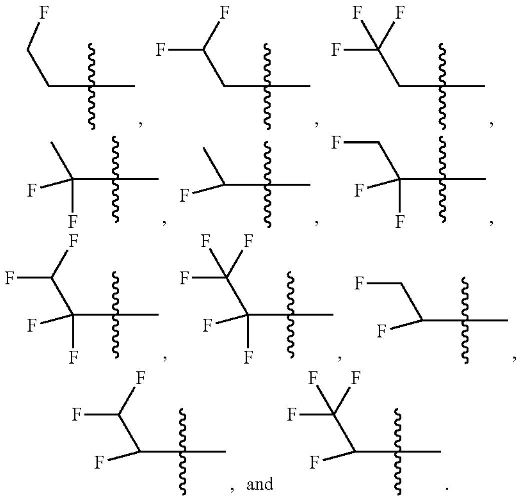

, , , , , , , , , , and .

Additional non-limiting examples of "halogen-$C_{1-6}$-alkyl" include:

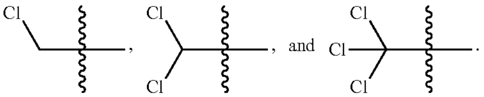

, , and .

Additional non-limiting examples of "halogen-$C_{1-6}$-alkyl" include:

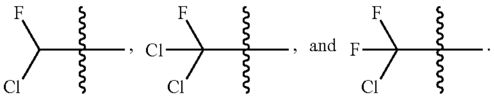

, , and .

The term "hydroxy-$C_{1-6}$-alkyl", alone or in combination with other groups, refers to $C_{1-6}$-alkyl as defined herein, which is substituted by one or multiple hydroxy groups, particularly by 1 hydroxy group. Examples are —$CH_2OH$, —$CH_2CH_2OH$ and the like.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two carbocycles having one or more carbon atoms in common, while one carbocycle is saturated, the other one may be aromatic. Particular cycloalkyl groups are monocyclic. Examples for monocyclic cycloalkyl are "$C_{3-7}$cycloalkyl" such as cyclopropyl, cyclobutanyl, cyclopentyl, cyclohexyl or cycloheptyl. Examples for saturated bicyclic cycloalkyl are bicyclo[2.2.1]heptanyl, or bicyclo [2.2.2]octanyl. Examples for bicyclic cycloalkyl wherein one ring is aromatic are 1H-indenyl or 1,2,3,4-tetrahydronaphthalenyl.

The term "hydroxy", alone or in combination with other groups, refers to OH.

The term "Bz" stands for benzyl (i.e., phenyl-$CH_2$—).

The term "halogen", alone or in combination with other groups, denotes chloro (Cl), iodo (I), fluoro (F) and bromo (Br). A specific group is F.

The term "heteroaryl" denotes a monovalent heterocyclic mono- or bicyclic ring system of 5 to 12 ring atoms, comprising 1, 2, 3 or 4 heteroatoms selected from N, O and S, the remaining ring atoms being carbon and in which at least one ring is aromatic. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolinyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, quinoxalinyl, or 2,3-dihydropyrrolo[2,3-b] pyridinyl. Specific examples include benzimidazolyl, pyridinyl, thiazolyl, indolinyl, 1,2,3,4-tetrahydroquinolinyl, 3,4-dihydroquinolinyl, benzofuranyl, furanyl, imidazolyl, isoindolyl, and quinolinyl.

In one embodiment "heteroaryl" is a 5 membered aromatic group containing 1, 2, 3, or 4 nitrogen atoms.

Non-limiting examples of 5 membered "heteroaryl" groups include pyrrole, furan, thiophene, pyrazole, imidazole, triazole, tetrazole, isoxazole, oxazole, oxadiazole, oxatriazole, isothiazole, thiazole, thiadiazole, and thiatriazole.

Additional non-limiting examples of 5 membered "heteroaryl" groups include:

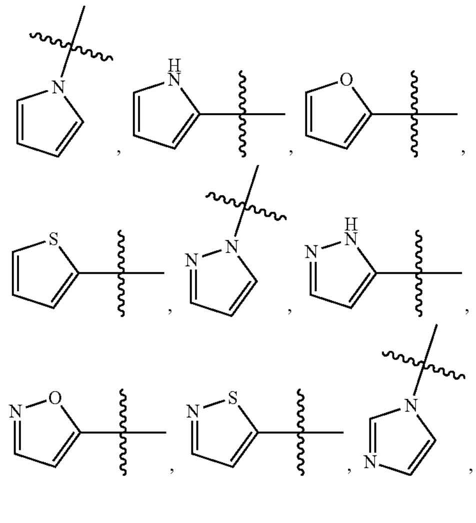

, , , , , , , , ,

-continued

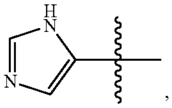, 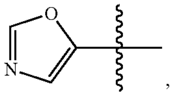, 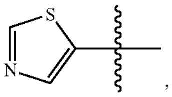,

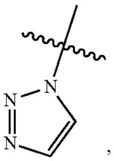, 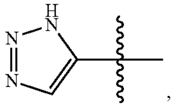, 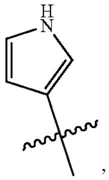, 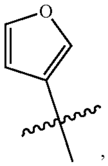,

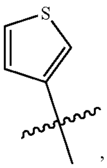, 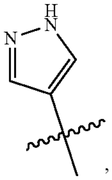, 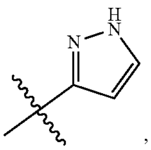, 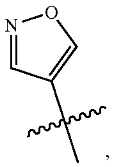,

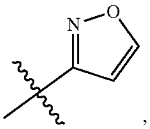, 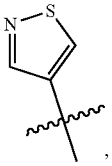, 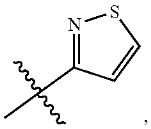, 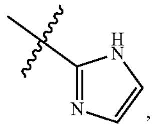,

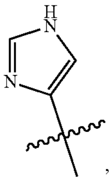, 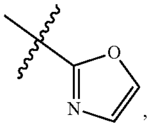, 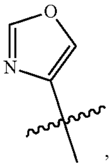, 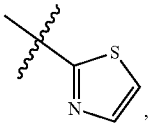,

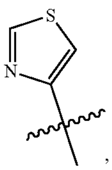, and 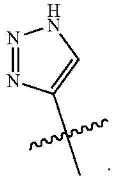.

In one embodiment "heteroaryl" is a 6 membered aromatic group containing 1, 2, or 3 nitrogen atoms (i.e. pyridinyl, pyridazinyl, triazinyl, pyrimidinyl, and pyrazinyl).

Non-limiting examples of 6 membered "heteroaryl" groups with 1 or 2 nitrogen atoms include:

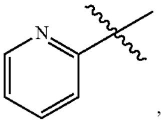, 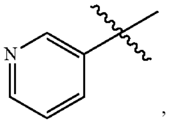, 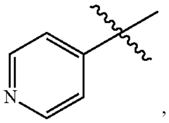,

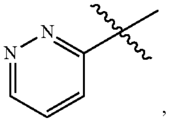, 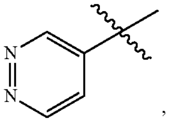, 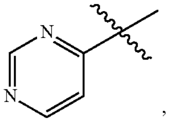,

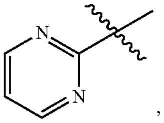, 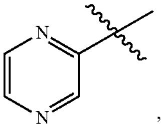, 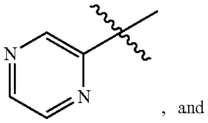, and

-continued

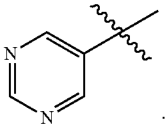.

In one embodiment "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

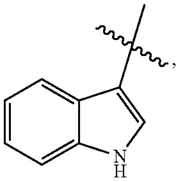, 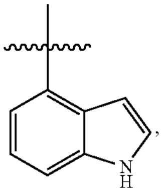,

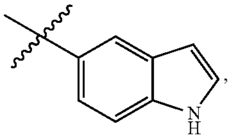, 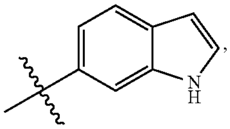,

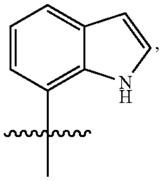, 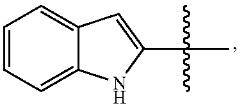, and

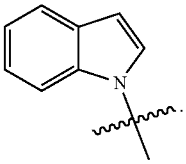.

Additional non-limiting examples of "heteroaryl" groups that are bicyclic include:

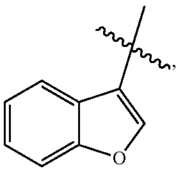, 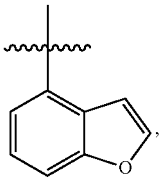,

-continued

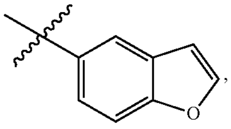,
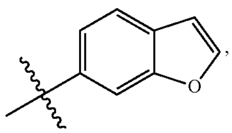,
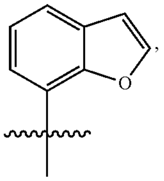, and
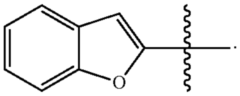.

Additional non-limiting examples of "heteroaryl" groups that are bicyclic include:

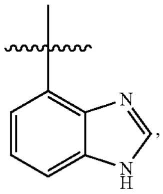,
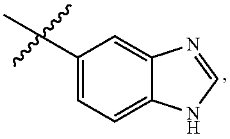,
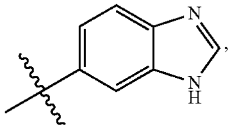,
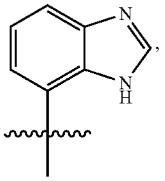,
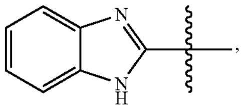, and
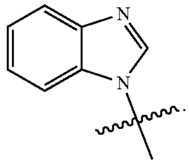.

In one embodiment "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

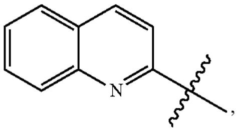,
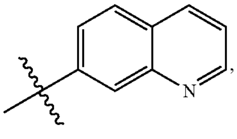,
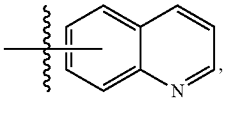,
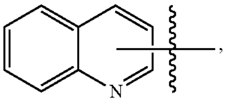,

-continued

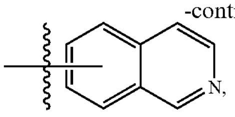, and
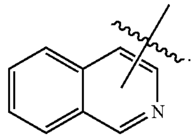.

In another embodiment "heteroaryl" is "optionally substituted" with 1, 2, 3, or 4 substituents.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Examples for monocyclic saturated heterocycloalkyl are azetidinyl, pyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Specific examples include piperazinyl, piperidinyl, pyrrolidinyl and 3,8-diazabicyclo[3.2.1]octanyl.

In one embodiment "heterocycloalkyl" refers to a cyclic ring with one nitrogen and 3, 4, 5, 6, 7, or 8 carbon atoms.

In one embodiment "heterocycloalkyl" refers to a cyclic ring with one nitrogen and one oxygen and 3, 4, 5, 6, 7, or 8 carbon atoms.

In one embodiment "heterocycloalkyl" refers to a cyclic ring with two nitrogens and 3, 4, 5, 6, 7, or 8 carbon atoms.

In one embodiment "heterocycloalkyl" refers to a cyclic ring with one oxygen and 3, 4, 5, 6, 7, or 8 carbon atoms.

In one embodiment "heterocycloalkyl" refers to a cyclic ring with one sulfur and 3, 4, 5, 6, 7, or 8 carbon atoms.

Non-limiting examples of "heterocycloalkyl" include aziridine, oxirane, thiirane, azetidine, 1,3-diazetidine, oxetane, and thietane.

Additional non-limiting examples of "heterocycloalkyl" include pyrrolidine, 3-pyrroline, 2-pyrroline, pyrazolidine, and imidazolidine.

Additional non-limiting examples of "heterocycloalkyl" include tetrahydrofuran, 1,3-dioxolane, tetrahydrothiophene, 1,2-oxathiolane, and 1,3-oxathiolane.

Additional non-limiting examples of "heterocycloalkyl" include piperidine, piperazine, tetrahydropyran, 1,4-dioxane, thiane, 1,3-dithiane, 1,4-dithiane, morpholine, and thiomorpholine.

Additional non-limiting examples of "heterocycloalkyl" include indoline, tetrahydroquinoline, tetrahydroisoquinoline, and dihydrobenzofuran wherein the point of attachment for each group is on the heterocyclic ring.

For example,

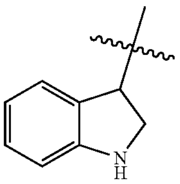 [SMILES: *C1CNc2ccccc21]

is a "heterocycloalkyl" group.

However,

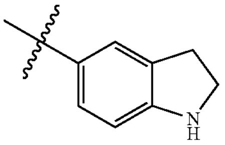 [SMILES: *c1ccc2c(c1)CCN2]

is an "aryl" group.

Non-limiting examples of "heterocycloalkyl" also include:

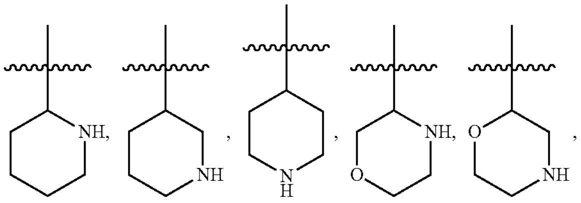

, , , ,

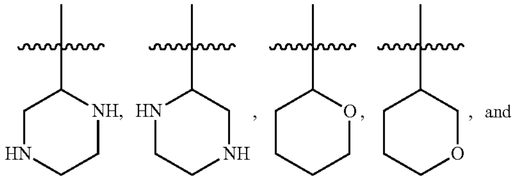

, , , and

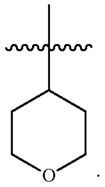

.

Additional non-limiting examples of "heterocycloalkyl" include:

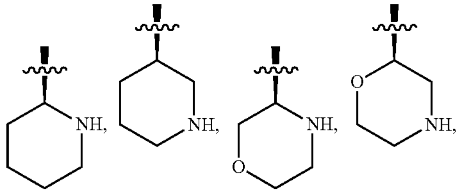

, , , ,

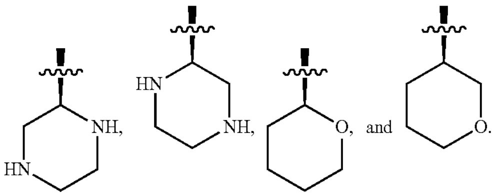

, , , and .

Additional non-limiting examples of "heterocycloalkyl" include:

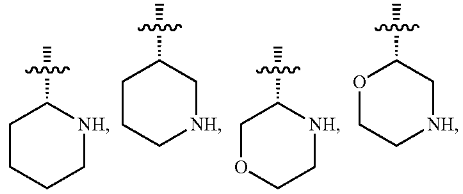

, , , ,

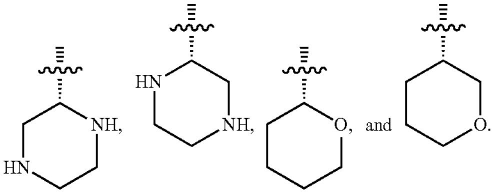

, , , and .

Non-limiting examples of "heterocycloalkyl" also include:

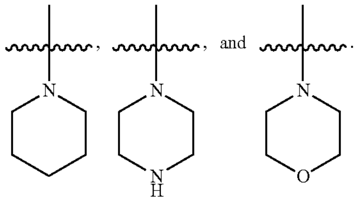

, , and .

Non-limiting examples of "heterocycloalkyl" also include:

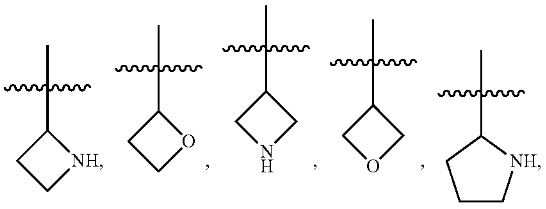

, , , , ,

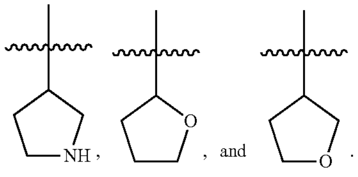

, , and .

Additional non-limiting examples of "heterocycloalkyl" include:

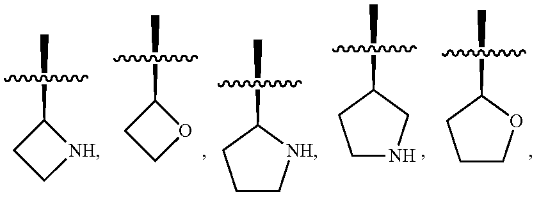

, , , , ,

-continued and

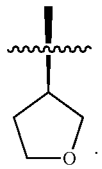.

Additional non-limiting examples of "heterocycloalkyl" include:

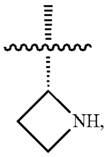, 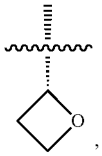, 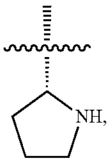, 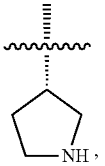, 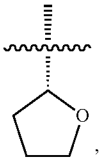, and

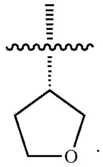.

In another embodiment "heterocycloalkyl" is "optionally substituted" with 1, 2, 3, or 4 substituents.

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. A specific group is methoxy.

The term "aryl" denotes a monovalent aromatic carbocyclic mono- or bicyclic ring system comprising 6 to 10 carbon ring atoms. Examples of aryl moieties include phenyl (Ph), and naphthyl. Specific "aryl" is phenyl.

In one embodiment "aryl" is a 6 carbon aromatic group (phenyl)

In one embodiment "aryl" is a 10 carbon aromatic group (napthyl)

In one embodiment "aryl" is a 6 carbon aromatic group fused to a heterocycle wherein the point of attachment is the aryl ring. Non-limiting examples of "aryl" include indoline, tetrahydroquinoline, tetrahydroisoquinoline, and dihydrobenzofuran wherein the point of attachment for each group is on the aromatic ring.

For example

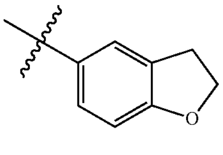 [SMILES: *c1ccc2c(c1)CCO2]

is an "aryl" group.

However,

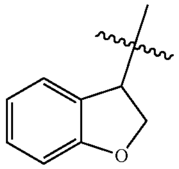 [SMILES: *C1COc2ccccc21]

is a "heterocycloalkyl" group.

In one embodiment "aryl" is a 6 carbon aromatic group fused to a cycloalkyl wherein the point of attachment is the aryl ring. Non-limiting examples of "aryl" include dihydroindene and tetrahydronaphthalene wherein the point of attachment for each group is on the aromatic ring.

For example

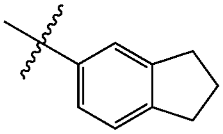 [SMILES: *c1ccc2c(c1)CCC2]

is an "aryl" group.

However,

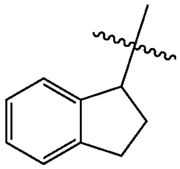 [SMILES: *C1CCc2ccccc21]

is a "cycloalkyl" group.

In another embodiment "aryl" is "optionally substituted" with 1, 2, 3, or 4 substitutents.

The term "optionally substituted" denotes the substitution of a group herein by a moiety including, but not limited to, $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, $C_1$-$C_{12}$ heterocycloalkyl, $C_3$-$C_{12}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{10}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, azido, acyl, thioacyl, acyloxy, carboxyl, and carboxylic ester.

In another embodiment any suitable group may be present on a "substituted" or "optionally substituted" position if indicated that forms a stable molecule and meets the desired purpose of the invention and includes, but is not limited to, e.g., halogen (which can independently be F, Cl, Br or I); cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; thioalkyl including those having one or more thioether linkages; alkylsulfinyl; alkylsulfonyl groups including those having one or more sulfonyl linkages; aminoalkyl groups including groups having more than one N atoms; aryl (e.g., phenyl, biphenyl, naphthyl, or the like, each ring either substituted or unsubstituted); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated or partially unsaturated heterocycle having 1 to 3 separate or fused rings with one or more N, O or S atoms, or a heteroaryl having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such groups may be further substituted, e.g. with hydroxy, alkyl, alkoxy, halogen and amino. In certain embodiments "optionally substituted" includes one or more substituents independently selected from halogen, hydroxyl, amino, cyano, —CHO, —COOH, —$CONH_2$, alkyl including $C_1$-$C_6$alkyl, alkenyl including $C_2$-$C_6$alkenyl, alkynyl including $C_2$-$C_6$alkynyl, —$C_1$-$C_6$alkoxy, alkanoyl including $C_2$-$C_6$alkanoyl, $C_1$-$C_6$alkyl ester, (mono- and di-$C_1$-$C_6$alkylamino)$C_0$-$C_2$alkyl, haloalkyl including $C_1$-$C_6$haloalkyl, hydoxy$C_1$-$C_6$alkyl, ester, carbamate, urea, sulfonamide, —$C_1$-$C_6$alkyl(heterocyclo), $C_1$-$C_6$alkyl(heteroaryl), —$C_1$-$C_6$alkyl($C_3$-$C_7$cycloalkyl), O—$C_1$-$C_6$alkyl($C_3$-$C_7$cycloalkyl), $B(OH)_2$, phosphate, phosphonate and haloalkoxy including $C_1$-$C_6$haloalkoxy. In some embodiments, the suitable group present on a "substituted" or "optionally substituted" is divalent including, but not limited to, oxo (═O), ═S, ═$CH_2$, etc. The suitable group on a "substituted" or "optional substituted" position may be monovalent, divalent, or trivalent such that it forms a stable molecule and meets the desired purpose of the invention.

In one embodiment a group described herein that can be substituted with 1, 2, 3, or 4 substituents is substituted with one substituent.

In one embodiment a group described herein that can be substituted with 1, 2, 3, or 4 substituents is substituted with two substituents.

In one embodiment a group described herein that can be substituted with 1, 2, 3, or 4 substituents is substituted with three substituents.

In one embodiment a group described herein that can be substituted with 1, 2, 3, or 4 substituents is substituted with four substituents.

Terms like "a-b-x substituted by R" means that the "x" portion of the moiety is substituted by R. For example, "—$(CH_2)_{0-1}$-aryl substituted by $R^{10}$" means that the "aryl" portion of the moiety is substituted by $R^{10}$; "—$(CH_2)_{0-1}$—($C_{3-7}$cycloalkyl)-aryl substituted by $R^{10}$" means that the "aryl" portion of the moiety is substituted by $R^{10}$; "—$(CH_2)_{0-1}$-heteroaryl substituted by $R^9$" means that the "heteroaryl" portion of the moiety is substituted by $R^9$; and "—$CH_2$—O—$(CH_2)_{0-1}$-aryl substituted by $R^{10}$" means that the "aryl" portion of the moiety is substituted by $R^{10}$.

The term "pharmaceutically acceptable" denotes an attribute of a material which is useful in preparing a pharmaceutical composition that is generally safe, not unacceptable toxic, and neither biologically nor otherwise undesirable. In one aspect, the material is acceptable for veterinary as well as human pharmaceutical use.

The term "a pharmaceutically acceptable salt" refers to a salt that is suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. Specific acids are hydrochloric acid, trifluoroacetic acid and fumaric acid.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like, or using a different acid that produces the same counterion. Lists of additional suitable salts may be found, e.g., in *Remington's Pharmaceutical Sciences,* 17th ed., Mack Publishing Company, Easton, Pa., p. 1418 (1985).

The terms "pharmaceutically acceptable auxiliary substance" refer to carriers and auxiliary substances such as diluents or excipients that are compatible with the other ingredients of the formulation.

"Therapeutically effective amount", when administered to a subject for treating a disease state, will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC-Compendium of Chemical Terminology, 2$^{nd}$ Edition, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

All separate embodiments may be combined.

The term "treatment" as used herein includes: (1) inhibiting the state, disorder or condition (e.g. arresting, reducing or delaying the development of the disease, or a relapse thereof in case of maintenance treatment, of at least one clinical or subclinical symptom thereof); and/or (2) relieving the condition (i.e., causing regression of the state, disorder or condition or at least one of its clinical or subclinical symptoms). However, it will be appreciated that when a medicament is administered to a patient to treat a disease, the outcome may not always be effective treatment.

The term "prophylaxis" as used herein includes: preventing or delaying the appearance of clinical symptoms of the state, disorder or condition developing in a mammal and especially a human that may be afflicted with or predisposed to the state, disorder or condition but does not yet experience or display clinical or subclinical symptoms of the state, disorder or condition.

Isotopic Substitution

The present invention includes compounds of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compound of the invention include isotopes of hydrogen, carbon, nitrogen, oxygen, fluorine, chlorine and iodine such as $^{2}H$, $^{3}H$, $^{11}C$, $^{13}C$, $^{14}C$, $^{15}N$, $^{17}O$, $^{18}O$, $^{18}F$, $^{35}S$, $^{36}Cl$, and $^{125}I$ respectively. In one non-limiting embodiment, isotopically labelled compounds can be used in metabolic studies (with, for example $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Isotopic substitutions, for example deuterium substitutions, can be partial or complete. Partial deuterium substitution means that at least one hydrogen is substituted with deuterium. In certain embodiments, the isotope is 90, 95, or 99% or more enriched in an isotope at any location of interest. In one non-limiting embodiment, deuterium is 90, 95, or 99% enriched at a desired location.

In one non-limiting embodiment, the substitution of a hydrogen atom for a deuterium atom can be provided in any compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1). In one non-limiting embodiment, the substitution of a hydrogen atom for a deuterium atom occurs within one or more groups selected from the variables described herein. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CHDCHD_2$, $OCDH_2$, $OCD_2H$, or $OCD_3$, etc.). In certain other embodiments, when two substitutions are combined to form a cycle, the unsubstituted carbons may be deuterated.

II. Compounds of the Present Invention

The present invention provides compounds of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, and pharmaceutically acceptable salts thereof. The invention also provides the use of compounds of Formula XIV or Formula XIV(1) as further described herein.

Embodiments of Formulas I-XIII

In one embodiment, a compound of Formula I is provided:

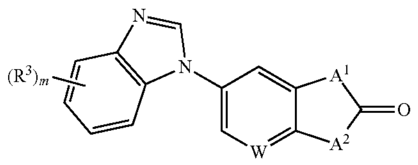

wherein all variables are as defined herein.

In one embodiment, a compound of Formula I is provided selected from:

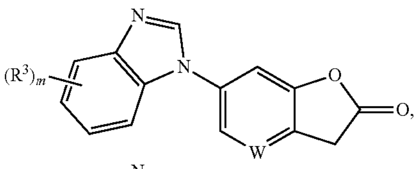

,

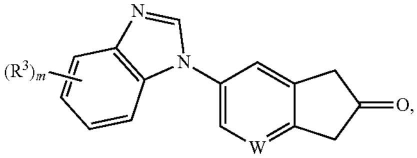

,

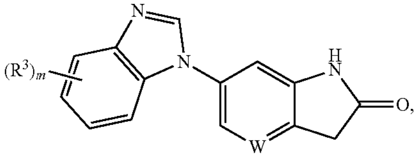

,

-continued
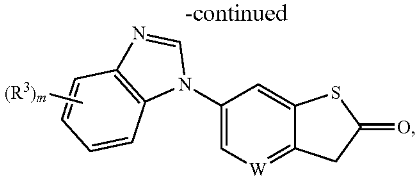
and
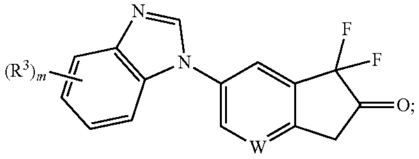
Wherein all variables are as defined herein.
In one embodiment, a compound of Formula I is selected from:
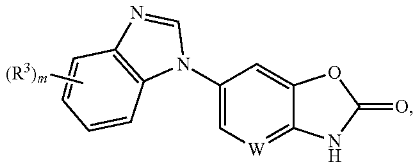
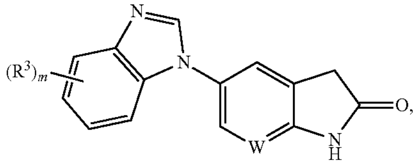
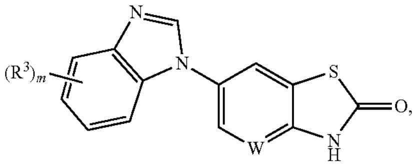
and
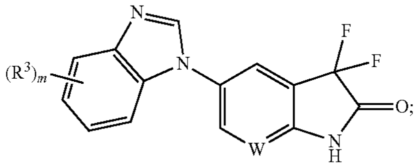
wherein all variables are defined as herein.
In one embodiment of Formula I,
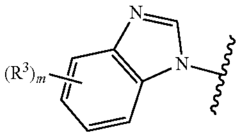
is selected from:
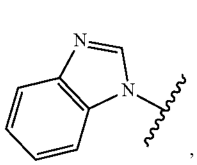
,
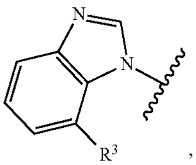
,
-continued
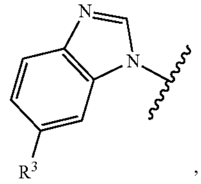
,
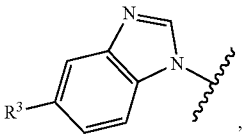
,
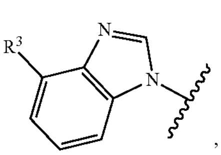
,
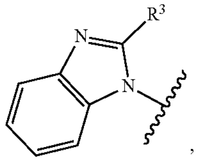
,
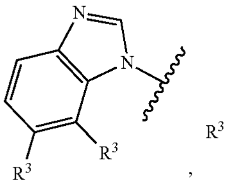
,
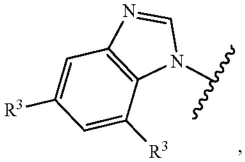
,
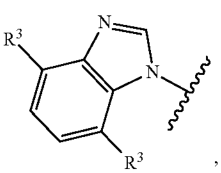
,
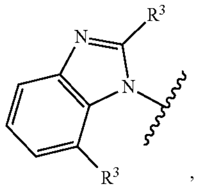
,
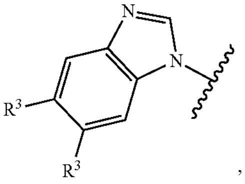
,
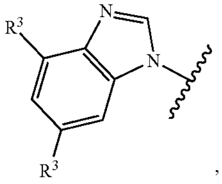
,
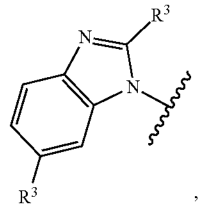
,
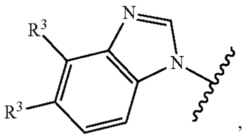
,
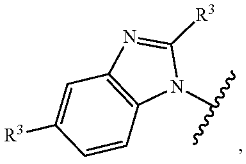
, and
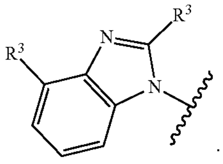
.
In one embodiment, a compound is provided of Formula II-a and Formula II-b:
(II-a)
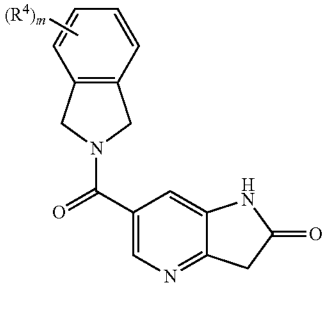
and -continued
(II-b)
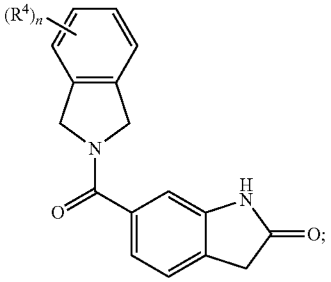
wherein all variables are defined as herein.
In one embodiment, a compound is provided of Formula II-c and Formula II-d:
(II-c)
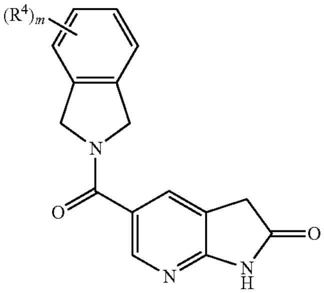
and
(II-d)
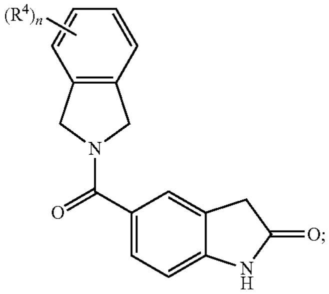
wherein all variables are defined as herein.
In one embodiment, a compound is provided of one of the following formulas:
(II-e)
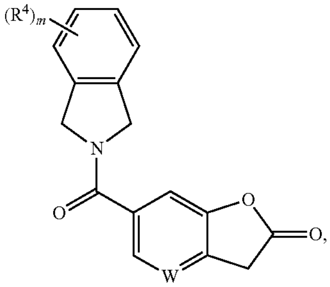
-continued
(II-f)
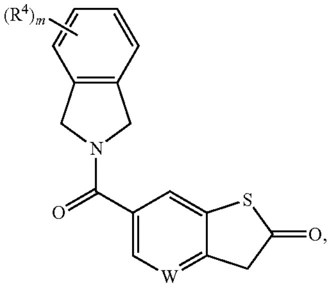
(II-g)
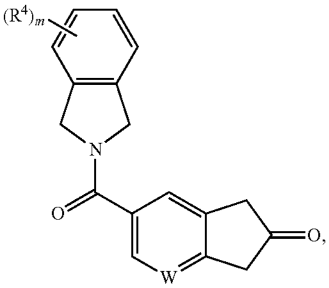
(II-h)
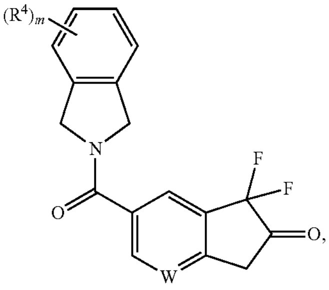
(II-i)
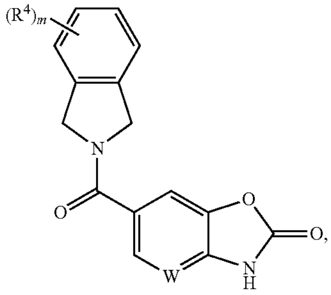
(II-j)
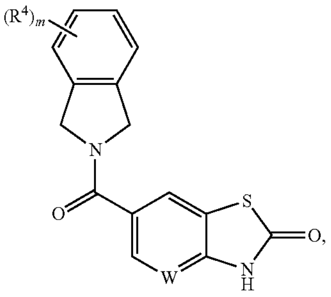
and -continued (II-k)

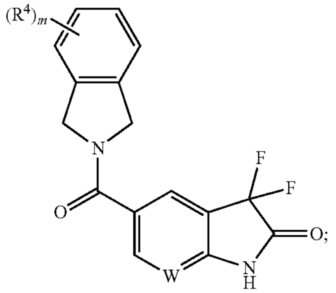

wherein all variables are defined as herein.

In any one embodiment of Formulas II-a to II-k,

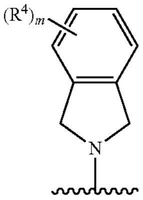

or

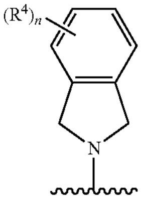

is selected from:

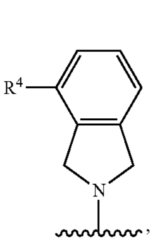

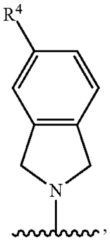

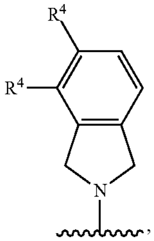

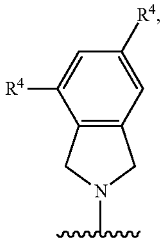

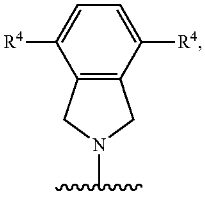

and

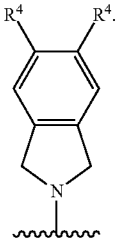

In one embodiment, a compound is provided of Formula III:

(III)

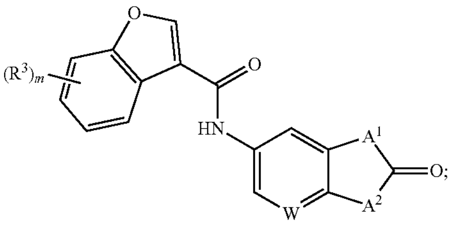

wherein all variables are as defined herein.

In one embodiment, a compound of Formula III is selected from:

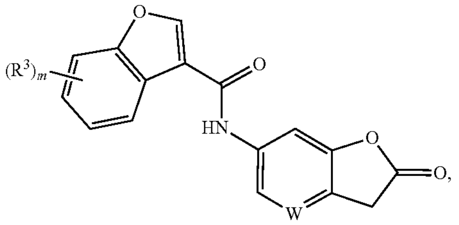

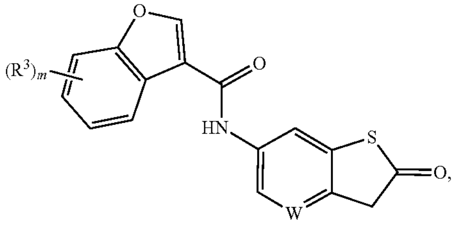

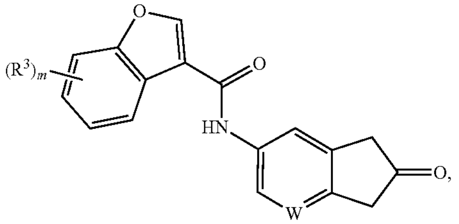

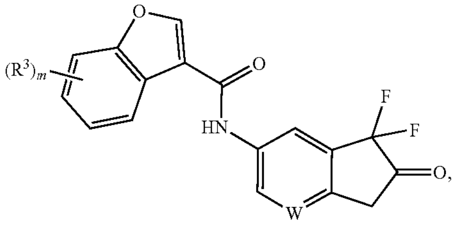

and

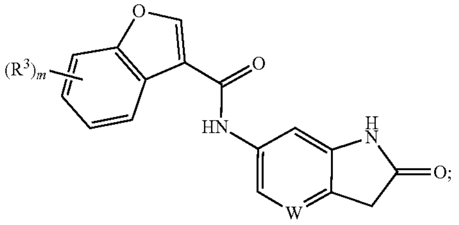

wherein all variables are defined as herein.

In one embodiment, a compound of Formula III is selected from:

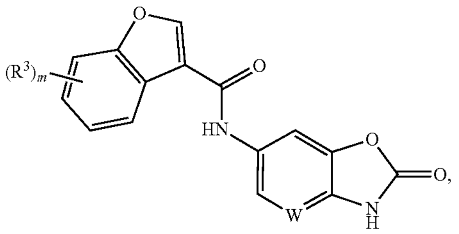

-continued
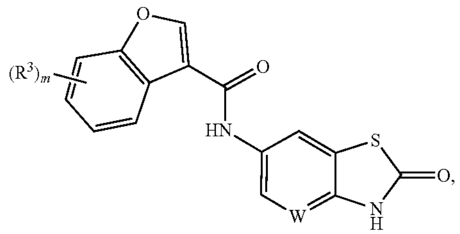
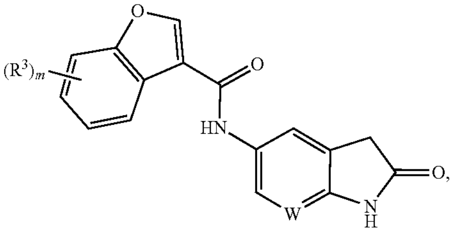
and
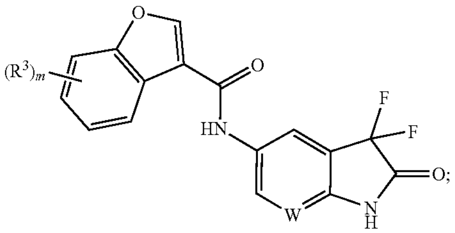
Wherein all variables are defined as herein.
In one embodiment of Formula III,
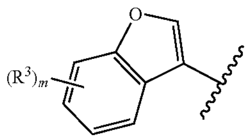
is selected from:
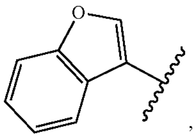
,
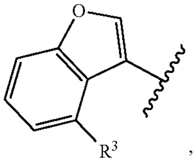
,
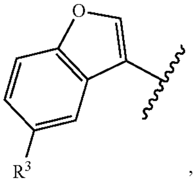
,
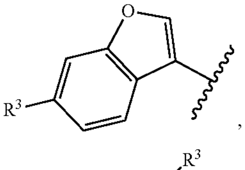
,
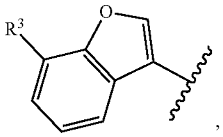
,
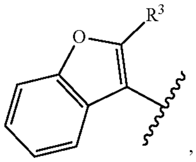
,
-continued
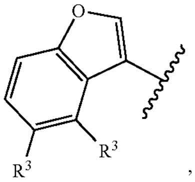
,
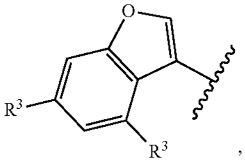
,
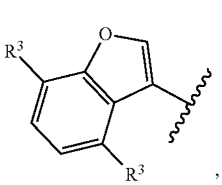
,
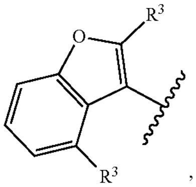
,
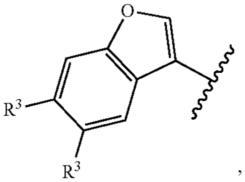
,
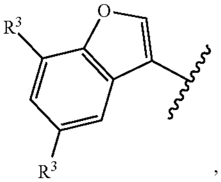
,
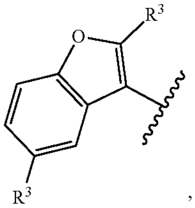
,
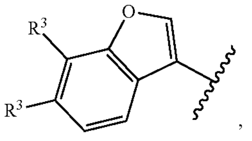
,
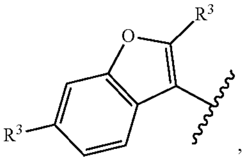
, and
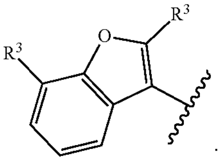
.
In one embodiment, a compound is provided of Formula IV-a and Formula IV-b:
(iIV-a)
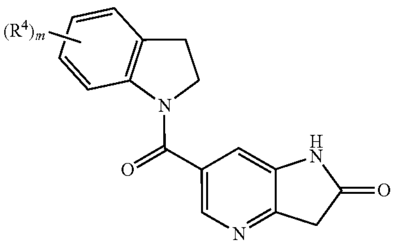
and
(IV-b)
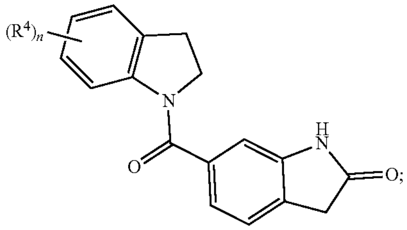
wherein all variables are as defined herein.

In one embodiment, a compound is provided of one of the following formulas:

(IV-c)

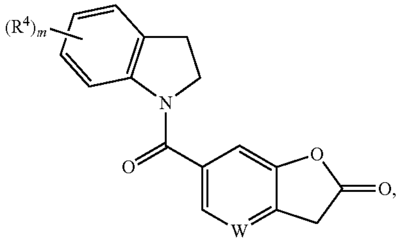

(IV-d)

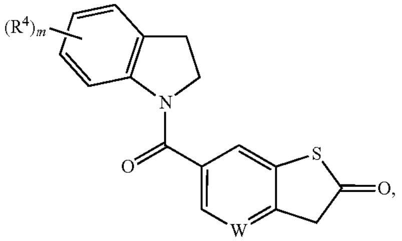

(IV-e)

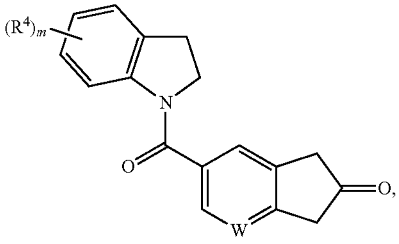

and (IV-f)

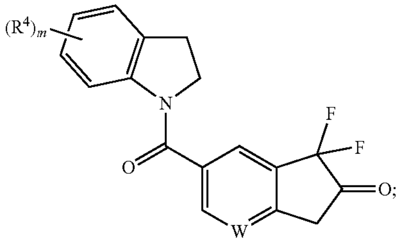

wherein all variables are as defined herein.

In one embodiment, a compound is provided selected Formula IV-g and Formula IV-h:

(IV-g)

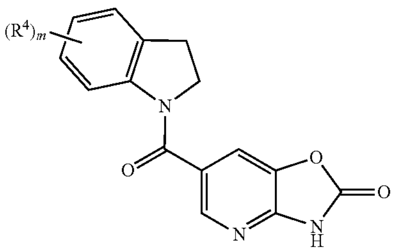

and

-continued (IV-h)

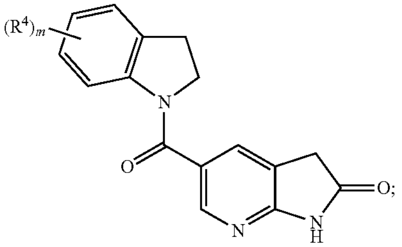

wherein all variables are as defined herein.

In some embodiments of any one of Formula IV-i to IV-j, (IV-i)

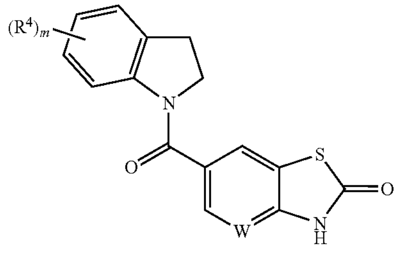

and (IV-j)

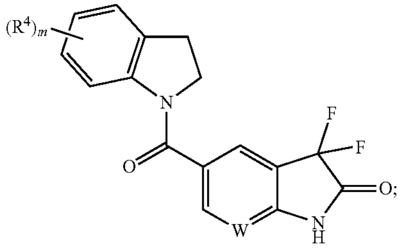

wherein all variables are as defined herein.

In some embodiments of any one of Formula IV-a to IV-j,

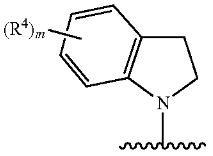

or

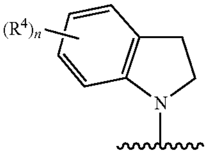

is selected from:

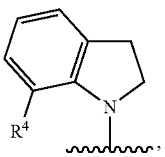

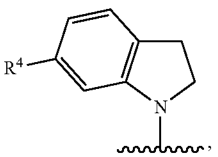

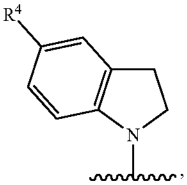

-continued
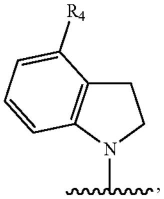
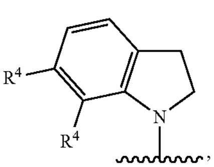
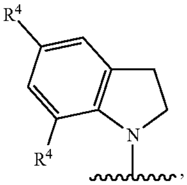
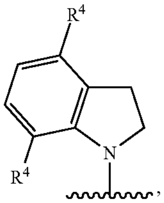
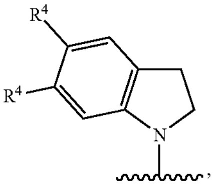
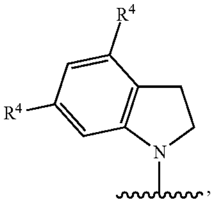
and
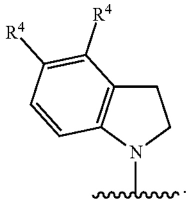
In one embodiment, a compound is provided of Formula V:
(V)
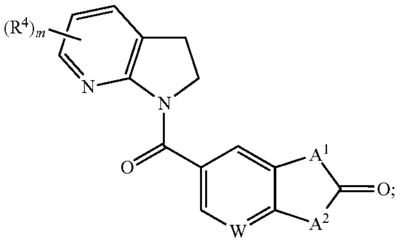
wherein all variables are as defined herein.
In one embodiment, a compound of Formula V is selected from:
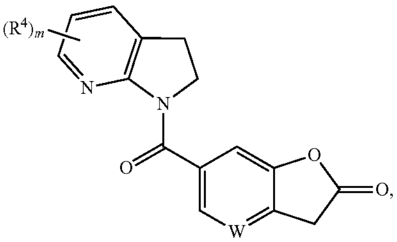
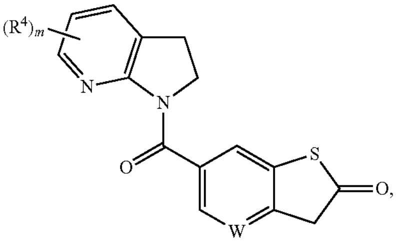
-continued
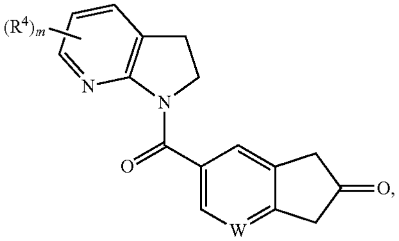
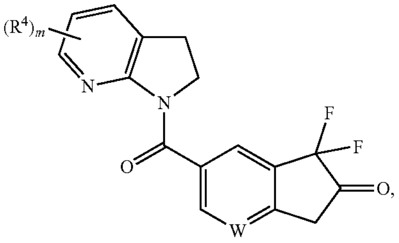
and
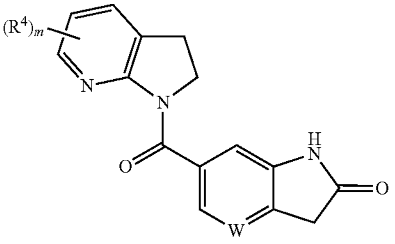
In one embodiment, a compound of Formula V is selected from:
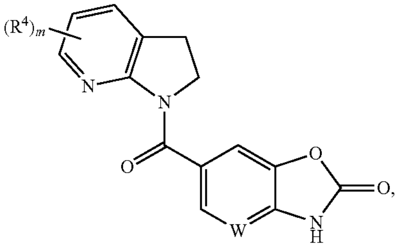
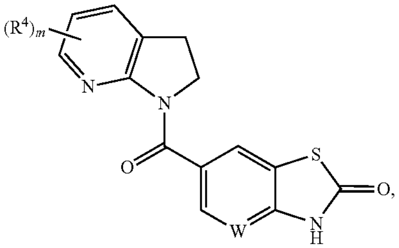
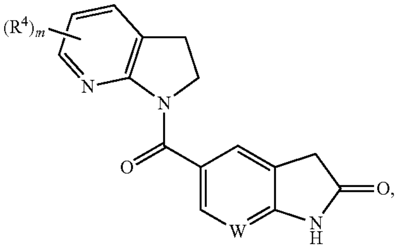
and -continued
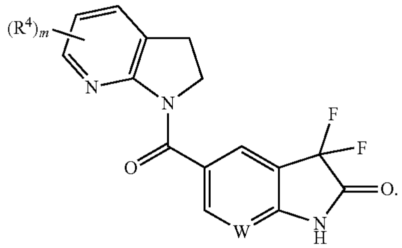
In one embodiment of Formula V,
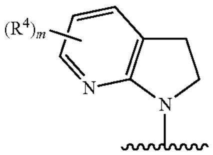
is selected from:
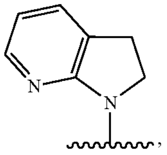
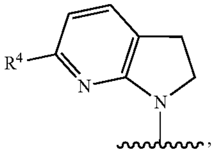
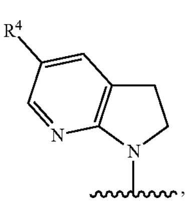
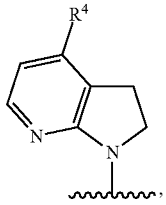
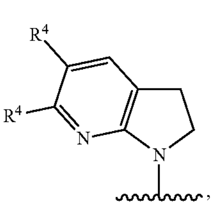
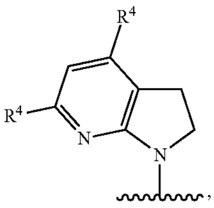 and
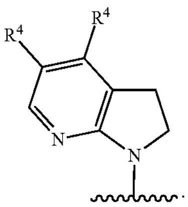
In one embodiment, a compound is provided of Formula VI:
(VI)
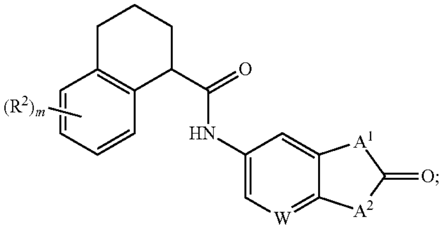
wherein all variables are as defined herein.
In one embodiment, a compound of Formula VI is selected from:
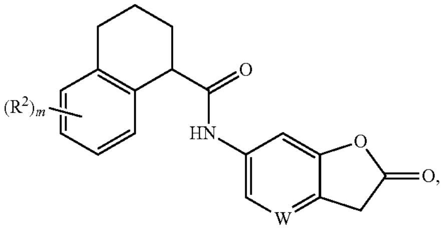
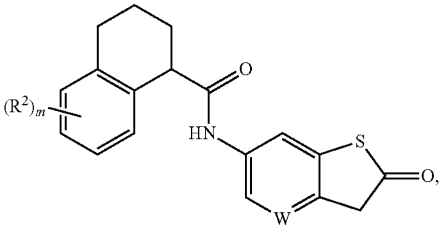
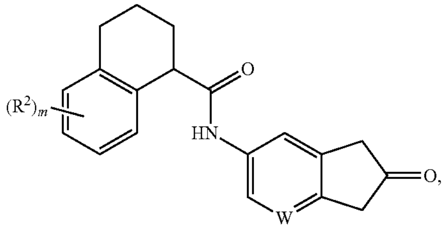
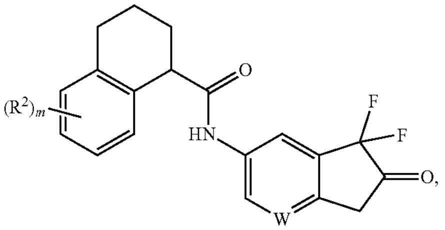 and
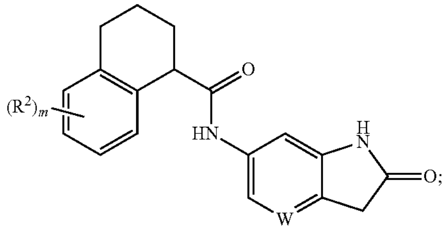
wherein all variables are as defined herein.

In one embodiment, a compound of Formula VI is selected from:
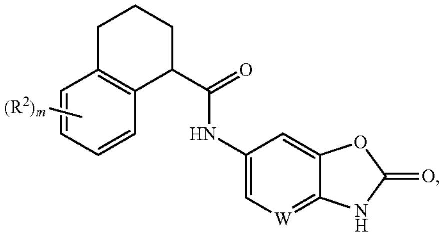
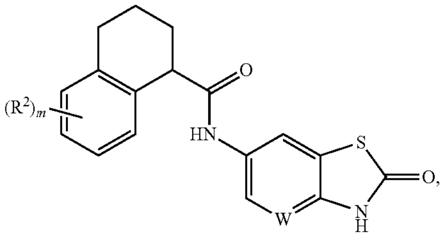
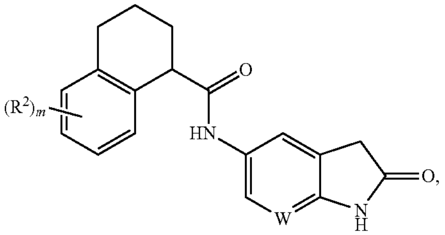
and
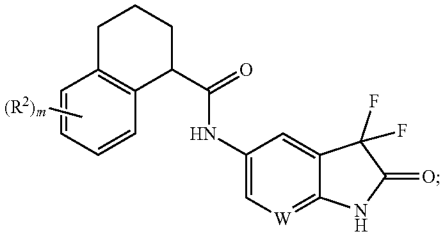
wherein all variables are as defined herein.
In one embodiment of Formula VI,
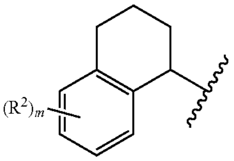
is selected from:
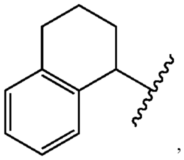
,
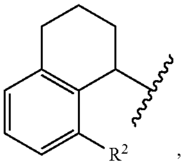
,
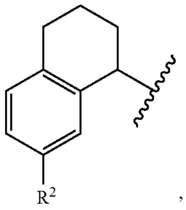
,
-continued
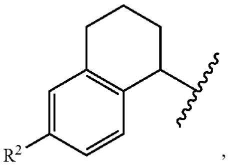
,
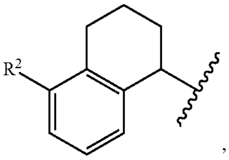
,
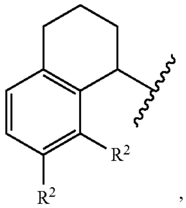
,
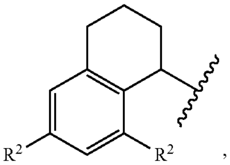
,
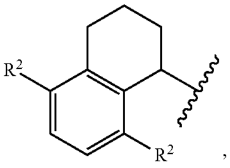
,
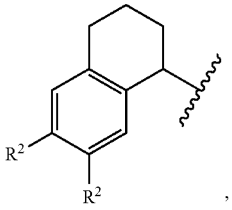
,
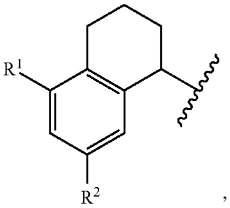
, and
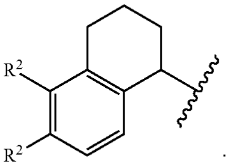
.
In one embodiment, a compound of Formula VII-a is selected from:
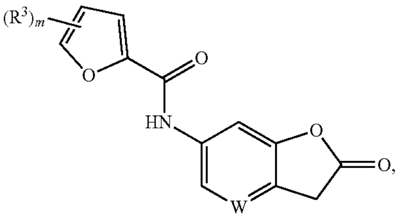
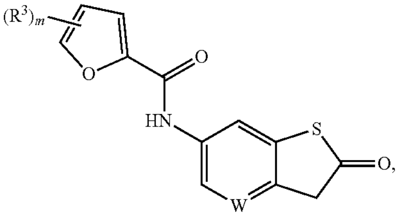
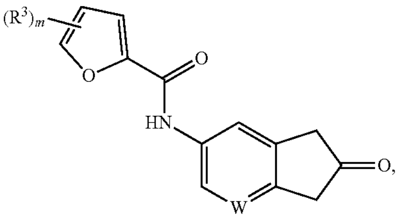

-continued

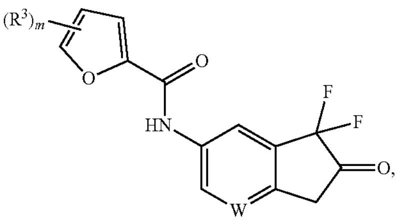

, and

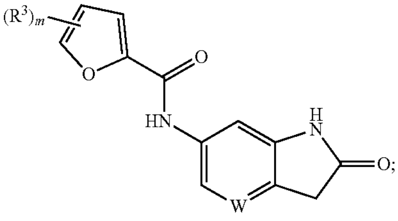

;

wherein all variables are as defined herein.

In one embodiment, a compound is provided of Formula VII-b, Formula VII-c, and Formula VII-d:

(VII-b)

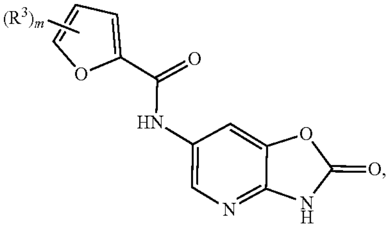

, (VII-c)

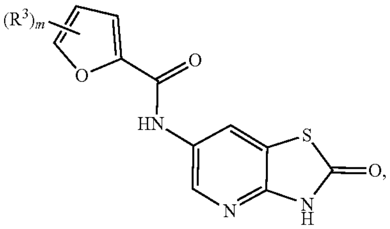

, and (VII-d)

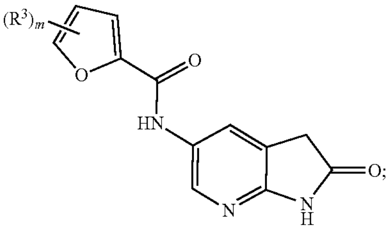

;

wherein all variables are as defined herein.

In one embodiment, a compound is provided of Formula VII-e:

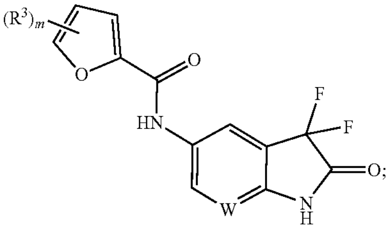

;

wherein all variables are as defined herein.

In one embodiment of any one of Formula VII-a to VII-e,

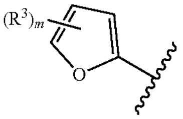

is selected from:

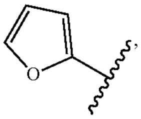

,

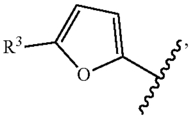

,

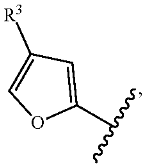

,

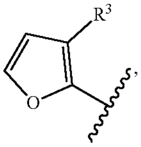

,

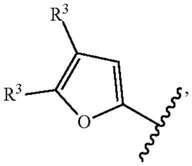

,

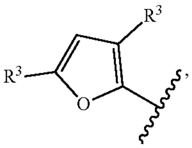

, and

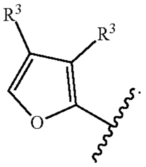

.

In one embodiment, a compound is provided of one of the following formulas:

(VIII-a)

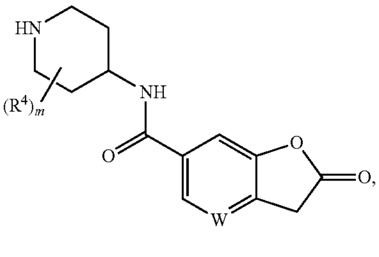

,

-continued (VIII-b)

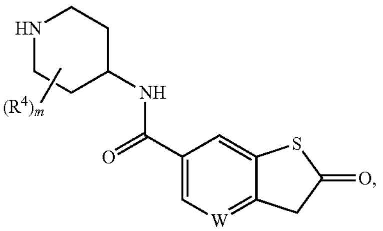

(VIII-c)

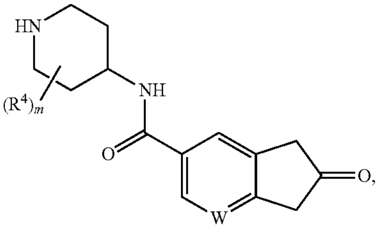

and (VIII-d)

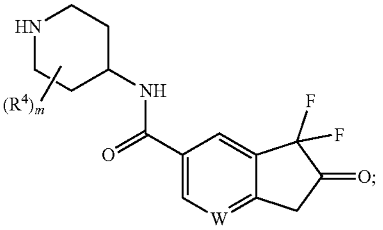

wherein all variables are as defined herein.

In one embodiment, a compound is provided of Formula VIII-e):

(VIII-e)

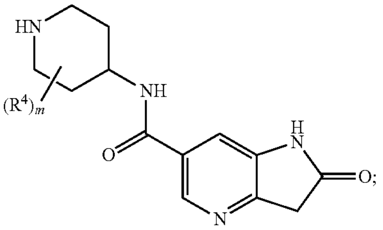

wherein all variables are as defined herein.

In one embodiment, a compound is provided of Formula VIII-f and Formula VIII-g:

(VIII-f)

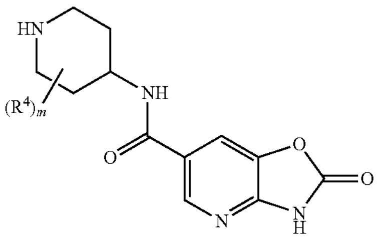

and

-continued (VIII-g)

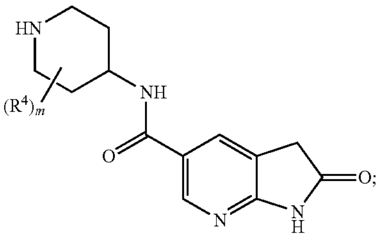

wherein all variables are as defined herein.

In one embodiment, a compound is provided of Formula VIII-h and VIII-i:

(VIII-h)

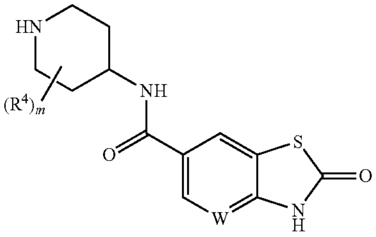

and (VIII-i)

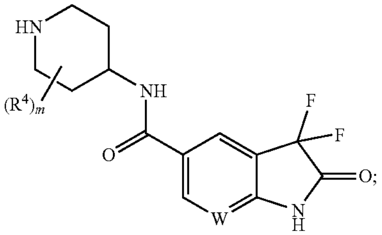

wherein all variables are as defined herein.

In one embodiment of any one of Formula VIII-a to VIII-i,

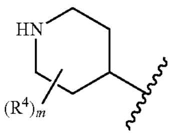

is selected from:

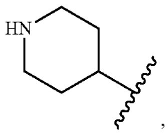,
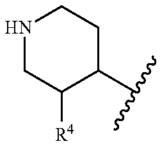,
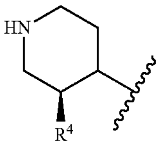,
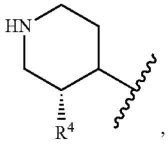,
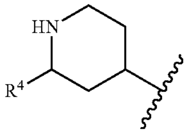,
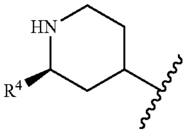,

-continued
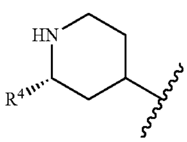 , 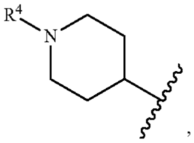 ,
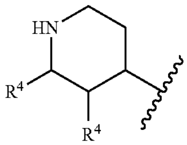 , 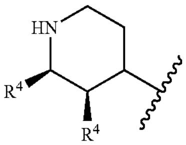 ,
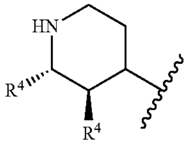 , 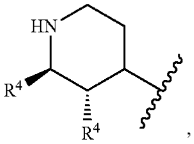 ,
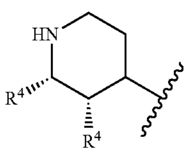 , 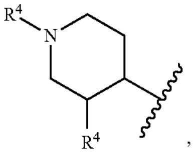 ,
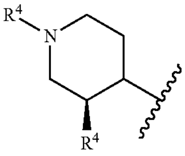 , 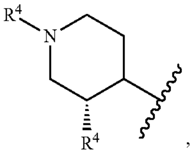 , 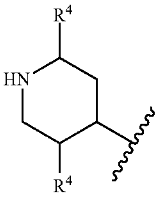 ,
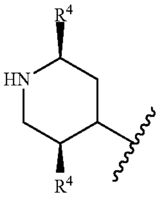 , 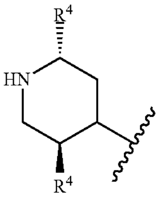 , 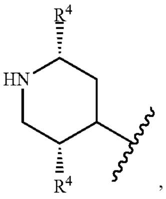 ,
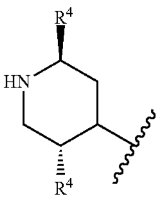 , 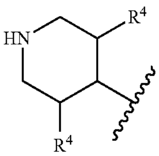 , 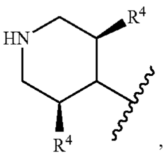 ,
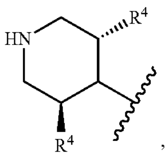 , 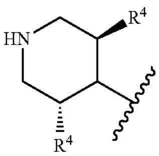 , 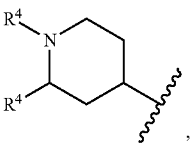 ,
-continued
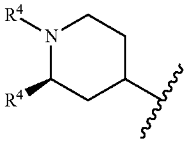 , 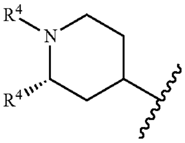 ,
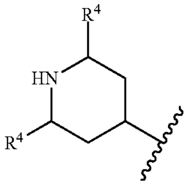 , 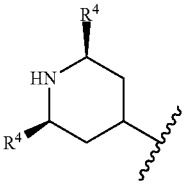 ,
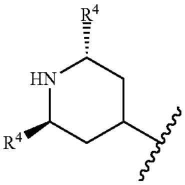 , and 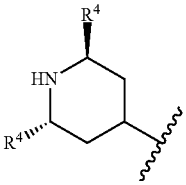 .
In one embodiment, a compound is provided of one of the following formulas:
(IX-a)
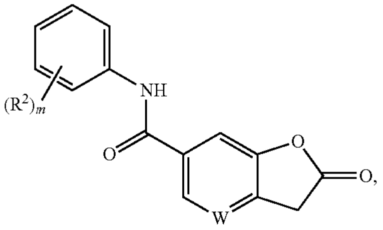
(IX-b)
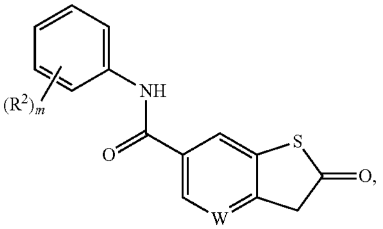
(IX-c)
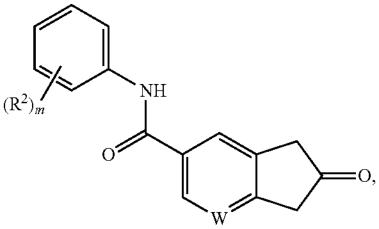
and
(IX-d)
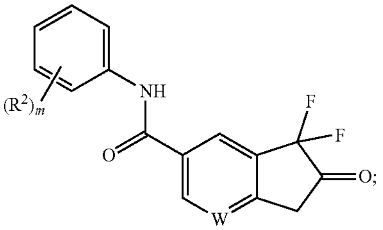
wherein all variables are as defined herein.

In one embodiment, a compound is provided of Formula IX-e:

(IX-e)

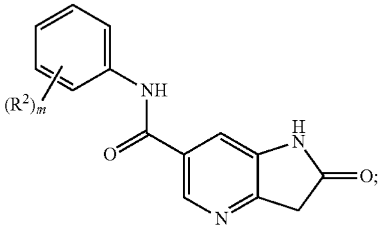

wherein all variables are as defined herein.

In one embodiment, a compound is provided of Formula IX-f and IX-g:

(IX-f)

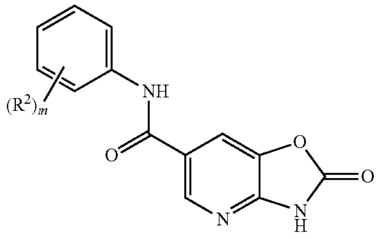

and (IX-g)

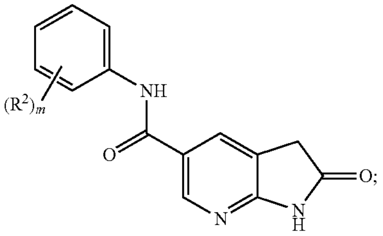

wherein all variables are as defined herein.

In one embodiment, a compound is provided of Formula IX-h and IX-i:

(IX-h)

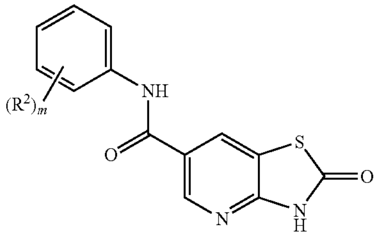

and (IX-i)

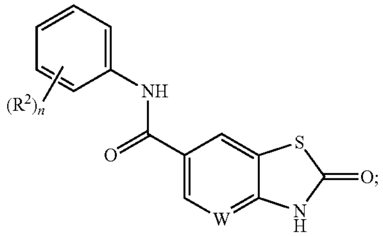

wherein all variables are as defined herein.

In one embodiment, a compound is provided of Formula IX-j:

(IX-j)

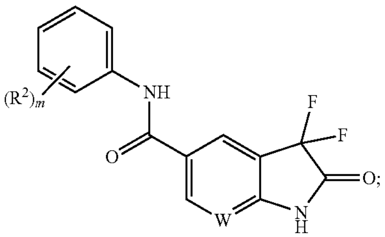

wherein all variables are as defined herein.

In one embodiment, a compound is provided of one of the following formulas:

(X-a)

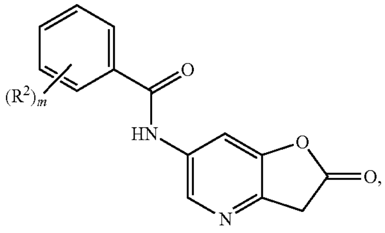

(X-b)

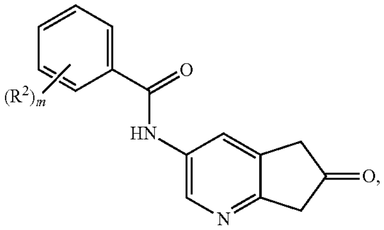

and (X-c)

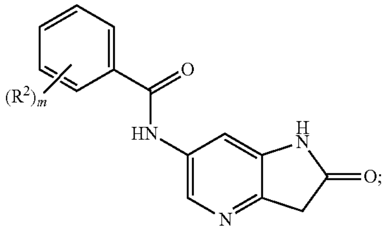

wherein all variables are as defined herein.

In one embodiment, a compound is provided of Formula X-d or X-e:

(X-d)

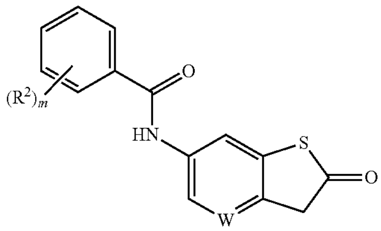

and

-continued (X-e)

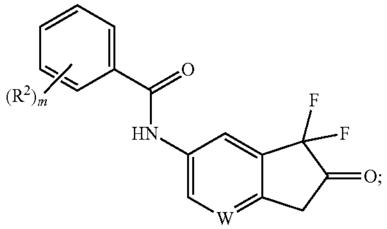

wherein all variables are as defined herein.

In one embodiment, a compound is provided of one of the following formulas:

(X-f)

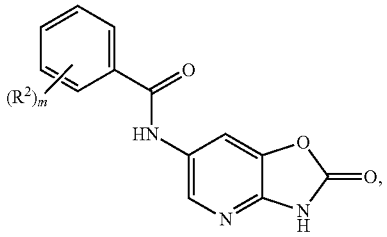

(X-g)

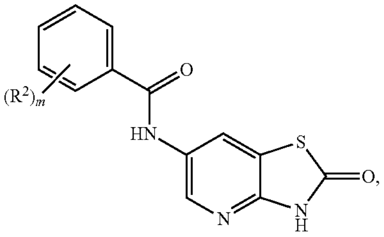

and (X-h)

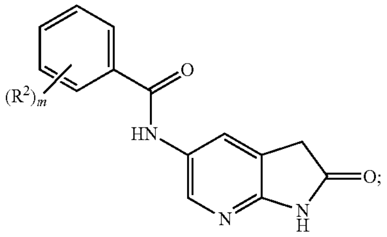

wherein all variables are as defined herein.

In one embodiment, a compound is provided of Formula X-i:

(X-i)

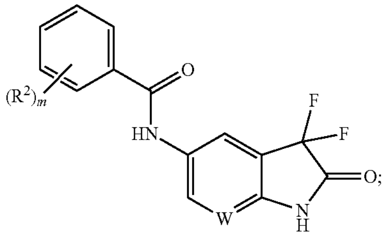

wherein all variables are as defined herein.

In one embodiment, a compound is provided of one of the following formulas:

(XI-a)

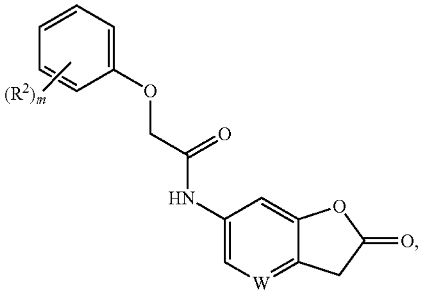

(XI-b)

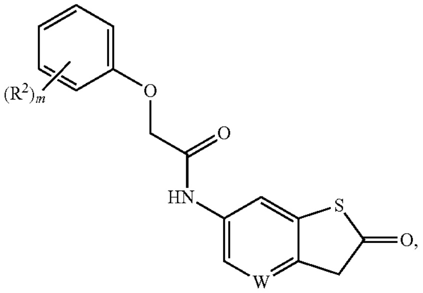

(XI-c)

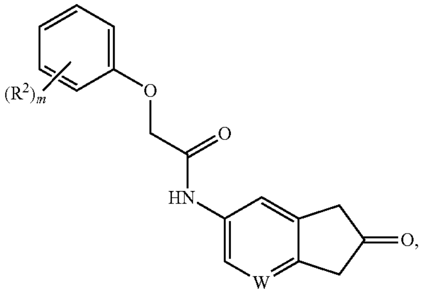

(XI-d)

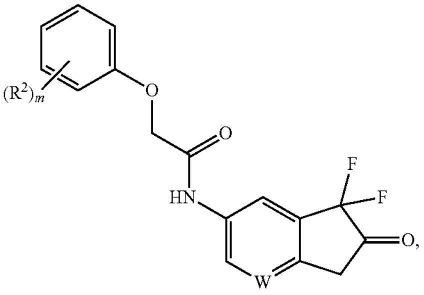

and (XI-e)

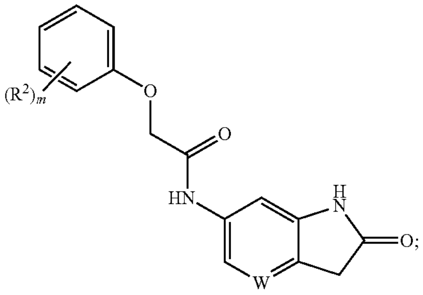

wherein all variables are as defined herein.

In one embodiment, a compound is provided of one of the following Formulas:

(XI-f)

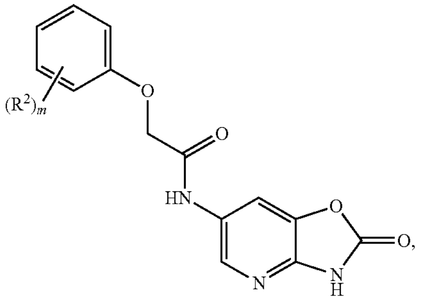

(XI-g)

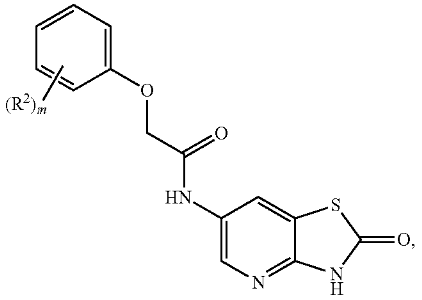

and (XI-h)

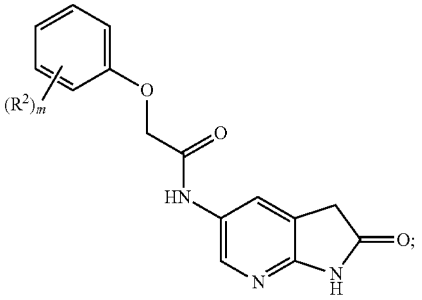

wherein all variables are as defined herein.

In one embodiment, a compound is provided of Formula XI-i:

(XI-i)

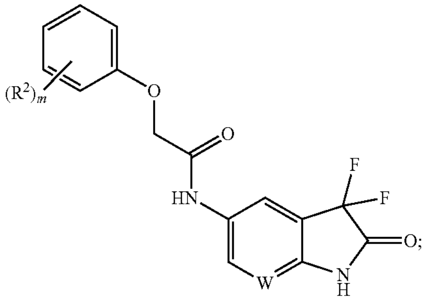

wherein all variables are as defined herein.

In one embodiment, a compound is provided of Formula XII:

(XII)

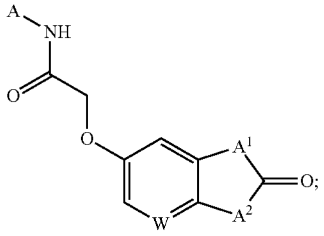

wherein all variables are as defined herein.

In one embodiment, a compound is provided of Formula XII selected from:

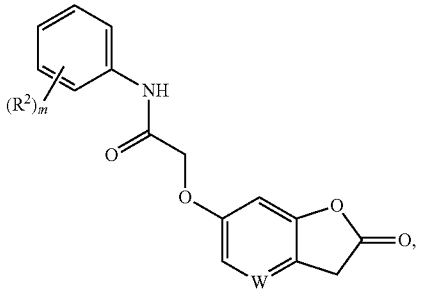

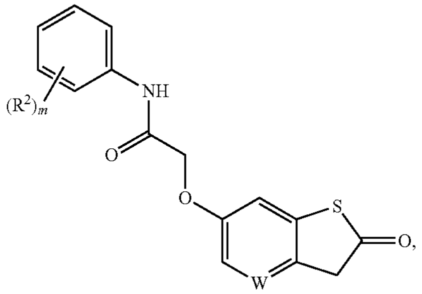

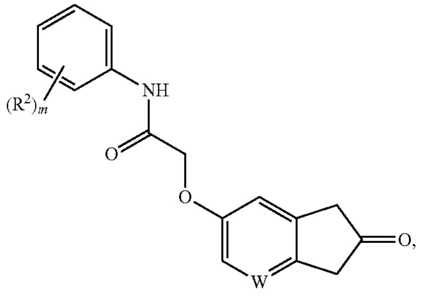

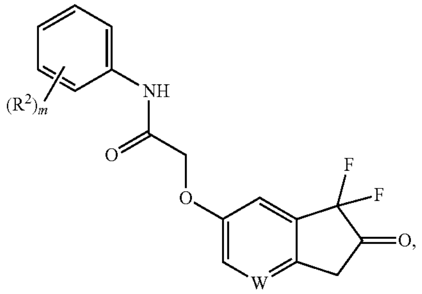

and

-continued
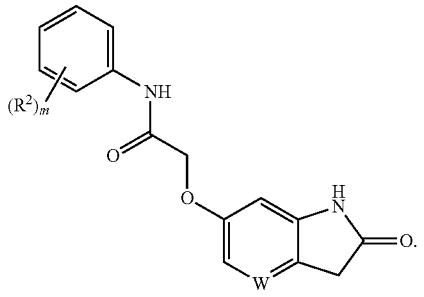
In one embodiment, a compound is provided of Formula XII selected from:
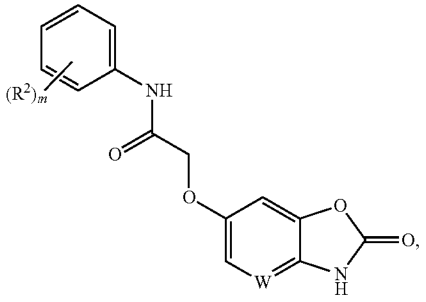
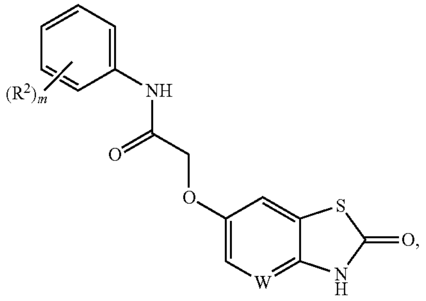
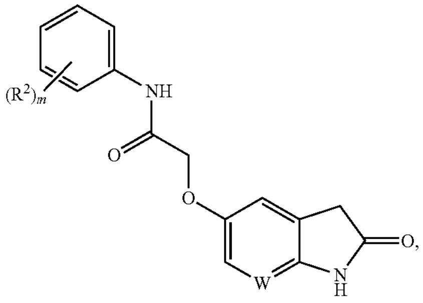
and
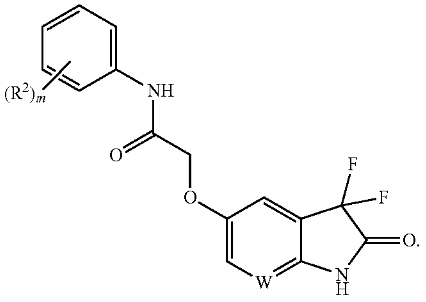
In one embodiment, a compound is provided of one of the following formulas:
(XIII-a)
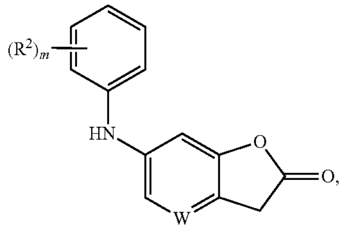
(XIII-b)
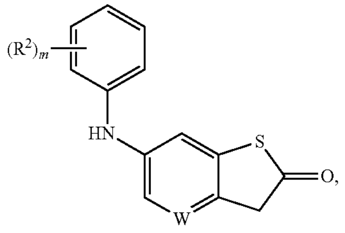
(XIII-c)
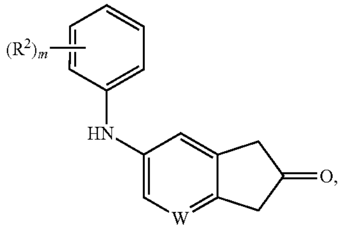
and
(XIII-d)
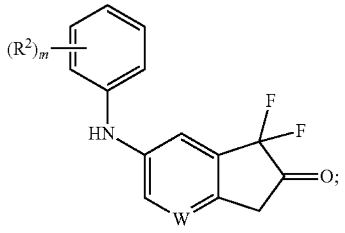
wherein all variables are as defined herein.
In one embodiment, a compound is provided of Formula XIII-e:
(XIII-e)
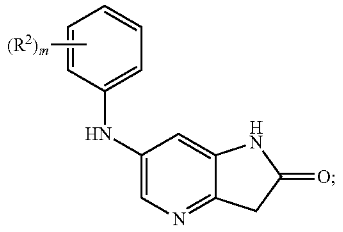
wherein all variables are as defined herein.

In one embodiment, a compound is provided of one of the following formulas:

(XIII-f)

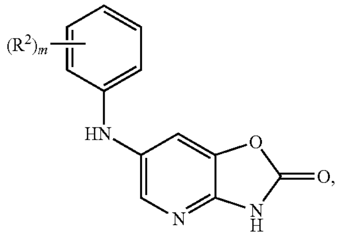

(XIII-g)

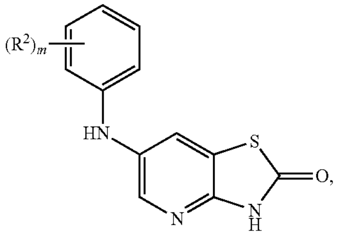

and (XIII-h)

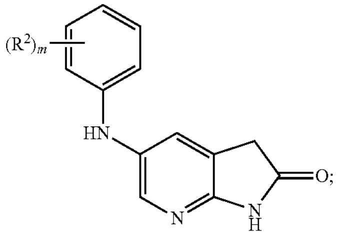

wherein all variables are as defined herein.

In one embodiment, a compound is provided of Formula XIII-i:

(XIII-i)

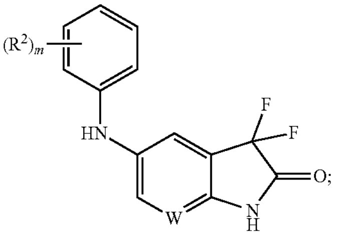

wherein all variables are as defined herein.

In any one embodiment of Formulas IX-a to IX-j, X-a to X-i, XI-a to XI-i, or XIII-a to XIII-I,

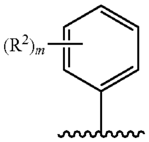

or

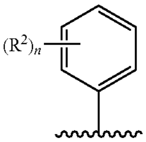

can be selected from:

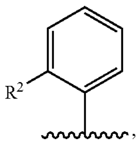

,

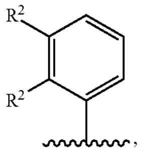

,

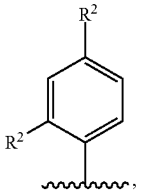

,

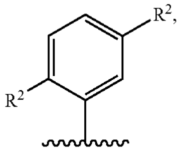

,

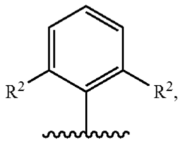

,

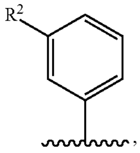

,

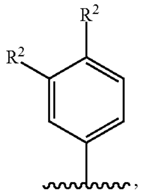

,

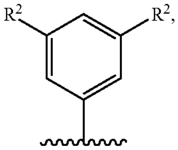

, and

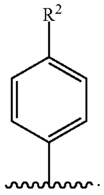

.

Embodiments of Formula XIV

In a first aspect (A1), the present invention provides a compound of Formula XIV (XIV)

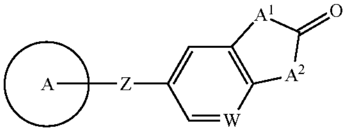

or a pharmaceutically acceptable salt thereof, wherein:

wherein all variables are as defined herein.

The invention also provides the following enumerated Embodiments (E):

E1: In one embodiment, the present invention provides a compound of Formula XIV according to A1, or a pharmaceutically acceptable salt thereof, wherein Z is selected from the group consisting of:

i) a covalent bond, ii) carbonyl, iii) $—NR^1—$, iv) $—O—CH_2—C(=O)—NR^1—$, v) $—C(=O)—NR^1—$, and vi) $—NR^1—C(=O)—$.

E2: In one embodiment, the present invention provides a compound of Formula XIV according to any one of A1 or E1, or a pharmaceutically acceptable salt thereof, wherein $R^1$ is hydrogen.

E3: In one embodiment, the present invention provides a compound of Formula XIV according to any one of A1 and E1 to E2, or a pharmaceutically acceptable salt thereof, wherein each $R^2$ is —$C_{1-6}$alkyl or —N($R^5$,$R^6$).

E4: In one aspect, the present invention provides a compound of Formula XIV according to any one of A1 and E1 to E2, or a pharmaceutically acceptable salt thereof, wherein each $R^2$ is methyl or —N($R^5$,$R^6$).

E5: In one embodiment, the present invention provides a compound of Formula XIV according to any one of A1 and E1 to E4, or a pharmaceutically acceptable salt thereof, wherein each $R^3$ is selected from the group consisting of —C(═O)—N($R^7$,$R^8$), —$C_{1-6}$alkyl, —OH, and —$NO_2$.

E6: In one embodiment, the present invention provides a compound of Formula XIV according to any one of A1 and E1 to E4, or a pharmaceutically acceptable salt thereof, wherein each $R^3$ is selected from the group consisting of —C(═O)—N($R^7$,$R^8$), isopropyl, —OH, and —$NO_2$.

E7: In one embodiment, the present invention provides a compound of Formula XIV according to any one of A1 and E1 to E6, or a pharmaceutically acceptable salt thereof, wherein each $R^4$ is —C(═O)$C_{1-6}$alkyl.

E8: In one aspect, the present invention provides a compound of Formula XIV according to any one of A1 and E1 to E6, or a pharmaceutically acceptable salt thereof, wherein each $R^4$ is acetyl.

E9: In one embodiment, the present invention provides a compound of Formula XIV according to any one of A1 and E1 to E8, or a pharmaceutically acceptable salt thereof, wherein each $R^5$ is hydrogen.

E10: In one embodiment, the present invention provides a compound of Formula XIV according to any one of A1 and E1 to E9, or a pharmaceutically acceptable salt thereof, wherein each $R^6$ is hydrogen.

E11: In one embodiment, the present invention provides a compound of Formula XIV according to any one of A1 and E1 to E10, or a pharmaceutically acceptable salt thereof, wherein each $R^7$ is $C_{1-6}$alkyl.

E12: In one embodiment, the present invention provides a compound of Formula XIV according to any one of A1 and E1 to E10, or a pharmaceutically acceptable salt thereof, wherein each $R^7$ is methyl.

E13: In one embodiment, the present invention provides a compound of Formula XIV according to any one of A1 and E1 to E12, or a pharmaceutically acceptable salt thereof, wherein each $R^8$ is hydrogen.

E14: In one embodiment, the present invention provides a compound of Formula XIV according to any one of A1 and E1 to E13, or a pharmaceutically acceptable salt thereof, wherein A is selected from the group consisting of:

i) aryl substituted with $R^2$,
ii) aryl,
iii) heteroaryl substituted with one or two $R^3$,
iv) heteroaryl, and
v) heterocycloalkyl substituted with $R^4$.

E15: In one aspect, the present invention provides a compound of Formula XIV according to any one of A1 and E1 to E13, or a pharmaceutically acceptable salt thereof, wherein A is selected from the group consisting of:

i) phenyl substituted with $R^2$,
ii) phenyl,
iii) tetralin-1-yl,
iv) benzimidazol-1-yl substituted with one or two $R^3$,
v) isoindolin-2-yl substituted with $R^3$,
vi) 2-furyl,
vii) indolin-1-yl,
viii) benzofuran-3-yl,
ix) 2,3-dihydropyrrolo[2,3-b]pyridin-1-yl, and
x) 4-piperidyl substituted with $R^4$.

E16: In one embodiment, the present invention provides a compound of Formula XIV according to A1, or a pharmaceutically acceptable salt thereof, wherein:

$A^1$ is selected from the group consisting of —O—, —S—, —$CH_2$—, —$CF_2$— and —NH—; and $A^2$ is —$CH_2$—; or
$A^1$ is selected from the group consisting of —O—, —S—, —$CH_2$—, and —$CF_2$—; and $A^2$ is —NH—;
Z is selected from the group consisting of:
i) a covalent bond,
ii) carbonyl,
iii) —NH—,
iv) —O—$CH_2$—C(═O)—NH—
v) —C(═O)—NH—, and
vi) —NH—C(═O)—;
W is CH or N;
A is selected from the group consisting of:
i) aryl substituted with $R^2$,
ii) aryl,
iii) heteroaryl substituted with one or two $R^3$,
iv) heteroaryl, and
v) heterocycloalkyl substituted with $R^4$;
$R^2$ is —$C_{1-6}$alkyl or —$NH_2$;
$R^3$ is selected from the group consisting of —C(═O)—NH—$C_{1-6}$alkyl, —$C_{1-6}$alkyl, —OH, and —$NO_2$; and
$R^4$ is —C(═O)$C_{1-6}$alkyl.

E17: In one aspect, the present invention provides a compound of Formula XIV according to A1, or a pharmaceutically acceptable salt thereof, wherein:

$A^1$ is selected from the group consisting of —O—, —S—, —$CH_2$—, —$CF_2$— and —NH—; and $A^2$ is —$CH_2$—; or
$A^1$ is selected from the group consisting of —O—, —S—, —$CH_2$—, and —$CF_2$—; and $A^2$ is —NH—;
Z is selected from the group consisting of:
i) a covalent bond,
ii) carbonyl,
iii) —NH—,
iv) —O—$CH_2$—C(═O)—NH—
v) —C(═O)—NH—, and
vi) —NH—C(═O)—;
W is CH or N;
A is selected from the group consisting of:
i) phenyl substituted with $R^2$,
ii) phenyl,
iii) tetralin-1-yl,
iv) benzimidazol-1-yl substituted with one or two $R^3$,
v) isoindolin-2-yl substituted with $R^3$,
vi) 2-furyl,
vii) indolin-1-yl,
viii) benzofuran-3-yl,
ix) 2,3-dihydropyrrolo[2,3-b]pyridin-1-yl, and
x) 4-piperidyl substituted with $R^4$;
$R^2$ is methyl or —$NH_2$;
$R^3$ is selected from the group consisting of —C(═O)—NH—$CH_3$, isopropyl, —OH, and —$NO_2$; and
$R^4$ is acetyl.

E18: In one embodiment, the present invention provides a compound of Formula XIV according to A1, or a pharmaceutically acceptable salt thereof, wherein:

$A^1$ is selected from the group consisting of —O—, —S—, —$CH_2$—, —$CF_2$— and —NH—; and $A^2$ is —$CH_2$—; or
$A^1$ is selected from the group consisting of —O—, —S—, —$CH_2$—, and —$CF_2$—; and $A^2$ is —NH—; and
W is CH or N.

E19: In one embodiment, the present invention provides a compound of Formula XIV according to A1, or a pharmaceutically acceptable salt thereof, wherein:

A is selected from the group consisting of:

i) aryl substituted with $R^2$, ii) aryl, iii) heteroaryl substituted with one or two $R^3$, iv) heteroaryl, and v) heterocycloalkyl substituted with $R^4$;

$R^2$ is-$C_{1-6}$alkyl or —$NH_2$;

$R^3$ is selected from the group consisting of —C(=O)—NH—$C_{1-6}$alkyl, —$C_{1-6}$alkyl, —OH, and —$NO_2$; and $R^4$ is —C(=O)$C_{1-6}$alkyl.

E20: In one aspect, the present invention provides a compound of Formula XIV according to A1, or a pharmaceutically acceptable salt thereof, wherein:

A is selected from the group consisting of:

i) phenyl substituted with $R^2$, ii) phenyl, iii) tetralin-1-yl, iv) benzimidazol-1-yl substituted with one or two $R^3$, v) isoindolin-2-yl substituted with $R^3$, vi) 2-furyl, vii) indolin-1-yl, viii) benzofuran-3-yl, ix) 2,3-dihydropyrrolo[2,3-b]pyridin-1-yl, and x) 4-piperidyl substituted with $R^4$;

$R^2$ is methyl or —$NH_2$;

$R^3$ is selected from the group consisting of —C(=O)—NH—$CH_3$, isopropyl, —OH, and —$NO_2$; and $R^4$ is acetyl.

E21: In one embodiment, the present invention provides a compound of Formula XIV according to A1, or a pharmaceutically acceptable salt thereof, wherein the compound of Formula XIV is selected from the group consisting of:

2-Isopropyl-A-methyl-1-(2-oxoindolin-6-yl)benzimidazole-5-carboxamide;

2-Isopropyl-A-methyl-1-(2-oxoindolin-5-yl)benzimidazole-5-carboxamide;

6-(2-Aminoanilino)-3H-1,3-benzothiazol-2-one;

6-(2-Isopropylbenzimidazol-1-yl)-3H-1,3-benzothiazol-2-one;

6-(2-Aminoanilino)-3H-1,3-benzoxazol-2-one;

6-(2-Isopropylbenzimidazol-1-yl)-3H-1,3-benzoxazol-2-one;

N-(1-Acetyl-4-piperidyl)-2-oxo-3H-1,3-benzoxazole-6-carboxamide;

6-(2,3-Dihydropyrrolo[2,3-b]pyridine-1-carbonyl)-3H-1,3-benzoxazol-2-one;

6-(Indoline-1-carbonyl)-3H-1,3-benzothiazol-2-one;

5-(Indoline-1-carbonyl)indolin-2-one;

2-Oxo-V-phenyl-3H-oxazolo[4,5-b]pyridine-6-carboxamide;

N-(1-Acetyl-4-piperidyl)-2-oxo-3H-oxazolo[4,5-b]pyridine-6-carboxamide;

5-(Indoline-1-carbonyl)-1,3-dihydropyrrolo[2,3-b]pyridin-2-one;

3,3-Difluoro-5-(2-isopropylbenzimidazol-1-yl)indolin-2-one;

6-(4-Hydroxyisoindoline-2-carbonyl)-3H-1,3-benzoxazol-2-one;

6-(4-Nitroisoindoline-2-carbonyl)-3H-1,3-benzoxazol-2-one;

N-(3,3-Difluoro-2-oxo-indolin-5-yl)tetralin-1-carboxamide;

N-(3,3-Difluoro-2-oxo-indolin-5-yl)benzofuran-3-carboxamide;

2-Isopropyl-A-methyl-1-(2-oxo-1,3-dihydropyrrolo[2,3-b]pyridin-5-yl)benzimidazole-5-carboxamide;

5-(2-Isopropylbenzimidazol-1-yl)-1,3-dihydropyrrolo[2,3-b]pyridin-2-one;

N-(2-Oxo-3H-1,3-benzoxazol-6-yl)benzamide;

N-(2-Oxoindolin-5-yl)furan-2-carboxamide;

2-(2-Methylphenoxy)-N-(2-oxo-3H-1,3-benzothiazol-6-yl)acetamide;

2-Oxo-N-phenylindoline-5-carboxamide;

2-Oxo-N-phenyl-3H-1,3-benzoxazole-6-carboxamide;

6-(Indoline-1-carbonyl)-3H-1,3-benzoxazol-2-one; and

2-Oxo-N-phenyl-3H-1,3-benzothiazole-6-carboxamide.

E22: In one embodiment, the present invention provides a compound of Formula XIV according to A1, or a pharmaceutically acceptable salt thereof, wherein the compound of Formula XIV is selected from the group consisting of:

2-Isopropyl-A-methyl-1-(2-oxoindolin-6-yl)benzimidazole-5-carboxamide;

2-Isopropyl-V-methyl-1-(2-oxoindolin-5-yl)benzimidazole-5-carboxamide;

6-(2-Aminoanilino)-3H-1,3-benzothiazol-2-one;

6-(2-Isopropylbenzimidazol-1-yl)-3H-1,3-benzothiazol-2-one;

6-(2-Isopropylbenzimidazol-1-yl)-3H-1,3-benzoxazol-2-one;

N-(1-Acetyl-4-piperidyl)-2-oxo-3H-1,3-benzoxazole-6-carboxamide;

6-(2,3-Dihydropyrrolo[2,3-b]pyridine-1-carbonyl)-3H-1,3-benzoxazol-2-one;

6-(Indoline-1-carbonyl)-3H-1,3-benzothiazol-2-one;

2-Oxo-A-phenyl-3H-oxazolo[4,5-b]pyridine-6-carboxamide;

N-(1-Acetyl-4-piperidyl)-2-oxo-3H-oxazolo[4,5-b]pyridine-6-carboxamide;

5-(Indoline-1-carbonyl)-1,3-dihydropyrrolo[2,3-b]pyridin-2-one;

3,3-Difluoro-5-(2-isopropylbenzimidazol-1-yl)indolin-2-one;

6-(4-Hydroxyisoindoline-2-carbonyl)-3H-1,3-benzoxazol-2-one;

6-(4-Nitroisoindoline-2-carbonyl)-3H-1,3-benzoxazol-2-one;

N-(3,3-Difluoro-2-oxo-indolin-5-yl)tetralin-1-carboxamide;

N-(3,3-Difluoro-2-oxo-indolin-5-yl)benzofuran-3-carboxamide;

2-Isopropyl-A-methyl-1-(2-oxo-1,3-dihydropyrrolo[2,3-b]pyridin-5-yl)benzimidazole-5-carboxamide; and 5-(2-Isopropylbenzimidazol-1-yl)-1,3-dihydropyrrolo[2,3-b]pyridin-2-one.

E23: In one embodiment, $R^3$ is independently selected at each occurrence from: —$(CH_2)_{0-1}$—($C_{3-7}$cycloalkyl)-aryl substituted by $R^{10}$; —$(CH_2)_{0-1}$—($C_{3-7}$cycloalkyl)-aryl; —$(CH_2)_{0-1}$—$C_{3-7}$ cycloalkyl substituted by $R^{10}$; —$(CH_2)_{0-1}$—$C_{3-7}$cycloalkyl; —$(CH_2)_{0-1}$-heterocycloalkyl; —C(=O)$C_{1-6}$alkyl; —$(CH_2)_{0-2}$—C(=O)—N($R^7$,$R^8$); —C(=O)O$C_{1-6}$alkyl; —$C_{1-6}$alkoxy; —$C_{1-6}$alkyl; —OH; —$NO_2$; —$C_{1-6}$alkyl-N($R^{11}$)—C(=O)—$R^{12}$; —$CH_2$—O—$(CH_2)_{0-1}$-aryl substituted by $R^{10}$; —$CH_2$—O—$(CH_2)_{0-1}$-aryl; —O—$(CH_2)_{0-1}$-aryl; -halogen; -halogen-$C_{1-6}$alkyl; -hydroxy-$C_{1-6}$alkyl; —N($R^5$,$R^6$); —NH—C(=O)$C_{1-6}$alkyl; and —NH—C(=O)O$C_{1-6}$alkyl.

E24: In one embodiment, $R^2$ is independently selected at each occurrence from: —$(CH_2)_{0-1}$—($C_{3-7}$cycloalkyl)-aryl substituted by $R^{10}$; —$(CH_2)_{0-1}$—($C_{3-7}$cycloalkyl)-aryl; —$(CH_2)_{0-1}$—$C_{3-7}$ cycloalkyl substituted by $R^{10}$; —$(CH_2)_{0-1}$—$C_{3-7}$cycloalkyl; —$(CH_2)_{0-1}$-heterocycloalkyl; —C(=O)$C_{1-6}$alkyl; —$(CH_2)_{0-2}$—C(=O)—N($R^7$,$R^8$); —C(=O)

$OC_{1-6}$alkyl; —$C_{1-6}$alkoxy; —$C_{1-6}$alkyl; —OH; —$NO_2$; —$C_{1-6}$alkyl-N($R^{11}$)—C(═O)—$R^{12}$; —$CH_2$—O—$(CH_2)_{0-1}$-aryl substituted by $R^{10}$; —$CH_2$—O—$(CH_2)_{0-1}$-aryl; —O—$(CH_2)_{0-1}$-aryl; -halogen; -halogen-$C_{1-6}$alkyl; -hydroxy-$C_{1-6}$alkyl; —N($R^5$,$R^6$); —NH—C(═O)$C_{1-6}$alkyl; and —NH—C(═O)$OC_{1-6}$alkyl.

E25: The compound of any one of the above embodiments, wherein $A^1$ is selected from the group consisting of —O— and —NH—, and $A^2$ is —$CH_2$—.

E26: The compound of any one of the above embodiments, wherein $A^1$ is selected from the group consisting of —O—, —S—, —$CH_2$—, —$CF_2$—, and $A^2$ is —NH—.

E27: The compound of any one of the above embodiments, wherein W is CH.

E28: The compound of any one of the above embodiments, wherein W is N.

E29: The compound of any one of the above embodiments, wherein $R^2$ is independently selected at each occurrence from: -halogen; -halogen-$C_{1-6}$alkyl; -hydroxy-$C_{1-6}$alkyl; —N($R^5$,$R^6$); —$NO_2$; —NH—C(═O)$C_{1-6}$alkyl; and —$SO_2$—N($R^5$,$R^6$).

E30: The compound of any one of the above embodiments, wherein $R^2$ is independently selected at each occurrence from: —$(CH_2)_{0-1}$—($C_{3-7}$cycloalkyl)-aryl substituted by $R^{10}$; —$(CH_2)_{0-1}$—($C_{3-7}$cycloalkyl)-aryl; —$(CH_2)_{0-1}$—$C_{3-7}$cycloalkyl substituted by $R^{10}$; —$(CH_2)_{0-1}$—$C_{3-7}$cycloalkyl; —C(═O)$C_{1-6}$alkyl; —C(═O)—N($R^7$,$R^8$); —C(═O)$OC_{1-6}$alkyl; —$C_{1-6}$alkoxy; —$C_{1-6}$alkyl; —$CH_2$—O—$(CH_2)_{0-1}$-aryl substituted by $R^{10}$; —$CH_2$—O—$(CH_2)_{0-1}$-aryl; and —O—$(CH_2)_{0-1}$-aryl.

E31: The compound of any one of the above embodiments, wherein $R^3$ is independently selected at each occurrence from: —C(═O)$C_{1-6}$alkyl; —$(CH_2)_{0-2}$—C(═O)—N($R^7$,$R^8$); —C(═O)$OC_{1-6}$alkyl; —$C_{1-6}$alkoxy; —$C_{1-6}$alkyl; —OH; —$NO_2$; —$C_{1-6}$alkyl-N($R^{11}$)—C(═O)—$R^{12}$; —$CH_2$—O—$(CH_2)_{0-1}$-aryl substituted by $R^{10}$; —$CH_2$—O—$(CH_2)_{0-1}$-aryl; —O—$(CH_2)_{0-1}$-aryl; -halogen; -halogen-$C_{1-6}$alkyl; -hydroxy-$C_{1-6}$alkyl; -hydroxy-$C_{1-6}$alkyl-aryl; —N($R^5$,$R^6$); —NH—C(═O)$C_{1-6}$alkyl; —NH—C(═O)$OC_{1-6}$alkyl; and ═O.

E32: The compound of any one of the above embodiments, wherein $R^3$ is independently selected at each occurrence from: —$(CH_2)_{0-1}$—($C_{3-7}$cycloalkyl)-aryl substituted by $R^{10}$; —$(CH_2)_{0-1}$—($C_{3-7}$cycloalkyl)-aryl; —$(CH_2)_{0-1}$—$C_{3-7}$cycloalkyl substituted by $R^{10}$; —$(CH_2)_{0-1}$—$C_{3-7}$cycloalkyl; —$(CH_2)_{0-1}$-heteroaryl substituted by $R^9$; and —$(CH_2)_{0-1}$-heterocycloalkyl.

E33: The compound of any one of the above embodiments, wherein $R^4$ is independently selected at each occurrence from: —C(═O)$C_{1-6}$alkyl; —C(═O)—N($R^7$,$R^8$); —C(═O)$OC_{1-6}$alkyl; —$C_{1-6}$alkoxy; —$C_{1-6}$alkyl; —$CH_2$—O—$(CH_2)_{0-1}$-aryl substituted by $R^{10}$; —$CH_2$—O—$(CH_2)_{0-1}$-aryl; -halogen; -halogen-$C_{1-6}$alkyl; -hydroxy-$C_{1-6}$ alkyl; —N($R^5$,$R^6$); and —NH—C(═O)$C_{1-6}$alkyl.

E34: The compound of any one of the above embodiments, wherein $R^4$ is independently selected at each occurrence from: —$(CH_2)_{0-1}$—($C_{3-7}$cycloalkyl)-aryl substituted by $R^{10}$; —$(CH_2)_{0-1}$—($C_{3-7}$cycloalkyl)-aryl; —$(CH_2)_{0-1}$—$C_{3-7}$cycloalkyl substituted by $R^{10}$; and —$(CH_2)_{0-1}$—$C_{3-7}$ cycloalkyl.

E35: The compound of any one of the above embodiments, wherein $R^5$ and $R^6$ are independently selected at each occurrence from H, $C_{1-6}$alkyl and phenyl.

E36: The compound of any one of the above embodiments, wherein $R^5$ and $R^6$, taken together with the nitrogen to which they are attached, form a heterocycloalkyl ring.

E37: The compound of any one of the above embodiments, wherein $R^7$ and $R^8$ are independently selected at each occurrence from H and $C_{1-6}$alkyl.

E38: The compound of any one of the above embodiments, wherein $R^7$ and $R^8$, taken together with the nitrogen to which they are attached, form a heterocycloalkyl ring.

E39: The compound of any one of the above embodiments, wherein $X^1$ is selected from bond or $NR^{34}$.

E40: The compound of any one of the above embodiments, wherein $X^{22}$ is selected from halo, —$NH_2$, —$NHR^{34}$, —N($R^{34}$)$_2$, hydroxyl, thiol, —B(OH)$_2$, —Sn($R^{36}$)$_3$, —Si($R^{36}$)$_3$, —OS(O)$_2$alkyl, —OS(O)$_2$haloalkyl, alkenyl, alkynyl, ethynyl, ethenyl, —C(O)H, —$NR^{34}$C(O)alkene, —$NR^{34}$C(O)alkyne, cyano, —SC(O)alkyl, OC(O)alkyl, heterocycle, —C(O)OH, hydrogen, alkyl, aryl, heteroaryl, aliphatic, heteroaliphatic, and carbocyclic.

E41: The compound of any one of the above embodiments, wherein $R^{20}$, $R^{21}$, $R^{22}$, $R^{23}$, and $R^{24}$ are independently selected from bond, alkyl, —C(O)—, —C(O)O—, —OC(O)—, —C(O)alkyl, —C(O)Oalkyl, —C(S)—, —$SO_2$—, —S(O)—, —C(S)—, —C(O)NH—, —NHC(O)—, —N(alkyl)C(O)—, —C(O)N(alkyl)-, —O—, —S—, —NH—, —N(alkyl)-, —CH(—O—$R^{26}$)—, —CH(—$NR^{34}R^{34'}$)—, —C(—O—$R^{26}$)alkyl-, —C(—$NR^{34}R^{34'}$)alkyl-, —C($R^{40}R^{40}$)—, -alkyl($R^{27}$)-alkyl($R^{28}$)—, —C($R^{27}R^{28}$)—, —P(O)($OR^{26}$)O—, —P(O)($OR^{26}$)—, —$NR^{34}$C(O)$NR^{34'}$—, alkene, haloalkyl, alkoxy, alkyneheteroarylalkyl, aryl, arylalkyl, heterocycle, aliphatic, heteroaliphatic, heteroaryl, lactic acid, glycolic acid, carbocycle, -(ethylene glycol)$_{1-6}$-, -(lactic-co-glycolic acid)$_{1-6}$-, -(propylene glycol)$_{1-6}$-, —O—$(CH_2)_{1-12}$—O—, —NH—$(CH_2)_{1-12}$—NH—, —NH—$(CH_2)_{1-12}$—O—, —O—$(CH_2)_{1-12}$—NH—, —S—$(CH_2)_{1-12}$—O—, —O—$(CH_2)_{1-12}$—S—, —S—$(CH_2)_{1-12}$—S—, —S—$(CH_2)_{1-12}$—NH—, and —NH—$(CH_2)_{1-12}$—S—, wherein at least one of $R^{20}$, $R^{21}$, $R^{22}$, $R^{23}$, and $R^{24}$ is not a bond.

E42: The compound of any one of the above embodiments, wherein at least two of $R^{20}$, $R^{21}$, $R^{22}$, $R^{23}$, and $R^{24}$ are not a bond.

E43: The compound of any one of the above embodiments, wherein at least three of $R^{20}$, $R^{21}$, $R^{22}$, $R^{23}$, and $R^{24}$ are not a bond.

E44: The compound of any one of the above embodiments, wherein at least four of $R^{20}$, $R^{21}$, $R^{22}$, $R^{23}$, and $R^{24}$ are not a bond.

In one embodiment, the present invention provides pharmaceutically acceptable salts or esters of the compounds of Formula XIV as described herein. In a particular embodiment, the present invention provides pharmaceutically acceptable salts of the compounds according to Formula XIV as described herein, especially hydrochloride salts. In a further particular embodiment, the present invention provides pharmaceutically acceptable esters of the compounds according to Formula XIV as described herein. In yet a further particular embodiment, the present invention provides compounds according to Formula XIV as described herein.

Furthermore, the invention includes all optical isomers, i.e. diastereoisomers, diastereomeric mixtures, racemic mixtures, all their corresponding enantiomers and/or tautomers as well as their solvates of the compounds of Formula XIV.

The compounds of Formula XIV may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

In one embodiment of Formula XIV, Z is a covalent bond.

In another embodiment of Formula XIV, Z is C(=O).

In another embodiment of Formula XIV, Z is selected from:

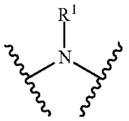 , 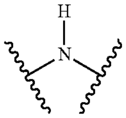 , 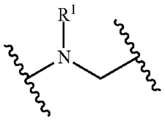 ,

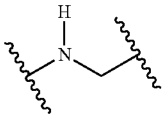 , 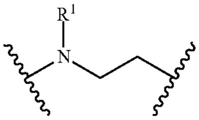 ,

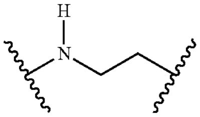 , 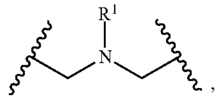 ,

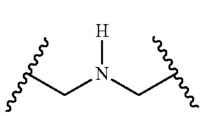 , 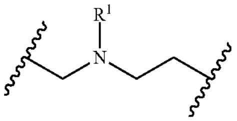 ,

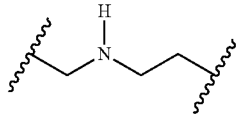 ,

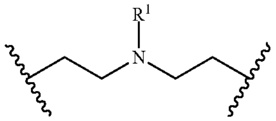 , and

-continued

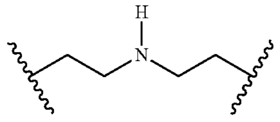 .

In another embodiment of Formula XIV, Z is selected from:

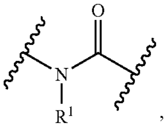 , 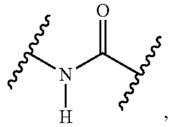 ,

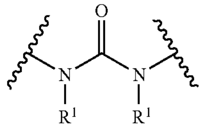 , and 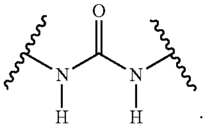 .

In another embodiment of Formula XIV, Z is selected from:

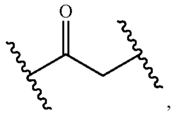 , 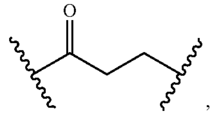 ,

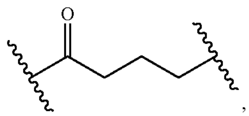 , 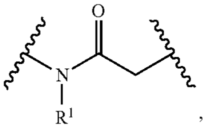 ,

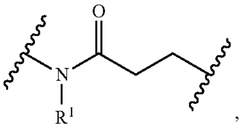 , 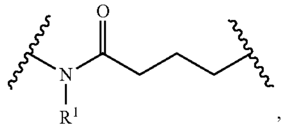 ,

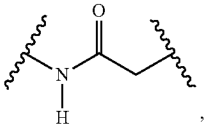 , 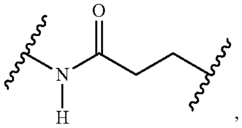 , and

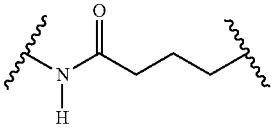 .

In another embodiment of Formula XIV, Z is selected from:

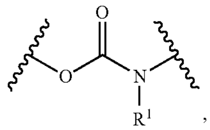 , 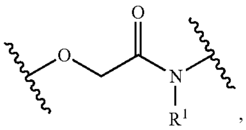 ,

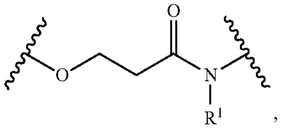 , 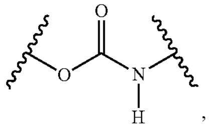 ,

-continued
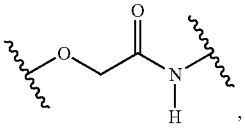
, and
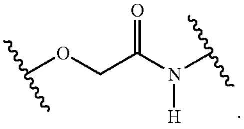
.
In another embodiment of Formula XIV, Z is selected from:
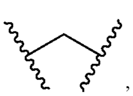
,
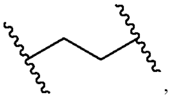
, and
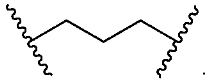
.
In another embodiment of Formula XIV, Z is selected from:
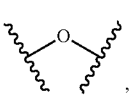
,
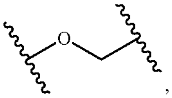
,
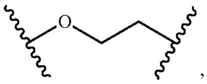
,
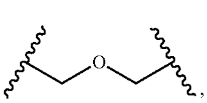
,
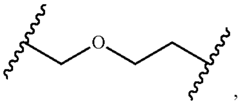
, and
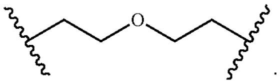
.
In another embodiment of Formula XIV, Z is selected from:
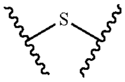
,
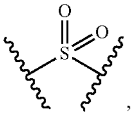
,
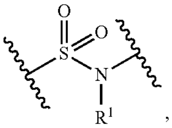
,
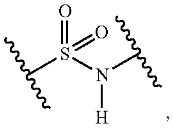
,
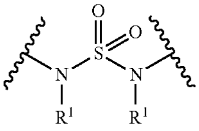
, and
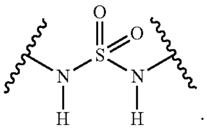
.
In another embodiment of Formula XIV,
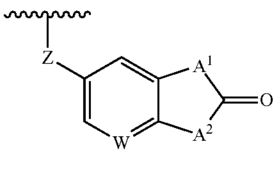
is
-continued
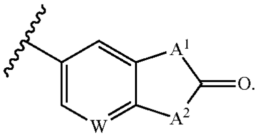
In one embodiment of Formula XIV,
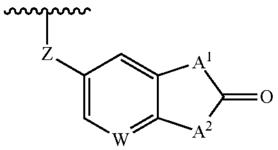
is
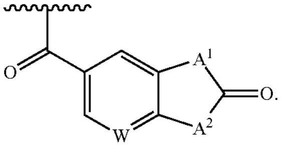
In one embodiment of Formula XIV,
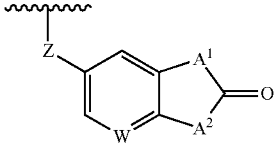
is selected from:
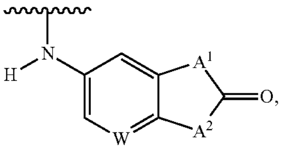
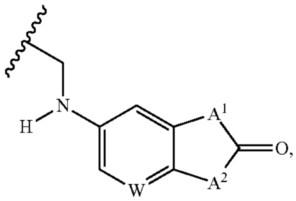
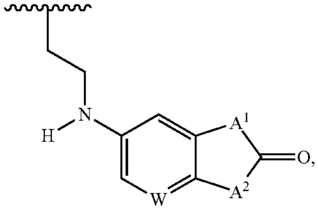
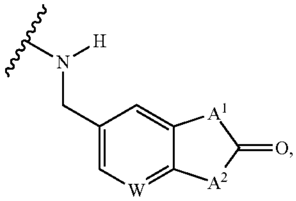

-continued
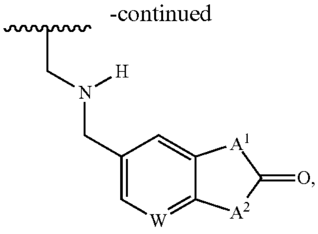
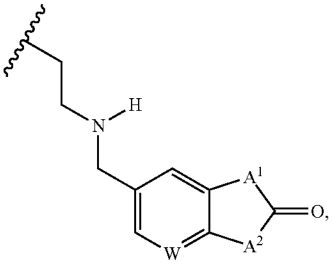
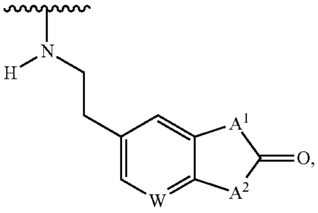
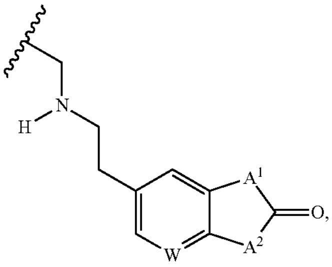
and
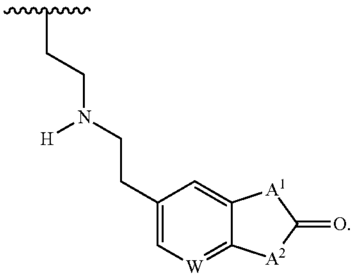
In one embodiment of Formula XIV,
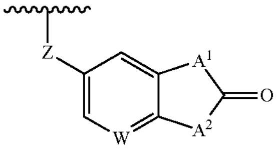
is selected from:
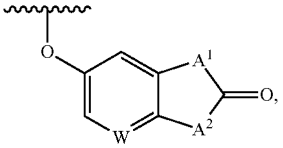
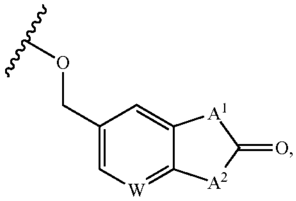
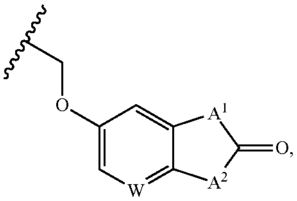
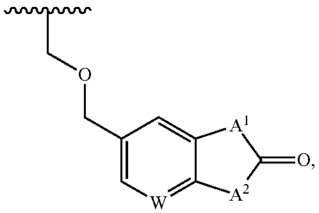
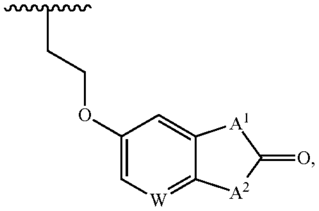
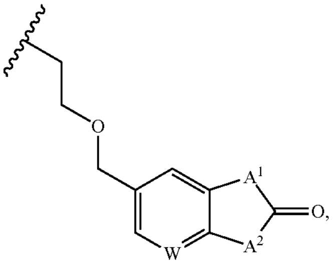
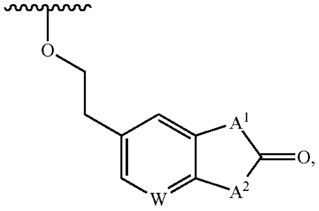

-continued
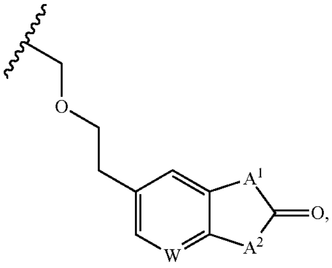
and
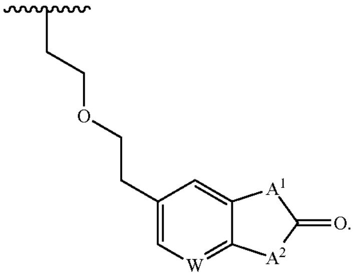
In one embodiment of Formula XIV,
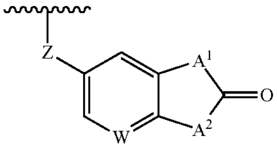
is selected from:
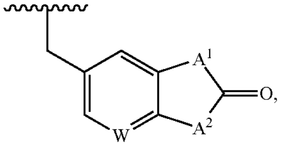
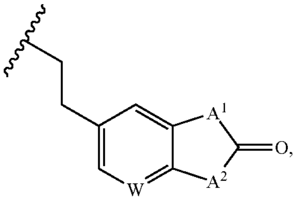
and
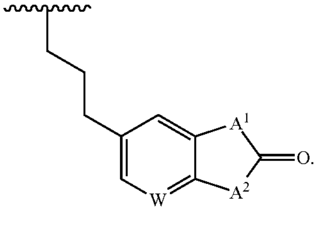
In one embodiment of Formula XIV,
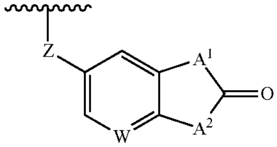
is selected from:
In one embodiment of Formula XIV,
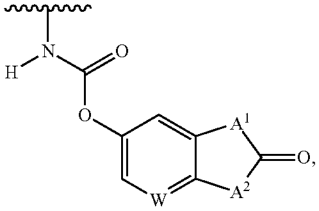
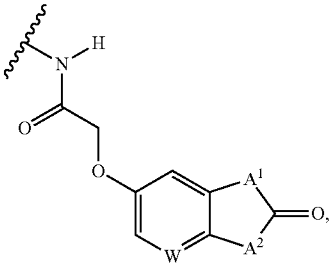
and
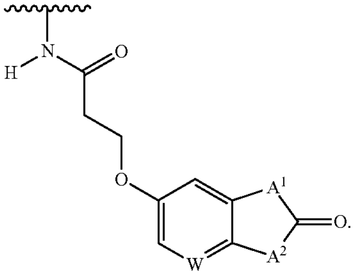
In one embodiment of Formula XIV,
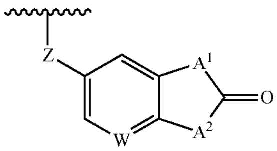
is selected from:
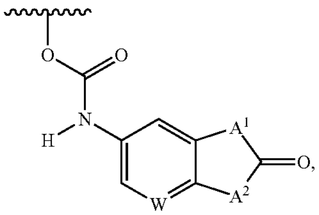

-continued
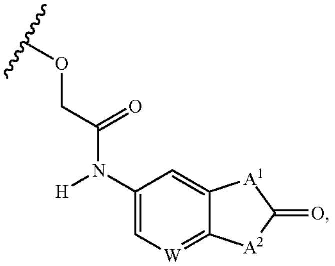
and
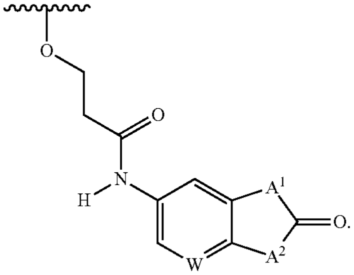
In one embodiment of Formula XIV,
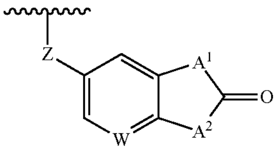
is selected from:
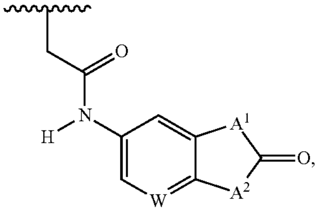
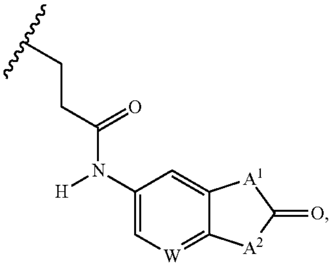
and
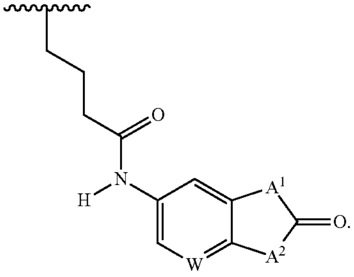
In one embodiment of Formula XIV,
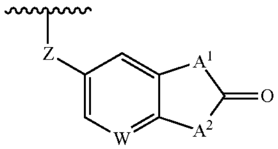
is selected from:
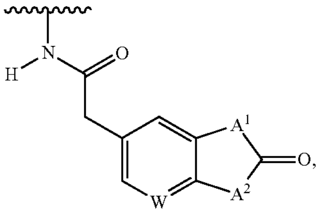
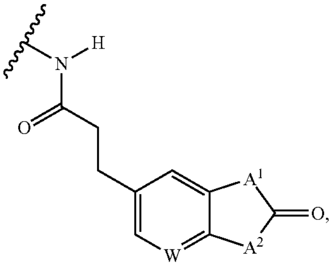
and
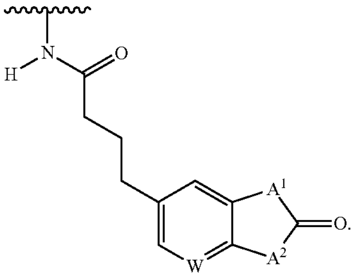
In one embodiment of Formula XIV,
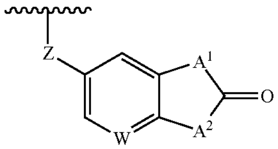
is selected from:
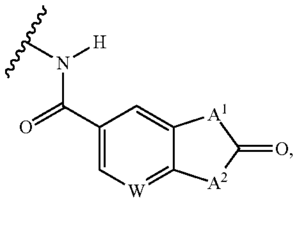

-continued
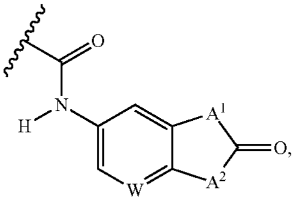
and
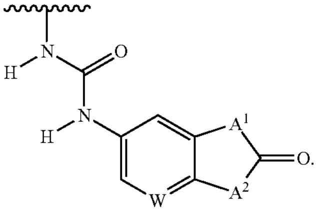
In one embodiment of Formula XIV,
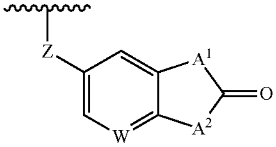
is selected from:
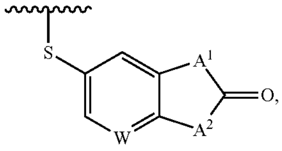
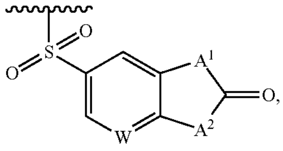
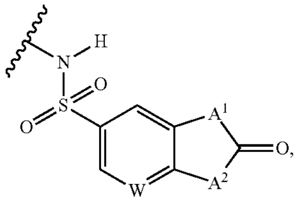
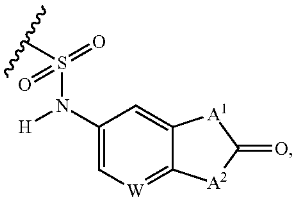
and
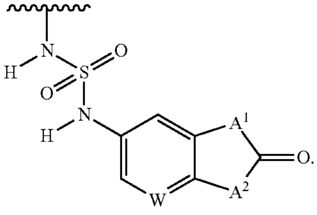
Embodiments of Formula XIV(1)
In one aspect, a compound of Formula XIV(1) selected from:
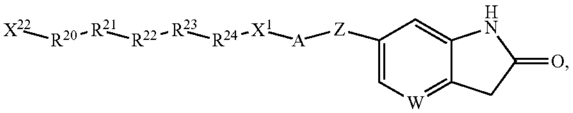
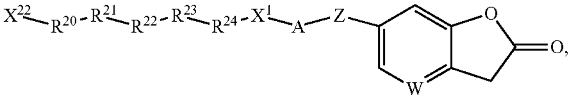
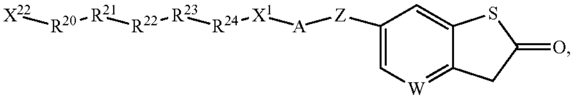
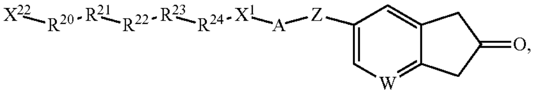
and
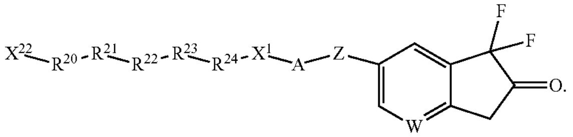
In one aspect, a compound of Formula XIV(1) selected from:
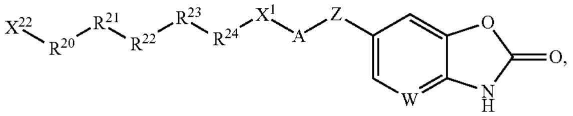
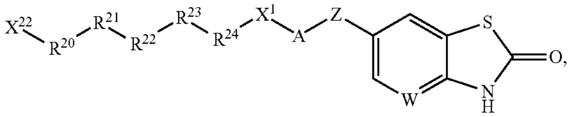
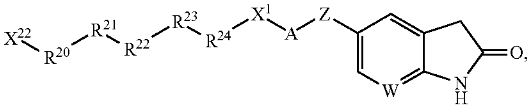
and
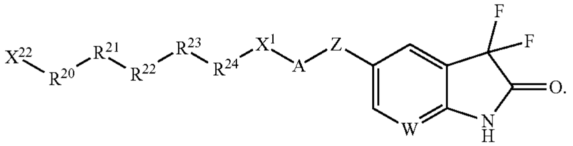
In one aspect, a compound of Formula XIV(1) selected from:
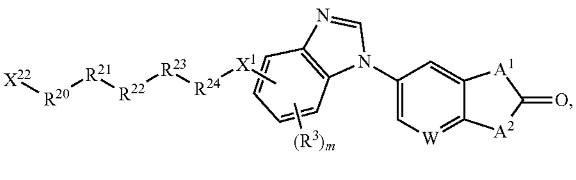

-continued
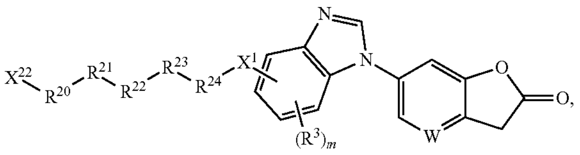
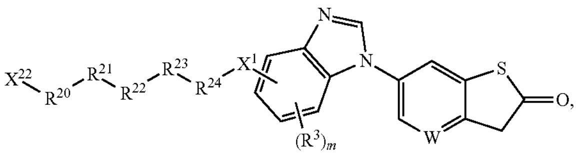
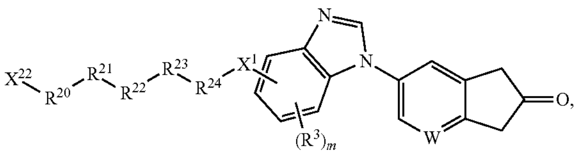
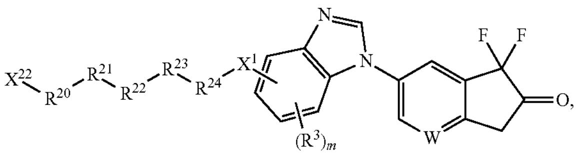
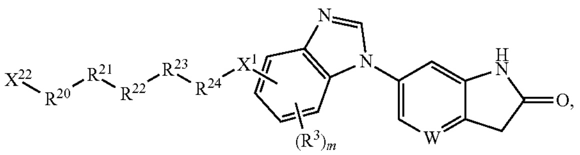
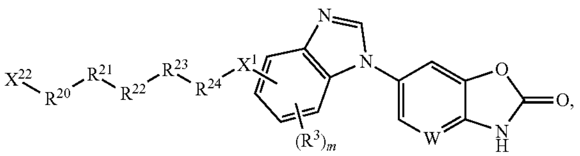
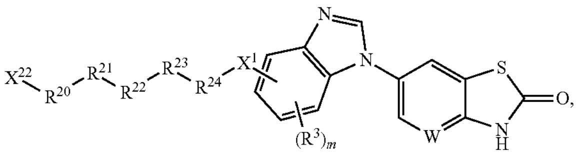
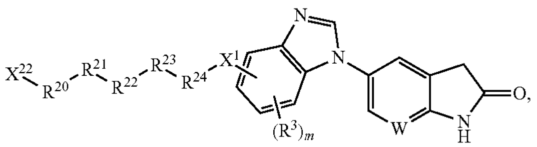
and
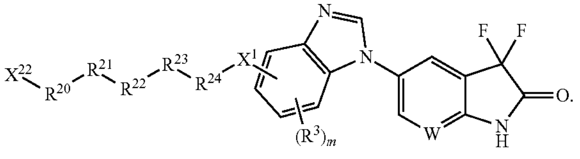
In one aspect, a compound of Formula XIV(1) selected from:
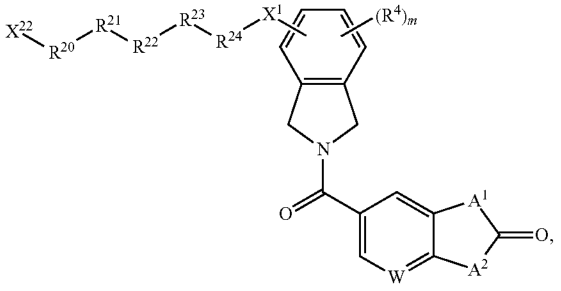
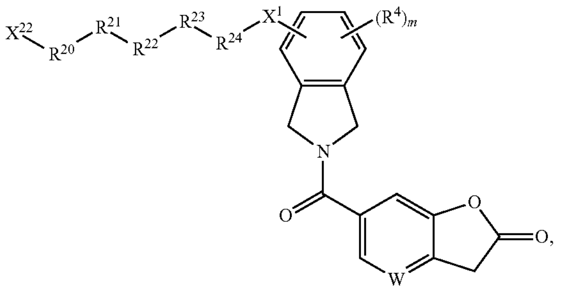
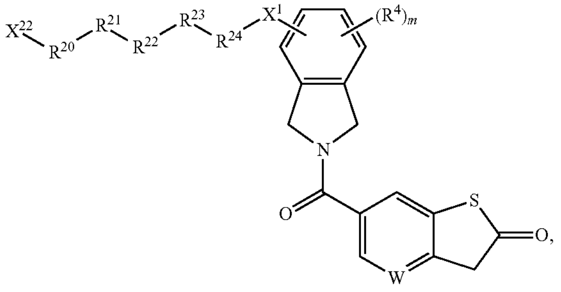
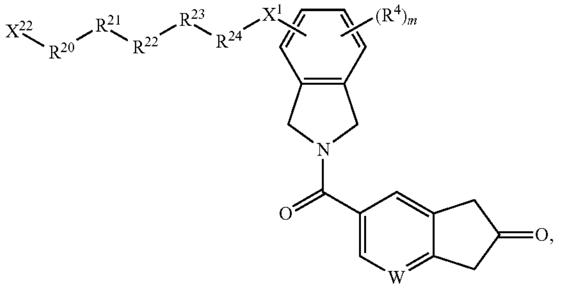
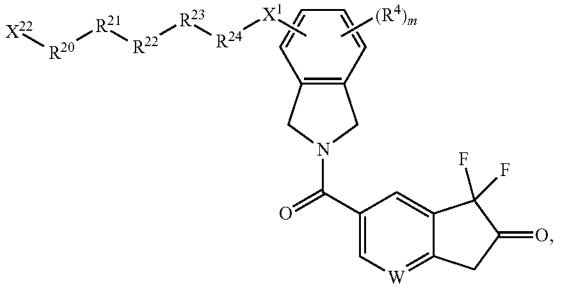

-continued
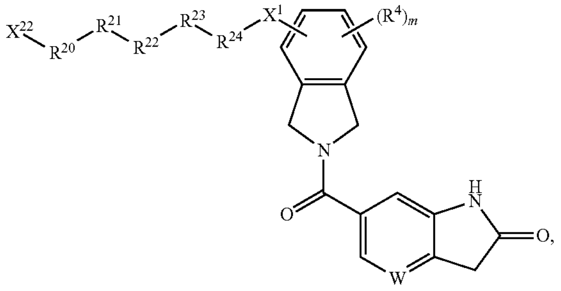
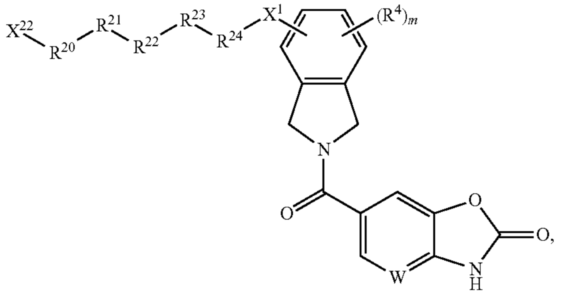
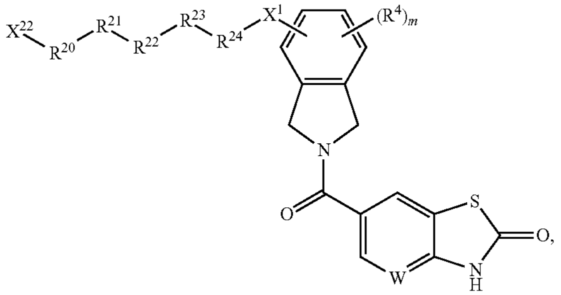
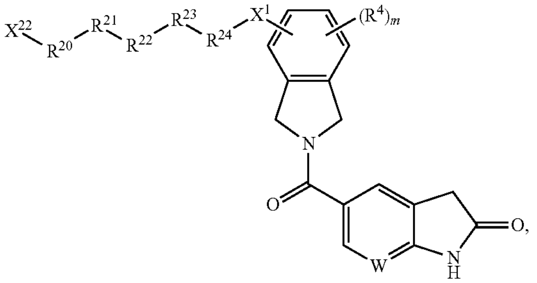
and
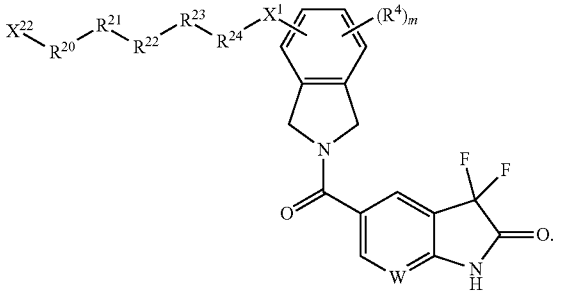
In one aspect, a compound of Formula XIV(1) selected from:
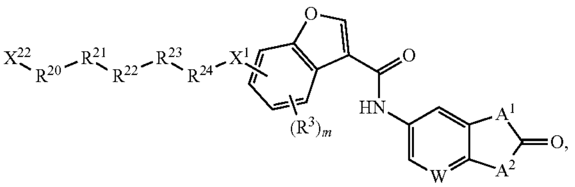
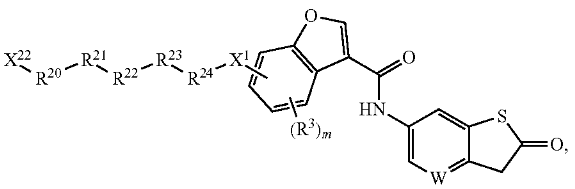
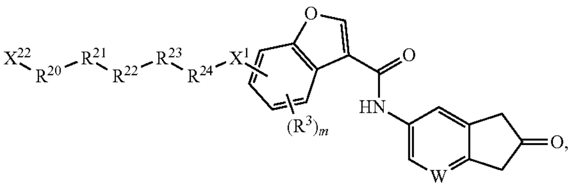
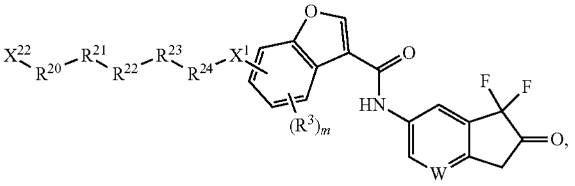
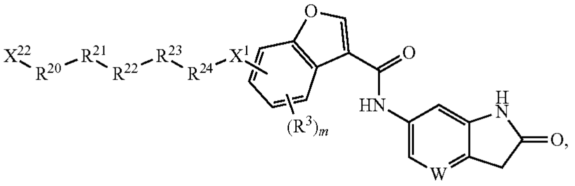
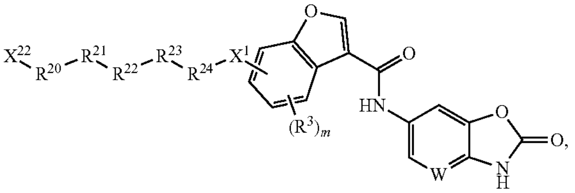
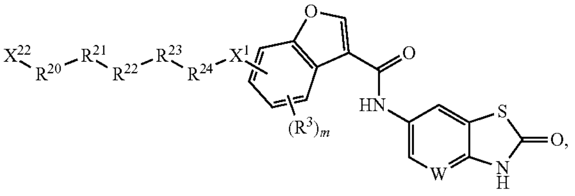
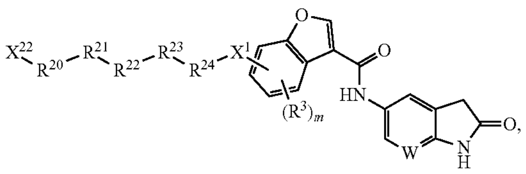
and -continued
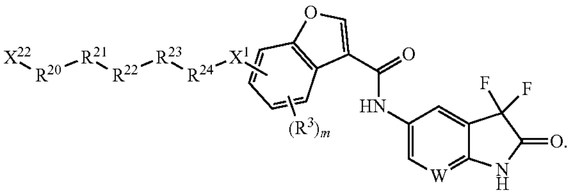
In one aspect, a compound of Formula XIV(1) selected from:
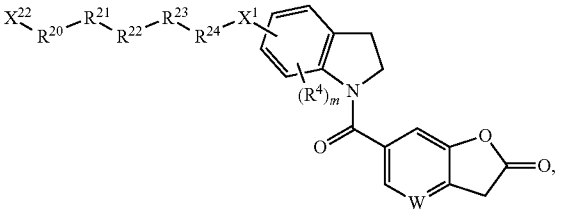
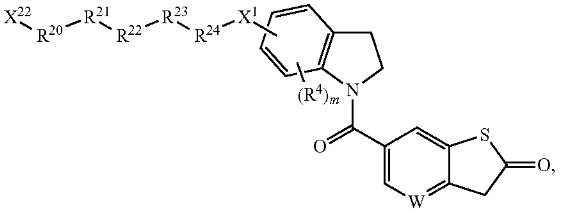
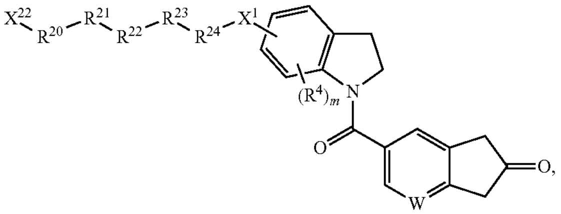
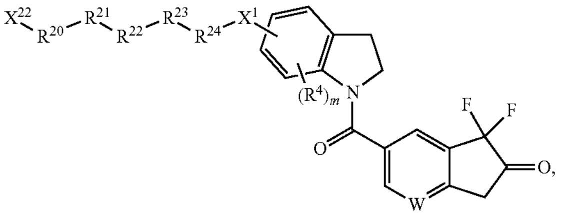
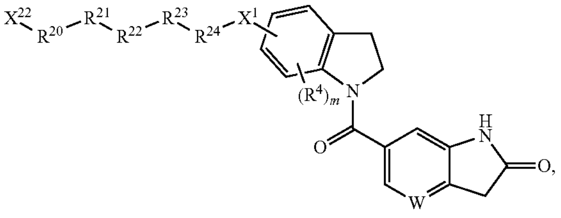
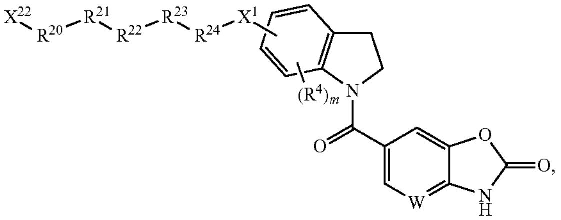
-continued
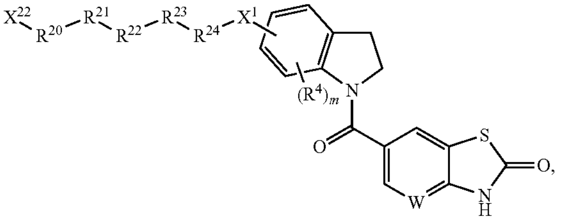
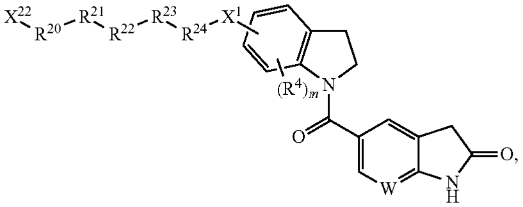
and
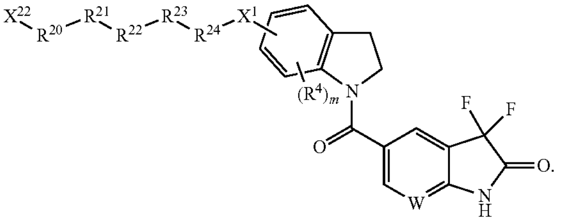
In one aspect, a compound of Formula XIV(1) selected from:
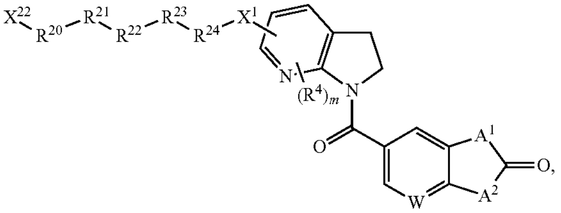
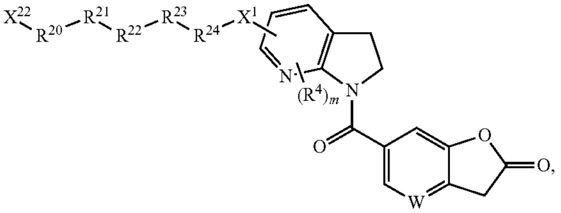
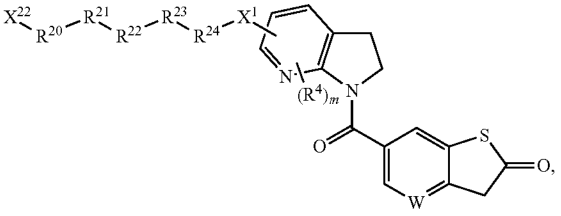
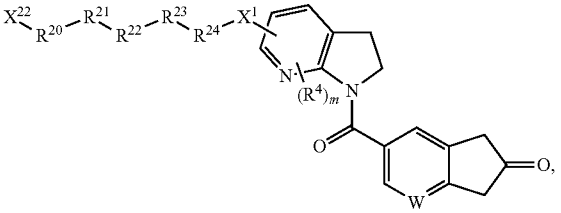

-continued
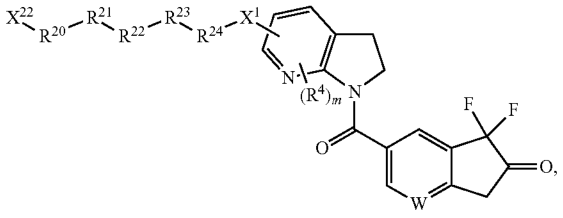
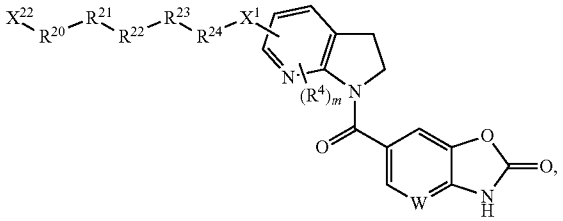
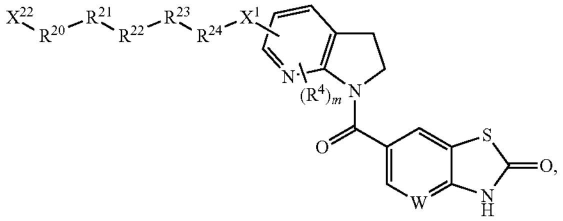
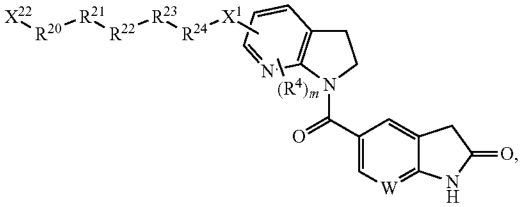
and
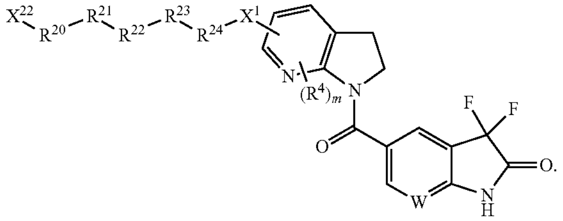
In one aspect, a compound of Formula XIV(1) selected from:
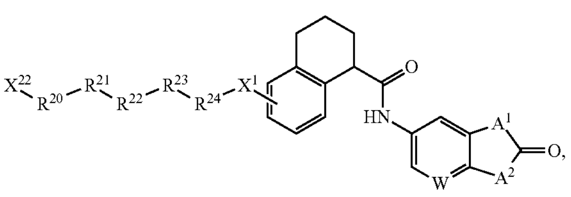
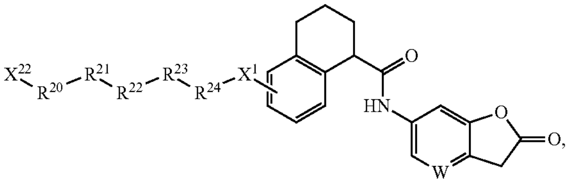
-continued
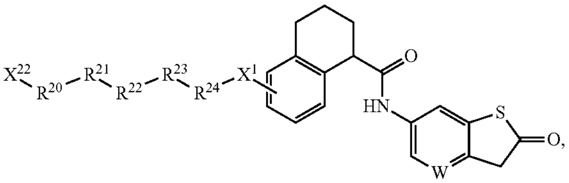
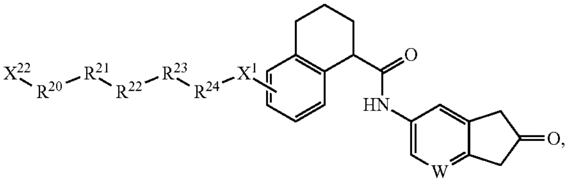
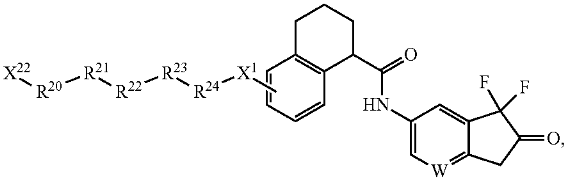
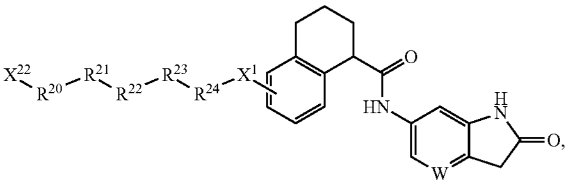
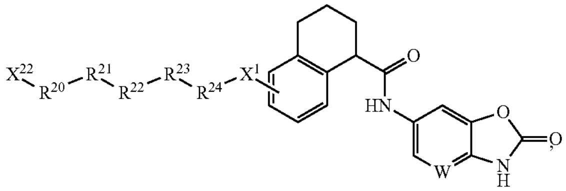
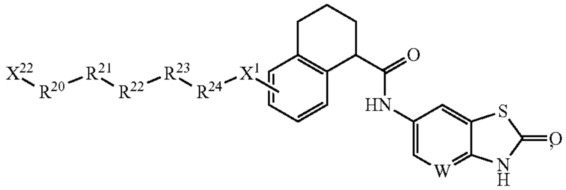
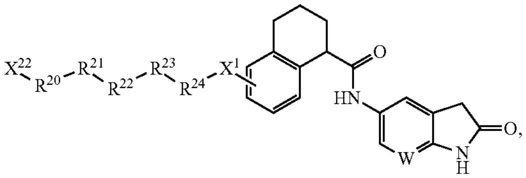
and
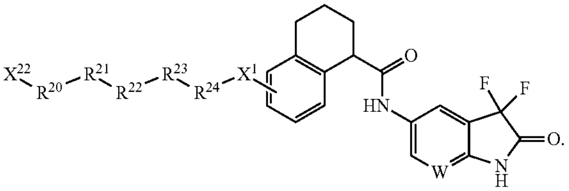

In one aspect, a compound of Formula XIV(1) selected from:
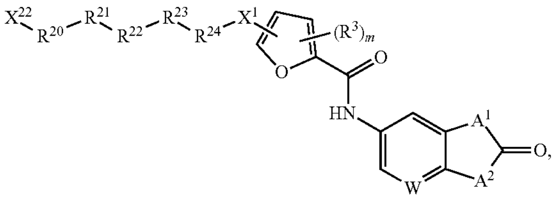
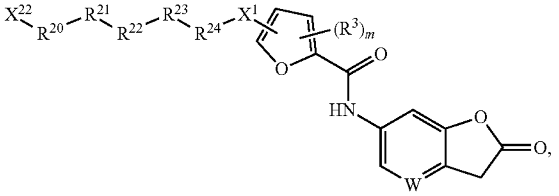
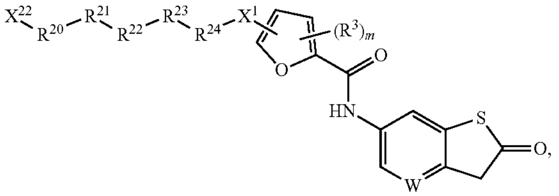
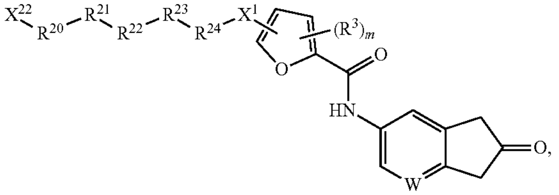
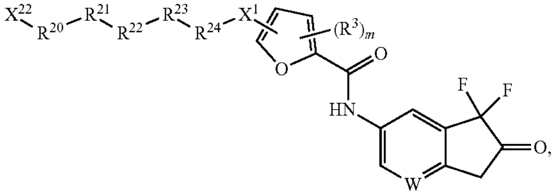
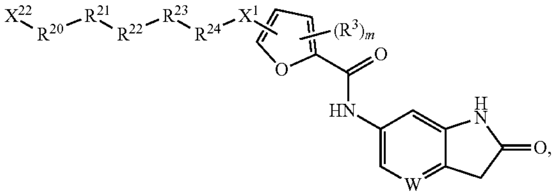
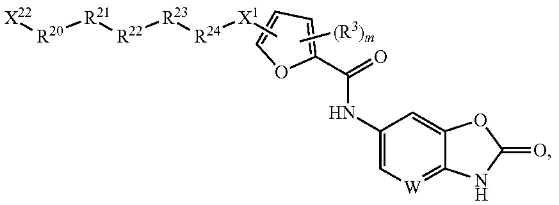
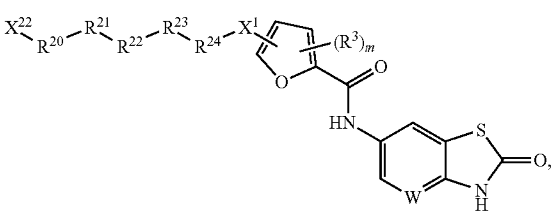
-continued
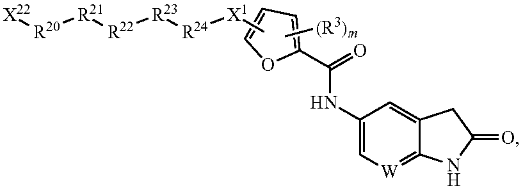
and
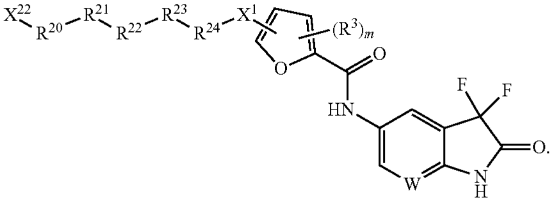
In one aspect, a compound of Formula XIV(1) selected from:
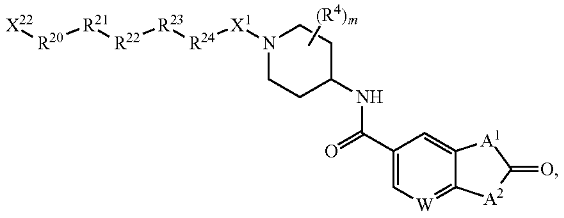
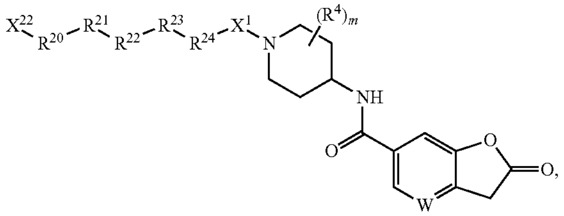
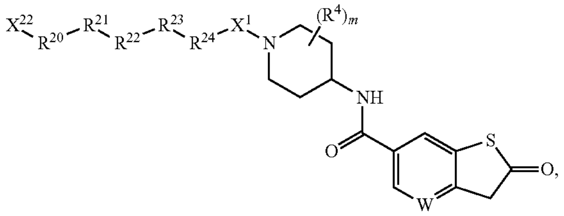
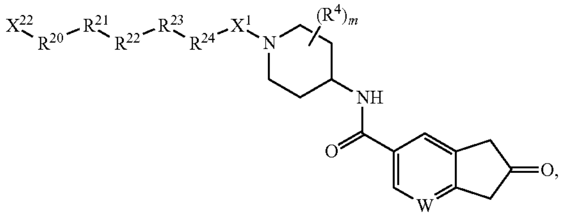
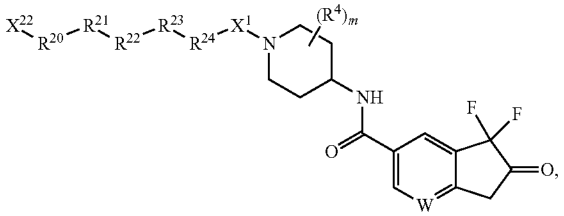

-continued
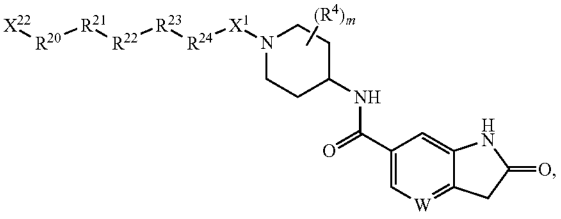
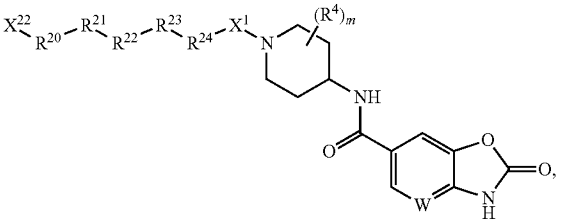
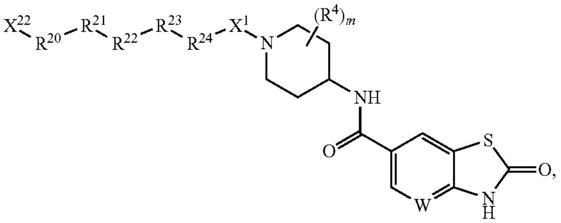
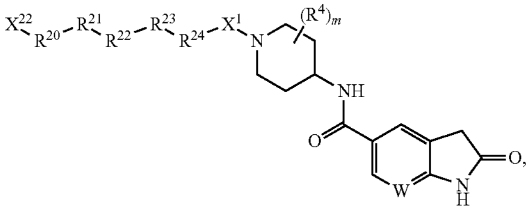
and
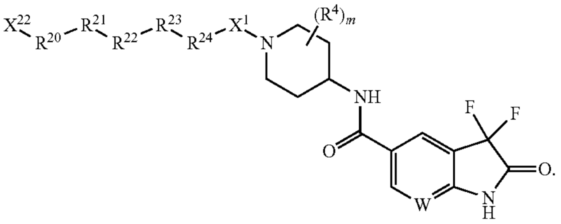
In one aspect, a compound of Formula XIV(1) selected from:
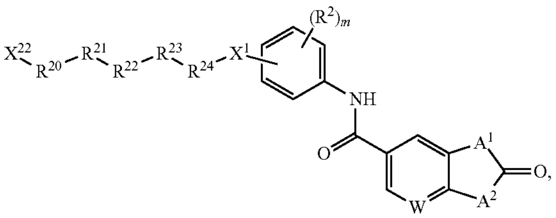
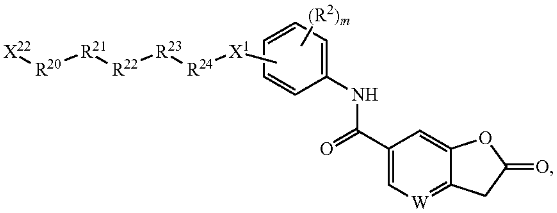
-continued
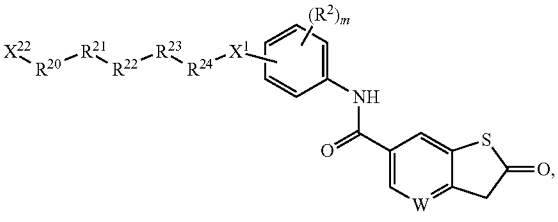
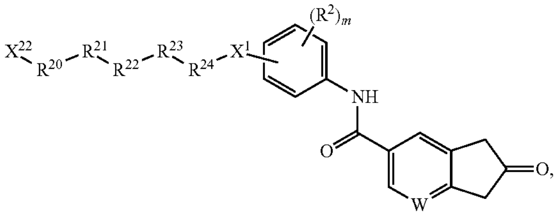
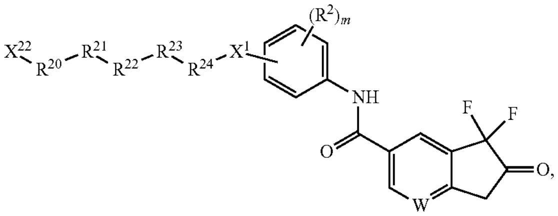
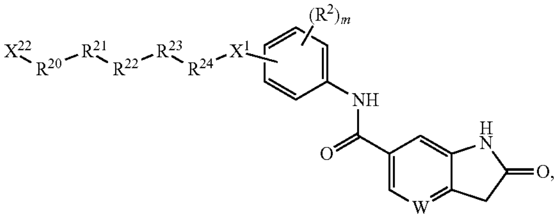
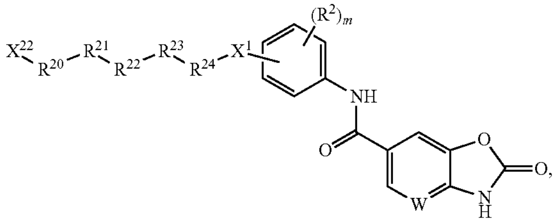
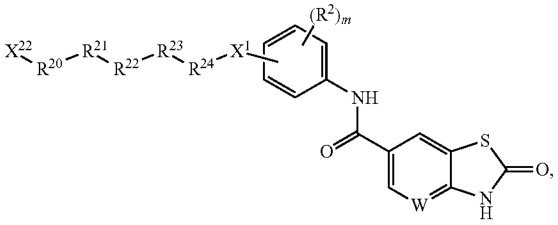
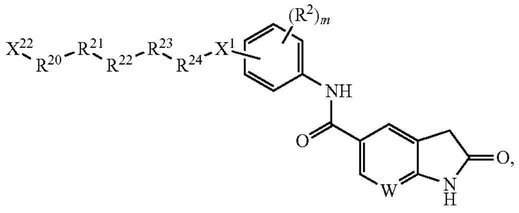
and -continued
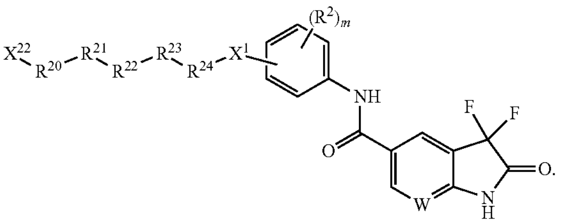
In one aspect, a compound of Formula XIV(1) selected from:
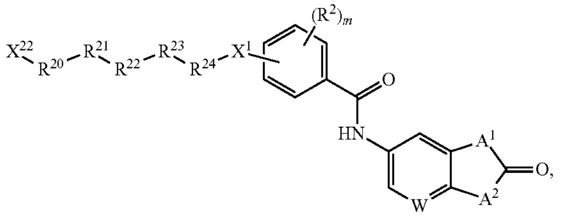
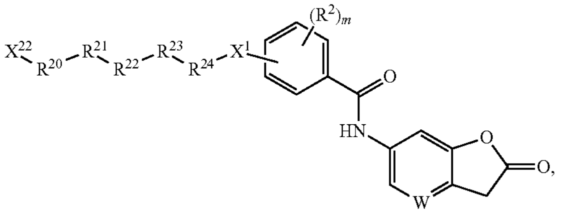
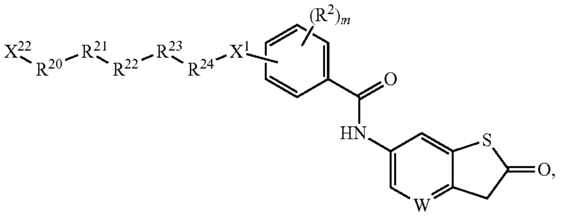
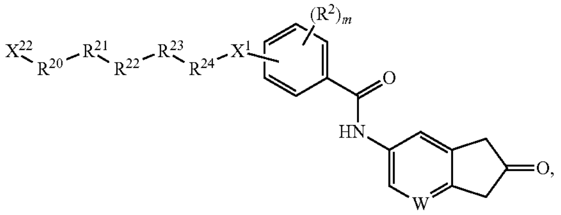
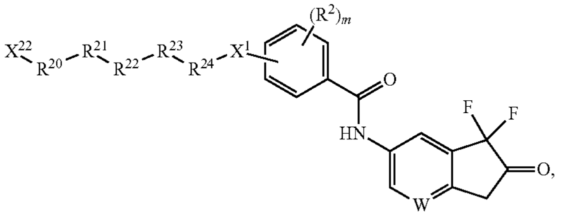
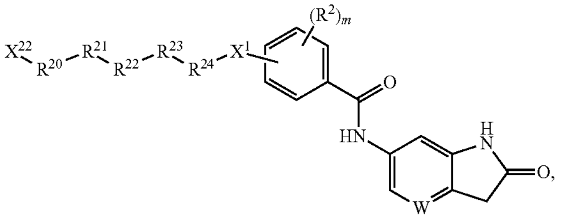
-continued
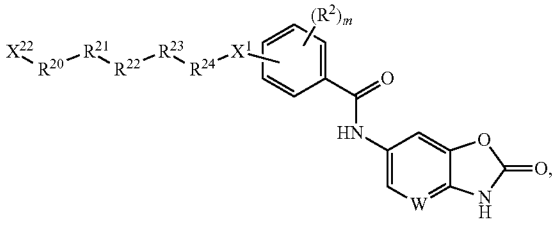
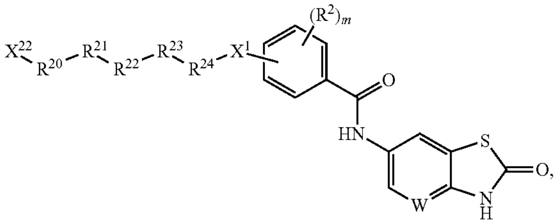
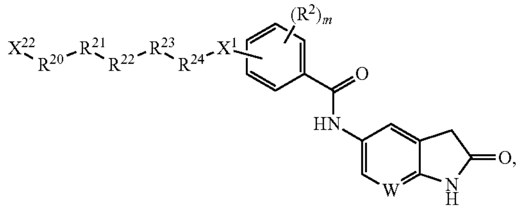
and
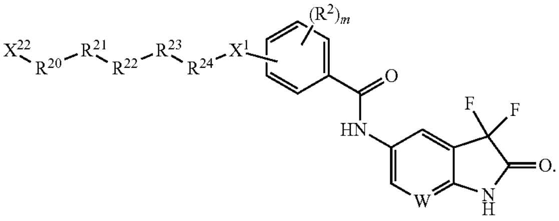
In one aspect, a compound of Formula XIV(1) selected from:
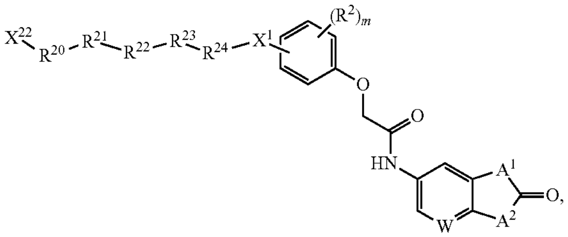
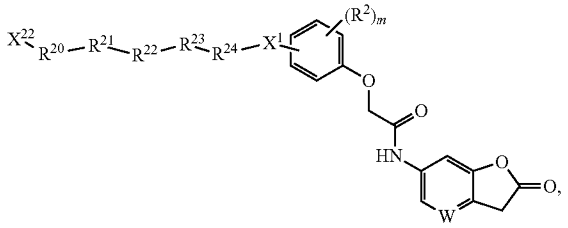
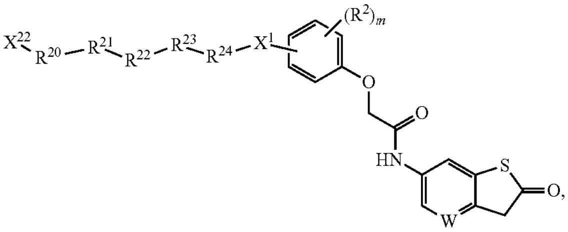

-continued
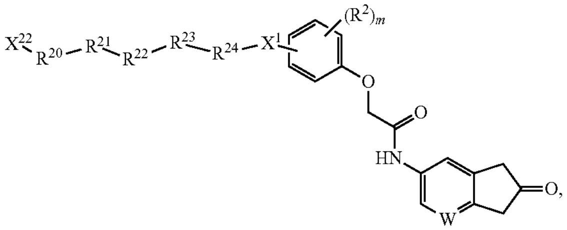
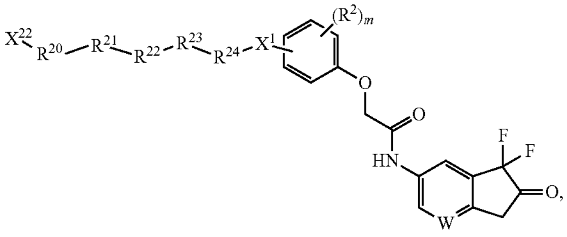
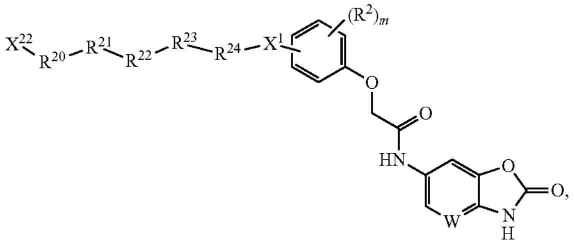
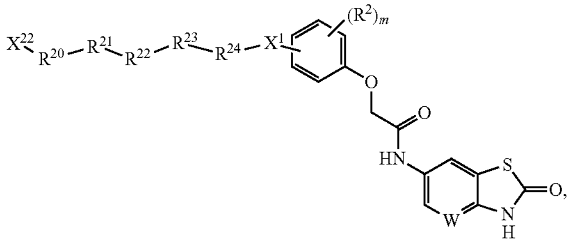
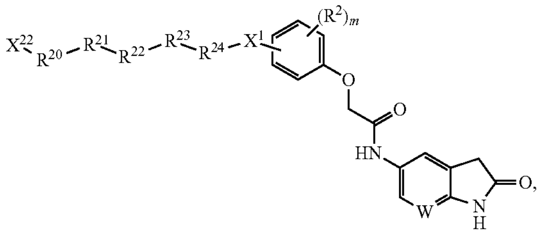
and
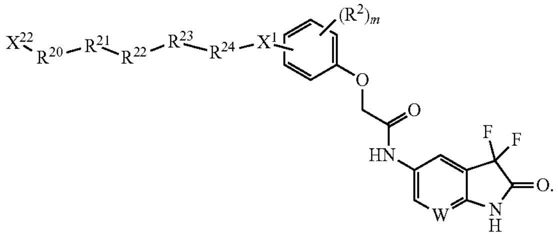
In one aspect, a compound of Formula XIV(1) selected from:
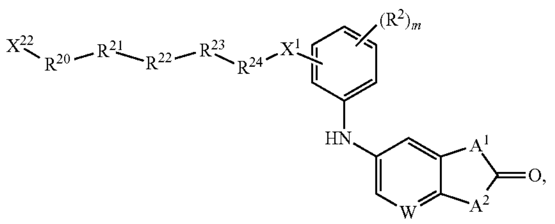
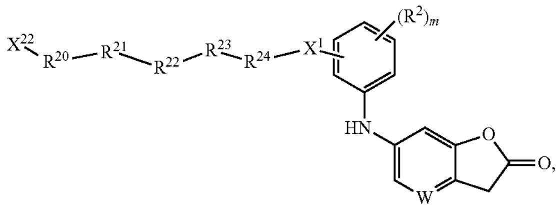
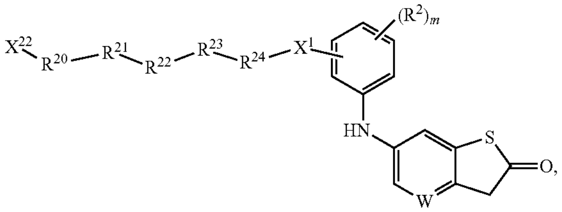
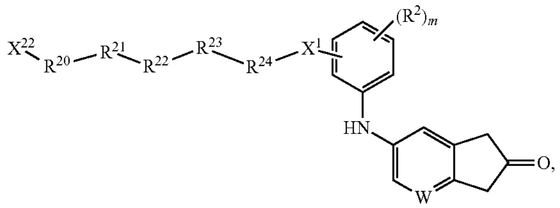
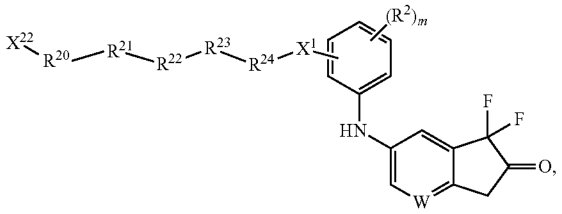
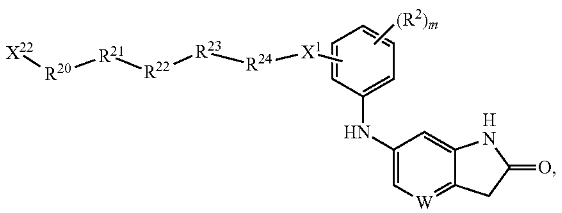
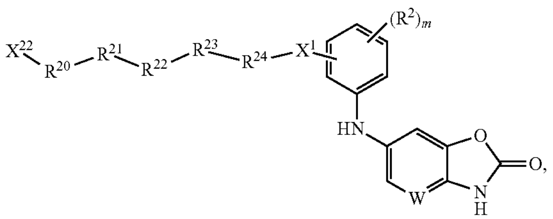

-continued
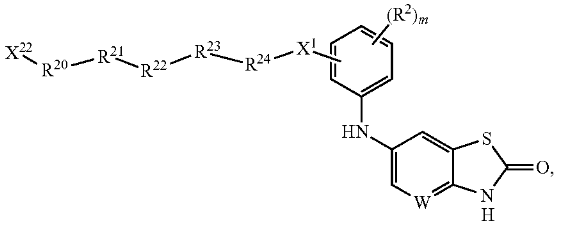
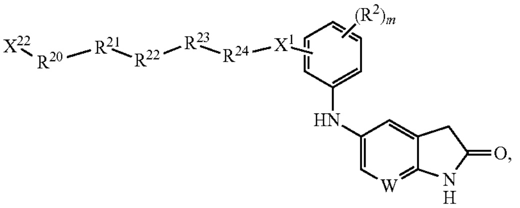
and
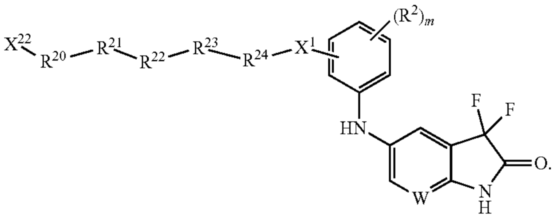
Embodiments of Formulas I(1)-XIII(1)
In one aspect, a compound is provided of Formula I(1)
[I(1)]
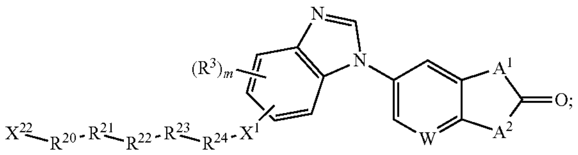
wherein all variables are as defined herein.
In one embodiment of Formula I(1),
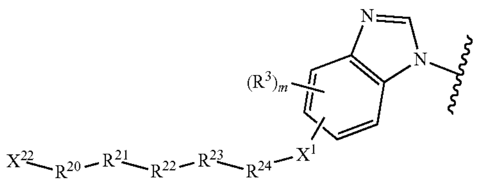
is selected from:
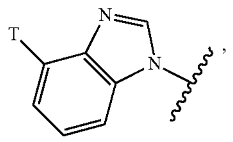
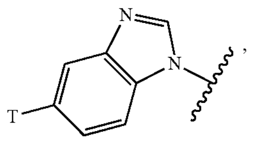
-continued
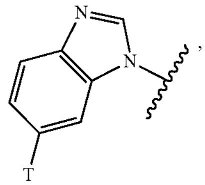
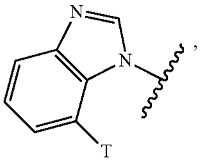
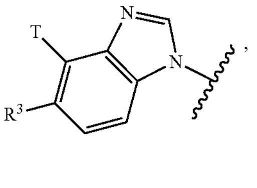
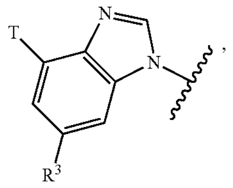
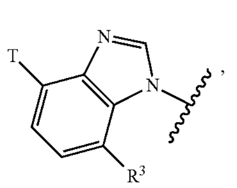
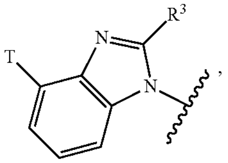
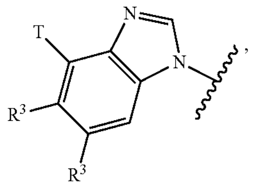
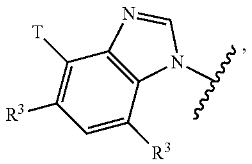
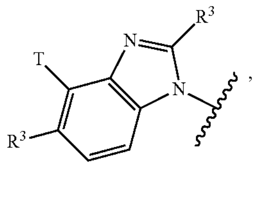
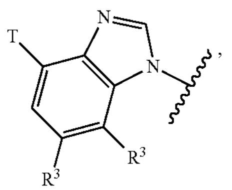
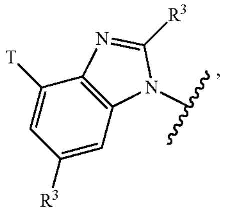
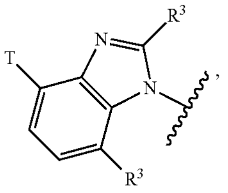
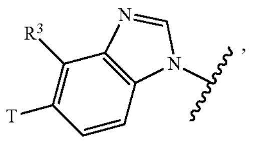
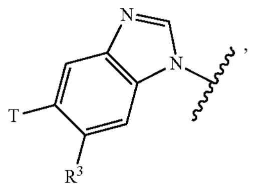
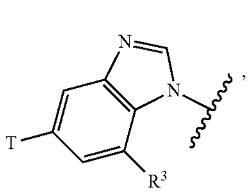
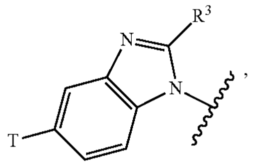
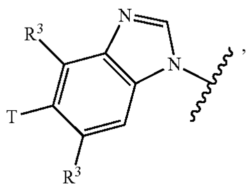
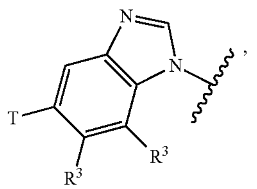

-continued
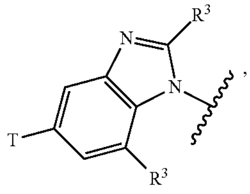 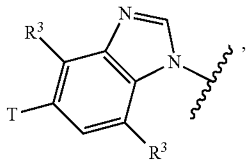
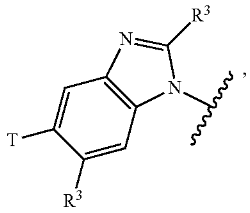 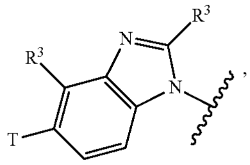
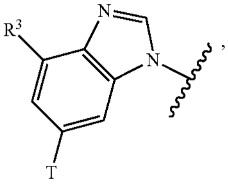 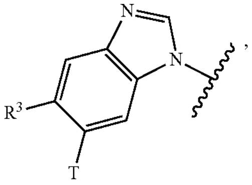
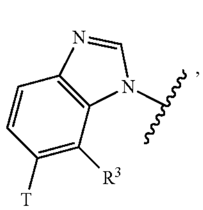 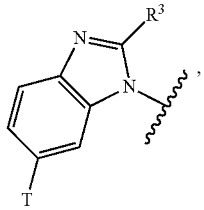
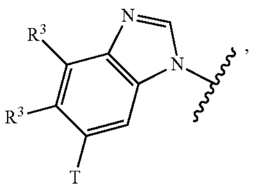 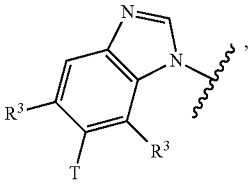
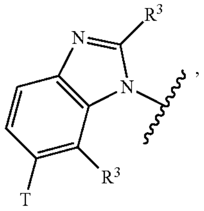 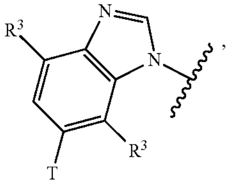
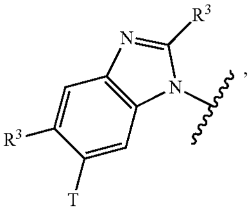 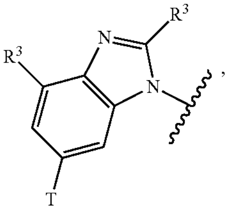
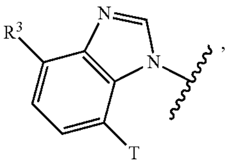 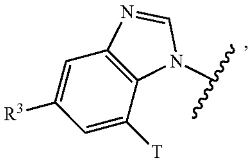
-continued
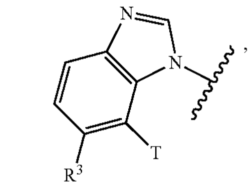 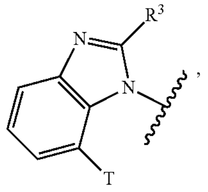
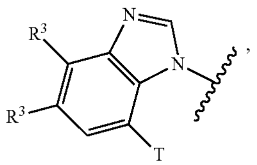 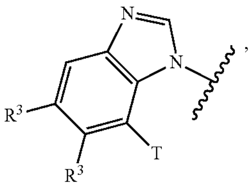
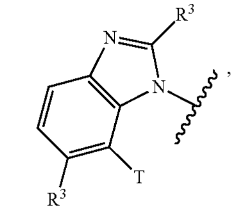 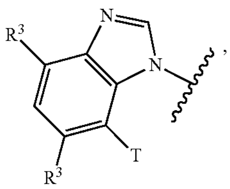
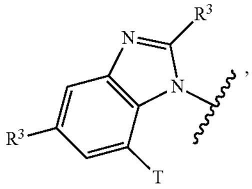 and 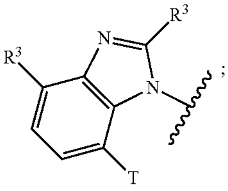
wherein T is
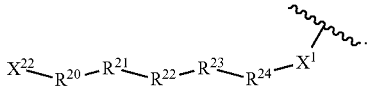
In one aspect, a compound is provided of one of the following formulas:
[II(1)-a]
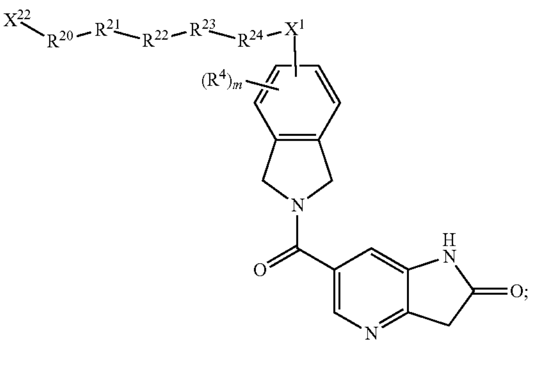

-continued
[II(1)-b]
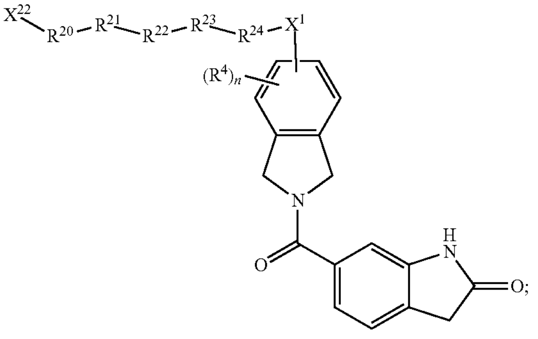
[II(1)-c]
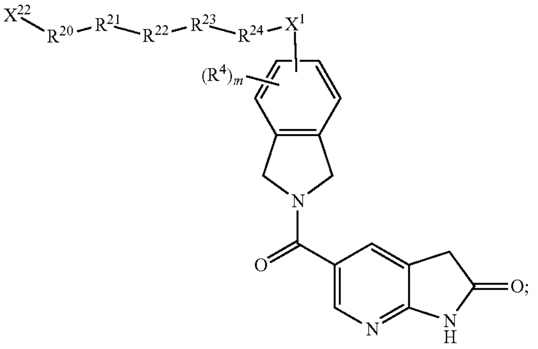
[II(1)-d]
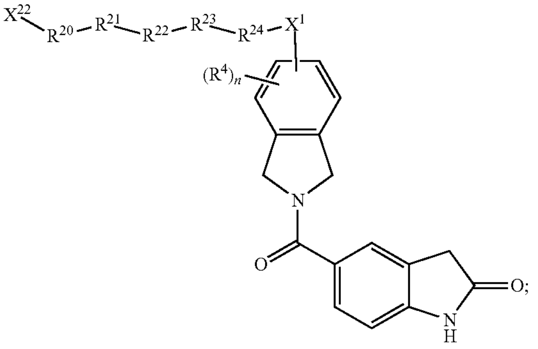
[II(1)-e]
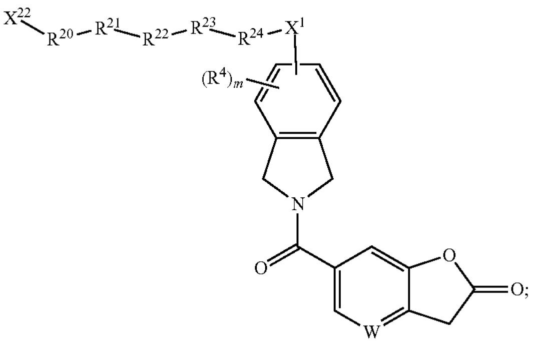
-continued
[II(1)-f]
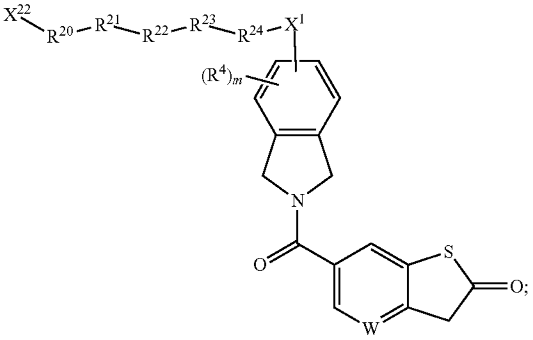
[II(1)-g]
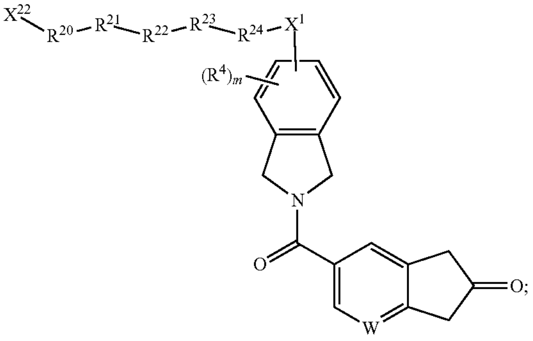
[II(1)-h]
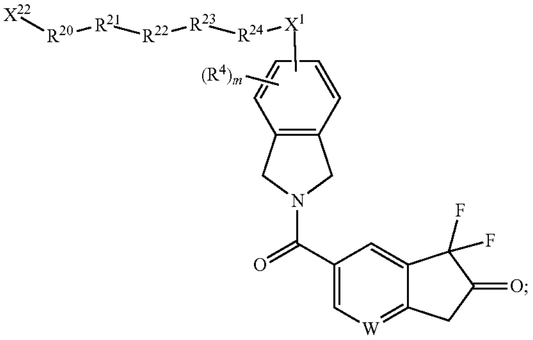
[II(1)-i]
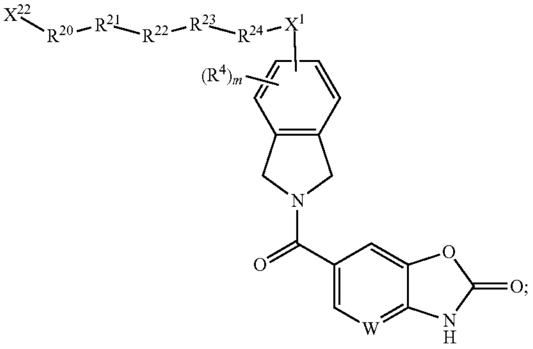

-continued
[II(1)-j]
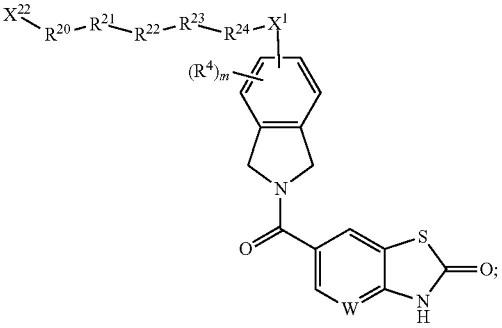
and
[II(1)-k]
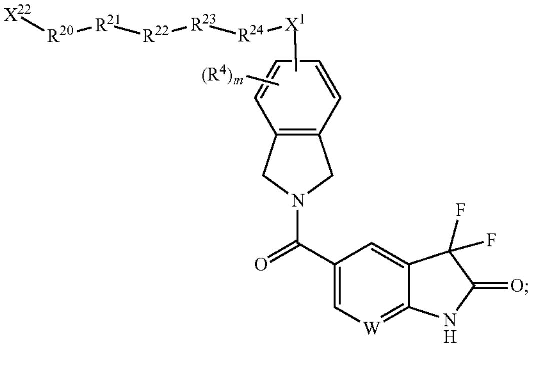
wherein all variables are as defined herein.
In any one embodiment of Formula II(1)a-II(1)-k,
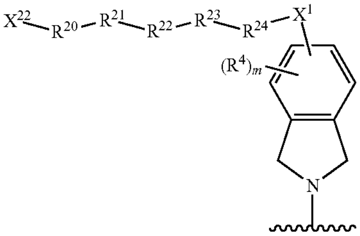
is selected from:
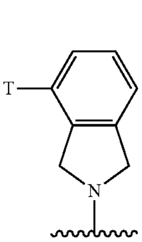,
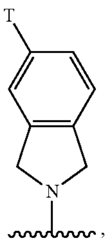,
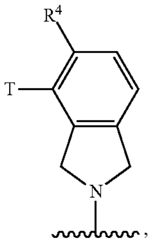,
-continued
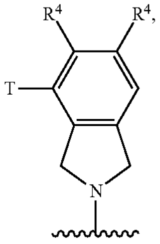
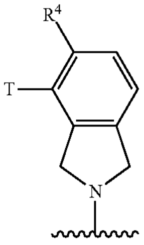
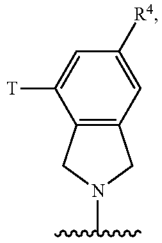
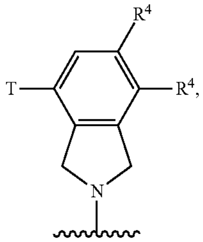
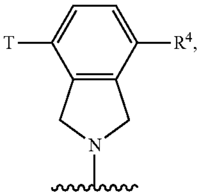
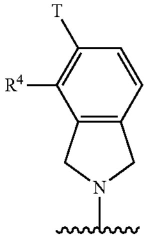,
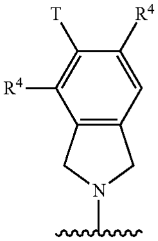,
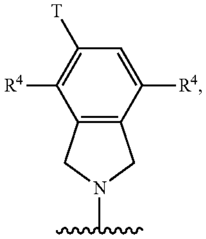
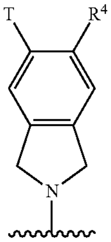,
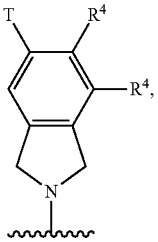
and
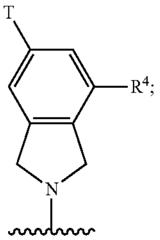
wherein T is
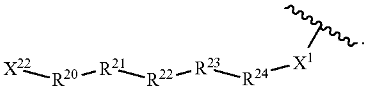.

In one aspect, a compound is provided of Formula III(1):
[III(1)]
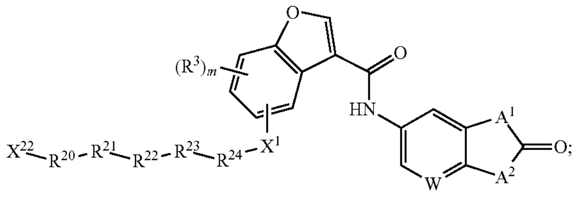
wherein all variables are as defined herein.
In one embodiment of Formula III(1),
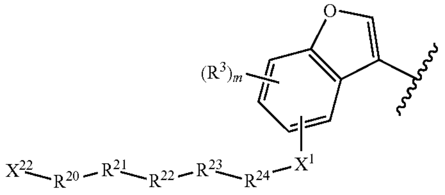
is selected from:
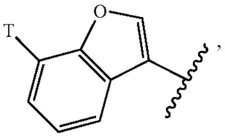,
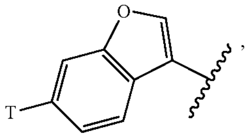,
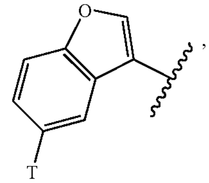,
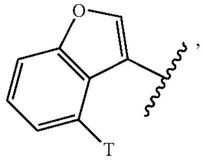,
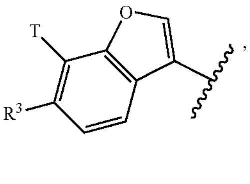,
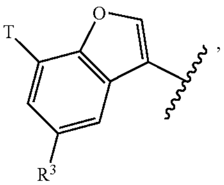,
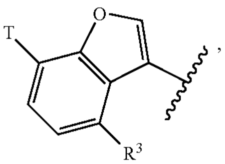,
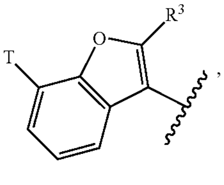,
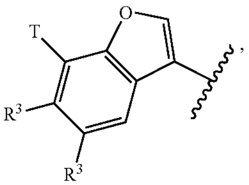,
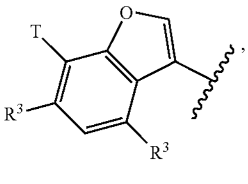,
-continued
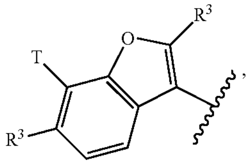,
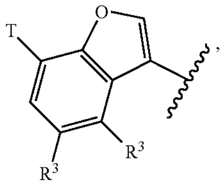,
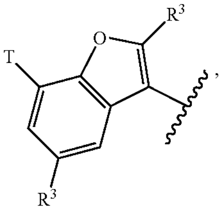,
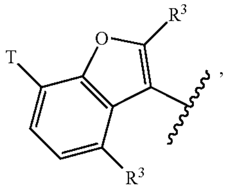,
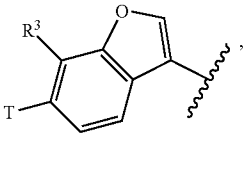,
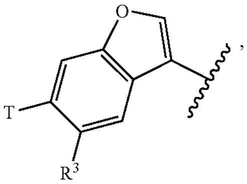,
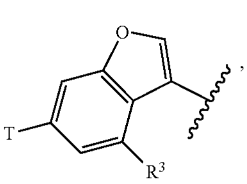,
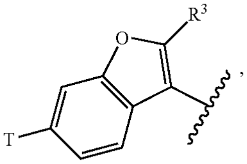,
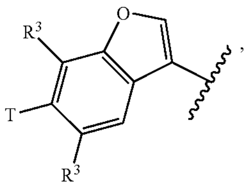,
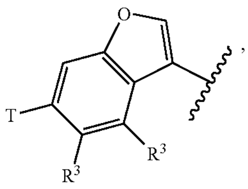,
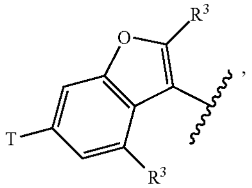,
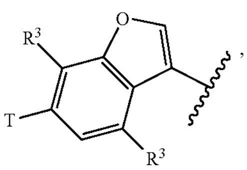,
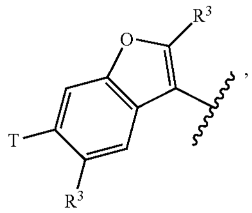,
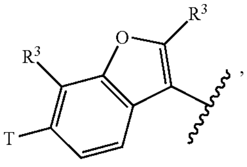,
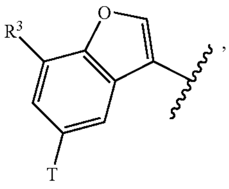,
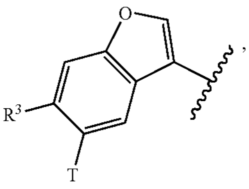, -continued
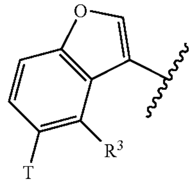,
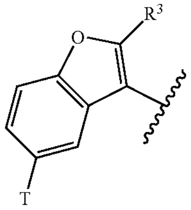,
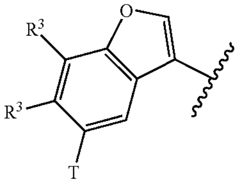,
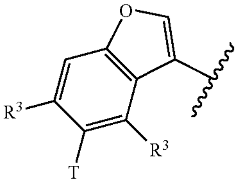,
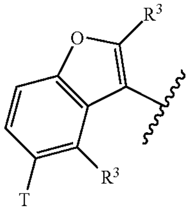,
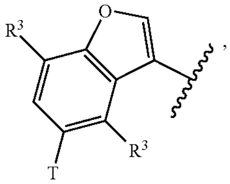,
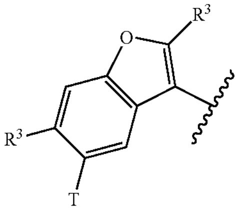,
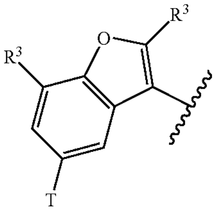,
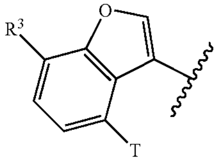,
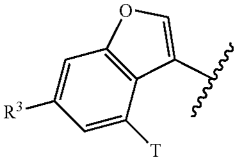,
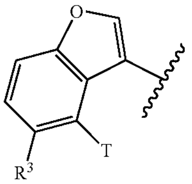,
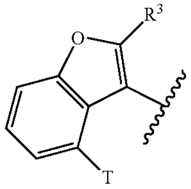,
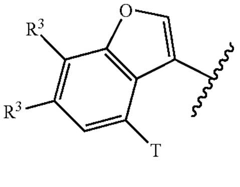,
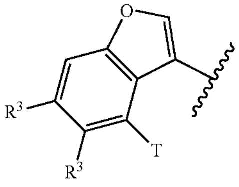,
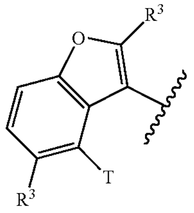,
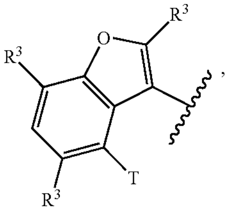,
-continued
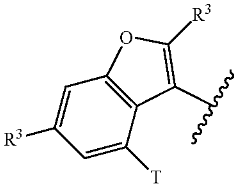, and
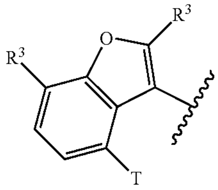;
wherein T is
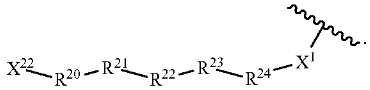
In one aspect, a compound is provided of one of the following formulas:
[IV(1)-a]
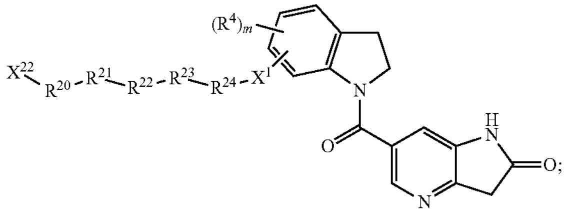
[IV(1)-b]
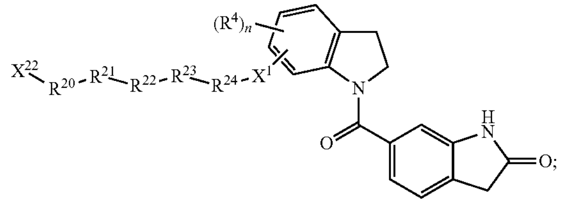
[IV(1)-c]
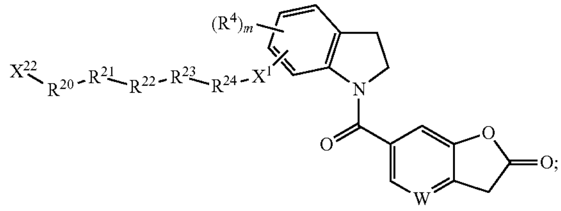
[IV(1)-d]
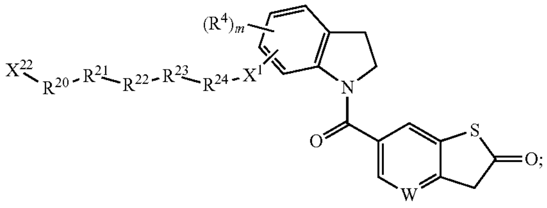

-continued
[IV(1)-e]
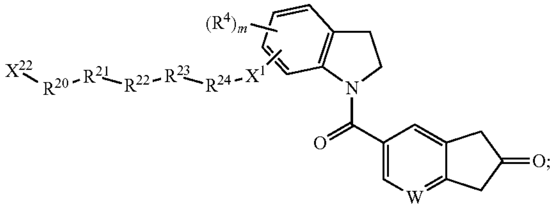
[IV(1)-f]
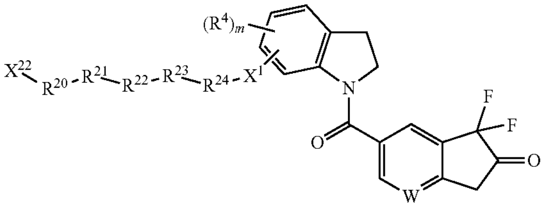
[IV(1)-g]
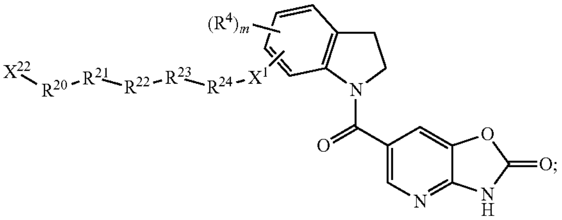
[IV(1)-h]
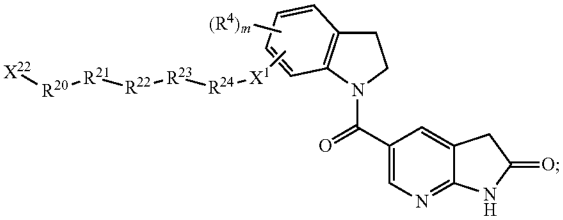
[IV(1)-i]
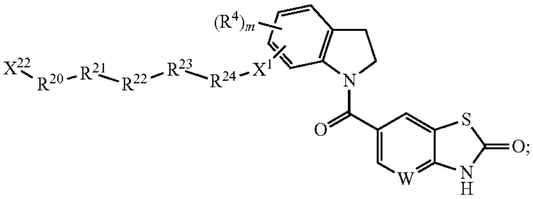
and
[IV(1)-j]
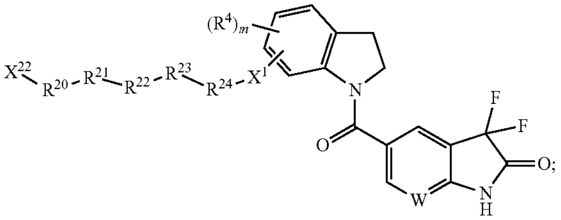
wherein all variables are as defined herein.
In one embodiment of any one of Formulas IV(1)-a to IV(1)-J,
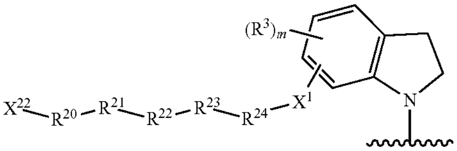
is selected from:
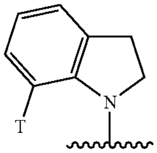 , 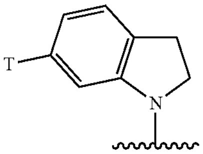 ,
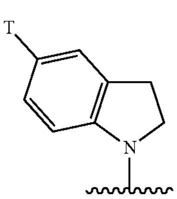 , 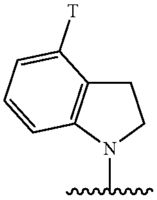 ,
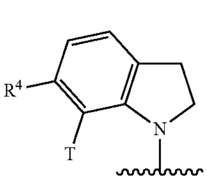 , 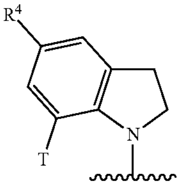 ,
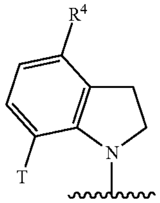 , 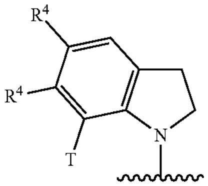 ,
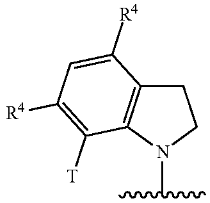 , 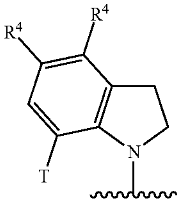 ,
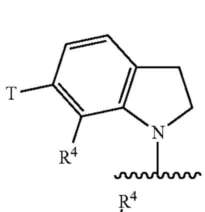 , 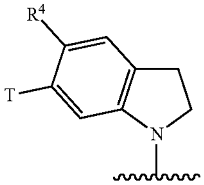 ,
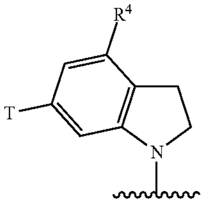 , 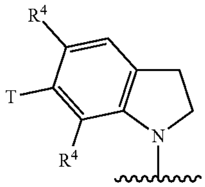 , -continued
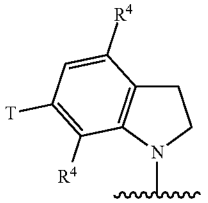,
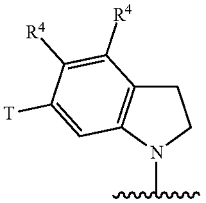,
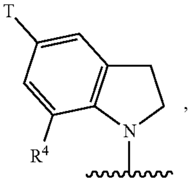,
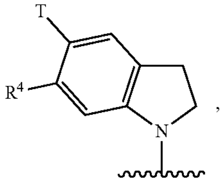,
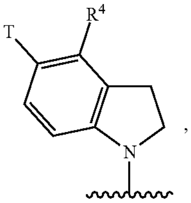,
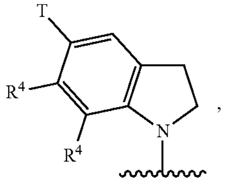,
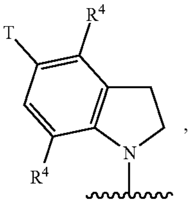,
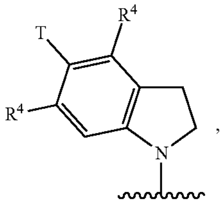,
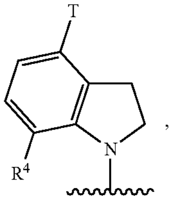,
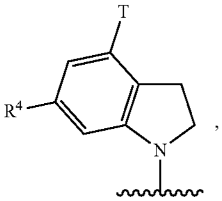,
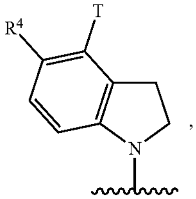,
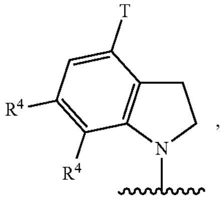,
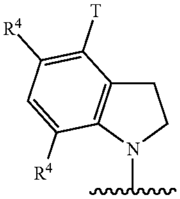, and
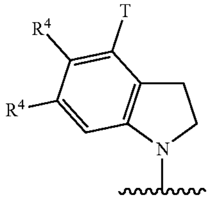;
wherein T is
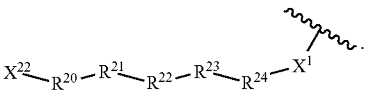.
In one aspect, a compound is provided of Formula V(1):
[V(1)]
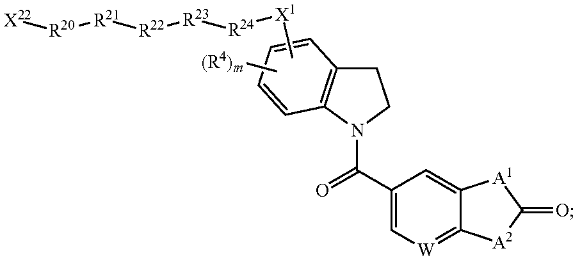
wherein all variables are as defined herein.
In one embodiment of Formula V(1),
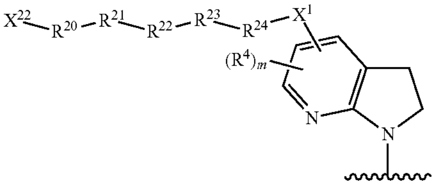
is selected from:
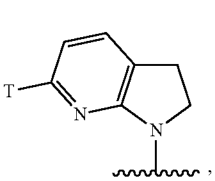,
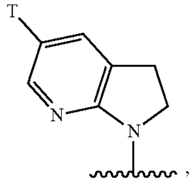,
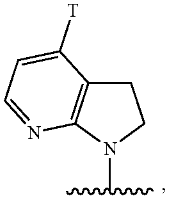,
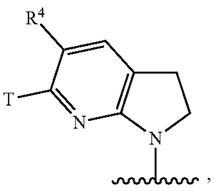,
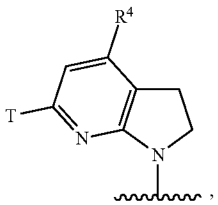,
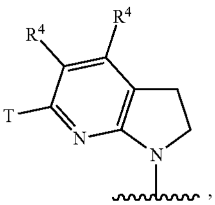,
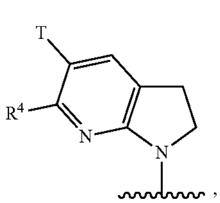,
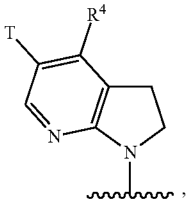, -continued
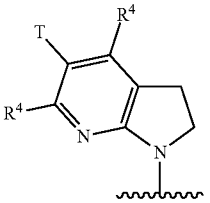
,
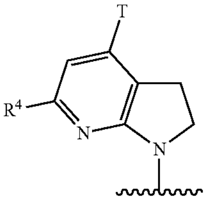
,
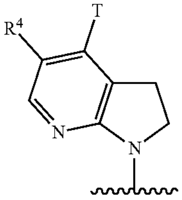
, and
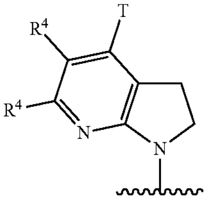
;
wherein T is
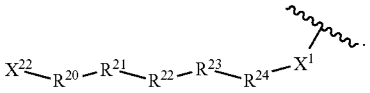
In one aspect, a compound is provided of Formula VI(1):
[VI(1)]
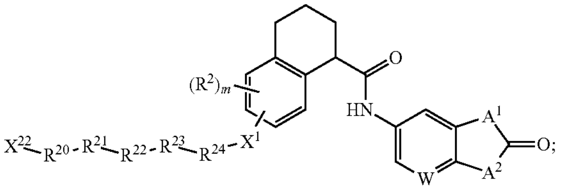
wherein all variables are as defined herein.
In one embodiment of Formula VI(1),
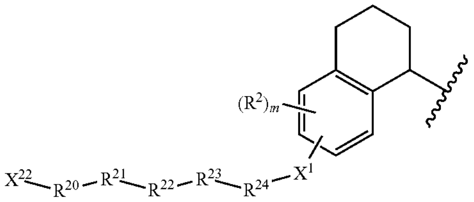
is selected from:
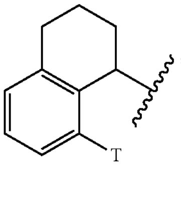
,
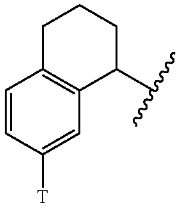
,
-continued
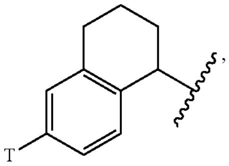
,
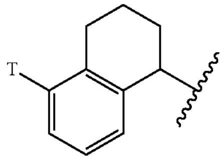
,
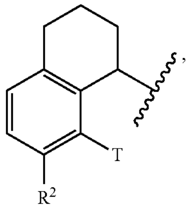
,
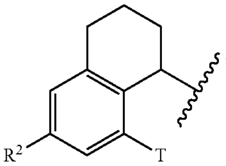
,
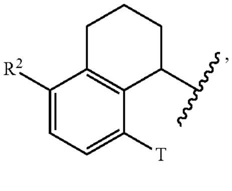
,
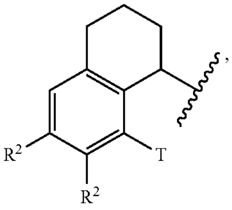
,
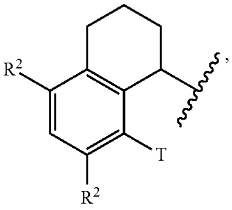
,
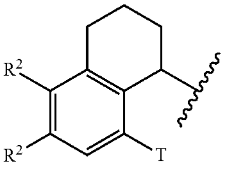
,
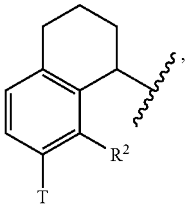
,
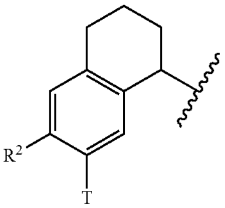
,
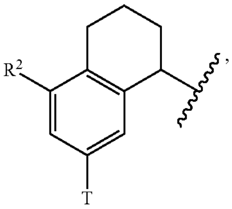
,
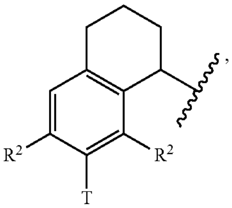
,
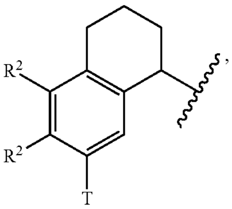
,
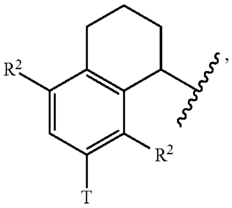
,
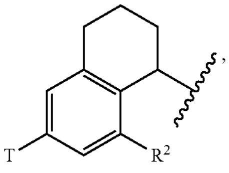
,
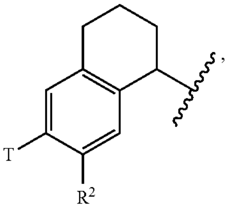
, -continued
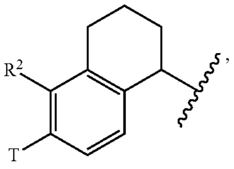
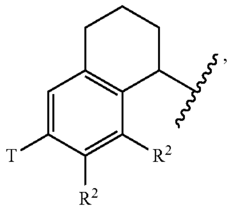
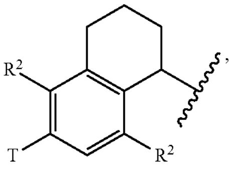
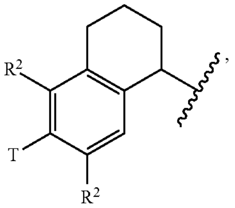
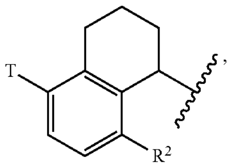
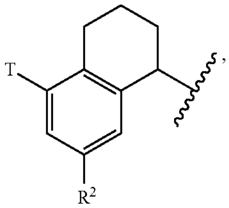
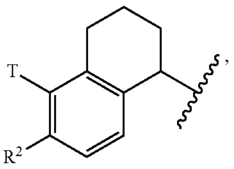
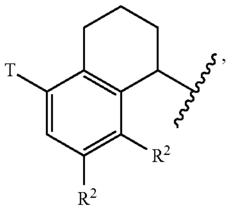
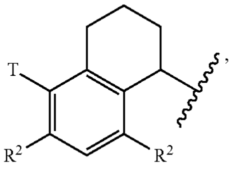
, and
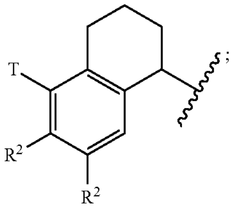
wherein T is
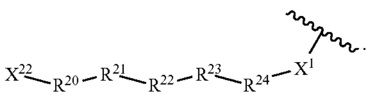
In one aspect, a compound is provided of one of the following formulas:
[VII(1)-a]
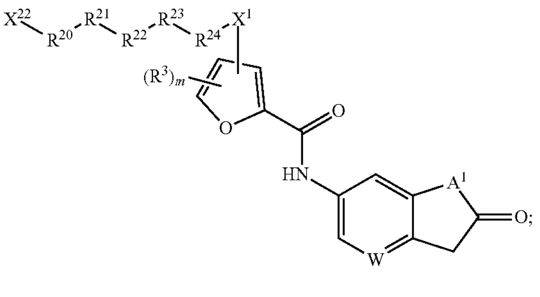
-continued
[VII(1)-b]
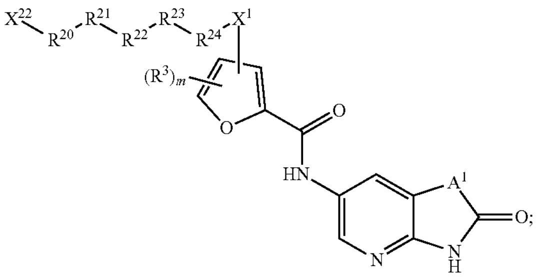
[VII(1)-c]
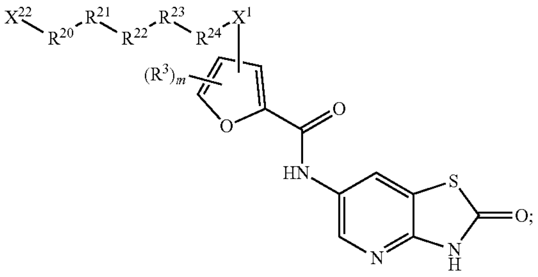
[VII(1)-d]
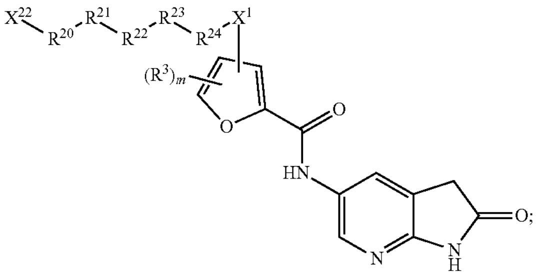
and
[VII(1)-e]
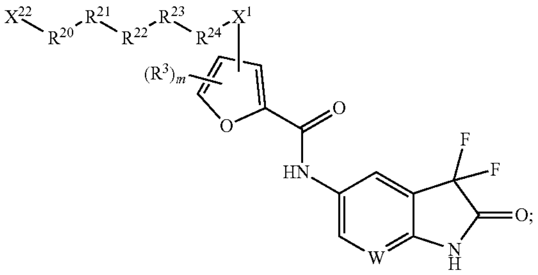
wherein all variables are as defined herein.
In one embodiment of any one of Formulas VII(1)a-VII (1)e,
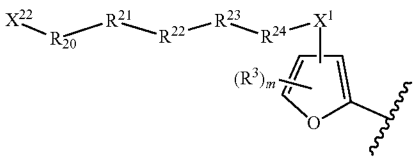

is selected from:
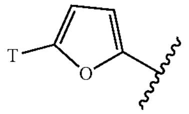,
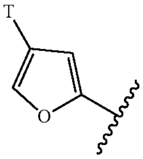,
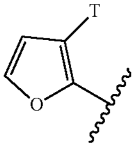,
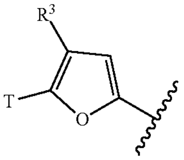,
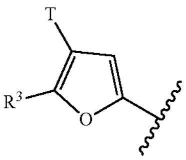,
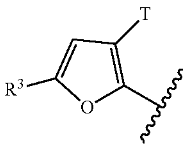,
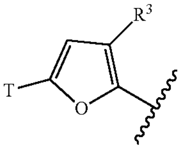,
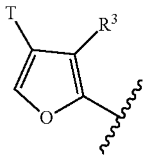,
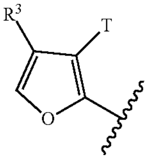,
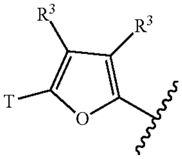,
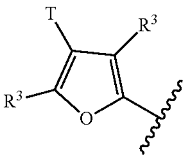, and
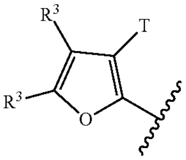;
wherein T is
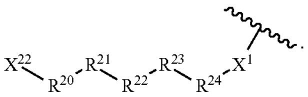
In one aspect, a compound is provided of one of the following formulas:
[VIII(1)-a]
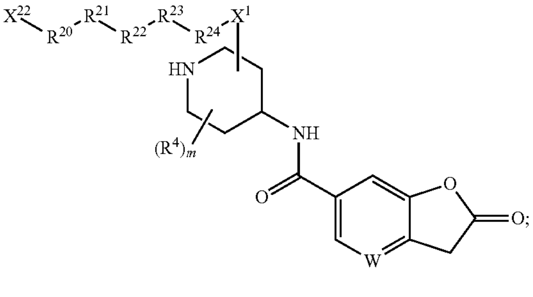
-continued
[VIII(1)-b]
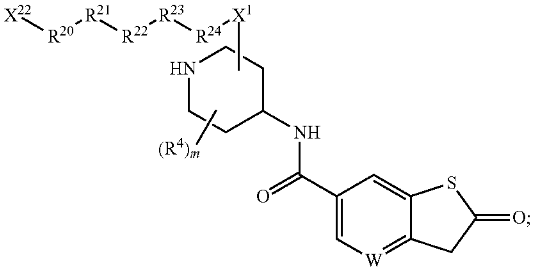
[VIII(1)-c]
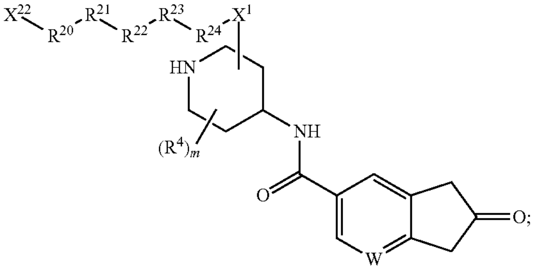
[VIII(1)-d]
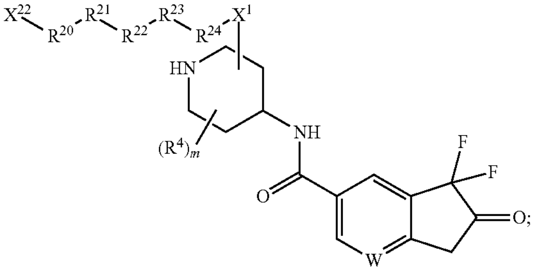
[VIII(1)-e]
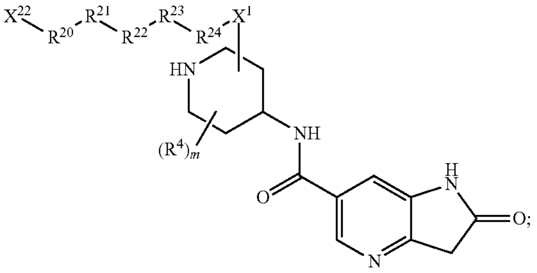
[VIII(1)-f]
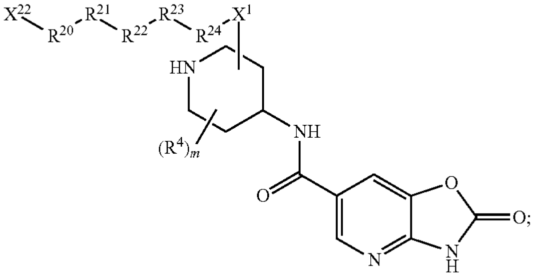

-continued
[VIII(1)-g]
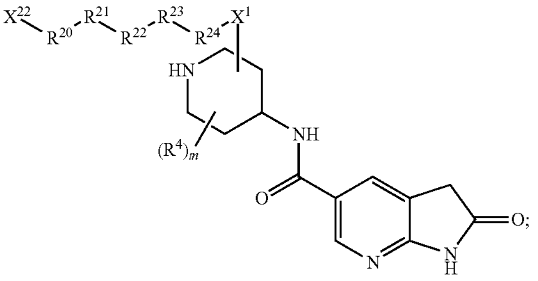
[VIII(1)-h]
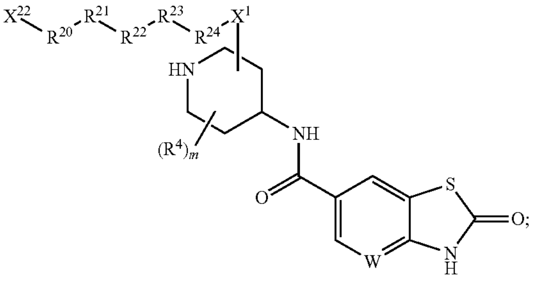
and
[VIII(1)-i]
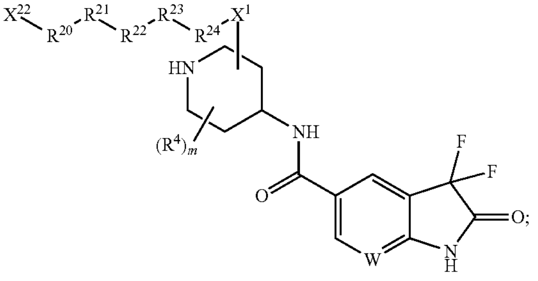
wherein all variables are as defined herein.
In one embodiment of any one of Formulas VIII(1)-a to VIII(1)-I, In one embodiment,
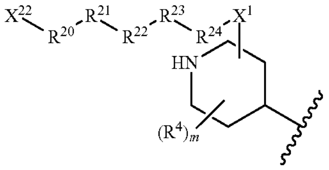
is selected from:
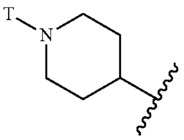,
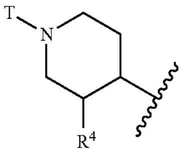,
-continued
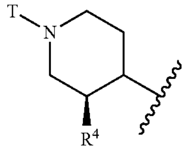,
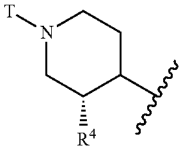,
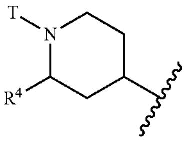,
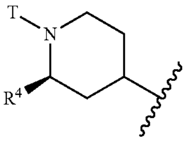,
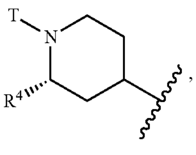,
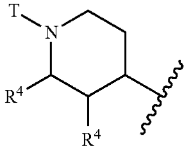,
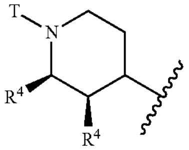,
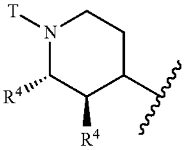,
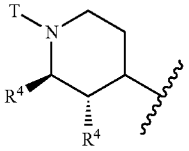,
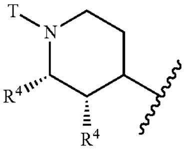,
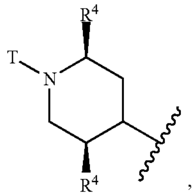,
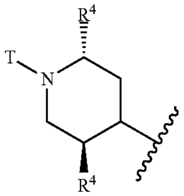,
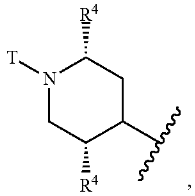,
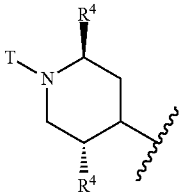,
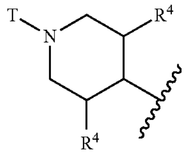,
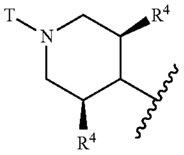,
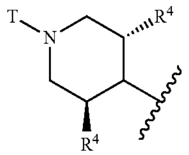,
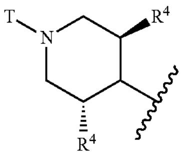,
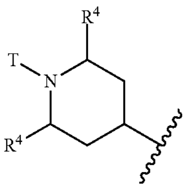,
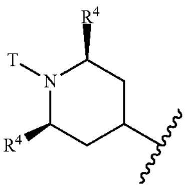, -continued
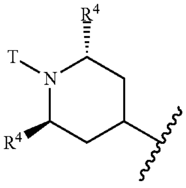
, and
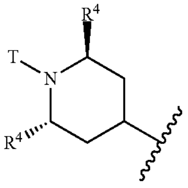
;
wherein T is
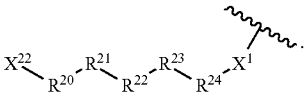
In one aspect, a compound is provided of one of the following formulas:
[IX(1)-a]
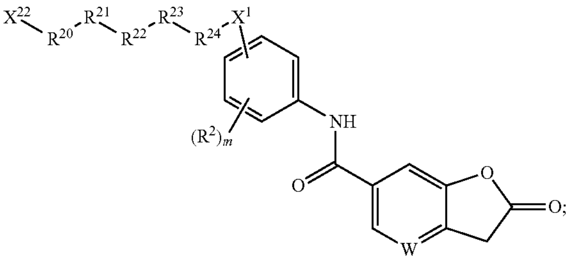
[IX(1)-b]
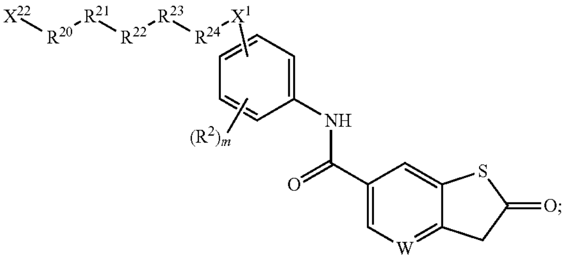
[IX(1)-c]
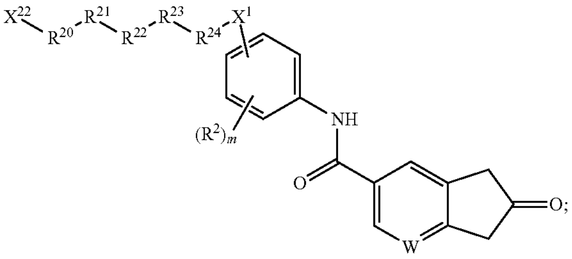
[IX(1)-d]
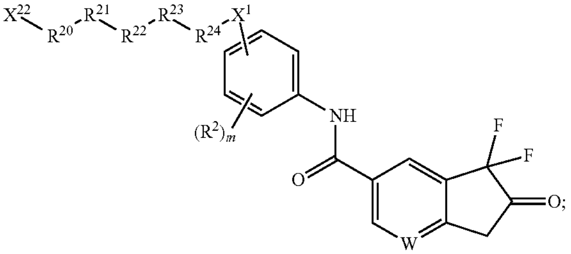
-continued
[IX(1)-e]
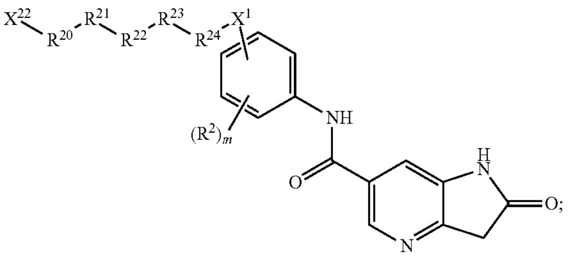
[IX(1)-f]
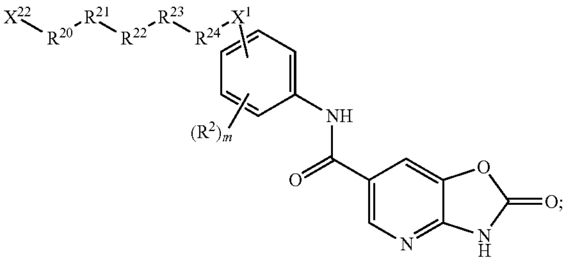
[IX(1)-g]
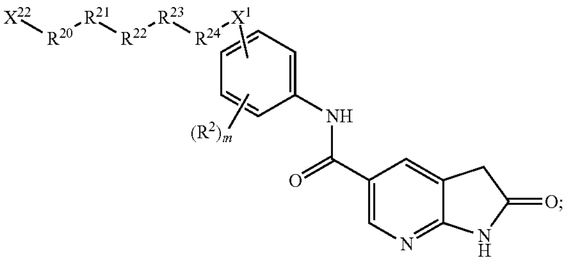
[IX(1)-h]
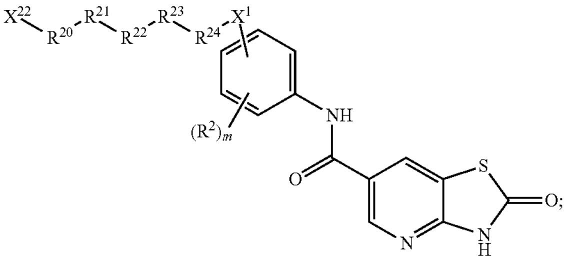
[IX(1)-i]
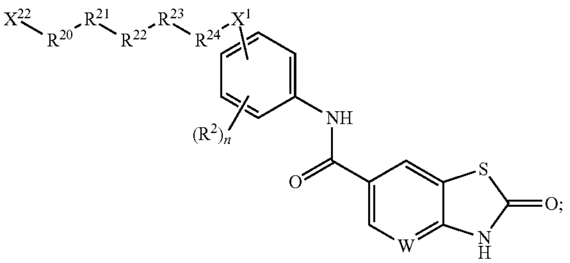
and -continued
[IX(1)-j]
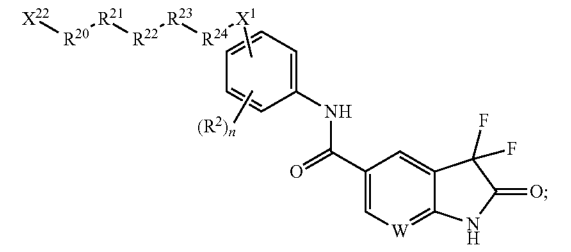
wherein all variables are as defined herein.
In one aspect, a compound is provided of one of the following formulas:
[X(1)-a]
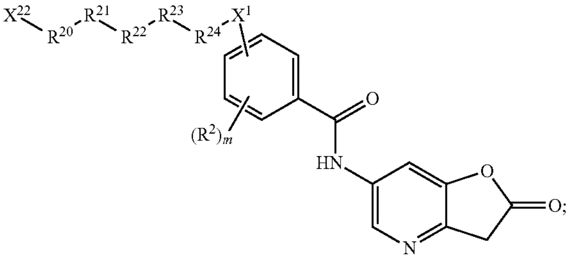
[X(1)-b]
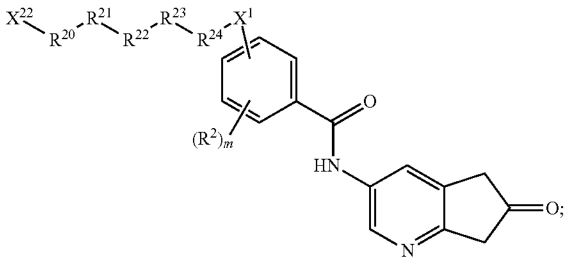
[X(1)-c]
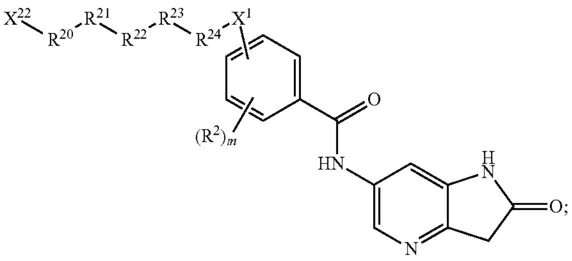
[X(1)-d]
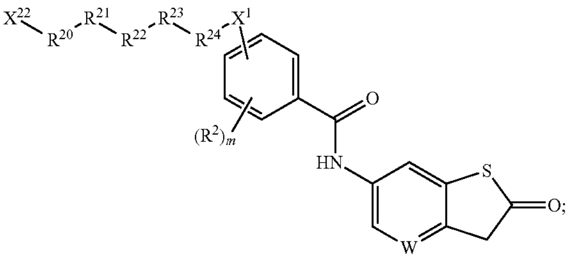
-continued
[X(1)-e]
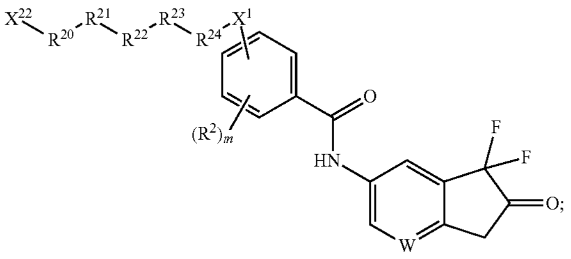
[X(1)-f]
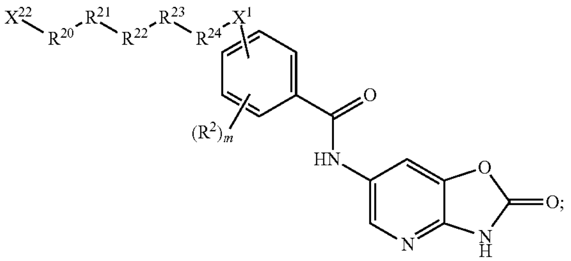
[X(1)-g]
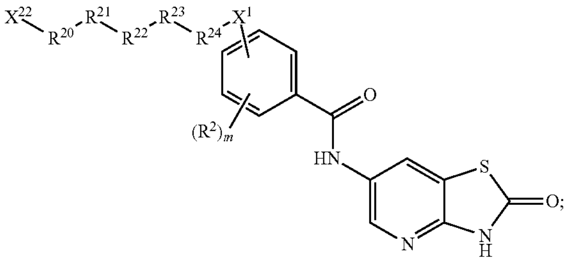
[X(1)-h]
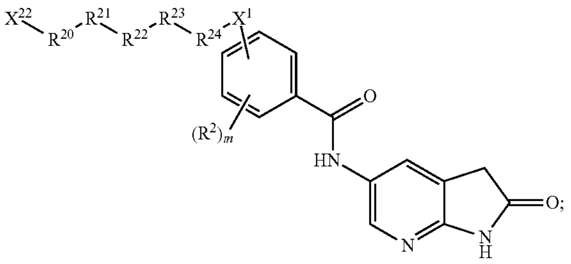
and
[X(1)-i]
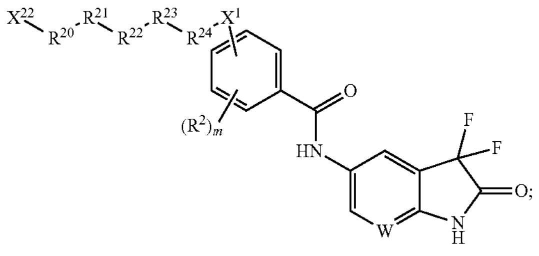
wherein all variables are as defined herein.

In one aspect, a compound is provided of one of the following formulas:
[X(1)-a]
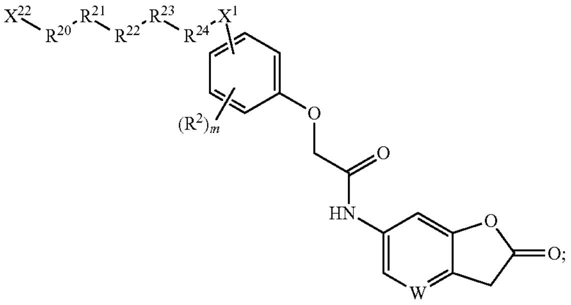
[X(1)-b]
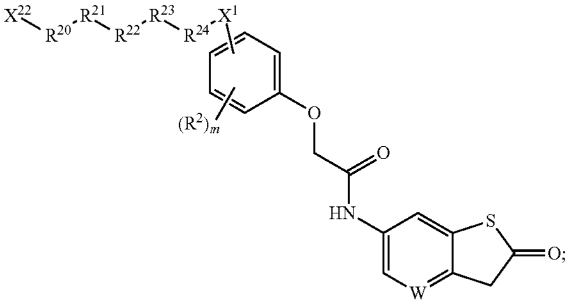
[X(1)-c]
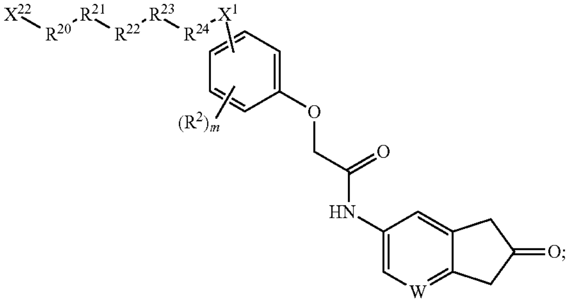
[X(1)-d]
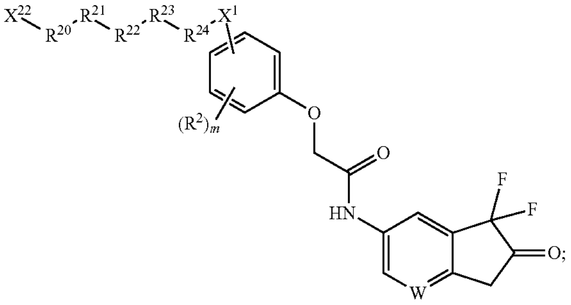
-continued
[X(1)-e]
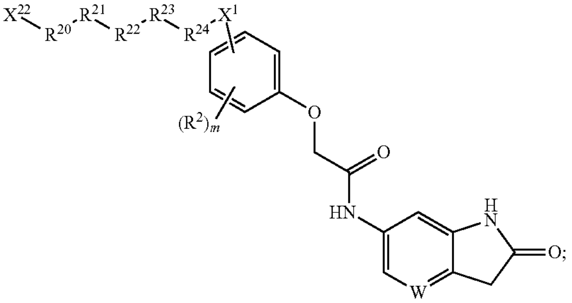
[X(1)-f]
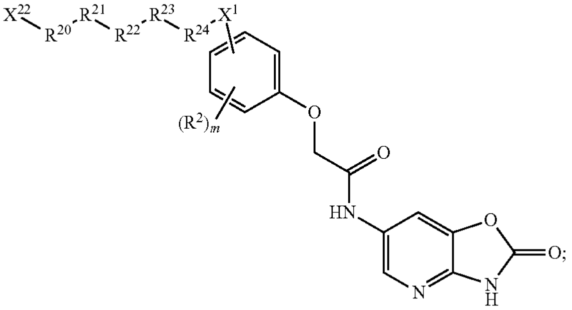
[X(1)-g]
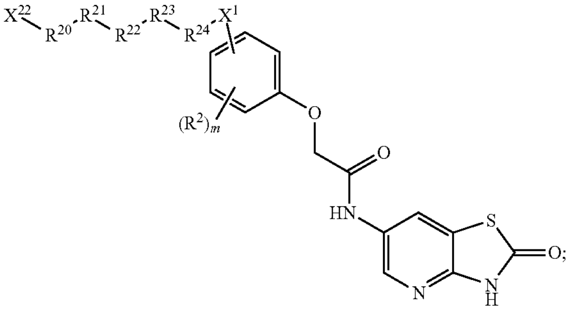
[X(1)-h]
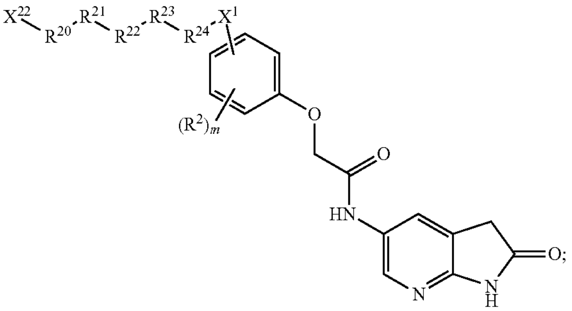
and -continued
[X(1)-i]
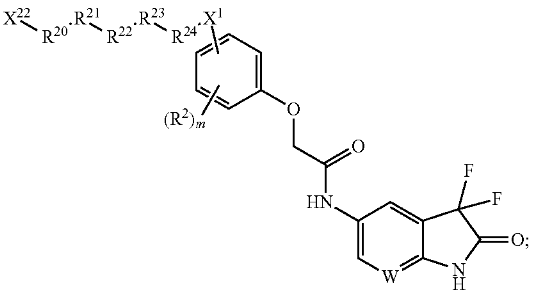
wherein all variables are as defined herein.
In one aspect, a compound is provided of Formula XII(1):
[XXI(1)]
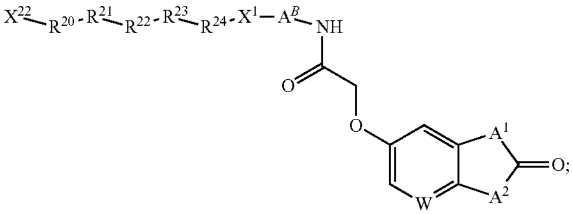
wherein all variables are as defined herein.
In one aspect, a compound is provided of one of the following formulas:
[XIII(1)-a]
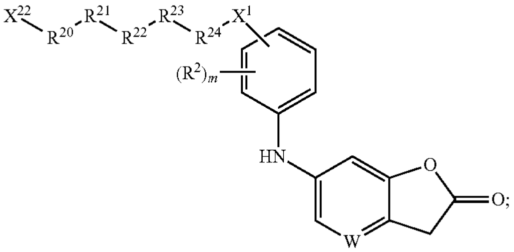
[XIII(1)-b]
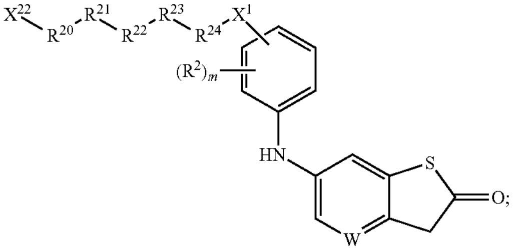
-continued
[XIII(1)-c]
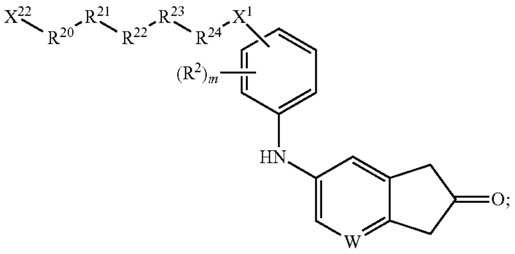
[XIII(1)-d]
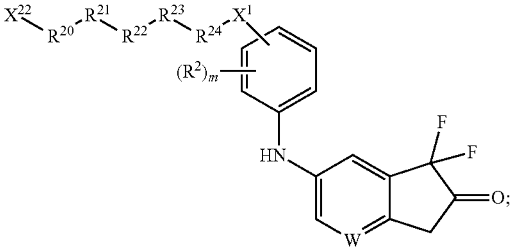
[XIII(1)-e]
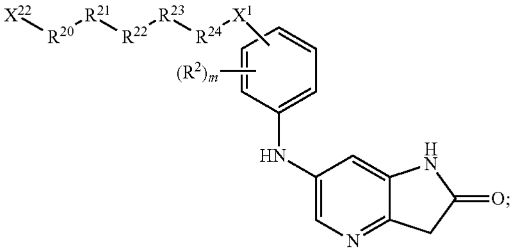
[XIII(1)-g]
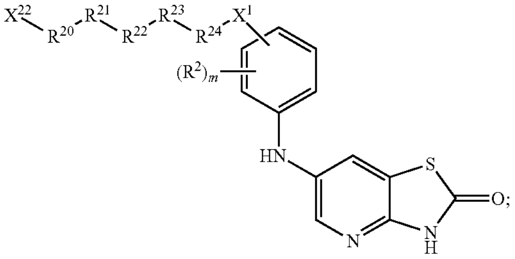
[XIII(1)-h]
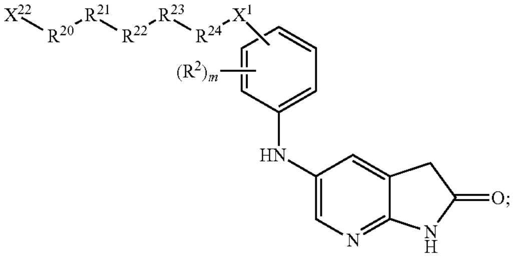
and -continued
[XIII(1)-i]
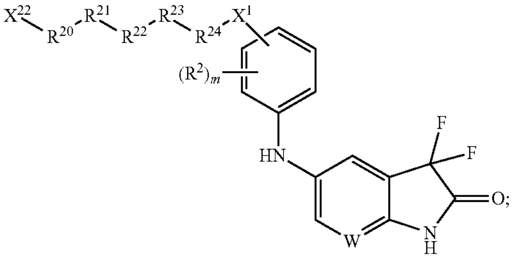
wherein all variables are as defined herein.
In one embodiment of any one compound of Formula IX(1)-1 to IX(1)-j, X(1)-a to X(1)-i, XI(1)-a to XI(1)-i, and XIII(1)-a to XIII(1)-i,
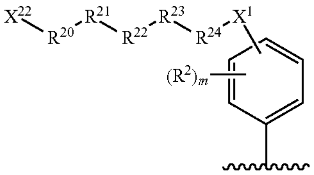
is selected from:
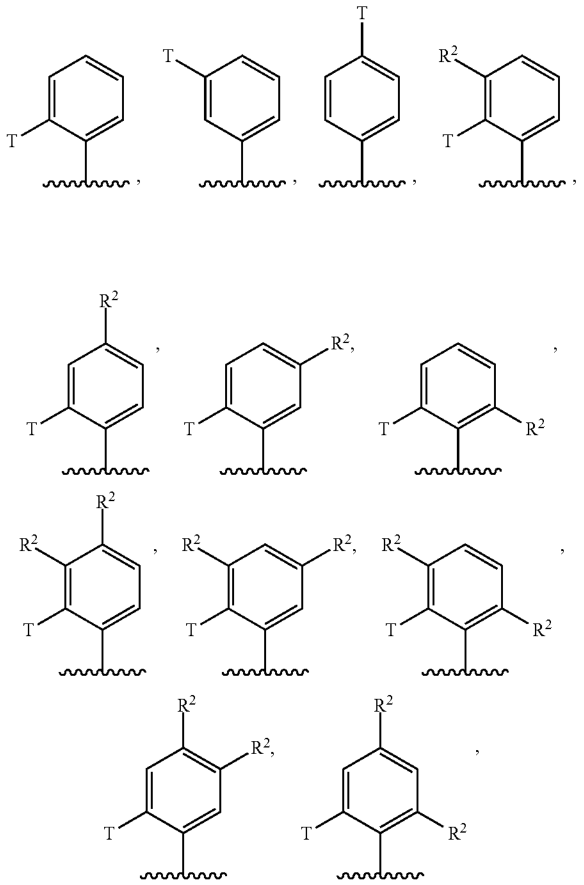
-continued
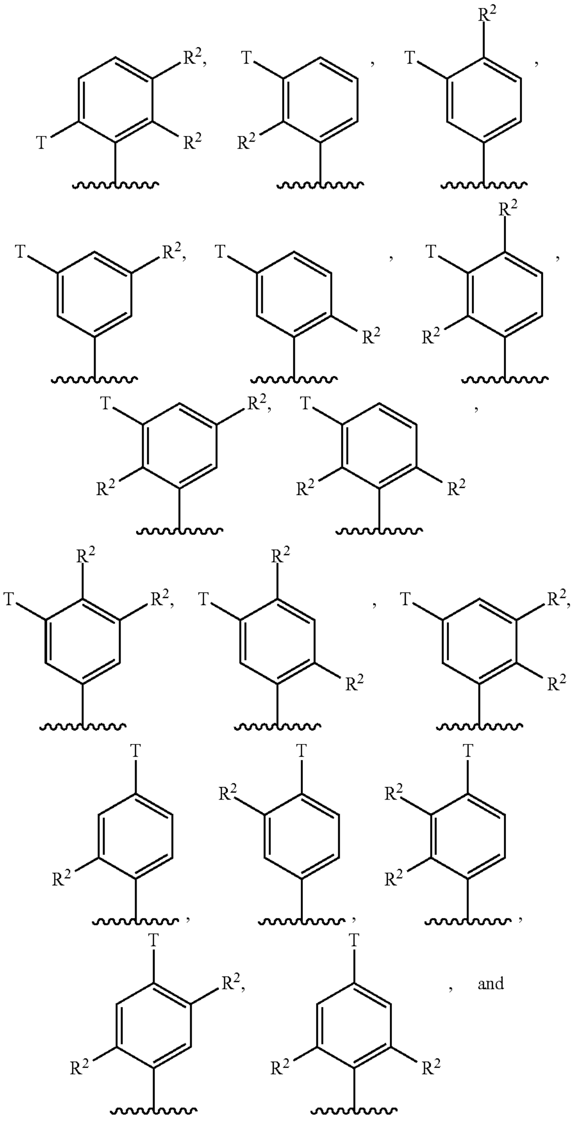
, and
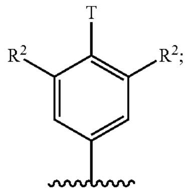
wherein T is
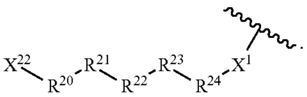
III. Tail Embodiments
In one embodiment, “Tail” is a moiety selected from Formula T-I, Formula T-II, Formula T-III, Formula T-IV, Formula T-V, Formula T-VI, and Formula T-VII:

(T-I)

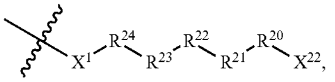

(T-II)

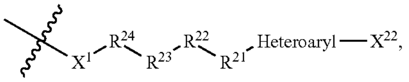

(T-III)

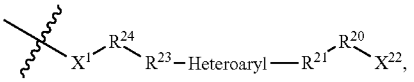

(T-IV)

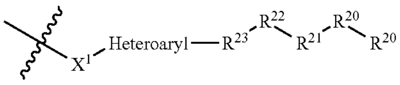

(T-V)

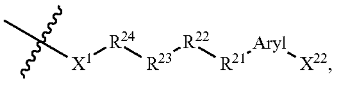

(T-VI)

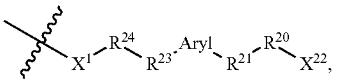

and (T-VII)

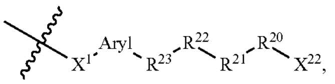

wherein all variables are defined as above.

In an additional embodiment, "Tail" is a moiety selected from Formula T-VIII, T-IX, and T-X:

(T-VIII)

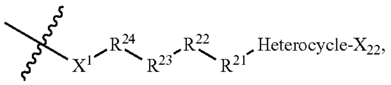

(T-IX)

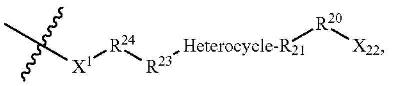

and (T-X)

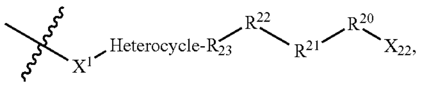

wherein all variables are defined as above. In other embodiments of T-VIII, T-IX and T-X, a carbocyclic ring is used in place of the heterocycle.

The following are non-limiting examples of "Tail" moieties that can be used in this invention. Based on this elaboration, those of skill in the art will understand how to use the full breadth of "Tail" moieties that will accomplish the goal of the invention.

As certain non-limiting examples, Formula T-I, Formula T-II, Formula T-III, Formula T-IV, Formula T-V, Formula T-VI, or Formula T-VII include:

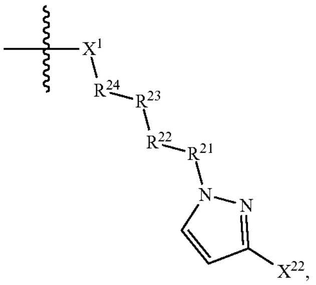

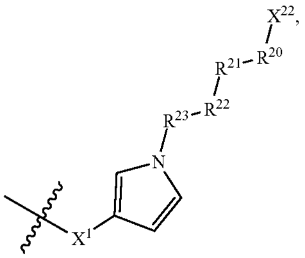

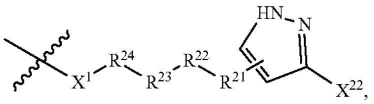

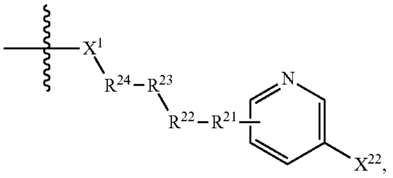

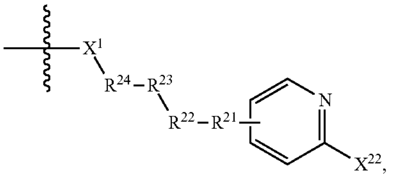

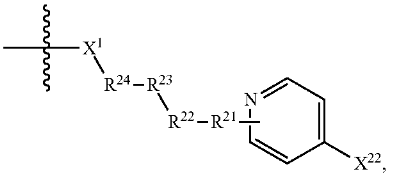

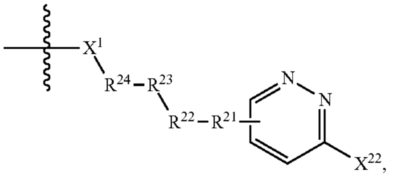

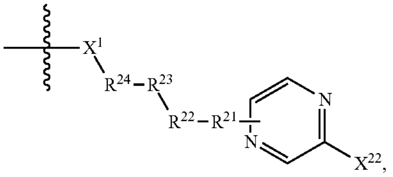

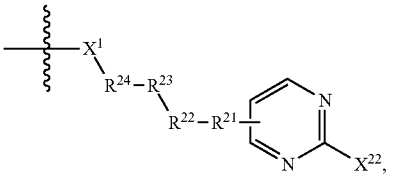

-continued
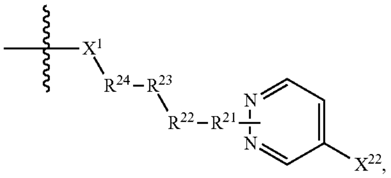
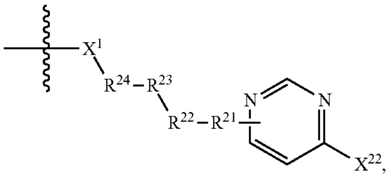
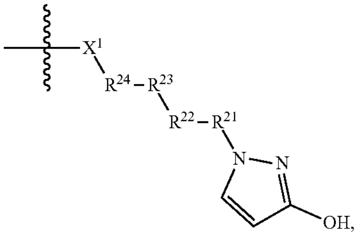
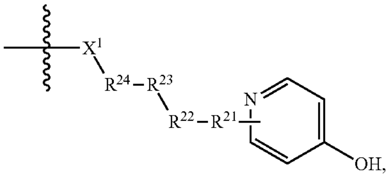
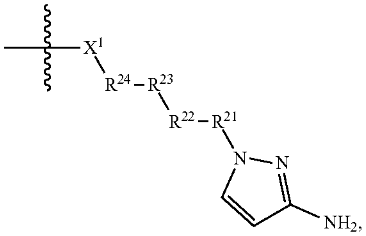
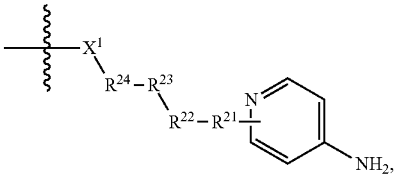
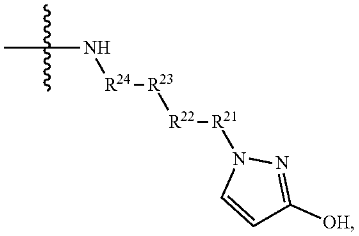
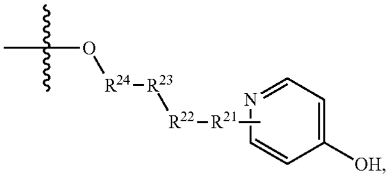
-continued
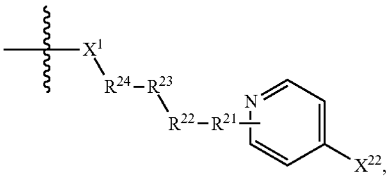
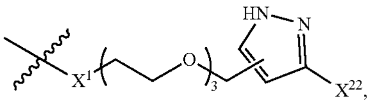
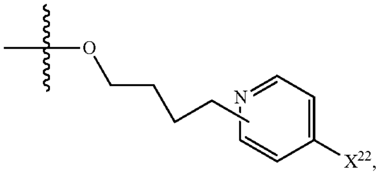
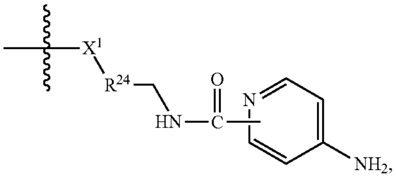
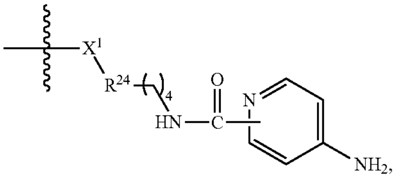
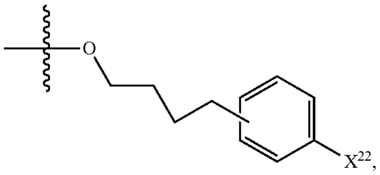
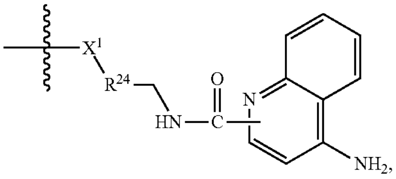
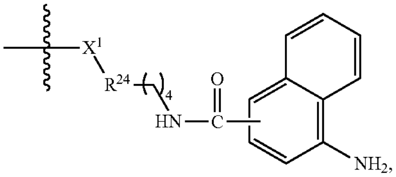
and
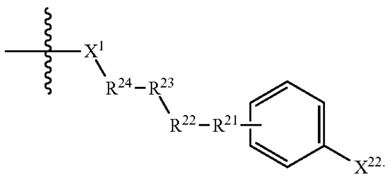

In an additional embodiment "Tail" is selected from:
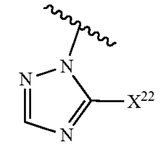
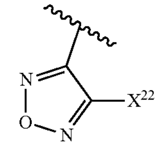
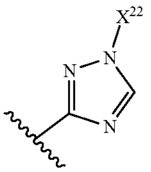
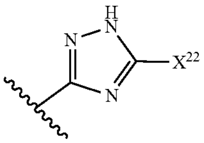
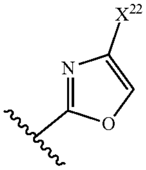
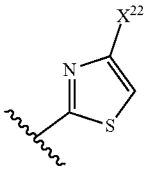
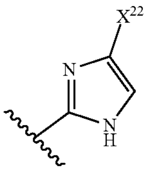
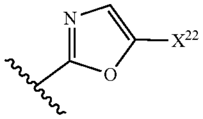
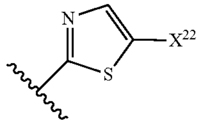
In an additional embodiment "Tail" is selected from:
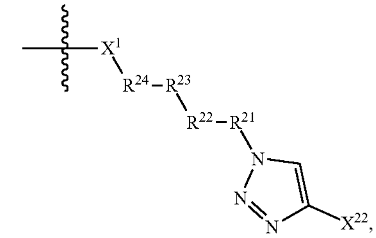
,
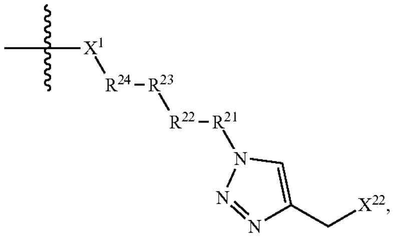
,
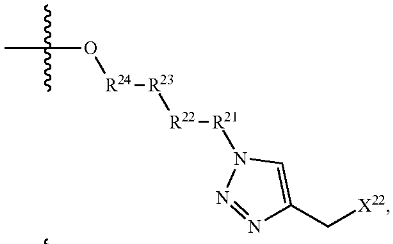
,
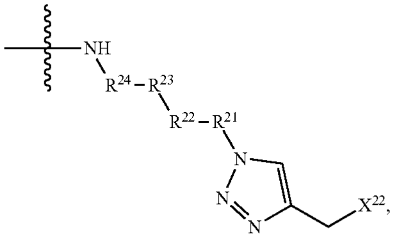
,
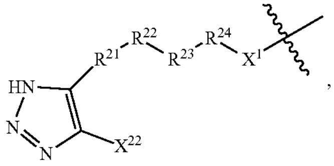
,
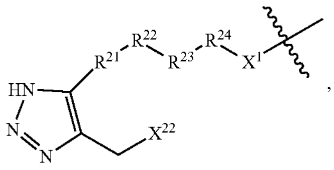
,
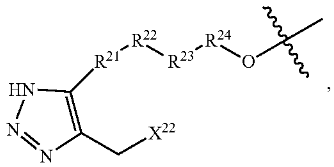
,
and
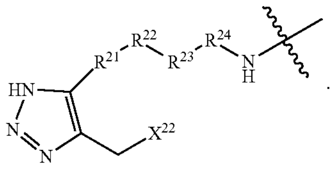
.

Non-limiting examples of moieties of $R^{20}$, $R^{21}$, $R^{22}$, $R^{23}$, and $R^{24}$ include:
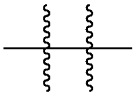,
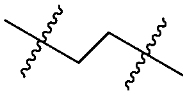,
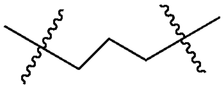,
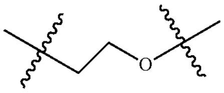,
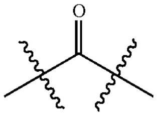,
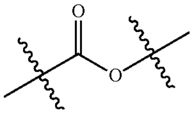,
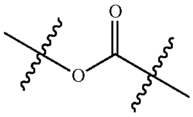,
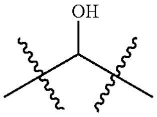,
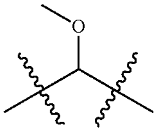,
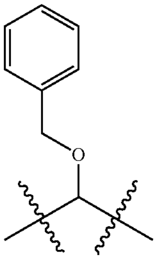,
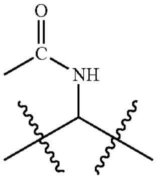,
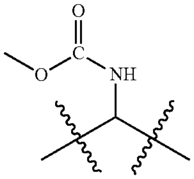,
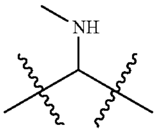,
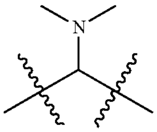,
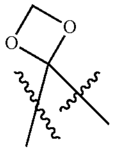,
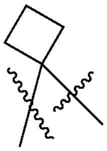,
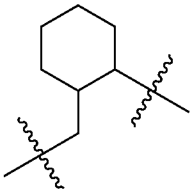,
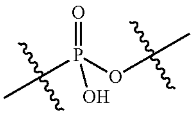, and
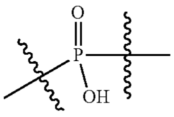.
Additional non-limiting examples of moieties of $R^{20}$, $R^{21}$, $R^{22}$, $R^{23}$, and $R^{24}$ include:
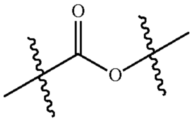,
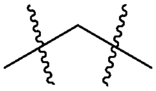,
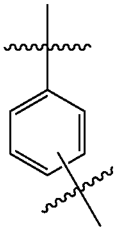,
-continued
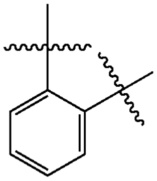,
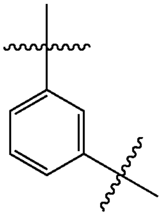,
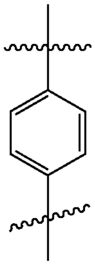,
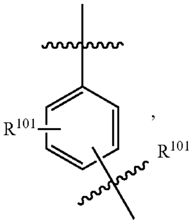,
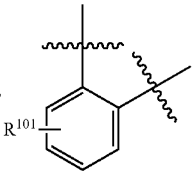,
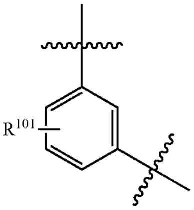,
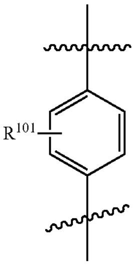,
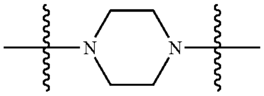,
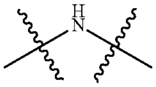,
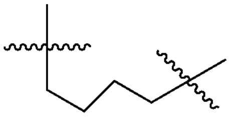,
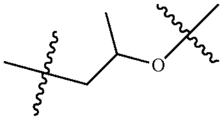,
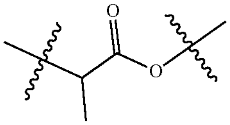,
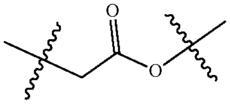,
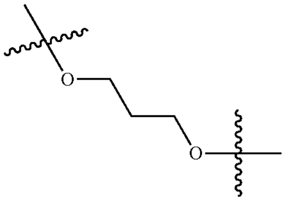,
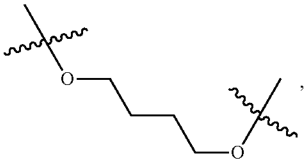,
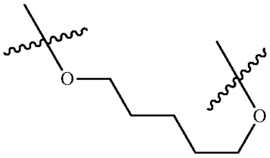,
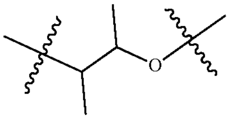,
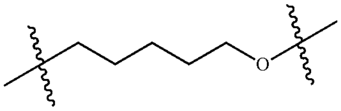, -continued
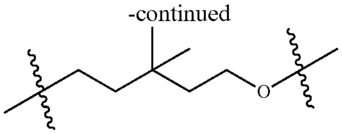,
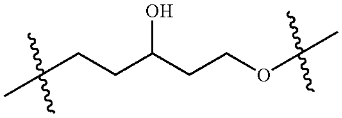,
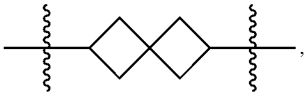,
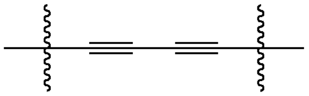,
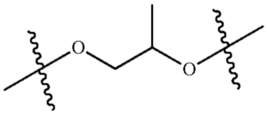, 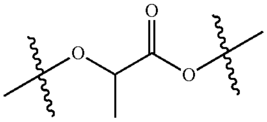,
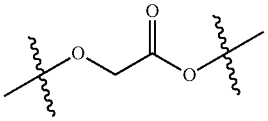, 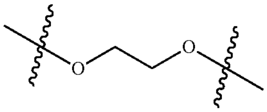,
and
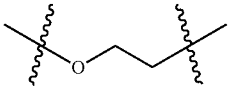.
Additional non-limiting examples of moieties of $R^{20}$, $R^{21}$, $R^{22}$, $R^{23}$, and $R^{24}$ include:
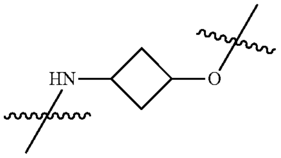,
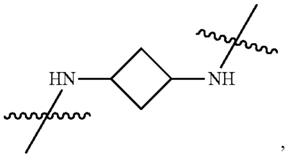,
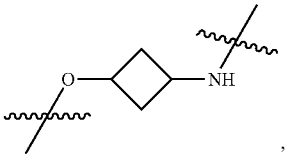,
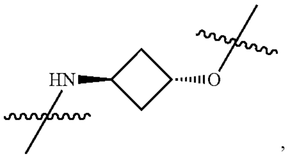,
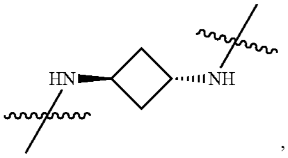,
-continued
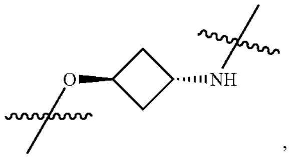,
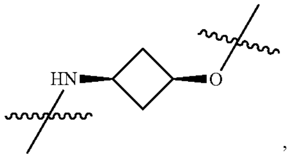,
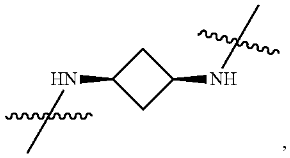,
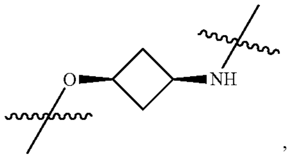,
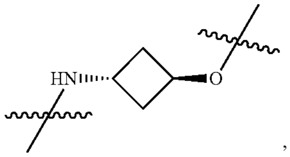,
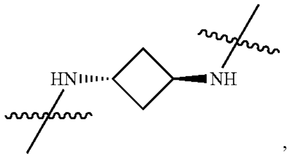,
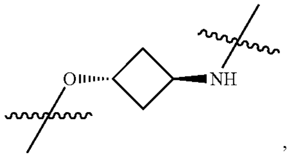,
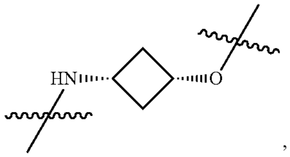,
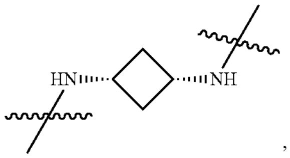,
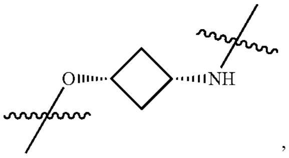, 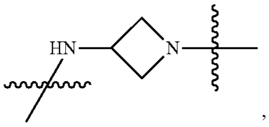,
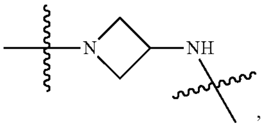, 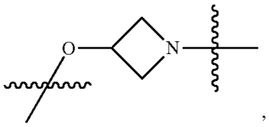, -continued

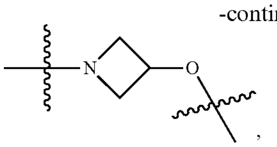,
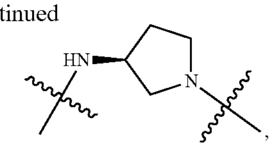,
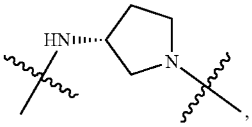,
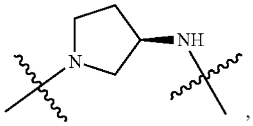,
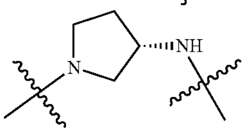,
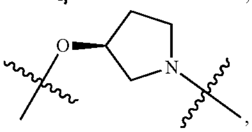,
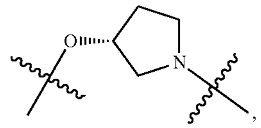,
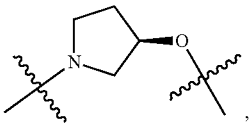, and
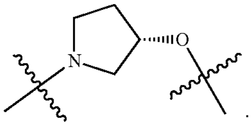.

In additional embodiments, "Tail" is an optionally substituted ethylene glycol having at least 1, at least 2, at least 3, at least 4, at least 5, at least 6, at least 7, at least 8, at least 9, at least 10, ethylene glycol units, or optionally substituted alkyl groups interspersed with optionally substituted, O, N, S, P or Si atoms. In certain embodiments, "Tail" is flanked, substituted, or interspersed with an aryl, phenyl, benzyl, alkyl, alkylene, or heterocycle group. In certain embodiments, "Tail" may be asymmetric or symmetrical. In some embodiments, "Tail" is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units. In any of the embodiments of the compounds described herein, "Tail" group may be any suitable moiety as described herein.

In additional embodiments, the "Tail" is selected from:

—$NR^{61}(CH_2)_{n1}$-(lower alkyl)-$X^{22}$, —$NR^{61}(CH_2)_{n1}$-(lower alkoxyl)-$X^{22}$,
—$NR^{61}(CH_2)_{n1}$-(lower alkoxyl)-$OCH_2$—$X^{22}$, —$NR^{61}(CH_2)_{n1}$-(lower alkoxyl)-(lower alkyl)-$OCH_2$—$X^{22}$,
—$NR^{61}(CH_2)_{n1}$-(cycloalkyl)-(lower alkyl)-$OCH_2$—$X^{22}$, —$NR^{61}(CH_2)_{n1}$-(heterocycloalkyl)-$X^{22}$,
—$NR^{61}(CH_2CH_2O)_{n1}$-(lower alkyl)-O—$CH_2$—$X^{22}$,
—$NR^{61}(CH_2CH_2O)_{n1}$-(heterocycloalkyl)-O—$CH_2$—$X^{22}$,
—$NR^{61}(CH_2CH_2O)_{n1}$-Aryl-O—$CH_2$—$X^{22}$, —$NR^{61}(CH_2CH_2O)_{n1}$-(heteroaryl)-O—$CH_2$—$X^{22}$,
—$NR^{61}(CH_2CH_2O)_{n1}$-(cycloalkyl)-O-(heteroaryl)-O—$CH_2$—$X^{22}$,
—$NR^{61}(CH_2CH_2O)_{n1}$-(cycloalkyl)-O-Aryl-O—$CH_2$—$X^{22}$,
—$NR^{61}(CH_2CH_2O)_{n1}$-(lower alkyl)-NH-Aryl-O—$CH_2$—$X^{22}$,
—$NR^{61}(CH_2CH_2O)_{n1}$-(loweralkyl)-O-Aryl-$CH_2$—$X^{22}$,
—$NR^{61}(CH_2CH_2O)_{n1}$-cycloalkyl-O-Aryl-$X^{22}$, —$NR^{61}(CH_2CH_2O)_{n1}$-cycloalkyl-O-heteroaryl-$X^{22}$,
—$NR^{61}(CH_2CH_2)_{n1}$-(cycloalkyl)-O-(heterocycle)-$CH_2$—$X^{22}$.

—$NR^{61}(CH_2CH_2)_{n1}$-(heterocycle)-(heterocycle)-$CH_2$—$X^{22}$, and —$NR^{61}$-(heterocycle)-$CH_2$—$X^{22}$;

wherein n1 is 0, 1, 2, 3, 4, 5, 6, 7, 8, 9, or 10; and $R^{61}$ is H, methyl, or ethyl.

In additional embodiments, "Tail" is selected from:

—$N(R^{61})$—$(CH_2)_{m1}$—$O(CH_2)_{n2}$—$O(CH_2)_{o1}$—$O(CH_2)_{p1}$—$O(CH_2)_{q1}$—$O(CH_2)_{r1}$—$OCH_2$—$X^{22}$,
—O—$(CH_2)_{m1}$—$O(CH_2)_{n2}$—$O(CH_2)_{o1}$—$O(CH_2)_{p1}$—$O(CH_2)_{q1}$—$O(CH_2)_{r1}$—$OCH_2$—$X^{22}$,
—O—$(CH_2)_{m1}$—$O(CH_2)_{n2}$—$O(CH_2)_{o1}$—$O(CH_2)_{p1}$—$O(CH_2)_{q1}$—$O(CH_2)_{r1}$—OH;
—$N(R^{61})$—$(CH_2)_{m1}$—$O(CH_2)_{n2}$—$O(CH_2)_{o1}$—$O(CH_2)_{p1}$—$O(CH_2)_{q1}$—$O(CH_2)_{r1}$—OH;
—$(CH_2)_{m1}$—$O(CH_2)_{n2}$—$O(CH_2)_{o1}$—$O(CH_2)_{p1}$—$O(CH_2)_{q1}$—$O(CH_2)_{r1}$—OH;
—$(CH_2)_{m1}$—$O(CH_2)_{n2}$—$O(CH_2)_{o1}$—$O(CH_2)_{p1}$—$O(CH_2)_{q1}$—$O(CH_2)_{r1}$—$OCH_2$—$X^{22}$;
—$O(CH_2)_{m1}O(CH_2)_{n2}O(CH_2)_{p1}O(CH_2)_{q1}OCH_2$—$X^{22}$;
—$O(CH_2)_{m1}O(CH_2)_{n2}O(CH_2)_{p1}O(CH_2)_{q1}OCH_2$—$X^{22}$;
wherein m1, n2, o1, p1, q1, and r1 are independently 1, 2, 3, 4, or 5; and $R^{61}$ is H, methyl, or ethyl.

In additional embodiments, "Tail" is selected from:

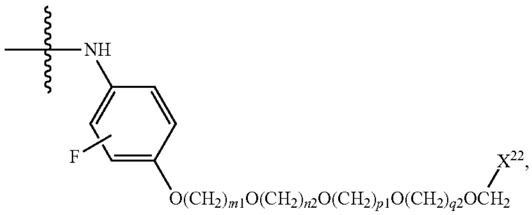,
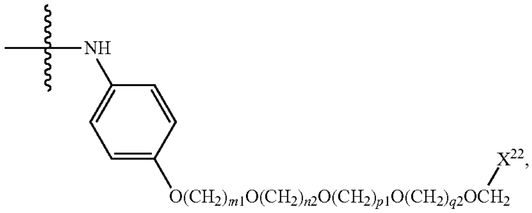,
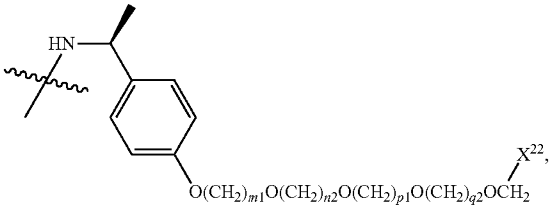,
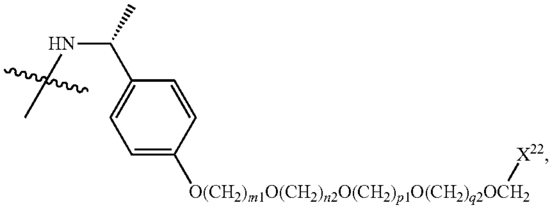,
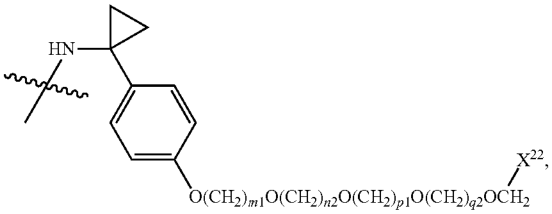,

-continued
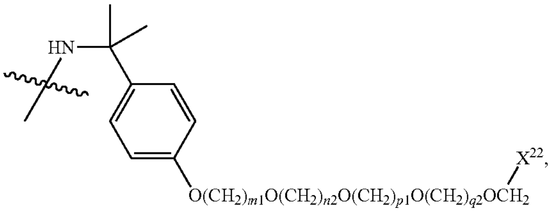
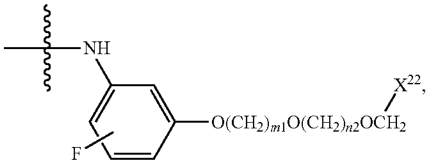
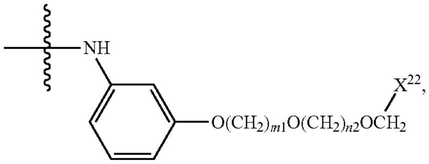
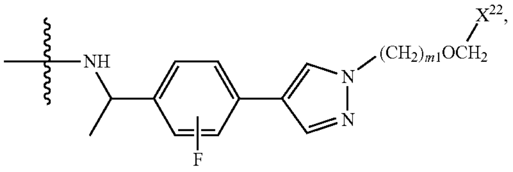
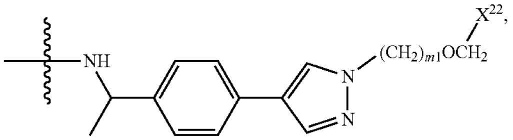
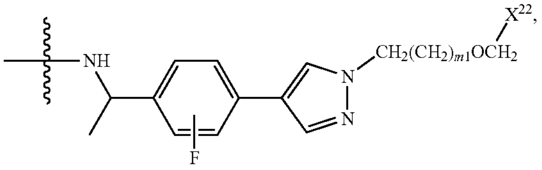
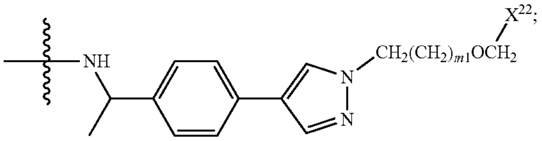
m1, n2, o1, p1, q2, and r1 are independently 1, 2, 3, 4, or 5.
In additional embodiments, "Tail" is selected from:
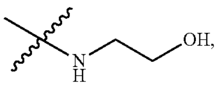
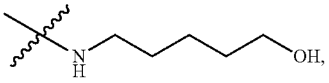
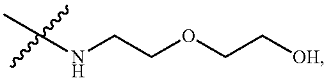
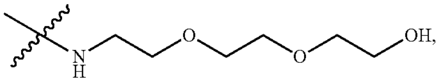
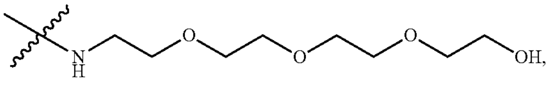
-continued
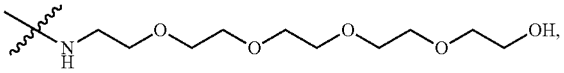
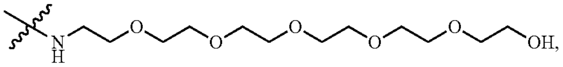
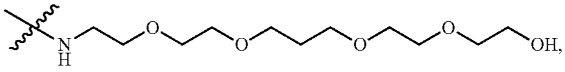
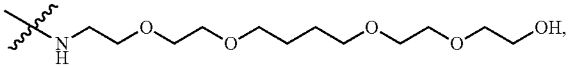
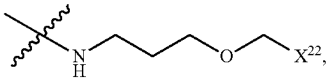
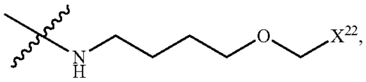
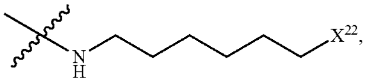
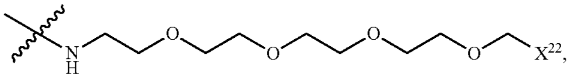
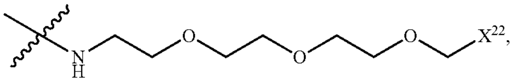
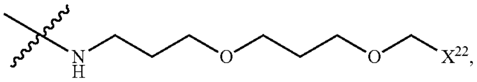
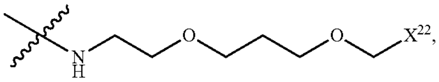
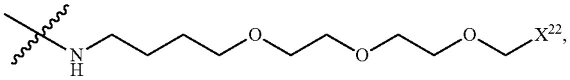
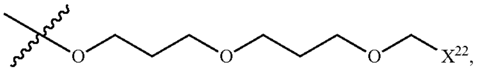
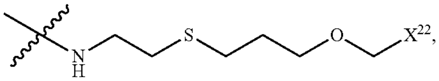
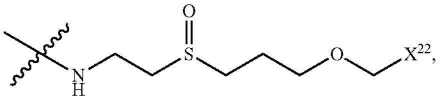
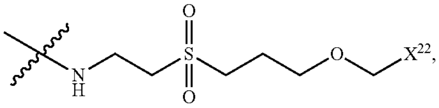
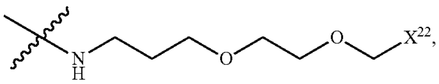
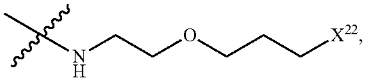
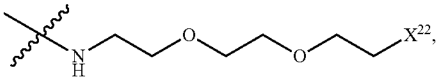
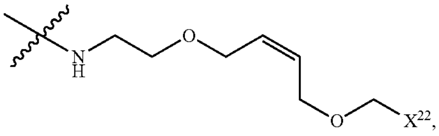

-continued
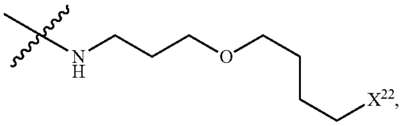
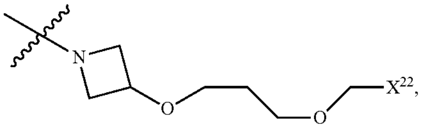
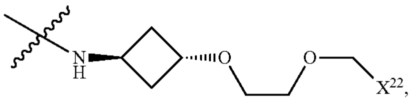
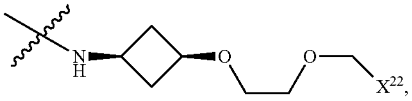
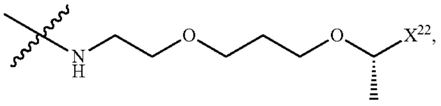
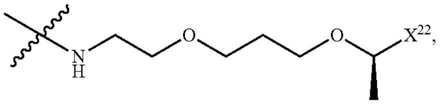
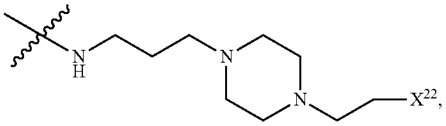
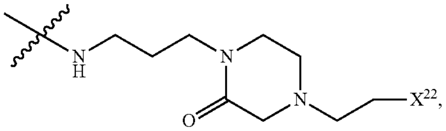
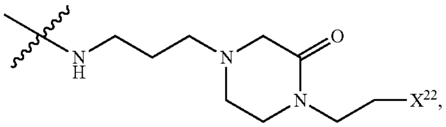
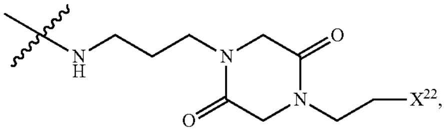
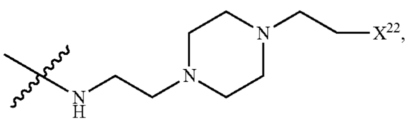
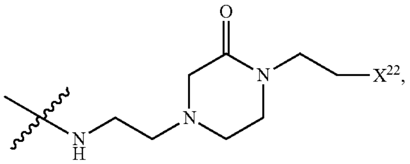
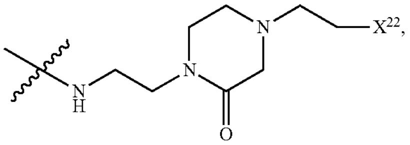
-continued
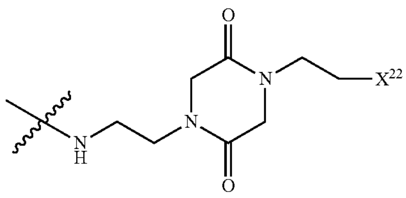
In additional embodiments, "Tail" is selected from:
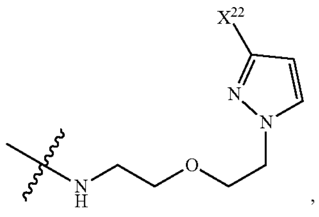
,
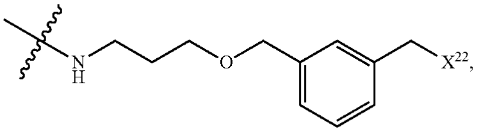
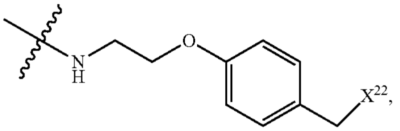
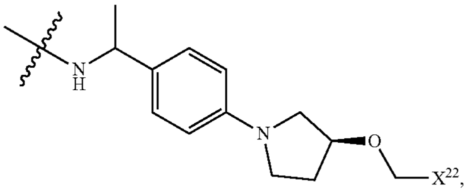
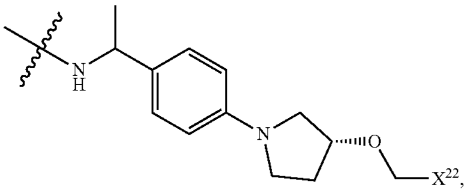
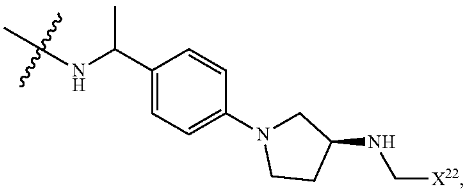
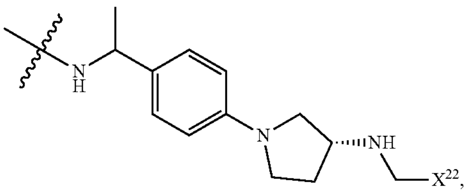

-continued
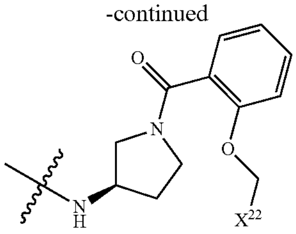
,
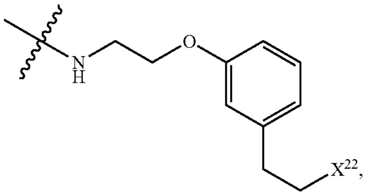
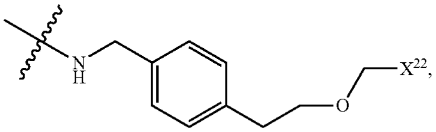
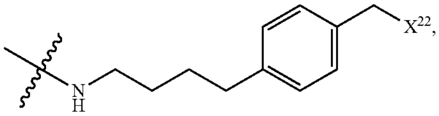
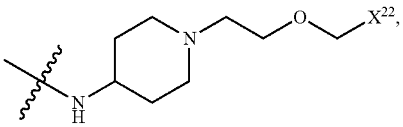
and
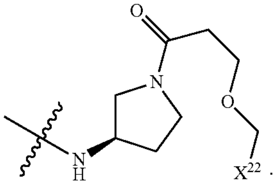
In additional embodiments, "Tail" is selected from:
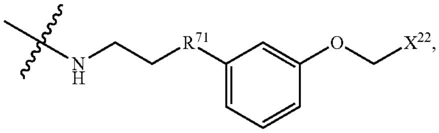
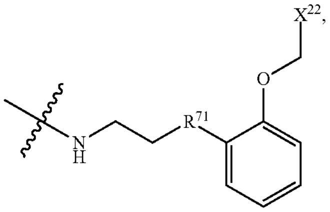
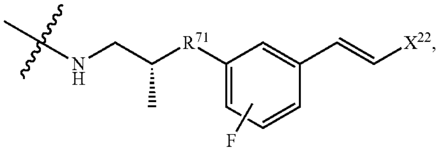
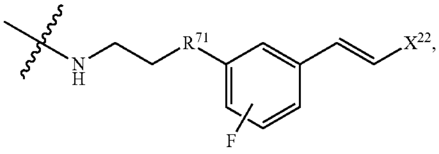
-continued
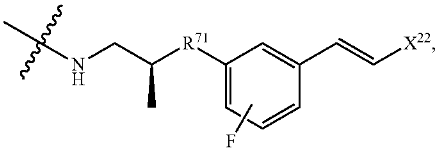
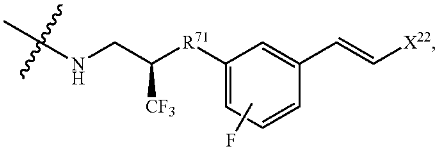
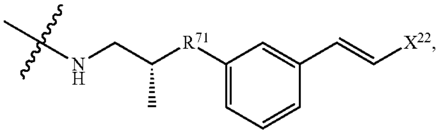
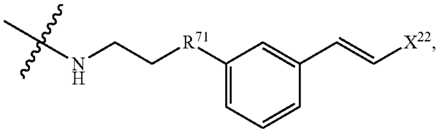
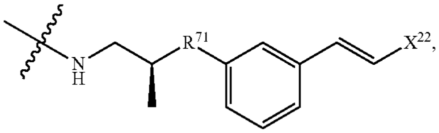
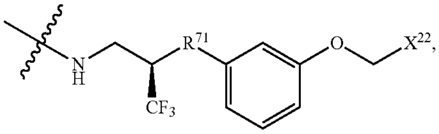
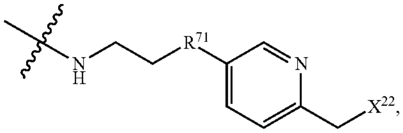
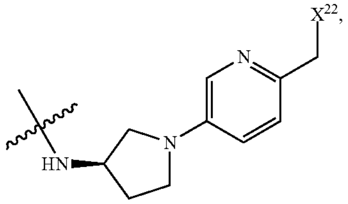
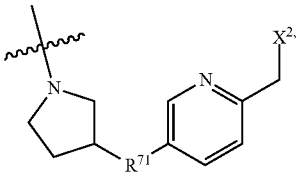
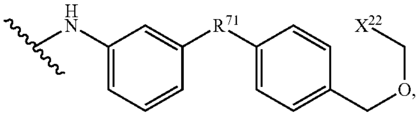
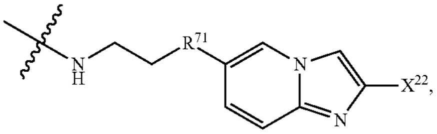
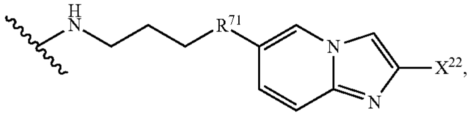

-continued
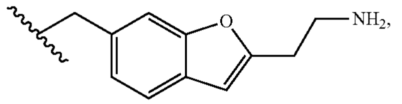
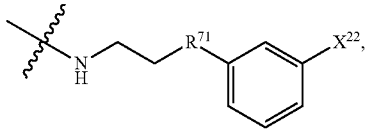
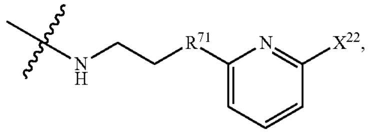
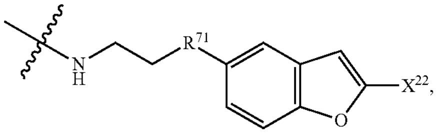
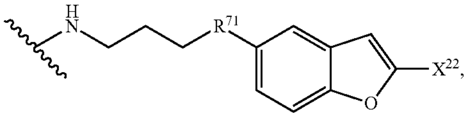
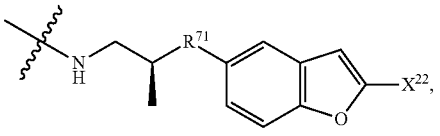
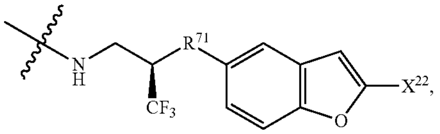
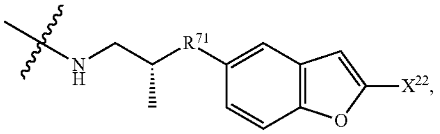
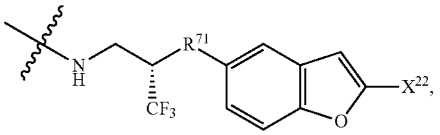
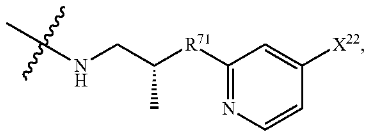
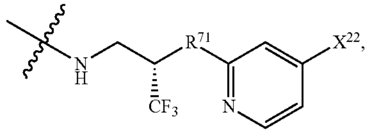
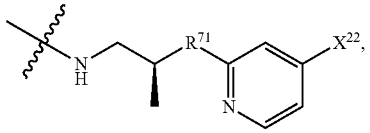
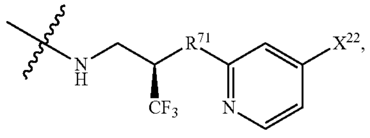
-continued
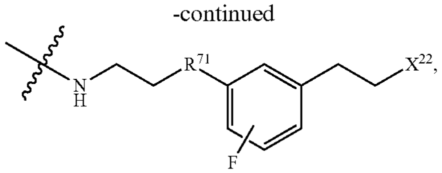
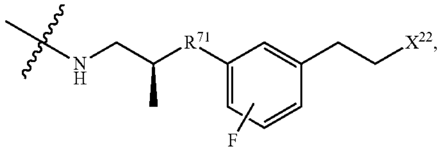
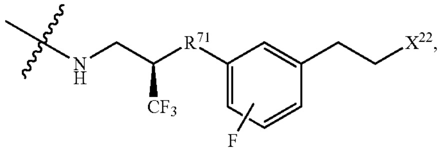
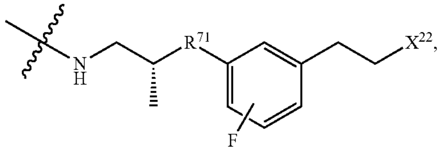
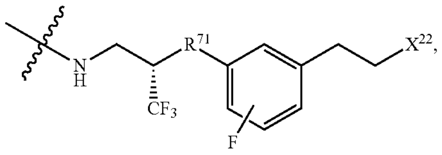
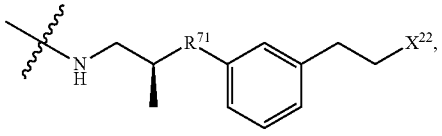
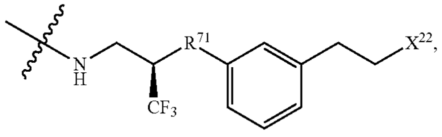
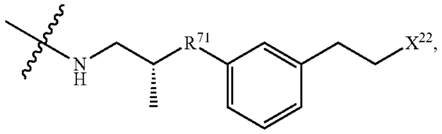
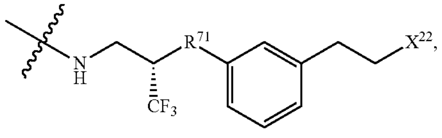
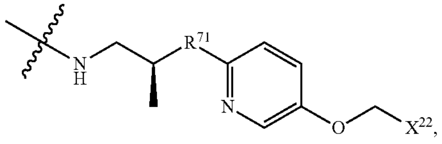
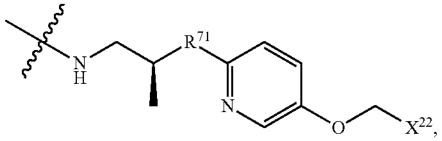
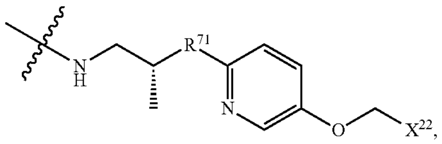

-continued
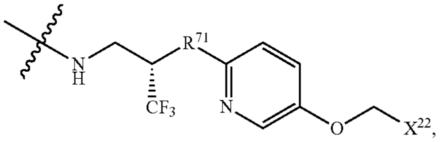
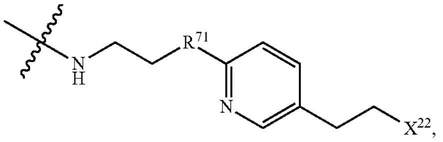
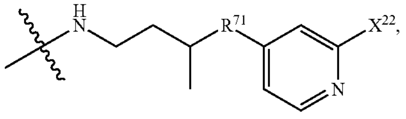
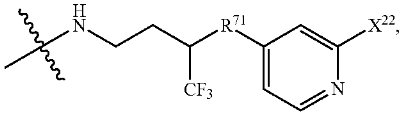
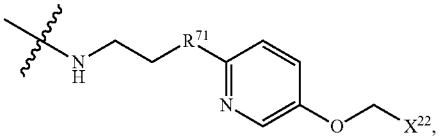
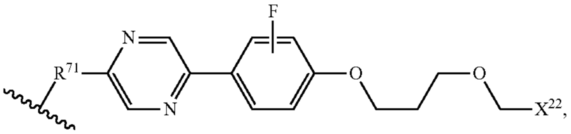
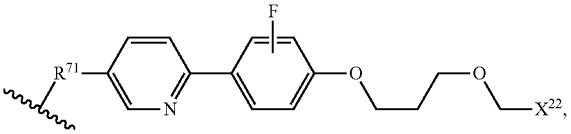
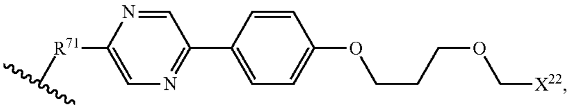
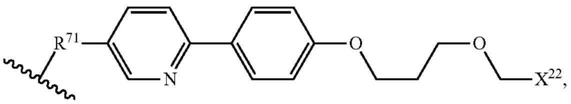
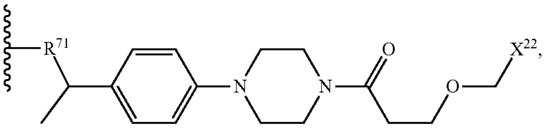
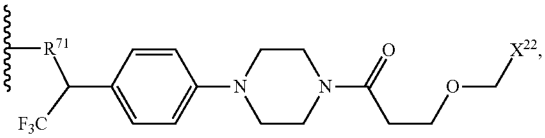
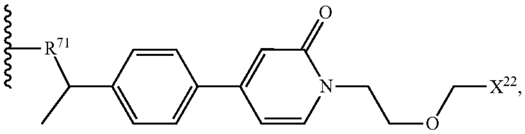
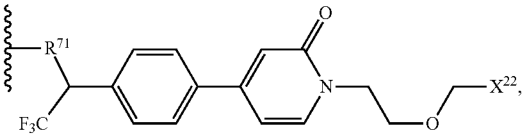
-continued
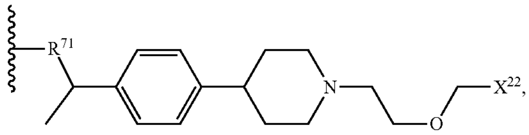
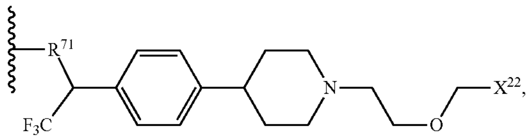
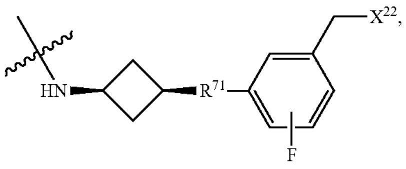
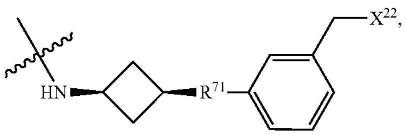
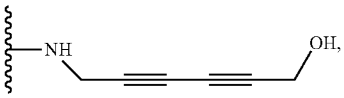
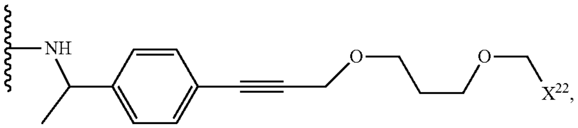
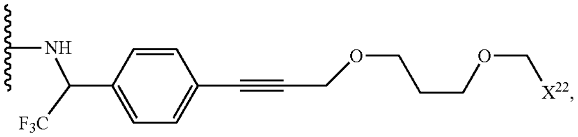
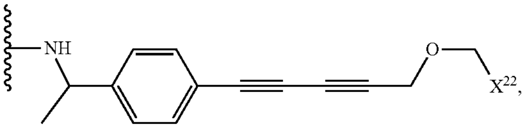
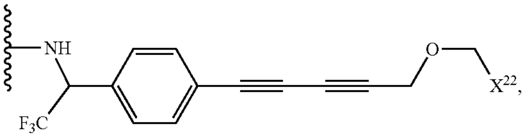
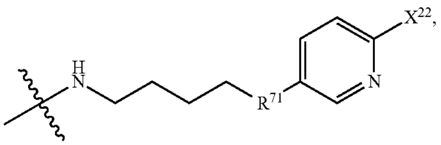
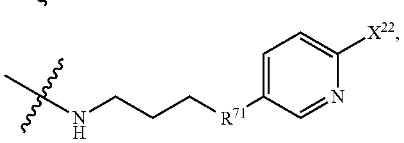
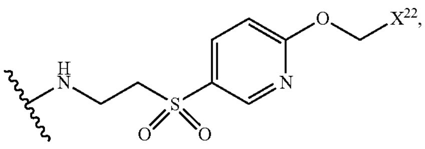

-continued
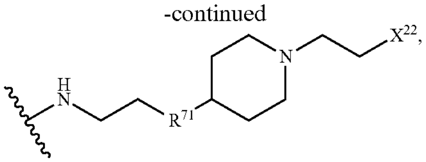
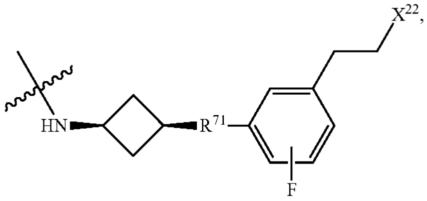
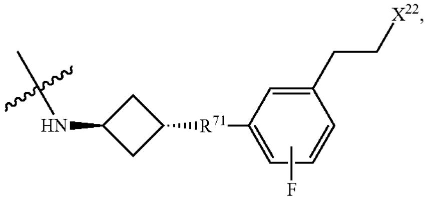
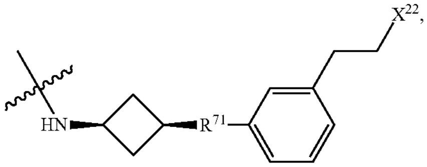
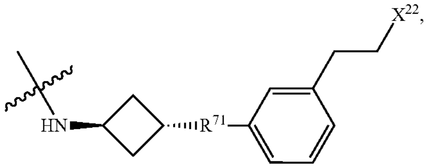
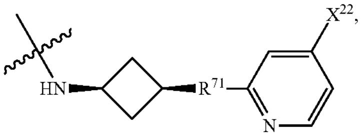
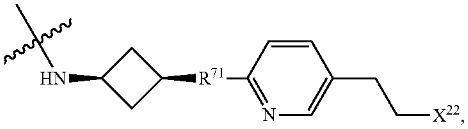
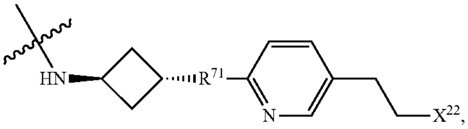
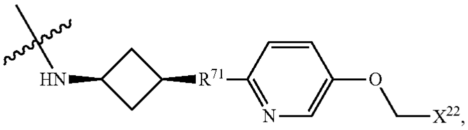
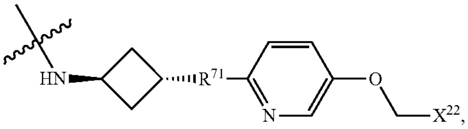
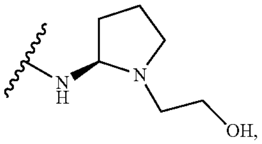
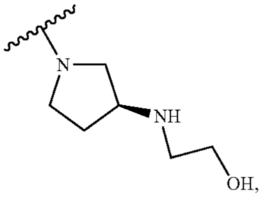
-continued
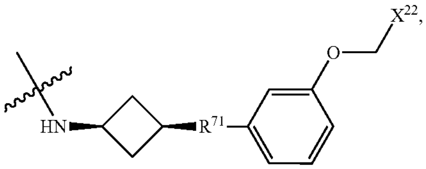
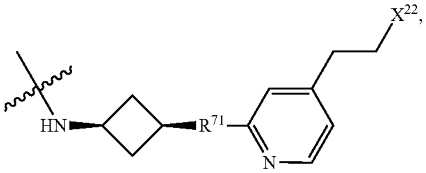
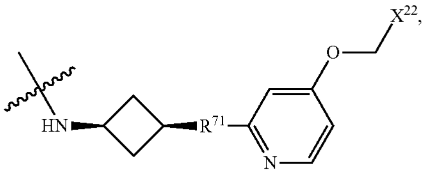
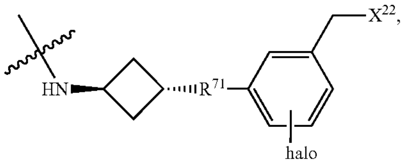
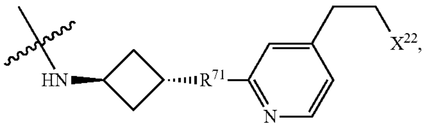
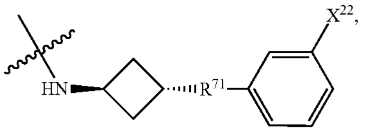
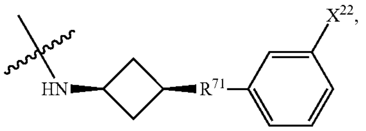
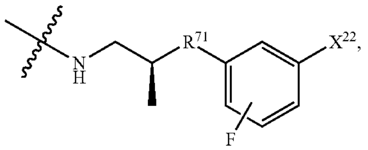
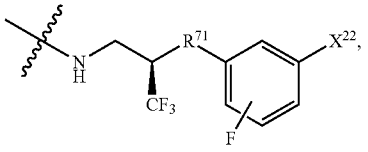
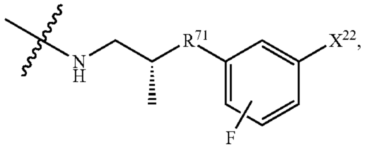
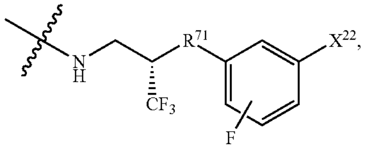

-continued
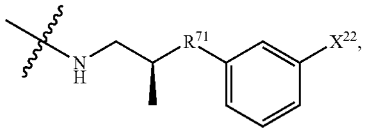
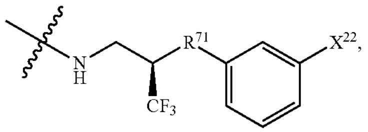
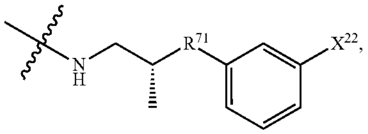
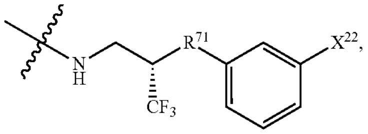
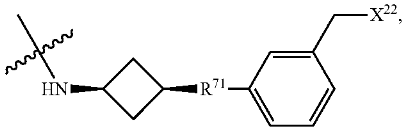
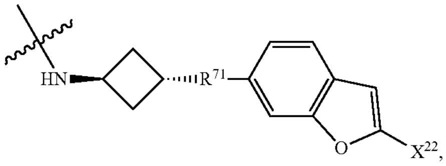
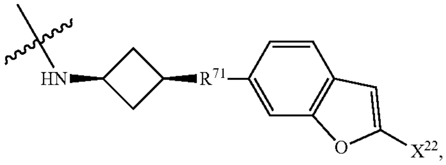
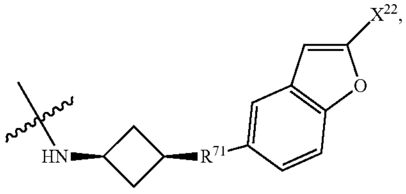
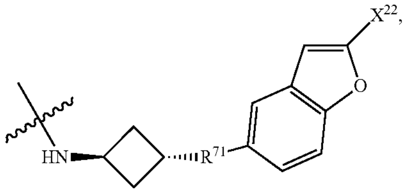
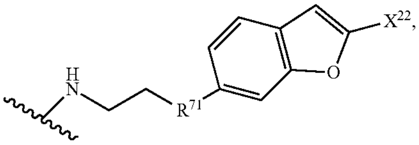
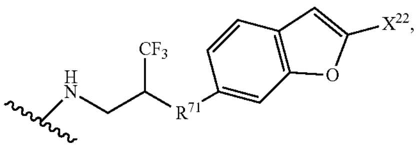
-continued
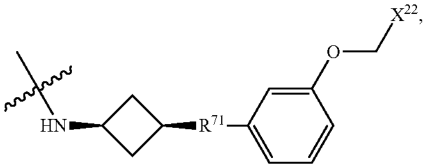
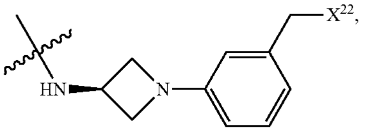
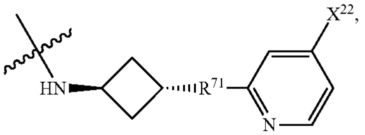
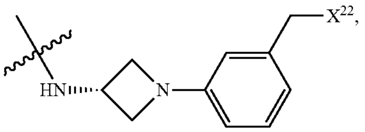
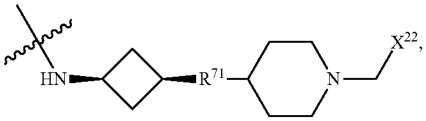
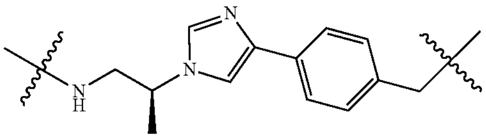
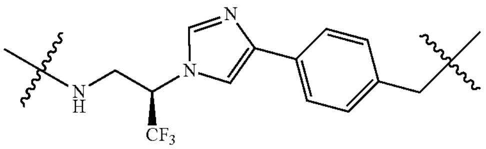
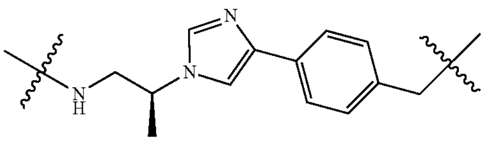
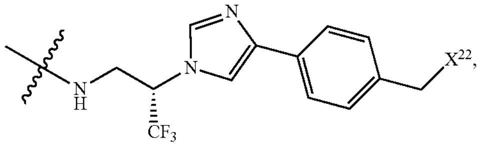
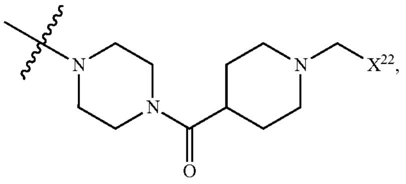
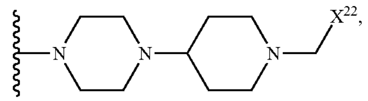
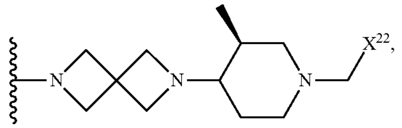

-continued
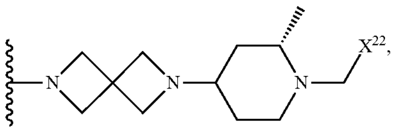
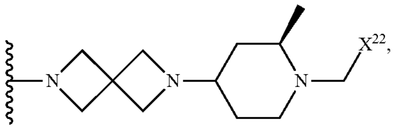
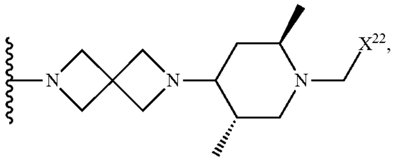
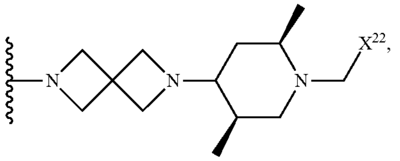
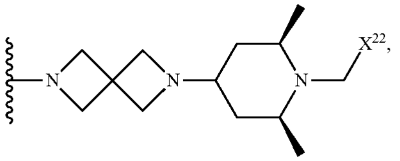
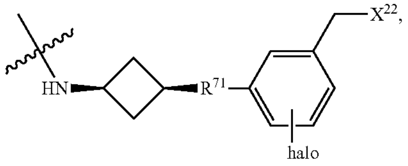
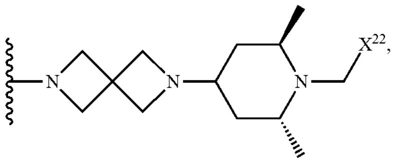
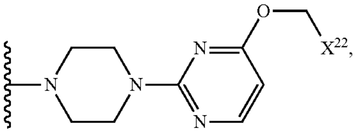
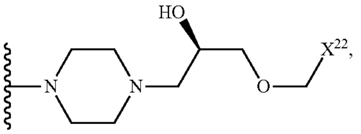
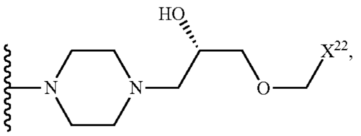
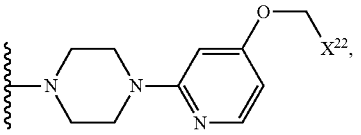
-continued
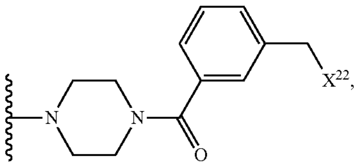
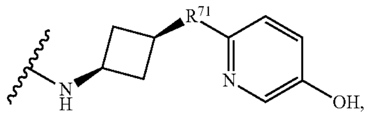
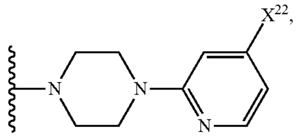
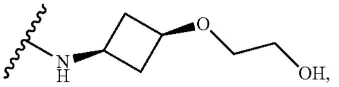
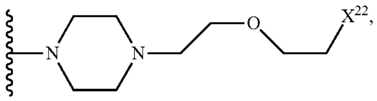
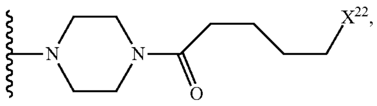
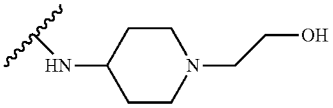
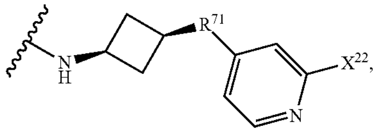
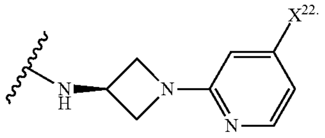
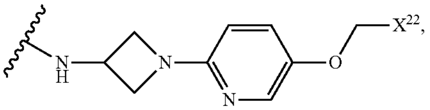
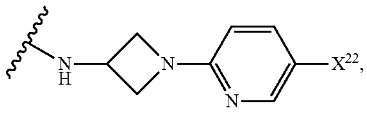
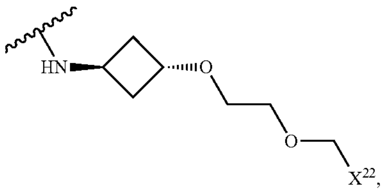

-continued
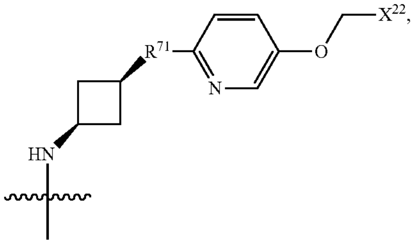
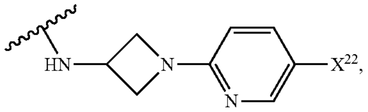
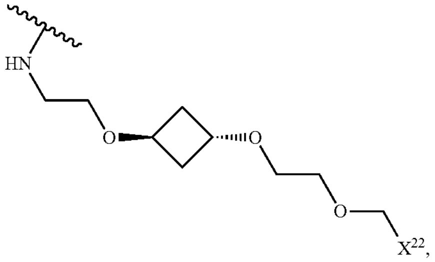
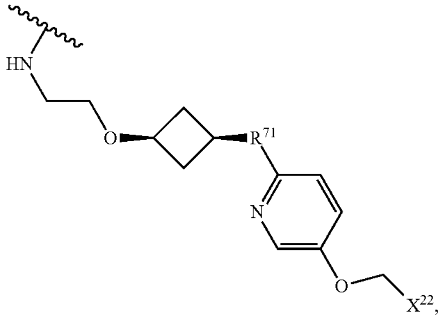
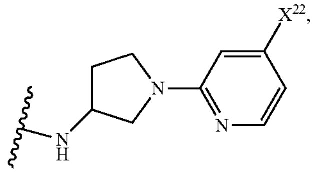
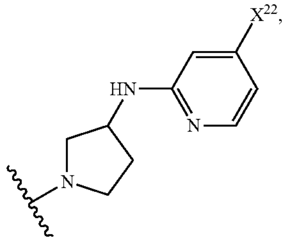
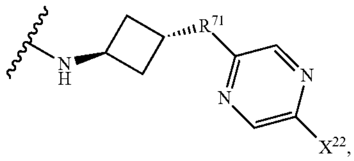
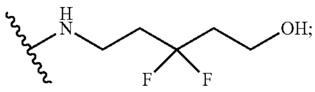
wherein $R^{71}$ is —O—, —NH, Nalkyl, heteroaliphatic, aliphatic, or —NMe.
In additional embodiments, "Tail" is selected from:
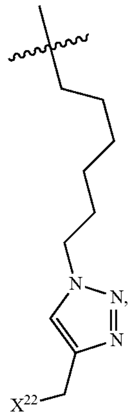
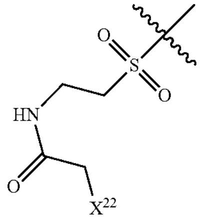
,
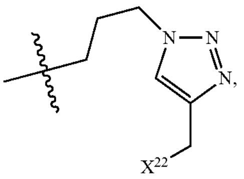
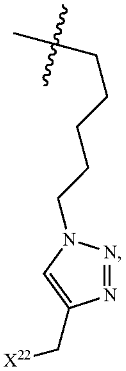
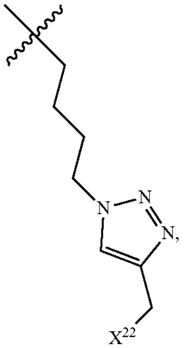
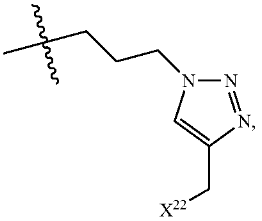
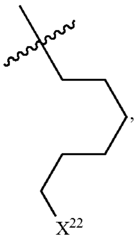
,
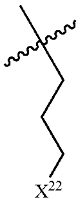
,
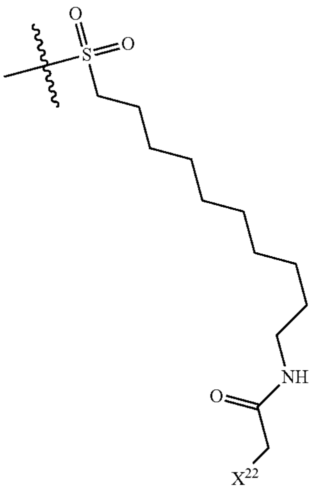
, -continued
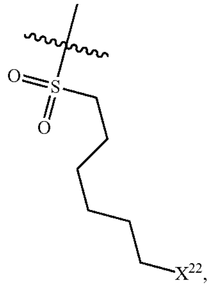
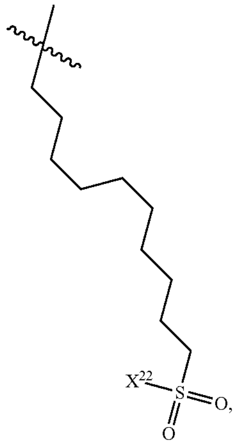
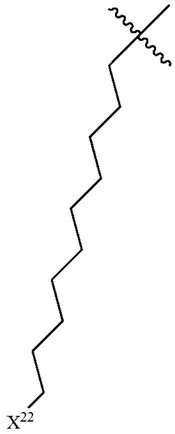
,
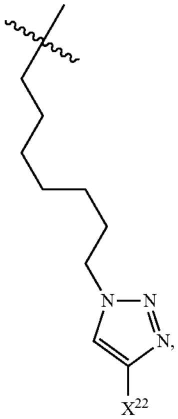
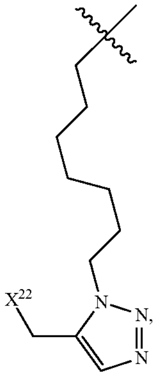
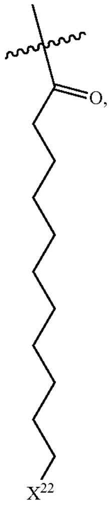
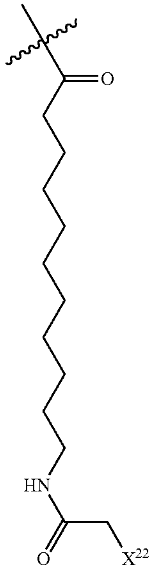
,
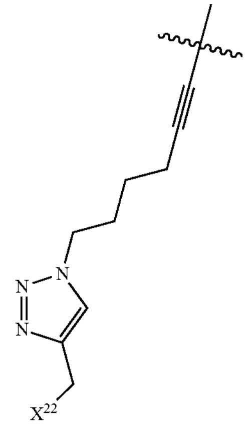
,
-continued
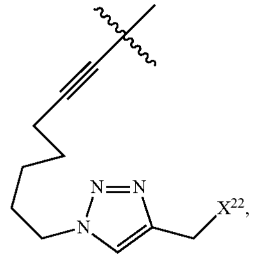
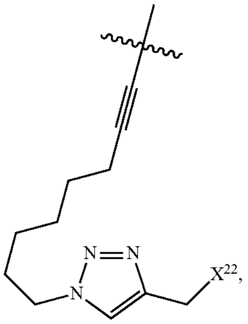
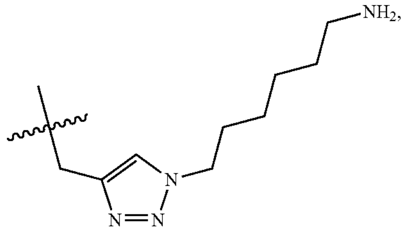
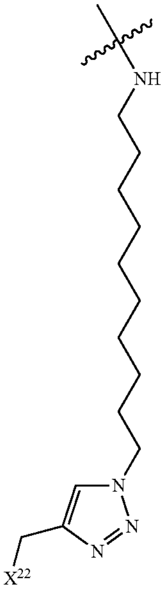
,
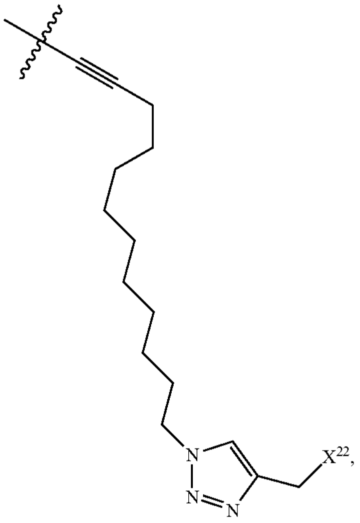
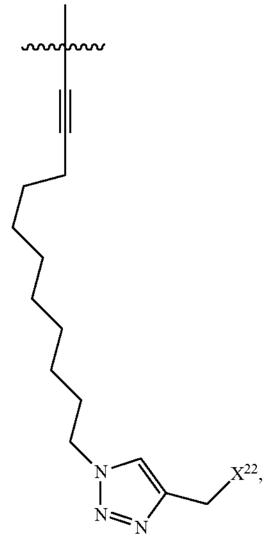
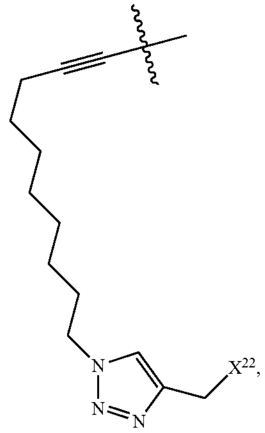

-continued
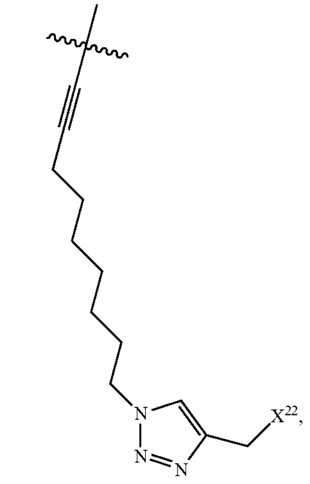
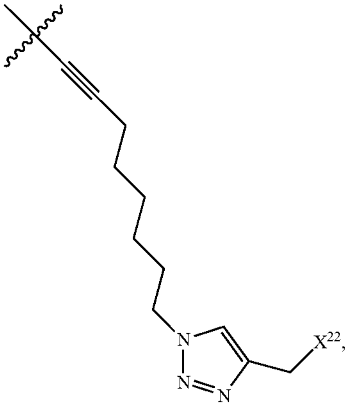
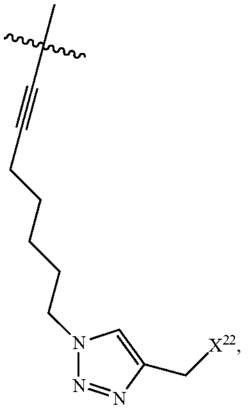
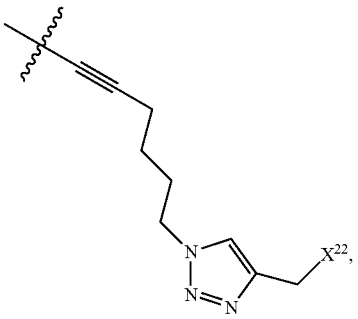
-continued
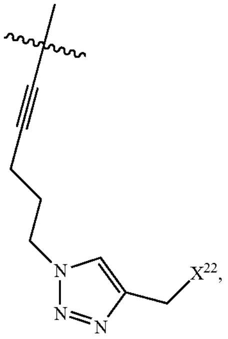
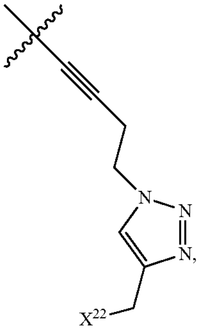
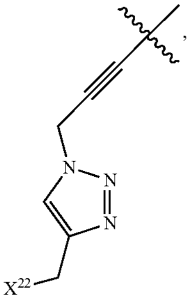
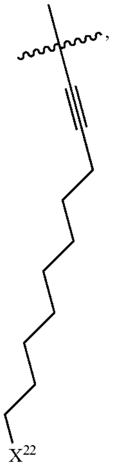
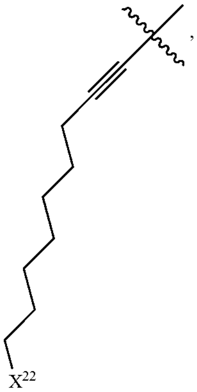
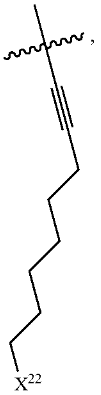
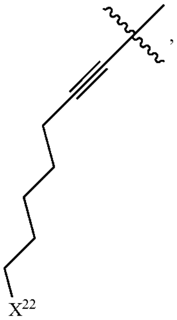
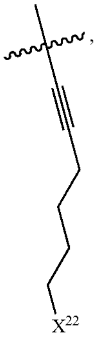
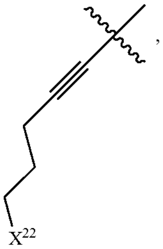
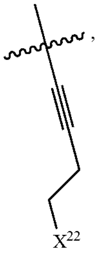
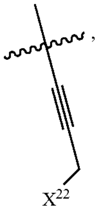
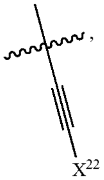
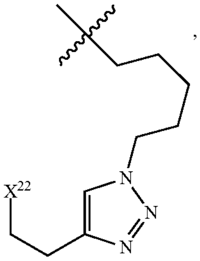

-continued
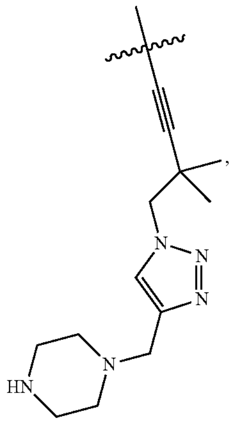
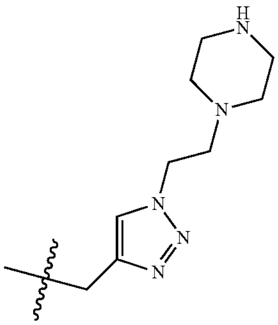
,
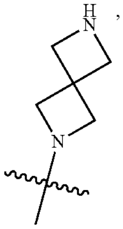
,
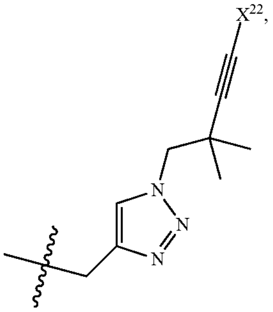
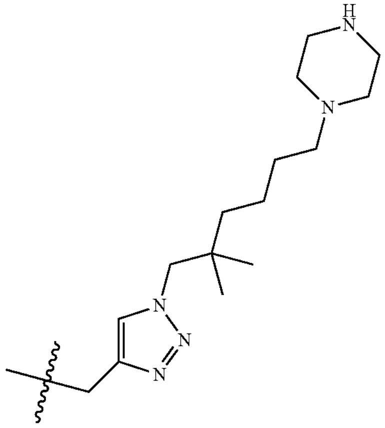
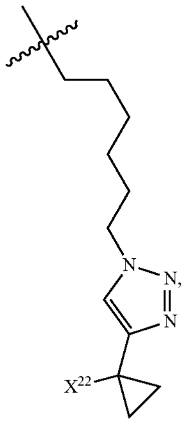
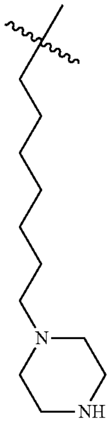
,
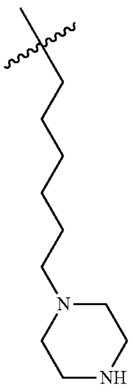
,
-continued
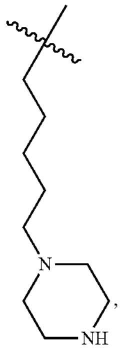
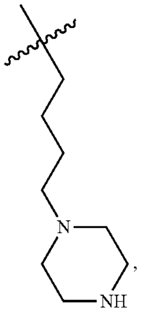
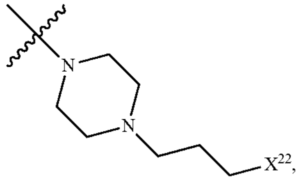
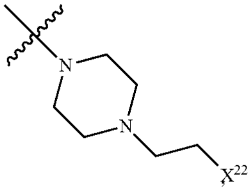
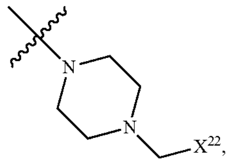
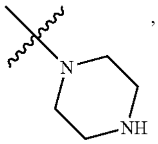
,
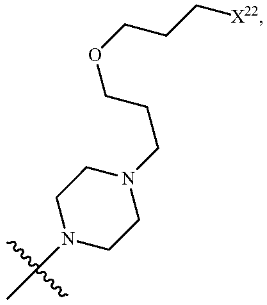
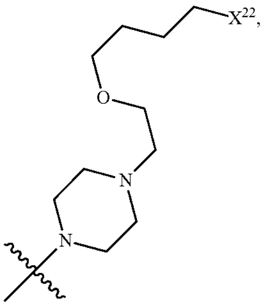
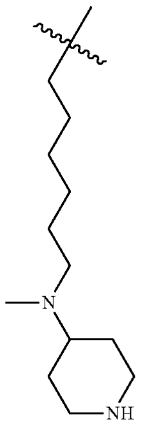
,
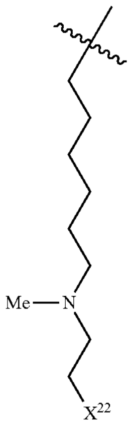

-continued
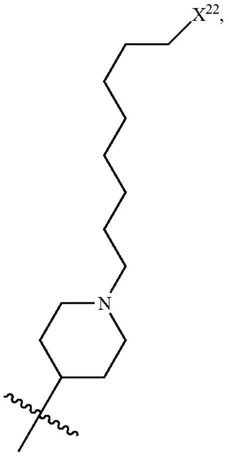
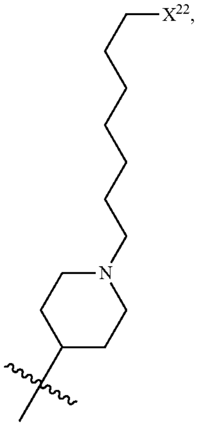
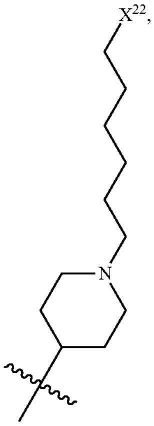
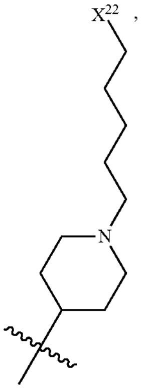
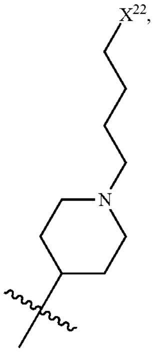
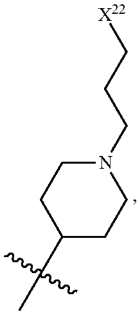
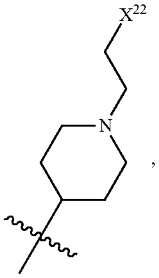
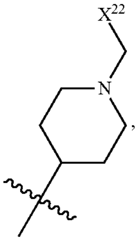
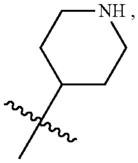
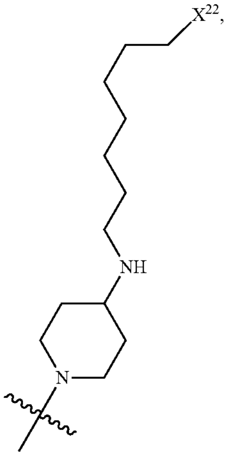
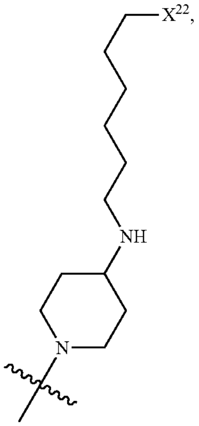
-continued
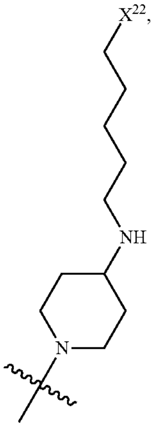
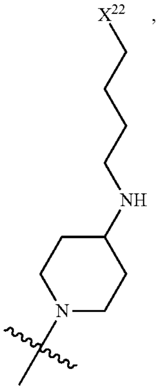
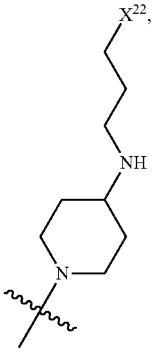
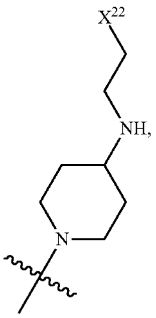
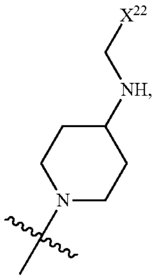
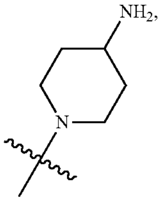
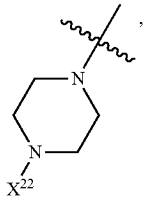
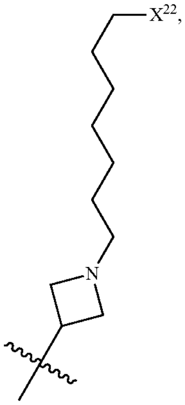
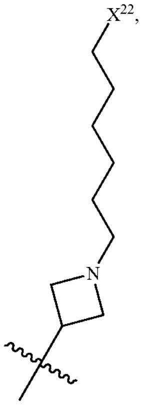
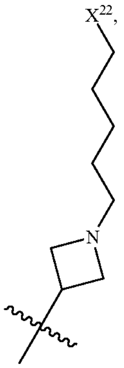
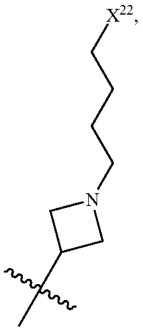
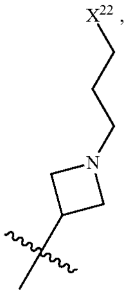
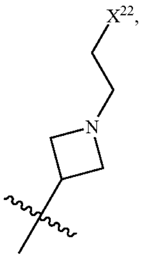

-continued
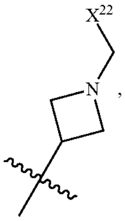
,
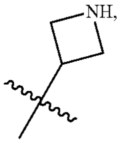
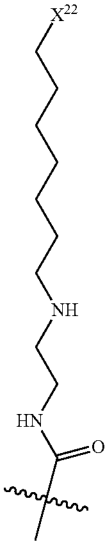
,
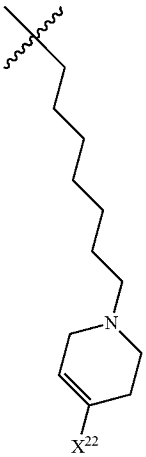
,
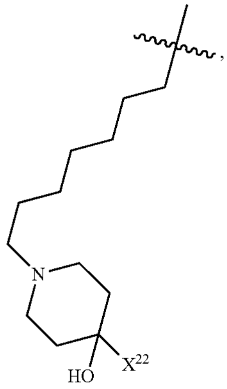
,
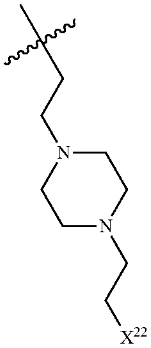
,
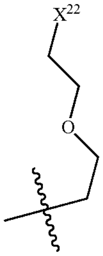
,
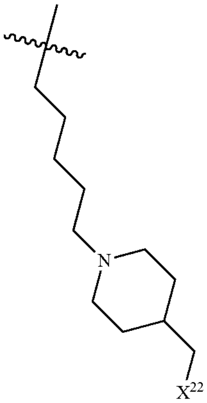
-continued
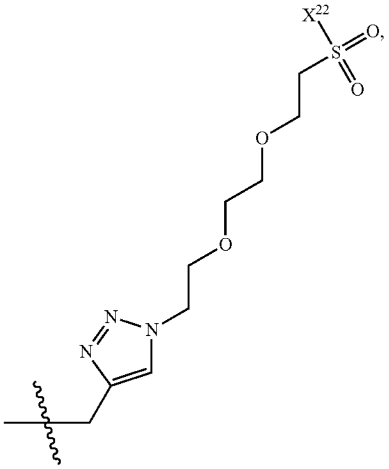
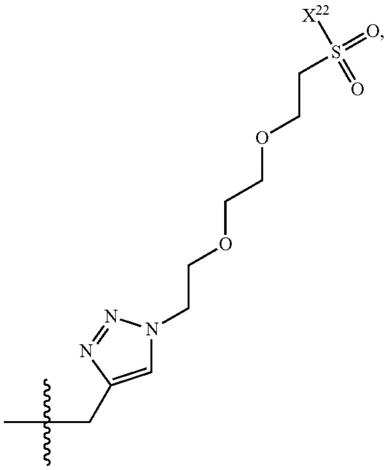
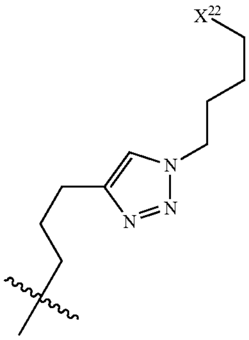
,
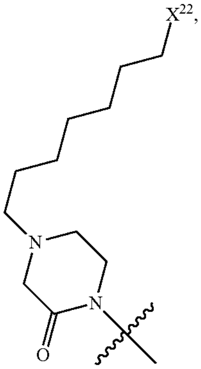

-continued
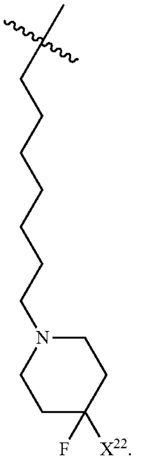
In additional embodiments, “Tail” is selected from:
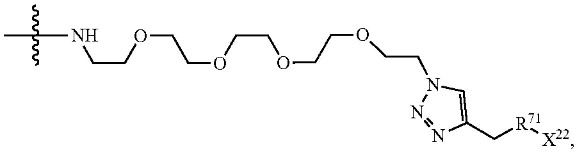
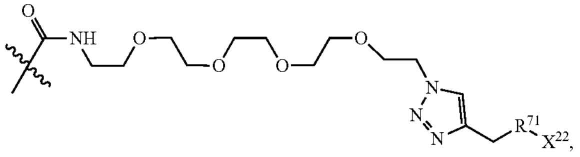
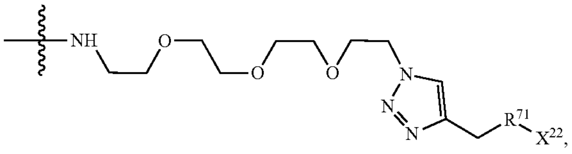
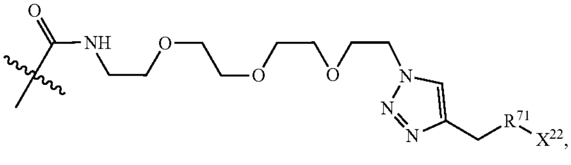
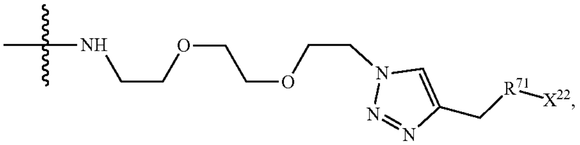
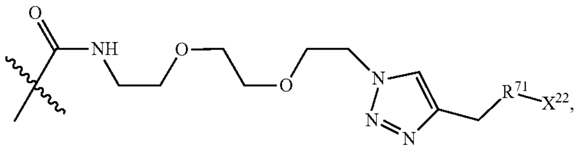
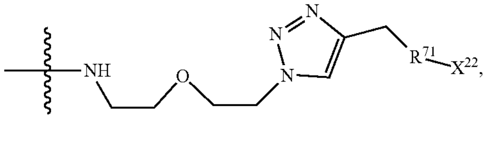
and
-continued
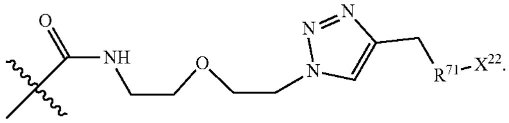
In additional embodiments, “Tail” is selected from:
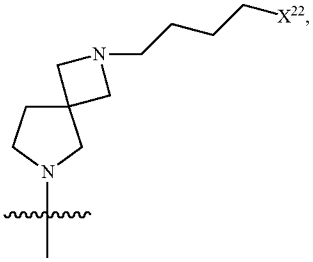
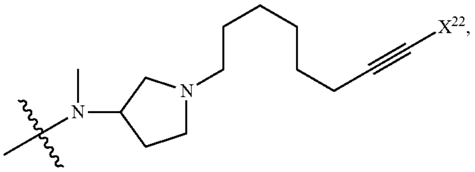
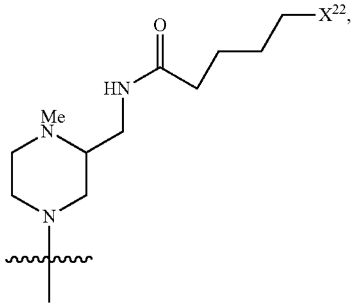
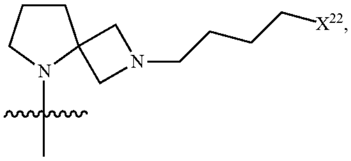
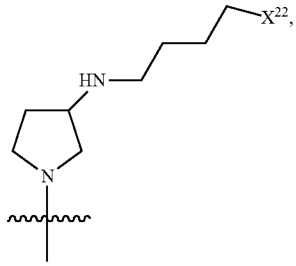
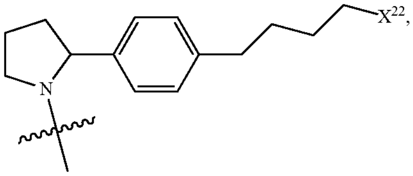

-continued
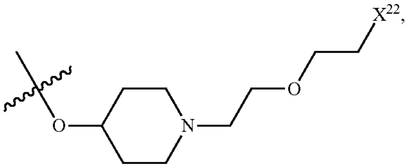
,
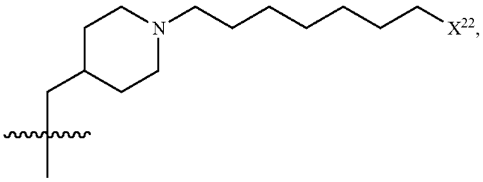
,
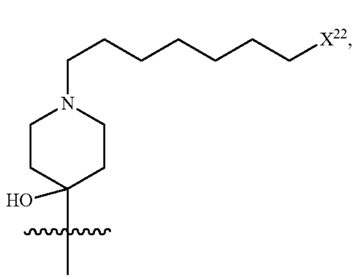
,
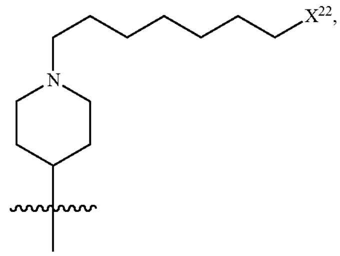
,
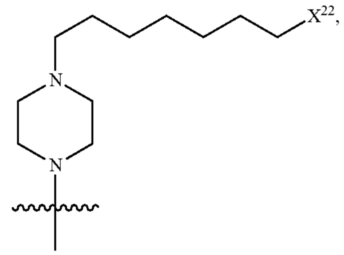
, and
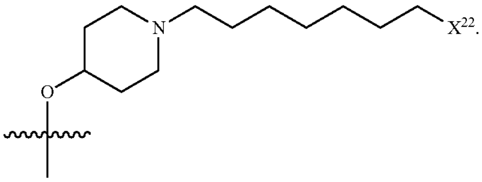
.
In additional embodiments, "Tail" is selected from:
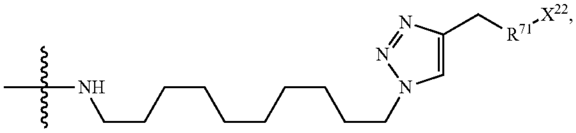
,
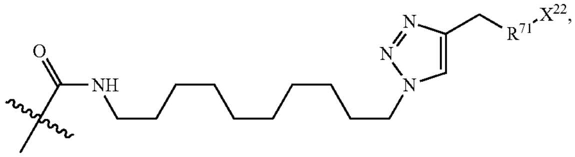
,
-continued
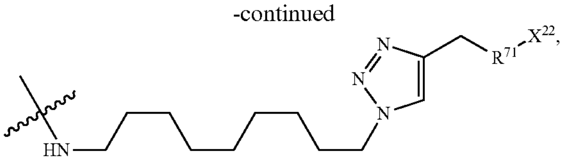
,
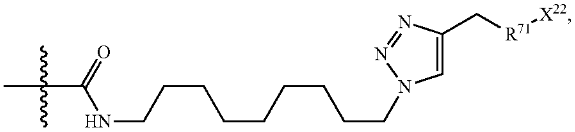
,
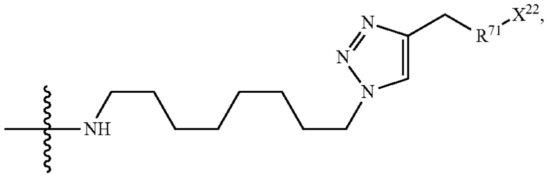
,
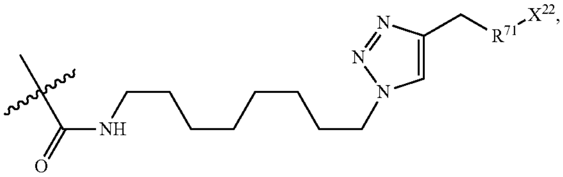
,
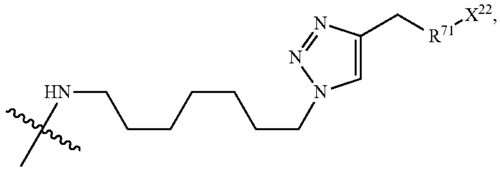
,
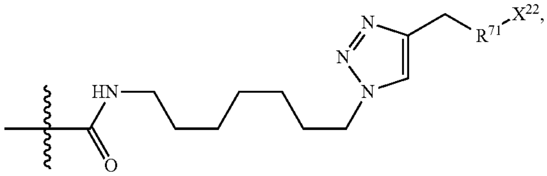
,
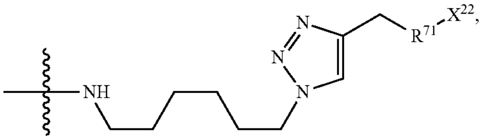
,
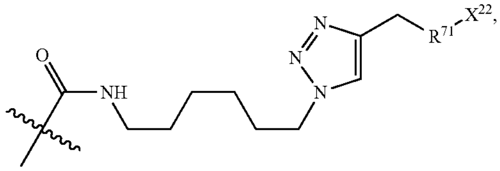
,
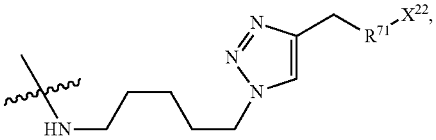
,
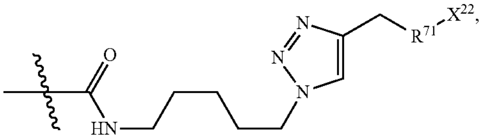
,
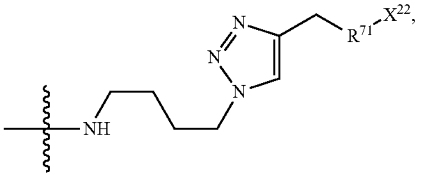
, and -continued
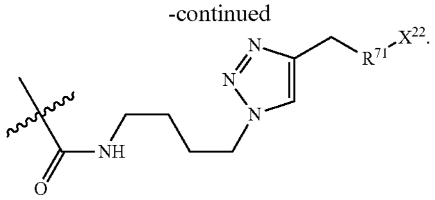
In additional embodiments, “Tail” is selected from:
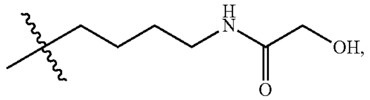
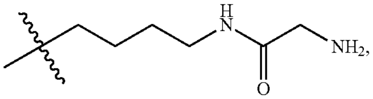
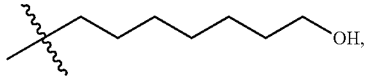
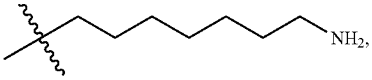
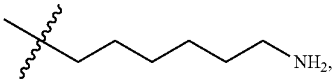
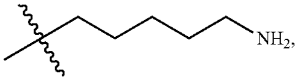
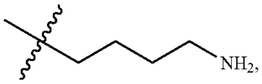 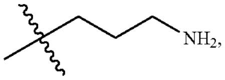
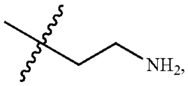
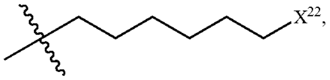
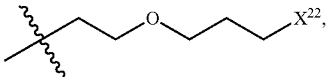
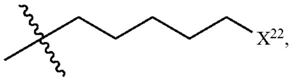
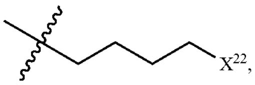
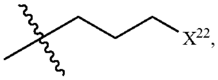 and 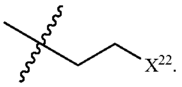
In the above embodiments $X^{22}$ is selected such that a compound sufficiently stable or the intended use results.
In additional embodiments, “Tail” is selected from:
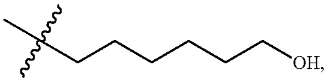
-continued
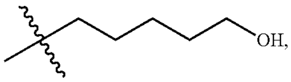
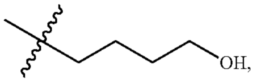
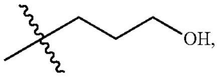 and
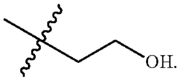
In certain embodiments, “Tail” is selected from:
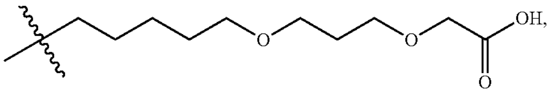
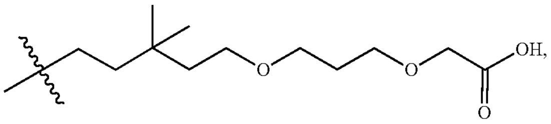
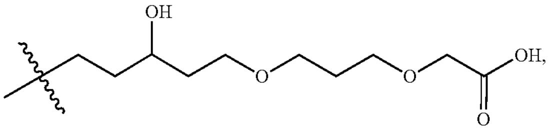
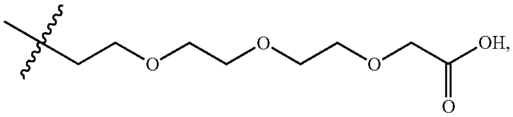
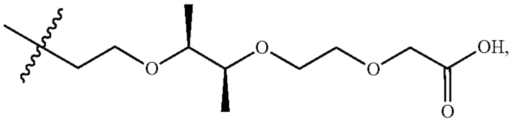
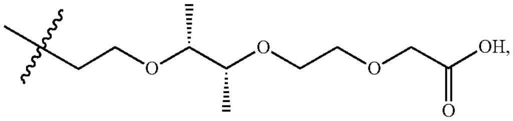
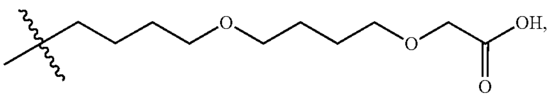
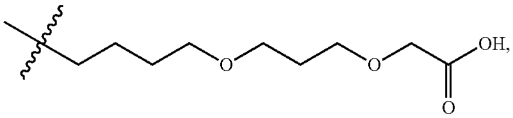
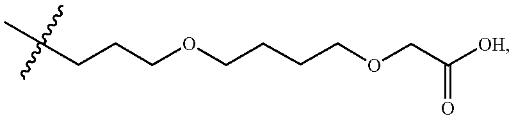

In certain embodiments "Tail" is selected from:
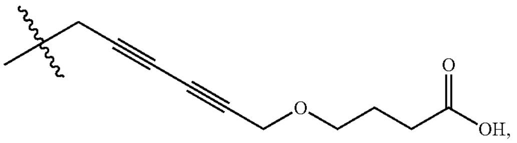
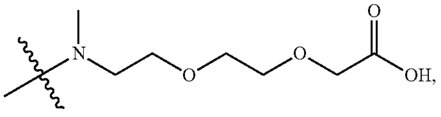
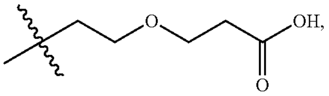
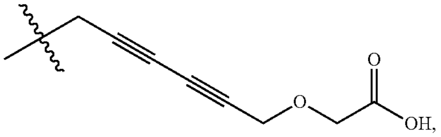
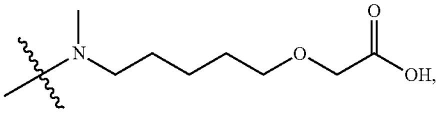
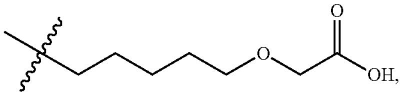
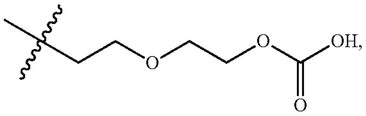
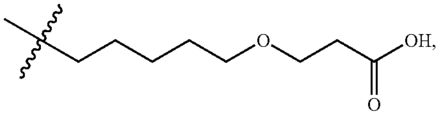
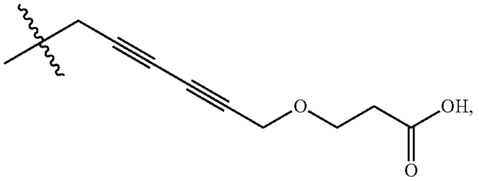
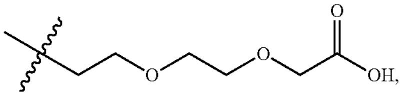
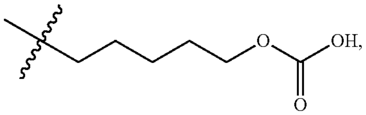
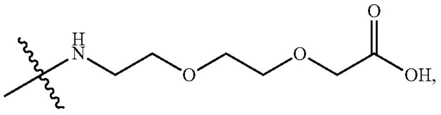
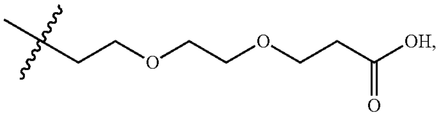
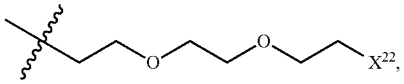
-continued
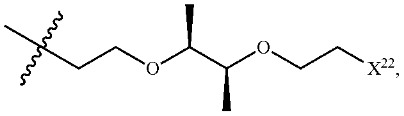
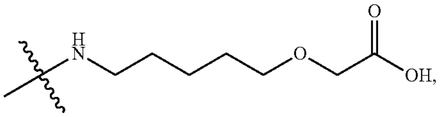
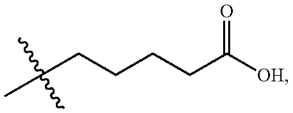
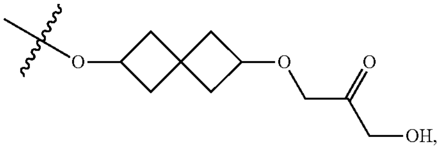
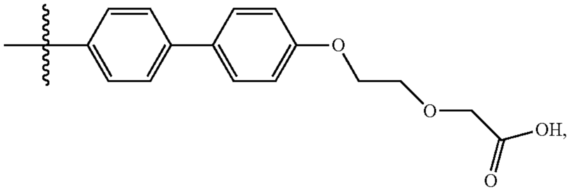
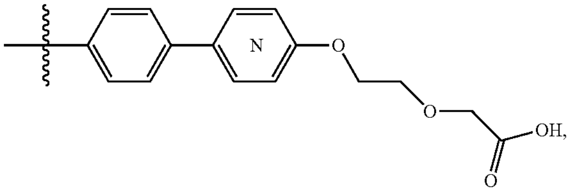
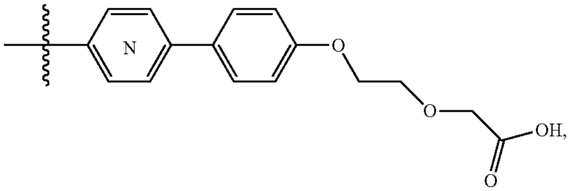
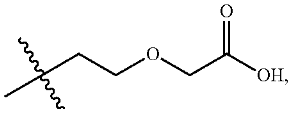
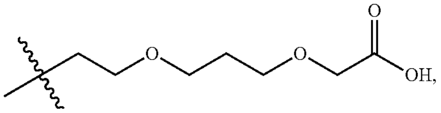
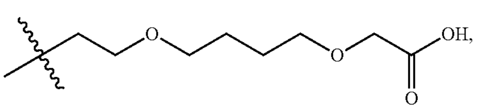
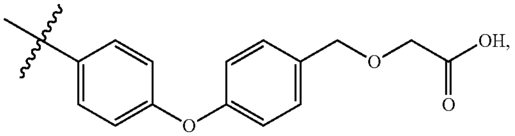
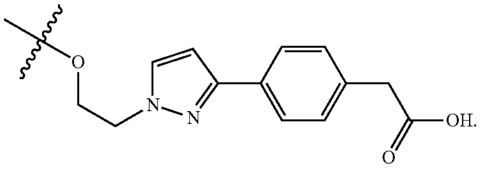

In the above structures
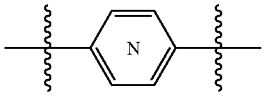
represents
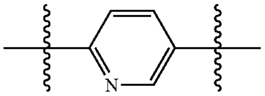
and
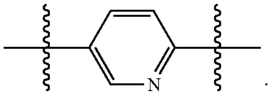
.
In certain embodiments, “Tail” can be a 4-24 carbon atom linear chains, wherein one or more the carbon atoms in the linear chain can be replaced or substituted with oxygen, nitrogen, amide, fluorinated carbon, etc., such as the following:
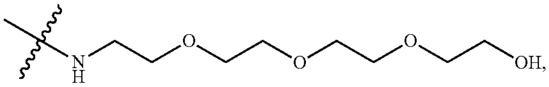
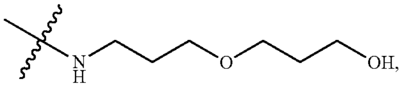
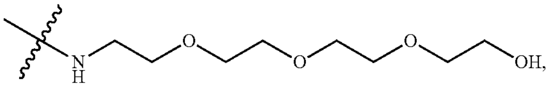
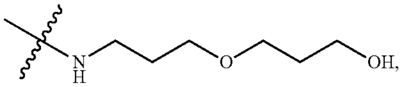
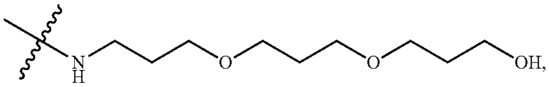
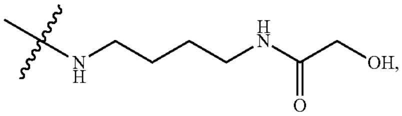
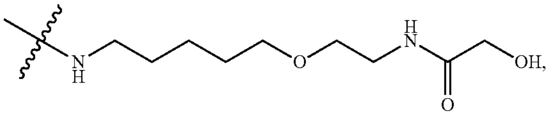
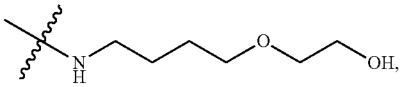
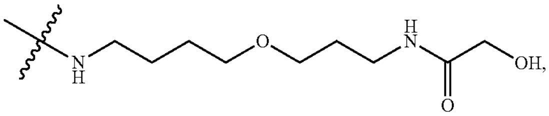
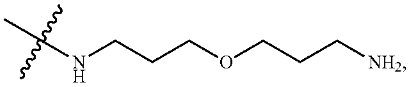
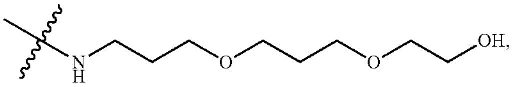
-continued
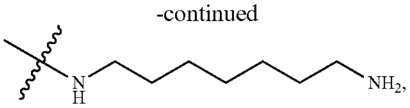
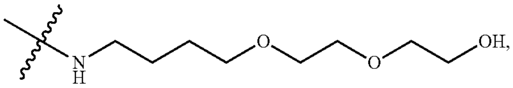
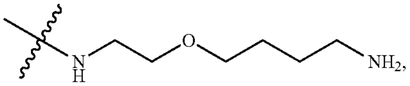
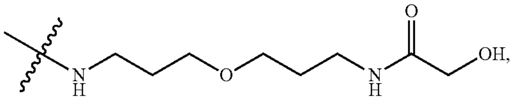
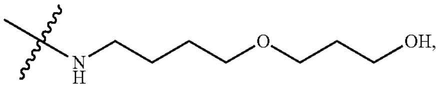
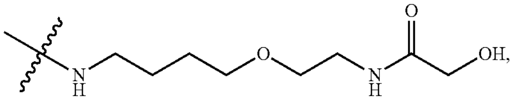
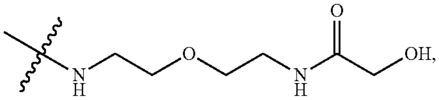
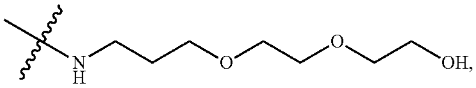
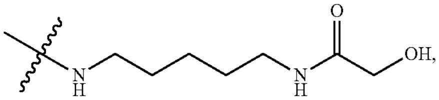
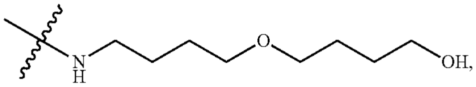
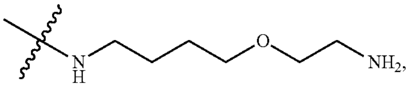
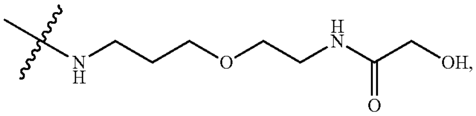
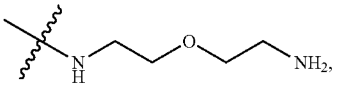
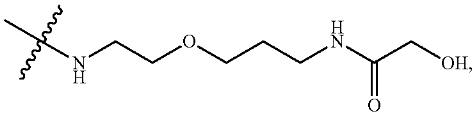
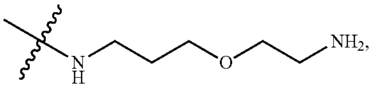
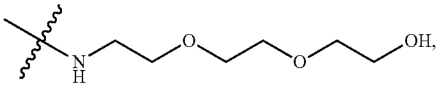
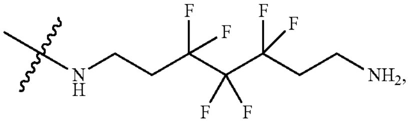
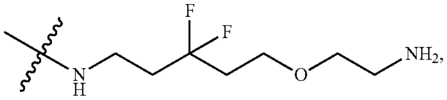

-continued

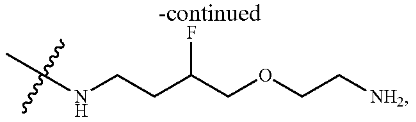,

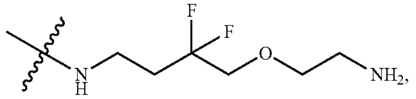,

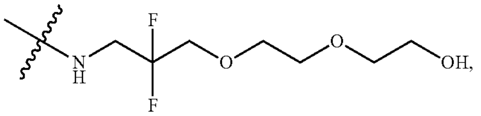,

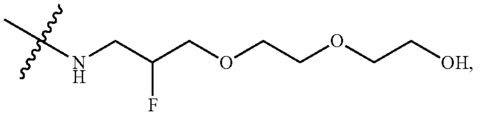,

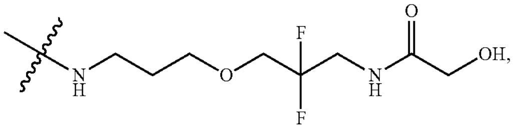,

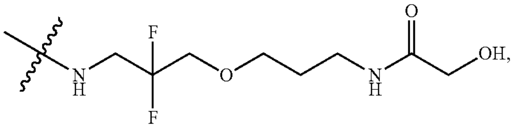,

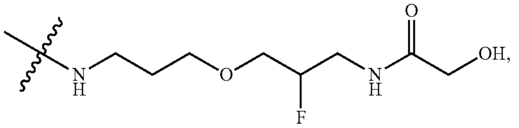,

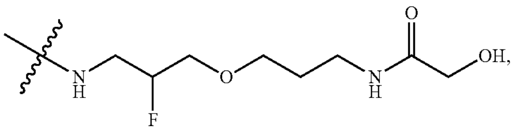,

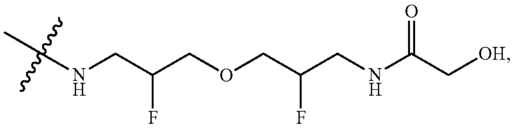,

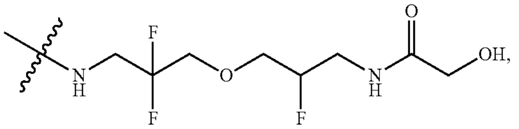,

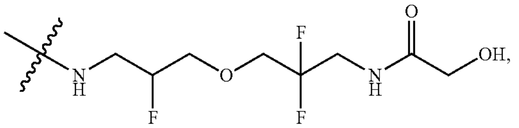,

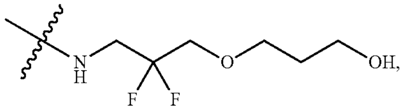,

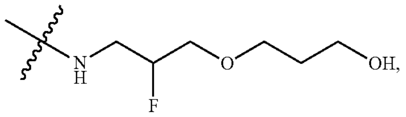,

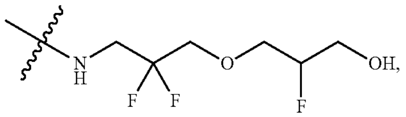,

-continued

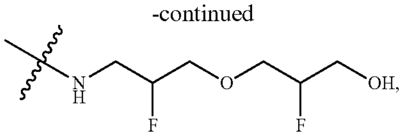,

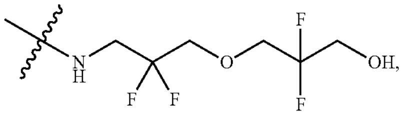,

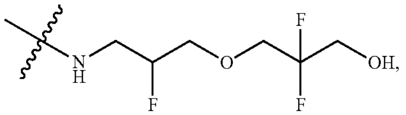,

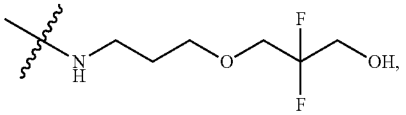,

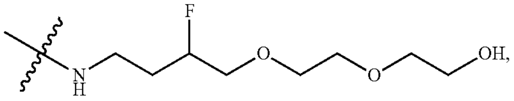, and

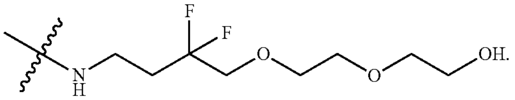.

In certain embodiments, "Tail" can be a nonlinear chain, and can be, or include, aliphatic or aromatic or heteroaromatic cyclic moieties.

In certain embodiments, "Tail" may include contiguous, partially contiguous or non-contiguous ethylene glycol unit groups ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units, for example, 1, 2, 3, 4, 6, 6, 7, 8, 9, 10, 11 or 12 ethylene glycol units.

In certain embodiments, "Tail" may have 1, 2, 3, 4, 5, 6, 7, 8, 9, 10, 11, 12, 13, 14, or 15 fluorine substituents. In another embodiment "Tail" is perfluorinated. In yet another embodiment "Tail" is a partially or fully fluorinated poly ether. Nonlimiting examples of fluorinated "Tail" moieties include:

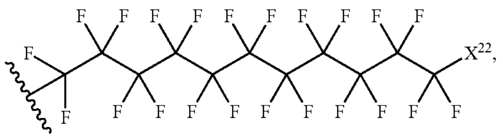,

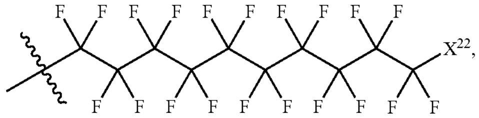,

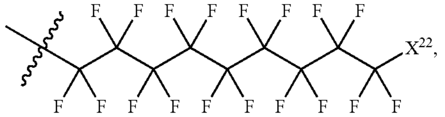,

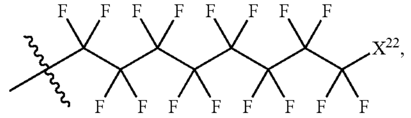,

-continued

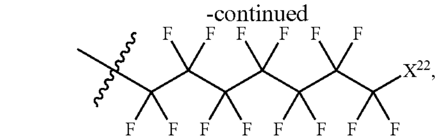,

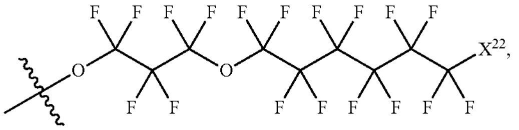,

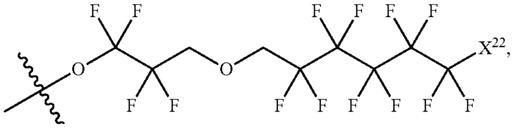,

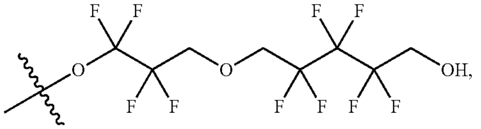,

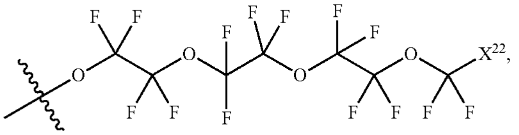,

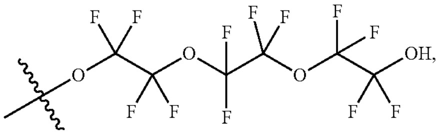,

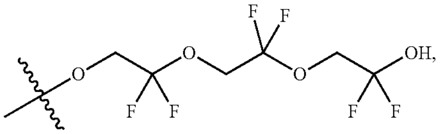,

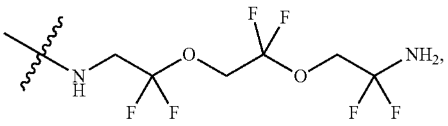, and

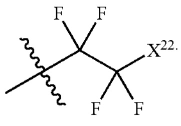.

Representative examples of $X^{22}$ include:

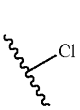, 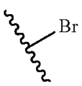, 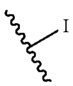, 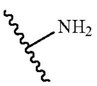, 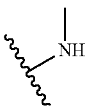,

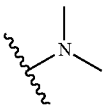, 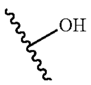, 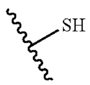, 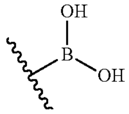,

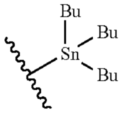, 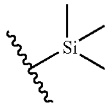,

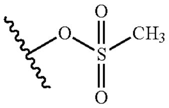, 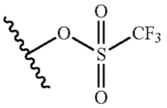,

-continued

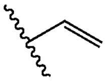, 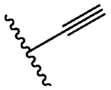, 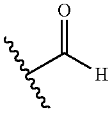,

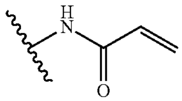 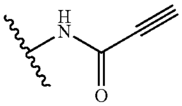,

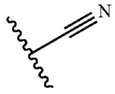, 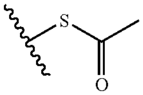,

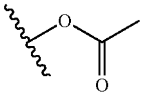, and 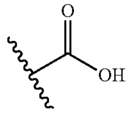,

In certain embodiments, the length can be adjusted as desired or as found necessary for the desired application.

IV. Methods of Treatment

The compounds of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII (1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) can be used in an effective amount to treat a host, including a human, in need thereof, optionally in a pharmaceutically acceptable carrier to treat any of the disorders described herein.

The terms "treat", "treating", and "treatment", etc., as used herein, refer to any action providing a benefit to a patient for which the present compounds may be administered, including the treatment of any disease state or condition which is modulated through the protein to which the present compounds bind. Illustrative non-limiting disease states or conditions, including cancer, which may be treated using compounds according to the present invention are set forth hereinabove.

The term "disease state or condition" when used in connection with a Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII (1)-a to XIII(1)-i, or Formula XIV(1) compound for example, refers to any therapeutic indication which can be treated by decreasing the activity of cereblon or a cereblon-containing E3 Ligase, including but not limited to uses known for the cereblon binders thalidomide, pomalidomide or lenalidomide. Nonlimiting examples of uses for cereblon binders are multiple myeloma, a hematological disorder such as myelodysplastic syndrome, cancer, tumor, abnormal cellular proliferation, HIV/AIDS, HBV, HCV, hepatitis, Crohn's disease, sarcoidosis, graft-versus-host disease, rheumatoid arthritis, Behcet's disease, tuberculosis, and myelofibrosis. Other indications include a myelo- or lymphoproliferative disorder such as B- or T-cell lymphomas, Waldenstrom's macroglobulinemia, Wiskott-Aldrich syndrome, or a post-transplant lymphoproliferative disorder; an immune disorder, including autoimmune disorders such as Addison disease, Celiac disease, dermatomyositis, Graves disease, thyroiditis, multiple sclerosis, pernicious anemia, arthritis, and in particular rheumatoid arthritis, lupus, or type I diabetes; a disease of cardiologic malfunction, including hypercholesterolemia; an infectious disease, including viral and/or bacterial infection, as described generally herein; an inflammatory condition, including asthma, chronic peptic ulcers, tuberculosis, rheumatoid arthritis, periodontitis and ulcerative colitis.

In certain embodiments, the present invention provides for administering a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) to a patient, for example, a human, having an infectious disease, wherein the therapy targets a protein of the infectious agent, optionally in combination with another bioactive agent. The disease state or condition may be a disease caused by a microbial agent or other exogenous agent such as a virus (as non-limiting examples, HIV, HBV, HCV, HSV, HPV, RSV, CMV, Ebola, Flavivirus, Pestivirus, Rotavirus, Influenza, Coronavirus, EBV, viral pneumonia, drug-resistant viruses, Bird flu, RNA virus, DNA virus, adenovirus, poxvirus, Picornavirus, Togavirus, Orthomyxovirus, Retrovirus or Hepadnovirus), bacteria (Gram-negative, Gram-positive, fungus, protozoa, helminth, worms, prion, parasite, or other microbe or may be a disease state, which is caused by overexpression of a protein, which leads to a disease state and/or condition.

In certain embodiments, the condition treated with a compound of the present invention is a disorder related to abnormal cellular proliferation. Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells, and to be caused by autoantibodies produced against collagen and IgE.

Other disorders that can include an abnormal cellular proliferative component include Bechet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

Cutaneous contact hypersensitivity and asthma are just two examples of immune responses that can be associated with significant morbidity. Others include atopic dermatitis, eczema, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Immunologically mediated leukocyte infiltration also occurs at sites other than the skin, such as in the airways in asthma and in the tear producing gland of the eye in keratoconjunctivitis sicca.

In one non-limiting embodiment compounds of the present invention are used as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions. The novel method may also be useful in reducing the infiltration of skin by malignant leukocytes in diseases such as mycosis fungoides. These compounds can also be used to treat an aqueous-deficient dry eye state (such as immune mediated keratoconjunctivitis) in a patient suffering therefrom, by administering the compound topically to the eye.

Disease states of conditions which may be treated using compounds according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease 1 (PKD1) or 2 (PKD2) Prader-Willi syndrome, Sickle-cell disease, Tay-Sachs disease, Turner syndrome.

Further disease states or conditions which may be treated by compounds according to the present invention include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barre syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present invention include aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alstrom syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome #arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Boumeville disease (tuberous sclerosis), prion disease, Birt-Hogg-Dube syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic *porphyria*), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia-familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysyl-hydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alstrom syndrome), Vrolik disease, Waardenburg syndrome, Warburg Sjo Fledelius Syndrome, Weissenbacher-Zweymiiller syndrome, Wolf-Hirschhorn syndrome, Wolff Periodic disease, Weissenbacher-Zweymiiller syndrome and Xeroderma pigmentosum, among others.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infdtrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+ DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

In one embodiment the cancer is NUT midline cardinioma.

In one embodiment the cancer is adenoid cystic carcinoma.

The term "bioactive agent" is used to describe an agent, other than a compound according to the present invention, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

V. Combination Therapy

The compounds of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII (1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) can be used in an effective amount alone or in combination to treat a host such as a human with a disorder as described herein.

The disclosed compounds described herein can be used in an effective amount alone or in combination with another compound of the present invention or another bioactive agent to treat a host such as a human with a disorder as described herein.

The term "bioactive agent" is used to describe an agent, other than the selected compound according to the present invention, which can be used in combination or alternation with a compound of the present invention to achieve a desired result of therapy. In one embodiment, the compound of the present invention and the bioactive agent are administered in a manner that they are active in vivo during overlapping time periods, for example, have time-period overlapping Cmax, Tmax, AUC or other pharmacokinetic parameter. In another embodiment, the compound of the present invention and the bioactive agent are administered to a host in need thereof that do not have overlapping pharmacokinetic parameter, however, one has a therapeutic impact on the therapeutic efficacy of the other.

In one aspect of this embodiment, the bioactive agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

VI. Pharmaceutical Compositions

The compounds of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII (1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) as disclosed herein can be administered as the neat chemical, but are more typically administered as a pharmaceutical composition, that includes an effective amount for a host, typically a human, in need of such treatment for any of the disorders described herein. Accordingly, the disclosure provides pharmaceutical compositions comprising an effective amount of compound or pharmaceutically acceptable salt together with at least one pharmaceutically acceptable carrier for any of the uses described herein. The pharmaceutical composition may contain a compound or salt as the only active agent, or, in an alternative embodiment, the compound and at least one additional active agent.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least 0.1, 1, 5, 10, 25, 50, 100, 200, 250, 300, 400, 500, 600, 700, or 750 mg of active compound, or its salt. The pharmaceutical composition may also include a molar ratio of the active compound and an additional active agent. For example the pharmaceutical composition may contain a molar ratio of about 0.5:1, about 1:1, about 2:1, about 3:1 or from about 1.5:1 to about 4:1 of an anti-inflammatory or immunosuppressing agent. Compounds disclosed herein may be administered orally, topically, parenterally, by inhalation or spray, sublingually, via implant, including ocular implant, transdermally, via buccal administration, rectally, as an ophthalmic solution, injection, including ocular injection, intravenous, intra-aortal, intracranial, subdermal, intraperitioneal, subcutaneous, transnasal, sublingual, or rectal or by other means, in dosage unit formulations containing conventional pharmaceutically acceptable carriers. For ocular delivery, the compound can be administered, as desired, for example, via intravitreal, intrastromal, intracameral, sub-tenon, sub-retinal, retro-bulbar, peribulbar, suprachorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device.

The pharmaceutical composition may be formulated as any pharmaceutically useful form, e.g., as an aerosol, a cream, a gel, a pill, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions can contain any amount of active compound that achieves the desired result, for example between 0.1 and 99 weight % (wt. %) of the compound and usually at least about 5 wt. % of the compound. Some embodiments contain from about 25 wt. % to about 50 wt. % or from about 5 wt. % to about 75 wt. % of the compound.

Formulations suitable for rectal administration are typically presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

The compounds described herein and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds described herein and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of the present invention or a pharmaceutically acceptable salt thereof and a therapeutically inert carrier are also provided by the present invention, as is a process for their production, which comprises bringing one or more compounds of Formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general Formula XIV or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of Formula XIV. Examples of compositions according to the invention are:

Example A

Tablets of the following composition are manufactured in the usual manner:

TABLE 1 possible tablet composition

| ingredient | mg/tablet 5 | 25 | 100 | 500 |
|---|---|---|---|---|
| Compound of Formula XIV | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 2 possible capsule ingredient composition

| ingredient | mg/capsule 5 | 25 | 100 | 500 |
|---|---|---|---|---|
| Compound of Formula XIV | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of Formula XIV, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 3 possible soft gelatin capsule ingredient composition

| ingredient | mg/capsule |
|---|---|
| Compound of Formula XIV | 5 |
| Yellow wax | 8 |
| Hydrogenated Soya bean oil | 8 |
| Partially hydrogenated plant oils | 34 |
| Soya bean oil | 110 |
| Total | 165 |

TABLE 4 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of Formula XIV is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 5

| possible suppository composition | |
|---|---|
| ingredient | mg/supp. |
| Compound of Formula XIV | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of Formula XIV is added thereto and stirred until it has dispersed completely. The mixture is poured into suppository molds of suitable size, left to cool; the suppositories are then removed from the molds and packed individually in wax paper or metal foil.

Example D

Injection solutions of the following composition are manufactured:

TABLE 6

| possible injection solution composition | |
|---|---|
| ingredient | mg/injection solution. |
| Compound of Formula XIV | 3 |
| Polyethylene Glycol 400 | 150 |
| acetic acid | q.s. ad pH 5.0 |
| water for injection solutions | ad 1.0 ml |

Manufacturing Procedure

The compound of Formula XIV is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 7

| possible sachet composition | |
|---|---|
| ingredient | mg/sachet |
| Compound of Formula XIV | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of Formula XIV is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

VII. Use of Compounds

The compounds of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) of the present invention bind to the ubiquitously expressed E3 ligase protein cereblon (CRBN) and alter the substrate specificity of the CRBN E3 ubiquitin ligase complex, resulting in breakdown of intrinsic downstream proteins. The present compounds are thus useful for the treatment or prophylaxis of various cancers.

In one aspect, the present invention provides compounds of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) as described herein for use as therapeutically active substance.

In a further aspect, the present invention provides compounds of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) as defined herein, for use in the treatment or prophylaxis of cancer.

In a further aspect, the present invention provides the use of a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) as defined herein for the treatment or prophylaxis of cancer.

In a further aspect, the present invention provides a method of treating or preventing cancer, comprising administering a therapeutically effective amount of a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to H(1)-k, Formula III(1), Formulas IV(1)-a to IV(1)-j, Formula V(1), Formula VI(1), Formulas VII(1)-a to VII (1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) as defined herein to a subject.

In a further aspect, the present invention provides the use of a compound of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII(1)-i, Formulas IX(1)-a to IX(1)-j, Formulas X(1)-a to X(1)-i, Formulas XI(1)-a to XI(1)-i, Formula XII(1), Formulas XIII (1)-a to XIII(1)-i, or Formula XIV(1) as defined herein for the manufacture of a medicament for the treatment or prophylaxis of cancer.

The compounds of Formula I, Formulas II-a to II-k, Formula III, Formulas IV-a to IV-j, Formula V, Formula VI, Formulas VII-a to VII-e, Formulas VIII-a to VIII-i, Formulas IX-a to IX-j, Formulas X-a to X-i, Formulas XI-a to XI-i, Formula XII, Formulas XIII-a to XIII-i, Formula XIV, Formula I(1), Formulas II(1)-a to II(1)-k, Formula III(1), Formulas IV(1)-a to IV(1)-j, Formula V(1), Formula VI(1), Formulas VII(1)-a to VII(1)-e, Formulas VIII(1)-a to VIII (1)-i, Formulas IX(1)-a to IX(1)-j, Formulas X(1)-a to X(1)-i, Formulas XI(1)-a to XI(1)-i, Formula XII(1), Formulas XIII(1)-a to XIII(1)-i, or Formula XIV(1) may also be used to prepare bifunctional degrader compounds by linking them to a protein-targeting moiety that binds to a target protein or to a target polypeptide, in analogy to the bifunctional compounds which have been described e.g. in WO2013020557, WO2013063560, WO 2013106643, WO2015160845, WO2016011906, WO2016105518, WO2017007612, WO2017024318, and WO2017117473.

VIII. General Synthesis and Processes of Manufacture

The compounds described herein can be prepared by methods known by those skilled in the art. In one non-limiting example the disclosed compounds can be made by the schemes provided below.

The preparation of compounds of the present invention may be carried out in sequential or convergent synthetic routes. Syntheses of the compounds of the invention are shown in the following schemes 1-3 and in the description of 27 specific examples. The skills required for carrying out the reaction and purification of the resulting products are known to those skilled in the art. The substituents and indices used in the following description of the processes have the significance given herein before unless indicated to the contrary.

In more detail, the compounds described herein can be manufactured by the methods given below, by the methods given in the examples or by analogous methods. Appropriate reaction conditions for the individual reaction steps are known to a person skilled in the art. The reaction sequence is not limited to the one displayed in schemes 1-3, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1

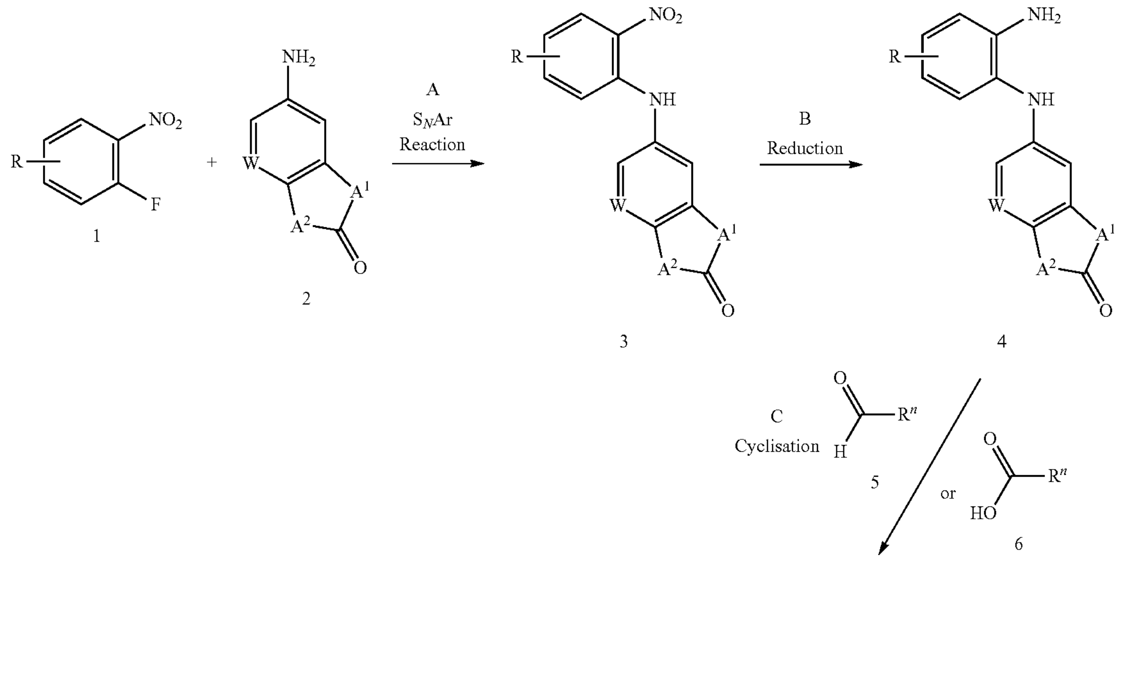

-continued

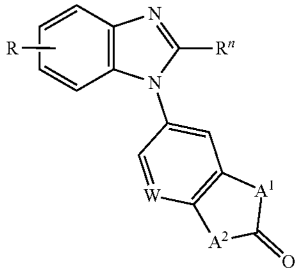

7

R = H, —C(O)NHMe, —C(O)OMe
W, $A^1$, $A^2$ = as defined herein
$R''$ = as defined herein Step A: Nitro-amino-arene compound 3 can be obtamed by an aromatic nucleophilic substitution (SNAT) reaction between a 1,2-fluoro-nitro-arene 1 and an aromatic amine compound 2.

Examples of suitable 1,2-fluoro-nitro-arenes 1 include, but are not limited to, l-fluoro-2-nitrobenzene (CAS 1493-27-2), 4-fluoro-N-methyl-3-nitrobenzamide (CAS 475216-25-2) and methyl 4-fluoro-3-nitro-benzoate (CAS 185629-31-6).

Examples of suitable aromatic amine compounds 2 include, but are not limited to, 6-amino-3H-1,3-benzoxazol-2-one (CAS 22876-17-1), 6-amino-3H-1,3-benzothiazol-2-one (CAS 56354-98-4), 5-aminoindolin-2-one (CAS 20876-36-2), 5-amino-3,3-difluoro-indolin-2-one (CAS 813424-17-8), 6-aminoindolin-2-one (CAS 150544-04-0) and 5-amino-1,3-dihydropyrrolo[2,3-b]pyridin-2-one (CAS 869371-00-6).

The $S_NAr$ reaction is carried out in the presence of an organic base such as N,N-diisopropylethylamine, triethylamine or N-methylmorpholine in a polar aprotic organic solvent such as N-methyl-2-pyrrolidinone or N,N-di methyl form amide at elevated temperatures. Preferred conditions are N,N-diisopropylethylamine in N-methyl-2-pyrrolidinone at 120° C. for 3 hours.

Step B. Reduction of nitro-amino-arene compound 3 to diamino-arene 4 can be effected by hydrogenation with hydrogen under normal or elevated pressure in the presence of a catalyst such as $PtO_2$, Pd—C or Raney nickel in polar solvents such as MeOH, EtOH, dioxane, THF, or mixtures thereof.

Preferred conditions are 1 atm of hydrogen in the presence of 10% palladium on charcoal in a mixture of methanol and THF at room temperature for 12 hours.

Step C. Benzimidazole 7 can be obtained by cyclisation of diamino-arene 4 with an aldehyde 5 in the presence of sodium metabisulfite. The cyclisation reaction is carried out in a polar aprotic organic solvent such as N-methyl-2-pyrrolidinone or N,N-dimethylformamide at elevated temperatures. Preferred conditions are N,N-dimethylformamide at 120° C. for 1 hour.

Benzimidazole 7 can also be obtained by cyclisation of diamino-arene 4 with a carboxylic acid 6 in the presence of another acid. The cyclisation reaction is carried out in an aqueous solution of a strong acid such as HCl or $H_2SO_4$. Preferred conditions are 6 M aq. HCl at 120° C. for 12 hours.

Scheme 2

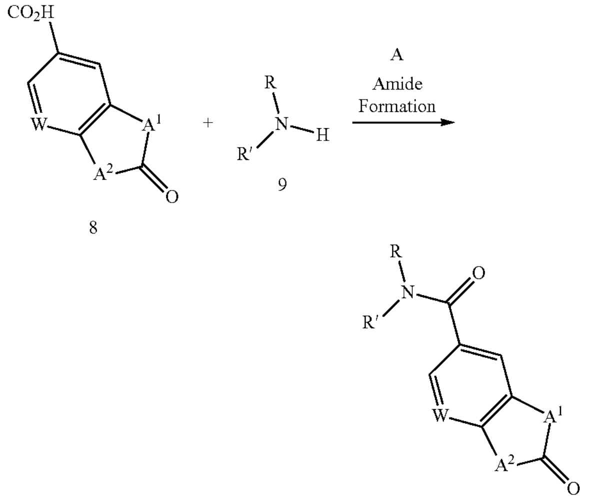

8 9 10

R,R' = H, aryl, heterocycloalkyl, heteroaryl or form together with the nitrogen they are attached to a heterocycloalkyl or a heteroaryl, as defined herein
W, $A^1$, $A^2$ = as described herein Step A: Amide bond formation can be accomplished by a coupling reaction between a suitable carboxylic acid 8 and a primary or secondary amine 9 in the presence of a coupling reagent such as DCC, EDC, TBTU or HATU in the presence of an organic base such as triethylamine, N,N-diisopropylethyl amine or N-methylmorpholine in halogenated solvents such as dichloromethane or 1,2-dichloroethane or ethereal solvents such as diethyl ether, dioxane, THF, DME or TBME or polar non-protic organic solvent such as N,N-di methyl form amide at room temperature or at elevated temperatures for 2-18 hours.

Examples of suitable carboxylic acids 8 include, but are not limited to, 2-oxo-3H-1,3-benzoxazole-6-carboxylic acid (CAS 54903-16-1), 2-oxo-3H-1,3-benzothiazole-6-carboxylic acid (CAS 99615-68-6), 2-oxoindoline-5-carboxylic acid (CAS 102359-00-2), 2-oxo-3H-oxazolo[4,5-b]pyridine-6-carboxylic acid (CAS 1555998-02-1) and 2-oxo-1,3-dihydropyrrolo[2,3-b]pyridine-5-carboxylic acid (CAS 1260665-66-4).

Preferred conditions are ELATU with N, N-diisopropylethylamine in N,N-dimethylformamide at room temperature for 4 hours.

Scheme 3

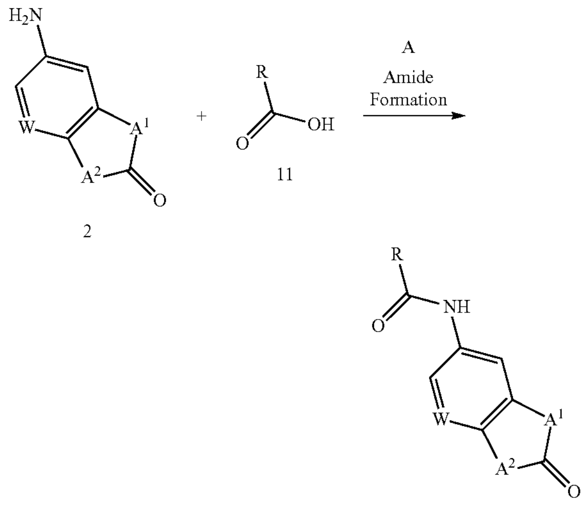

2 11 12

R = as defined herein
W, $A^1$, $A^2$ = as described herein

Step A: Amide bond formation can be accomplished by a coupling reaction between a suitable amine 2 and a carboxylic acid 11 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME or polar non-protic organic solvent such as N,N-di methyl form amide at room temperature or at elevated temperatures for 2-18 hours.

Alternatively, amide bond formation can be accomplished by a coupling reaction between a suitable amine 2 and a carboxylic acid 11 in the presence of a coupling reagent such as DMTMM in alcoholic solvents such as methanol, ethanol, n-propanol or isopropanol at room temperature for 1-4 hours.

Examples of suitable aromatic amine compounds 2 include, but are not limited to, 6-amino-3H-1,3-benzoxazol-2-one (CAS 22876-17-1), 6-amino-3H-1,3-benzothiazol-2-one (CAS 56354-98-4), 5-aminoindolin-2-one (CAS 20876-36-2), 5-amino-3,3-difluoro-indolin-2-one (CAS 813424-17-8), 6-aminoindolin-2-one (CAS 150544-04-0) and 5-amino-1,3-dihydropyrrolo[2,3-b]pyridin-2-one (CAS 869371-00-6).

Preferred conditions are DMTMM in methanol at room temperature for 4 hours.

Scheme 4

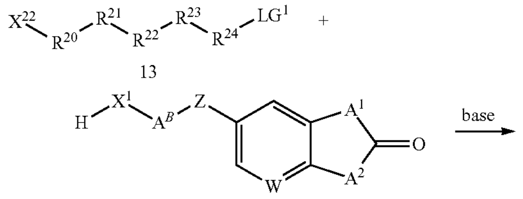

13 14

-continued

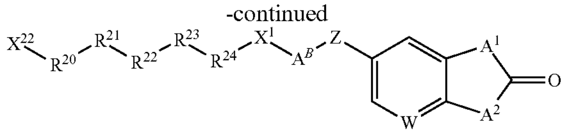

15

A compound of Formula XIV(1) may be synthesized as shown in Scheme 4 by coupling an intermediate 14 (wherein $X^1$ is $NR^{34}$, O, or S) with an intermediate 13 wherein $LG^1$ is an appropriate leaving group as would be understood by one of skill in the art, for example a halogen (e.g., Cl, Br, or I) or a sulfonate (for example —$O(SO_2)CH_3$, —$O(SO_2)CF_3$, or —$O(SO_2)$(4-methylphenyl)) in the presence of an appropriate base (for example, an inorganic base such as sodium carbonate or sodium hydride or an organic base such as triethylamine, DIPEA, or DBU) in an organic solvent (for example dichloromethane, dimethylformamide, or dimethylsulfoxide) at room temperature for 1-24 hours.

Scheme 5

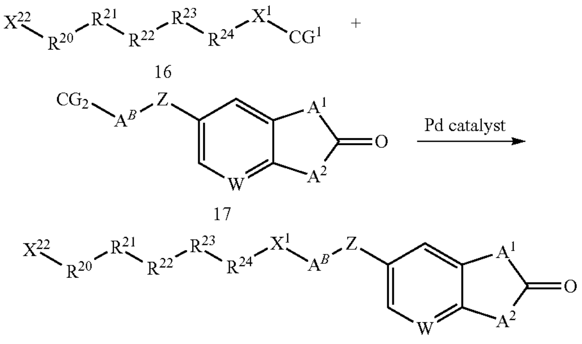

16 17 15

A compound of Formula XIV(1) may be synthesized as shown in Scheme 5 by coupling an intermediate 16 with a $CG^1$ group with an intermediate 17 with a $CG^2$ group in the presence of a palladium catalyst (for example $Pd(PPh_3)_4$, $PdCl_2(PPh_3)_2$, or similar catalyst as would be appropriately selected by a person of skill in the art) in an organic solvent at elevated temperature (for example, reflux of the organic solvent) for 1-48 hours. In some embodiments wherein $X^1$ is $NR^{34}$, O, or S, $CG^1$ is H and $CG^2$ can be selected from —$B(OH)_2$, —Zn(halogen), or $Sn(alkyl)_3$. In some embodiments, wherein $X^1$ is $CH_2$, $CHR^{34}$, or $C(R^{34})_2$, $CG^1$ is selected from a halogen or sulfonate and $CG^2$ can be selected from —$B(OH)_2$, —Zn(halogen), or $Sn(alkyl)_3$. In other embodiments, wherein $X^1$ is $CH_2$, $CHR^{34}$, or $C(R^{34})_2$, $CG^1$ can be selected from —$B(OH)_2$, —Zn(halogen), or $Sn(alkyl)_3$ and $CG^2$ can be selected from halogen or sulfonate.

Scheme 6

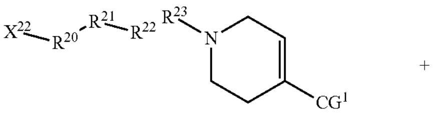

18

-continued

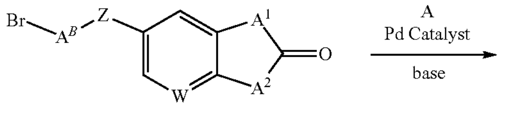

19

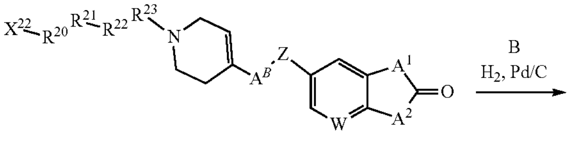

20

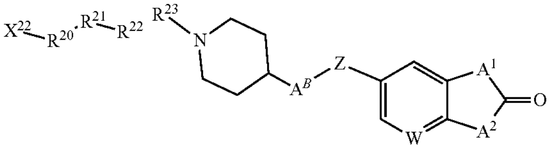

21

A compound 21 of Formula XIV(1) may be synthesized as shown in Scheme 6 by a sequential Heck reaction followed by a hydrogenation or other appropriate reduction. In Step A, heterocycloalkene 18 containing a $CG^1$ group is reacted with bromide 19 in the presence of a palladium catalyst (for example, $Pd(dppf)C_{1-2}$ or similar catalyst as would be appropriately selected by a person of skill in the art) and base (for example, sodium carbonate) in an organic solvent (for example, 1,4-dioxane) at elevated temperature (for example, 80° C.) for 1-24 hours. In one embodiment of Step A, the $CG^1$ group is a pinacolatoboron group. In Step B, heterocycloalkene 20 is reacted under a hydrogen atmosphere with palladium on carbon catalyst in organic solvent (for example, ethanol) for 1-48 hours. The heterocycloalkene group of 18 can be substituted by any cycloalkene or heterocycloalkene group as would be understood to be appropriate by a person having ordinary skill in the art.

Scheme 7

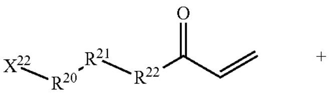

22

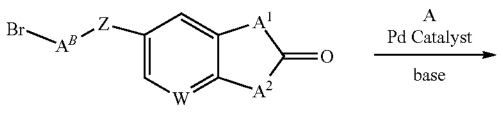

19

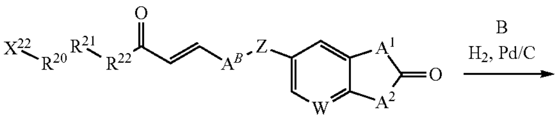

23

-continued

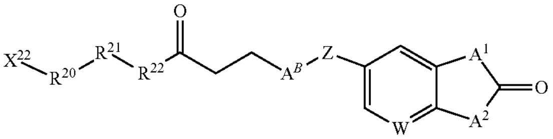

24

A compound 24 of Formula XIV(1) may be synthesized as shown in Scheme 7 by a Heck reaction followed by a hydrogenation or other appropriate reduction. In Step A, alkene 22 is reacted with bromide 19 in the presence of a palladium catalyst (for example, $Pd(PPh_3)_2C_{1-2}$ or similar catalyst as would be appropriately selected by a person of skill in the art) and base (for example, triethylamine) in an organic solvent (for example, DMF) at elevated temperature (for example, 90° C.) for 1-24 hours. In Step B, alkene 23 is reacted under a hydrogen atmosphere with palladium on carbon catalyst in organic solvent (for example, ethanol) for 1-48 hours.

Scheme 8

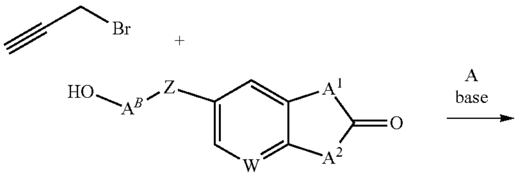

25

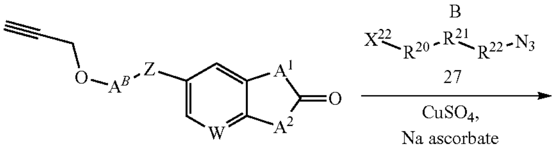

26

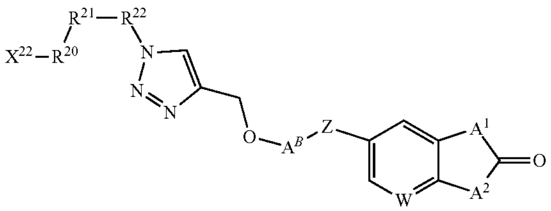

28

A compound 28 of Formula XIV(1) may be synthesized as shown in Scheme 8 by an azide-alkyne Huisgen cycloaddition sequence. In Step A, alcohol 25 is reacted with propargyl bromide in the presence of base (for example, cesium carbonate) in organic solvent (for example, DMF) at room temperature for 1-24 hours. In Step B, alkyne 27 is reacted with azide 27 in the presence of copper sulfate and sodium ascorbate in organic solvent (for example, DMSO).

Scheme 9

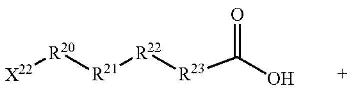

29

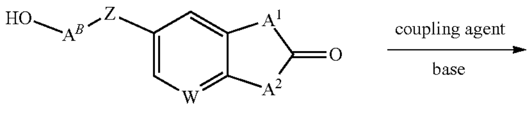

25

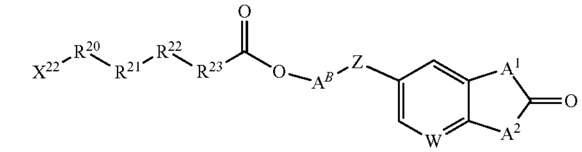

30

A compound 30 of Formula XIV(1) may be synthesized as shown in Scheme 9 by reacting a carboxylic acid 29 and an alcohol 25 in the presence of a coupling agent (for example, a mixture of 2,4,6-trichlorobenzoyl chloride and 4-dimethylaminopyridine) and a base (for example, triethylamine) in organic solvent (for example, THF) at room temperature for 1-24 hours. In some embodiment, the alcohol group of 25 may be substituted by an amino or thio group as would be readily understood by a person of skill in the art.

Scheme 10

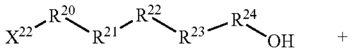

31

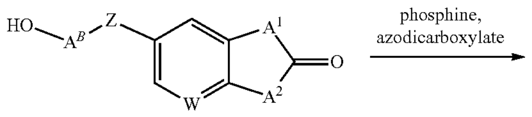

25

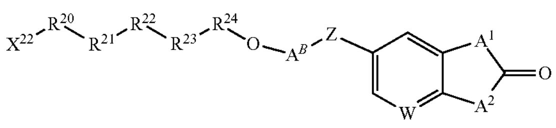

32

A compound 32 of Formula XIV(1) may be synthesized as shown in Scheme 10 by a Mitsunobu reaction by reacting an alcohol 31 with a second alcohol 25 in the presence of a phosphine (for example, triphenylphosphine) and an azodicarboxylate compound (for example, DEAD or DIAD) in organic solvent (for example, THF) at elevated temperature (for example, reflux) for 1-24 hours.

Scheme 11

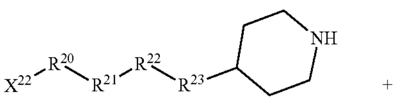

33

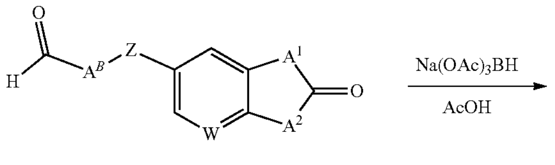

34

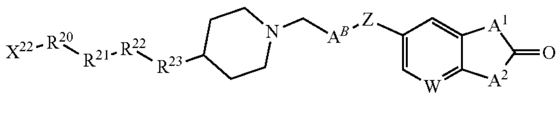

35

A compound 35 of Formula XIV(1) may be synthesized as shown in Scheme 11 by reductive amination by reacting a piperidine 33 with an aldehyde 34 in the presence of sodium triacetoxyborohydride and acetic acid optionally in an organic solvent (for example THF) at room temperature for 1-24 hours. In one embodiment, the piperidine group of compound 33 can be substituted with a heterocyclic amine group of different size or substitution as would be readily apparent to a person of ordinary skill in the art.

Scheme 12

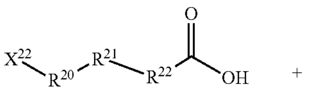

36

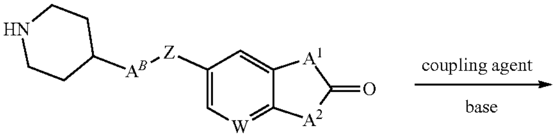

37

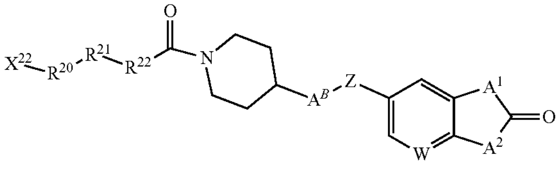

38

A compound 38 of Formula XIV(1) may be synthesized as shown in Scheme 12 by reacting a carboxylic acid 36 with a piperidine 37 in the presence of a coupling agent (for example, COMU) and a base (for example, diisopropylethylamine) in organic solvent (for example, DMF) at room temperature for 1-24 hours. In one embodiment, the piperidine group of compound 37 can be substituted by a heterocyclic amine group of different size or substitution as would be readily apparent to a person of ordinary skill in the art.

Scheme 13

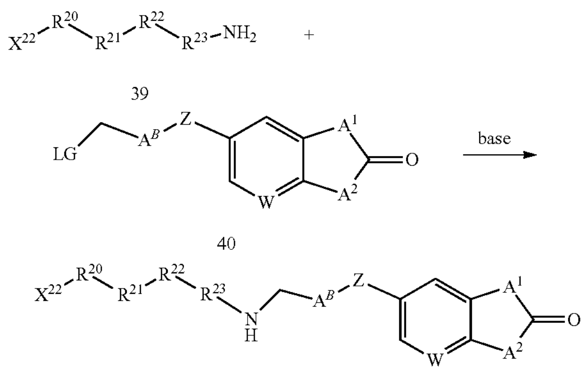

39

40

41

A compound 41 of Formula XIV(1) may be synthesized as shown in Scheme 13 by reacting an amine 39 with compound 40 substituted with a leaving group (LG), for example a bromide, iodide, or sulfonate group, in the presence of a base (for example, diisopropylethylamine) in organic solvent (for example, DMF) at elevated temperature (for example, 60° C.) for 1-24 hours. In some embodiments, the amino group of 39 can be substituted by an alcohol or thio group as would be readily understood by a person of skill in the art.

Scheme 14

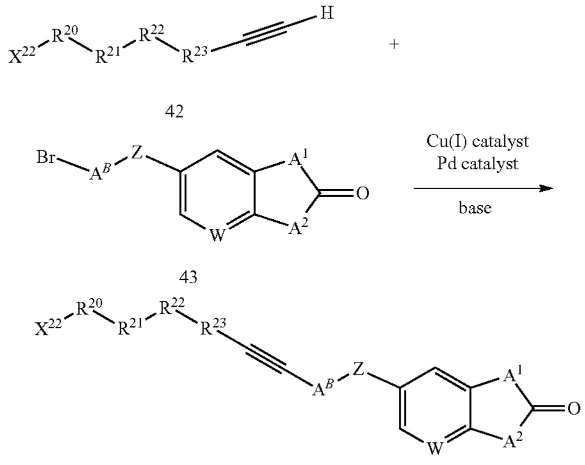

42

43

44

A compound 44 of Formula XIV(1) may be synthesized as shown in Scheme 14 by a Sonagashira reaction by reacting a terminal alkyne 41 with a bromide 43 in the presence of a copper(I) catalyst (for example, CuI) and a palladium catalyst (for example, $Pd(PPh_3)_4$) in the presence of a base (for example, triethylamine) in organic solvent (for example, DMF) at elevated temperature (for example, 80° C.) for 1-24 hours.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of Formula XIV can be separated using chiral HPLC. Racemic mixtures of chiral synthetic intermediates may also be separated using chiral HPLC.

In cases where the compounds of Formula XIV are basic they may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

Insofar as their preparation is not described in the examples, the compounds of Formula XIV as well as all intermediate products can be prepared according to analogous methods or according to the methods set forth herein. Starting materials are commercially available, known in the art or can be prepared by methods known in the art or in analogy thereto.

It will be appreciated that the compounds of general Formula XIV in this invention may be derivatised at functional groups to provide derivatives which are capable of conversion back to the parent compound in vivo.

Stereochemistry

Compounds of the present invention with stereocenters may be drawn without stereochemistry for convenience. One skilled in the art will recognize that pure enantiomers and diastereomers can be prepared by methods known in the art. Examples of methods to obtain optically active materials include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;
ii) simultaneous crystallization—a technique whereby the individual enantiomers are separately crystallized from a solution of the racemate, possible only if the latter is a conglomerate in the solid state;
iii) enzymatic resolutions—a technique whereby partial or complete separation of a racemate by virtue of differing rates of reaction for the enantiomers with an enzyme;
iv) enzymatic asymmetric synthesis—a synthetic technique whereby at least one step of the synthesis uses an enzymatic reaction to obtain an enantiomerically pure or enriched synthetic precursor of the desired enantiomer;
v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including via chiral HPLC). The stationary phase can be made of chiral material or the mobile phase can contain an additional chiral material to provoke the differing interactions;

xi) chiral gas chromatography-a technique whereby the racemate is volatilized and enantiomers are separated by virtue of their differing interactions in the gaseous mobile phase with a column containing a fixed non-racemic chiral adsorbent phase;

xii) extraction with chiral solvents-a technique whereby the enantiomers are separated by virtue of preferential dissolution of one enantiomer into a particular chiral solvent;

xiii) transport across chiral membranes-a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

xiv) simulated moving bed chromatography, is used in one embodiment. A wide variety of chiral stationary phases are commercially available.

REPRESENTATIVE EXAMPLES OF THE PRESENT INVENTION

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography (e.g., chiral SFC or chiral HPLC) or crystallization.

All reaction examples and intermediates were prepared under a nitrogen atmosphere if not specified otherwise.

Example 1

N-(2-Oxo-3H-1,3-benzoxazol-6-yl)benzamide

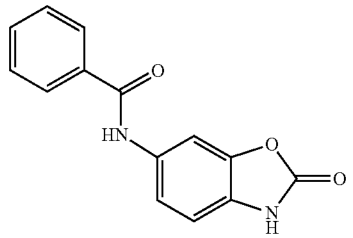 [SMILES: O=C(Nc1ccc2[nH]c(=O)oc2c1)c1ccccc1]

The title compound (CAS 932474-64-1) can be purchased from commercial vendors as listed, for instance, in chemical databases such as SciFinder® (American Chemical Society).

Example 2

N-(2-Oxoindolin-5-yl)furan-2-carboxamide

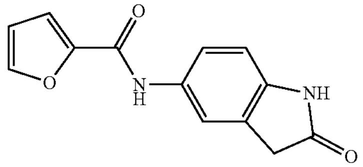 [SMILES: O=C1Cc2cc(NC(=O)c3ccco3)ccc2N1]

The title compound (CAS 921814-32-6) can be purchased from commercial vendors as listed, for instance, in chemical databases such as SciFinder® (American Chemical Society).

Example 3

2-(2-Methylphenoxy)-N-(2-oxo-3H-1,3-benzothiazol-6-yl)acetamide

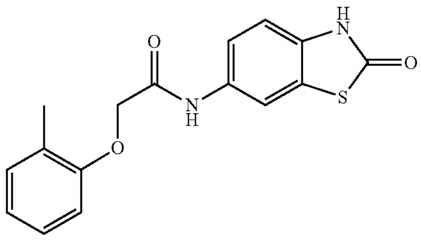 [SMILES: Cc1ccccc1OCC(=O)Nc1ccc2[nH]c(=O)sc2c1]

The title compound (CAS 931736-40-2) can be purchased from commercial vendors as listed, for instance, in chemical databases such as SciFinder® (American Chemical Society).

Example 4

2-Isopropyl-N-methyl-1-(2-oxoindolin-6-yl)benzimidazole-5-carboxamide

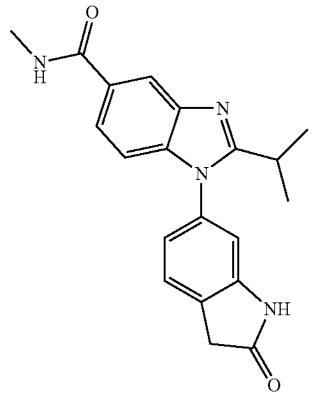 [SMILES: CNC(=O)c1ccc2c(c1)nc(C(C)C)n2-c1ccc2c(c1)NC(=O)C2]

a) N-Methyl-3-nitro-4-[(2-oxoindolin-6-yl)amino]benzamide

A stirred solution of 4-fluoro-A-methyl-3-nitrobenzamide (1264 mg, CAS 475216-25-2), 6-aminoindolin-2-one (151 mg, CAS 150544-04-0) and N,N-diisopropylethylamine (1.59 ml) in N-methyl-2-pyrrolidinone (20 ml) was heated at 120° C. for three hours. The reaction mixture was then cooled to room temperature and poured into water and extracted three times with ethyl acetate. The combined organic layers were dried with sodium sulfate, filtered, and dried in vacuo to afford N-methyl-3-nitro-4-[(2-oxoindolin-6-yl)amino]benzamide (1800 mg, 36%) as a black oil which was used in the next step without further purification. MS (ISP): 327.2 ([M+H]$^+$).

b) 3-Amino-A-methyl-4-[(2-oxoindolin-6-yl)amino]benzamide

To a stirred suspension of N-methyl-3-nitro-4-[(2-oxoindolin-6-yl)amino]benzamide (1800 mg) in methanol (20 ml) and THF (20 ml) was added 10% palladium on charcoal (200 mg). The reaction mixture was stirred at room temperature for 12 hours under an atmosphere of hydrogen. The catalyst was collected by filtration, washing with methanol. The filtrate was then concentrated in vacuo. The crude material was purified by flash chromatography (silica gel, eluent: 0 to 10% of methanol in dichloromethane) to afford 3-amino-A-methyl-4-[(2-oxoindolin-6-yl)amino]benzamide (800 mg, 49%) as a brown solid. MS (ISP): 297.2 ([M+H]$^+$).

c) 2-Isopropyl-N-methyl-1-(2-oxoindolin-6-yl)benzimidazole-5-carboxamide

To a stirred solution of 3-amino-A-methyl-4-[(2-oxoindolin-6-yl)amino]benzamide (199 mg) and isobutyraldehyde (48.5 mg, CAS 78-84-2) in N,N-dimethylformamide (10 ml) was added sodium metabisulfite (153.4 mg) at room temperature. The reaction mixture was then heated at 120° C. for 1 hour. Subsequent TLC and LC-MS analysis showed the reaction was complete. The reaction mixture was poured into water and extracted three times with ethyl acetate. The combined organic phases were dried over $MgSO_4$, filtered, and concentrated in vacuo. The crude material was purified by preparative reversed phase HPLC to afford 2-isopropyl-A-methyl-1-(2-oxoindolin-6-yl)benzimidazole-5-carboxamide (90 mg, 35%) as a brown solid. MS (ISP): 349.1 ([M+H]$^+$).

Example 5

2-Isopropyl-N-methyl-1-(2-oxoindolin-5-yl)benzimidazole-5-carboxamide

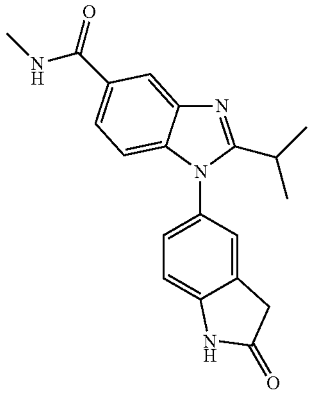 [SMILES: CNC(=O)c1ccc2c(c1)nc(C(C)C)n2-c1ccc2c(c1)CC(=O)N2]

The title compound was obtained in analogy to example 4 using 5-aminoindolin-2-one (CAS 20876-36-2) in place of 6-aminoindolin-2-one for step a. White solid. MS (ISP): 349.1 ([M+H]$^+$).

Example 6

6-(2-Aminoanilino)-3H-1,3-benzothiazol-2-one

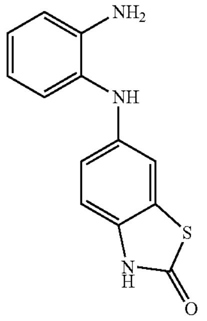 [SMILES: Nc1ccccc1Nc1ccc2[nH]c(=O)sc2c1]

The title compound was obtained in analogy to example 4 steps a and b using 1-fluoro-2-nitrobenzene (CAS 1493-27-2) in place of 4-fluoro-N-methyl-3-nitrobenzamide and 6-aminobenzo[d]thiazol-2(3H)-one (CAS 56354-98-4) in place of 6-aminoindolin-2-one in step a. Brown solid. MS (ISP): 258.3 ([M+H]$^+$).

Example 7

6-(2-Isopropylbenzimidazol-1-yl)-3H-1,3-benzothiazol-2-one

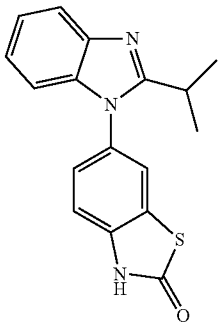 [SMILES: CC(C)c1nc2ccccc2n1-c1ccc2[nH]c(=O)sc2c1]

The title compound was obtained in analogy to example 4 step c using 6-(2-Aminoanilino)-3H-1,3-benzothiazol-2-one in place of 3-amino-X-methyl-4-[(2-oxoindolin-6-yl)amino]benzamide. White solid. MS (ISP): 310.2 ([M+H]$^+$).

Example 8

6-(2-Aminoanilino)-3H-1,3-benzoxazol-2-one

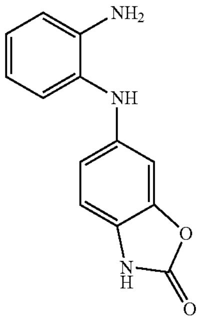 [SMILES: Nc1ccccc1Nc1ccc2[nH]c(=O)oc2c1]

The title compound was obtained in analogy to example 4 steps a and b using 1-fluoro-2-nitrobenzene (CAS 1493-27-2) in place of 4-fluoro-A-methyl-3-nitrobenzamide and 6-aminobenzo[d]oxazol-2(3H)-one (CAS 22876-17-1) in place of 6-aminoindolin-2-one in step a. Brown solid. MS (ISP): 242.2 ([M+H]+).

Example 9

6-(2-Isopropylbenzimidazol-1-yl)-3H-1,3-benzoxazol-2-one

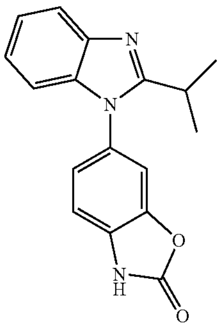 [SMILES: CC(C)c1nc2ccccc2n1-c1ccc2[nH]c(=O)oc2c1]

The title compound was obtained in analogy to example 4 step c using 6-(2-aminoanilino)-3H-1,3-benzoxazol-2-one in place of 3-amino-A-methyl-4-[(2-oxoindolin-6-yl)amino]benzamide. White solid. MS (ISP): 294.3 ([M+H]$^+$).

Example 10

2-Oxo-N-phenylindoline-5-carboxamide

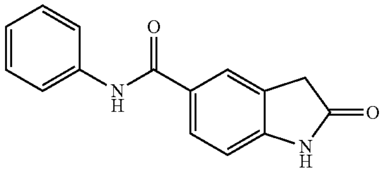

The title compound (CAS 1168720-81-7) can be purchased from commercial vendors as listed, for instance, in chemical databases such as SciFinder® (American Chemical Society).

Example 11

2-Oxo-N-phenyl-3H-1,3-benzoxazole-6-carboxamide

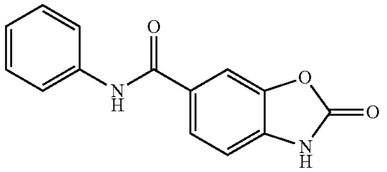 [SMILES: O=C(Nc1ccccc1)c1ccc2[nH]c(=O)oc2c1]

The title compound (CAS 1791206-26-2) can be purchased from commercial vendors as listed, for instance, in chemical databases such as SciFinder® (American Chemical Society).

Example 12

N-(1-Acetyl-4-piperidyl)-2-oxo-3H-1,3-benzoxazole-6-carboxamide

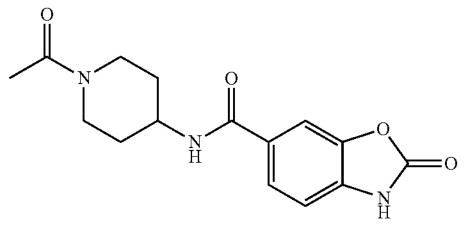

To a mixture of 1-(4-aminopiperidin-1-yl)ethan-1-one (50 mg, CAS 160357-94-8) and 2-oxo-2,3-dihydrobenzo[d]oxazole-6-carboxylic acid (69.3 mg, CAS 54903-16-1) was added dropwise N,N-diisopropylethyl amine (181 μl) followed by a solution of HATU in N,N-dimethylformamide (245 mg, 1.8 ml, 0.358 M solution). The reaction mixture was shaken at 25° C. for 4 hours. The reaction mixture was directly purified by preparative HPLC followed by lyophilisation to afford N-(1-acetyl-4-piperidyl)-2-oxo-3H-1,3-benzoxazole-6-carboxamide (45.5 mg, 43%) as a white solid. MS (ISP): 304.2 ($[M+H]^+$).

Example 13

6-(Indoline-1-carbonyl)-3H-1,3-benzoxazol-2-one

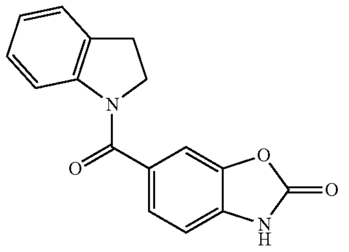 [SMILES: O=C(c1ccc2[nH]c(=O)oc2c1)N1CCc2ccccc21]

The title compound (CAS 1787518-86-8) can be purchased from commercial vendors as listed, for instance, in chemical databases such as SciFinder® (American Chemical Society).

Example 14

6-(2,3-Dihydropyrrolo[2,3-b]pyridine-1-carbonyl)-3H-1,3-benzoxazol-2-one

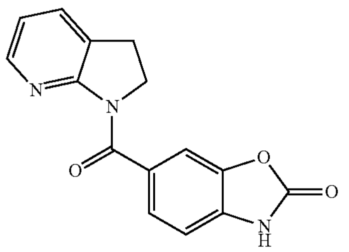 [SMILES: O=C(c1ccc2[nH]c(=O)oc2c1)N1CCc2cccnc21]

The title compound was obtained in analogy to example 12 using 2,3-dihydro-1H-pyrrolo[2,3-b]pyridine (CAS 10592-27-5) in place of 1-(4-aminopiperidin-1-yl)ethan-1-one. White solid. MS (ISP): 282.1 ($[M+H]^+$).

Example 15

2-Oxo-N-phenyl-3H-1,3-benzothiazole-6-carboxamide

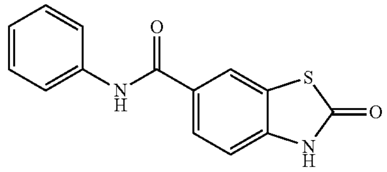 [SMILES: O=C(Nc1ccccc1)c1ccc2[nH]c(=O)sc2c1]

The title compound (CAS 503443-01-4) can be purchased from commercial vendors as listed, for instance, in chemical databases such as SciFinder® (American Chemical Society).

Example 16

6-(Indoline-1-carbonyl)-3H-1,3-benzothiazol-2-one

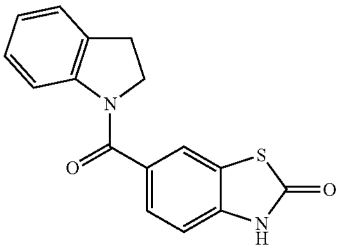

The title compound was obtained in analogy to example 12 using indoline (CAS 496-15-1) in place of 1-(4-aminopiperidin-1-yl)ethan-1-one and 2-oxo-2,3-dihydrobenzo[d]thiazole-6-carboxylic acid (CAS 99615-68-6) in place of 2-oxo-2,3-dihydrobenzo[d]oxazole-6-carboxylic acid. White solid. MS (ISP): 297.2 ($[M+H]^+$).

Example 17

5-(Indoline-1-carbonyl)indolin-2-one

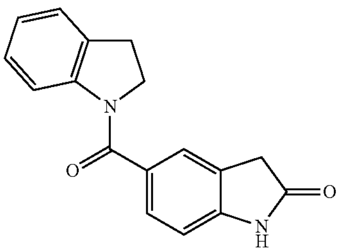 [SMILES: O=C1Cc2cc(C(=O)N3CCc4ccccc43)ccc2N1]

The title compound was obtained in analogy to example 12 using indoline (CAS 496-15-1) in place of 1-(4-aminopiperidin-1-yl)ethan-1-one and 2-oxoindoline-5-carboxylic acid (CAS 102359-00-2) instead of 2-oxo-2,3-dihydrobenzo[d]oxazole-6-carboxylic acid. White solid. MS (ISP): 279.3 ([M+H]$^+$).

Example 18

2-Oxo-N-phenyl-3H-oxazolo[4,5-b]pyridine-6-carboxamide

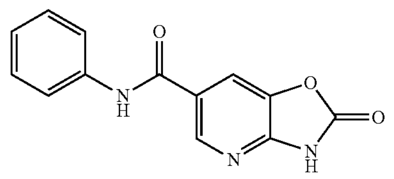 [SMILES: O=C(Nc1ccccc1)c1cnc2[nH]c(=O)oc2c1]

The title compound was obtained in analogy to example 12 using aniline in place of 1-(4-aminopiperidin-1-yl)ethan-1-one and 2-oxo-2,3-dihydrooxazolo[4,5-b]pyridine-6-carboxylic acid (CAS 1555998-02-1) instead of 2-oxo-2,3-dihydrobenzo[d]oxazole-6-carboxylic acid. White solid. MS (ISP): 256.3 ([M+H]$^+$).

Example 19

N-(1-Acetyl-4-piperidyl)-2-oxo-3H-oxazolo[4,5-b]pyridine-6-carboxamide

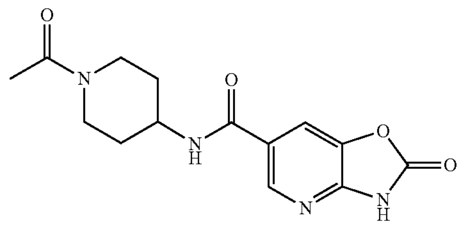 [SMILES: CC(=O)N1CCC(NC(=O)c2cnc3[nH]c(=O)oc3c2)CC1]

The title compound was obtained in analogy to example 12 using 2-oxo-2,3-dihydrooxazolo[4,5-b]pyridine-6-carboxylic acid (CAS 1555998-02-1) instead of 2-oxo-2,3-dihydrobenzo[d]oxazole-6-carboxylic acid. White solid. MS (ISP): 305.3 ([M+H]$^+$).

Example 20

5-(Indoline-1-carbonyl)-1,3-dihydropyrrolo[2,3-b]pyridin-2-one

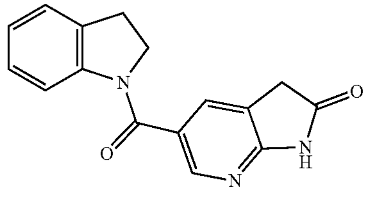 [SMILES: O=C1Cc2cc(C(=O)N3CCc4ccccc43)cnc2N1]

The title compound was obtained in analogy to example 12 using indoline (CAS 496-15-1) in place of 1-(4-aminopiperidin-1-yl)ethan-1-one and 2-oxo-2,3-dihydro-1H-pyrrolo[2,3-b]pyridine-5-carboxylic acid (CAS 1260665-66-4) instead of 2-oxo-2,3-dihydrobenzo[d]oxazole-6-carboxylic acid. White solid. MS (ISP): 280.2 ([M+H]$^+$).

Example 21

3,3-Difluoro-5-(2-isopropylbenzimidazol-1-yl)indolin-2-one

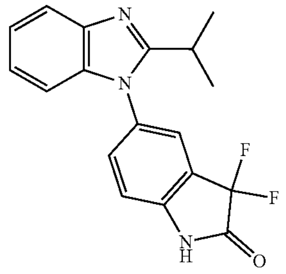 [SMILES: CC(C)c1nc2ccccc2n1-c1ccc2c(c1)C(F)(F)C(=O)N2]

The title compound was obtained in analogy to example 4 using 1-fluoro-2-nitrobenzene (CAS 1493-27-2) in place of 4-fluoro-A-methyl-3-nitrobenzamide and 5-amino-3,3-difluoroindolin-2-one (CAS 813424-17-8) in place of 6-aminoindolin-2-one in step a. White solid. MS (ISP): 328.1 ([M+H]$^+$).

Example 22

6-(4-Hydroxyisoindoline-2-carbonyl)-3H-1,3-benzoxazol-2-one

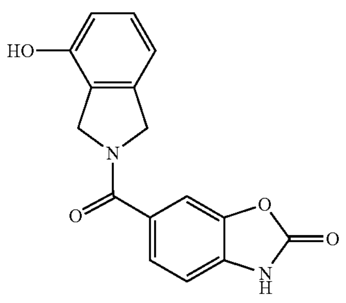 [SMILES: O=C(c1ccc2[nH]c(=O)oc2c1)N1Cc2cccc(O)c2C1]

The title compound was obtained in analogy to example 12 using isoindolin-4-ol hydrochloride (CAS 72695-20-6) in place of 1-(4-aminopiperidin-1-yl)ethan-1-one. White solid. MS (ISP): 295.2 ([M−H]$^-$).

Example 23

6-(4-Nitroisoindoline-2-carbonyl)-3H-1,3-benzoxazol-2-one

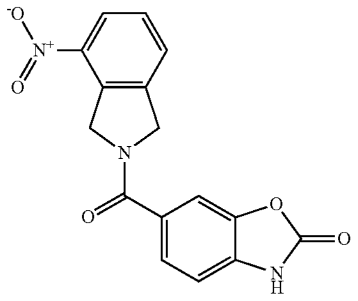

The title compound was obtained in analogy to example 12 using 4-nitroisoindoline hydrochloride (CAS 1159826-78-4) in place of 1-(4-aminopiperidin-1-yl)ethan-1-one. White solid. MS (ISP): 326.5 ([M+H]$^+$).

Example 24

N-(3,3-difluoro-2-oxo-indolin-5-yl)tetralin-1-carboxamide

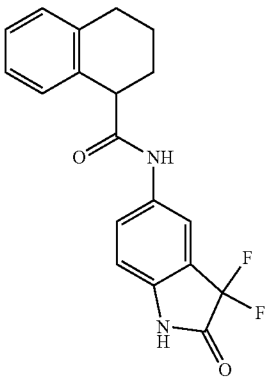 [SMILES: O=C(Nc1ccc2c(c1)C(F)(F)C(=O)N2)C1CCCc2ccccc21]

To a stirred solution of 1,2,3,4-tetrahydronaphthalene-1-carboxylic acid (47.8 mg, CAS 1914-65-4) and 5-amino-3,3-difluoroindolin-2-one (50 mg, CAS 813424-17-8) in methanol (1.67 ml) at room temperature was added DMTMM (90.2 mg, CAS 3945-69-5). The reaction mixture was stirred at room temperature for 4 h. The reaction mixture was then poured into 20 ml brine and extracted twice with EtOAc/THF (1:1). The organic layers were dried over sodium sulfate and concentrated in vacuo. The crude material was purified by preparative HPLC (Gemini NX, 12 nm, 5 µm, 100×30 mm, flow rate: 40 ml/min, eluant: $CH_3CN$/$H_2O$+$Et_3N$). The product was lyophilised to afford N-(3,3-difluoro-2-oxo-indolin-5-yl)tetralin-1-carboxamide (16 mg, 17%) as a light orange solid. MS (ISP): 343.1 ([M+H]$^+$).

Example 25

N-(3,3-Difluoro-1-oxo-indolin-5-yl)benzofuran-3-carboxamide

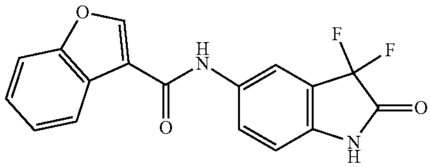 [SMILES: O=C(Nc1ccc2c(c1)C(F)(F)C(=O)N2)c1coc2ccccc12]

The title compound was obtained in analogy to example 24 using benzofuran-3-carboxylic acid (CAS 26537-68-8) in place of 1,2,3,4-tetrahydronaphthalene-1-carboxylic acid. White solid. MS (ISP): 327.1 ([M−H]$^-$).

Example 26

2-Isopropyl-A-methyl-1-(2-oxo-1,3-dihydropyrrolo[2,3-b]pyridin-5-yl)benzimidazole-5-carboxamide

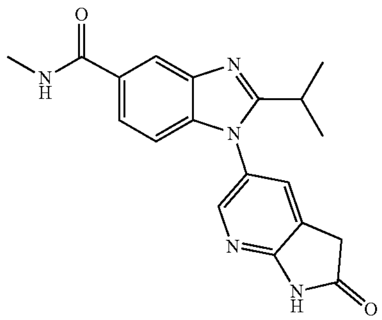 [SMILES: CNC(=O)c1ccc2c(c1)nc(C(C)C)n2-c1cnc2c(c1)CC(=O)N2]

a) N-Methyl-3-nitro-4-(1H-pyrrolo[2,3-b]pyridin-5-ylamino)benzamide

The title compound was obtained in analogy to example 4 step a using 1H-pyrrolo[2,3-b]pyridin-5-amine (CAS 100960-07-4) in place of 6-aminoindolin-2-one for step a. Red solid. MS (ISP): 312.0 ([M+H]$^+$).

b) 4-[(3,3-Dibromo-2-oxo-1H-pyrrolo[2,3-b]pyridin-5-yl)amino]-N-methyl-3-nitro-benzamide To a stirred solution of N-methyl-3-nitro-4-(1H-pyrrolo[2,3-b]pyridin-5-ylamino)benzamide (3.0 g) in tert-butanol (100 ml) was added in small portions pyridinium tribromide (8.32 g) over 7 min. The reaction was stirred at 25° C. for 12 hours. According to TLC the reaction was finished. The solvent was removed by concentration in vacuo and the resulting residue was dissolved in a 1:1 mixture of ethyl acetate/water (400 ml). The organic layer was separated and the aqueous layer was further extracted with ethyl acetate (2×100 ml). The combined organic extracts were washed sequentially with water and with saturated brine, then dried over magnesium sulfate and concentrated in vacuo to afford 4-[(3,3-dibromo-2-oxo-1H-pyrrolo[2,3-b]pyridin-5-yl)amino]-N-methyl-3-nitro-benzamide (2.2 g, 18%). Brown solid. MS (ISP): 485.9 ([M+H]$^+$).

c) 3-Amino-N-methyl-4-[(2-oxo-1,3-dihydropyrrolo [2,3-b]pyridin-5-yl)amino]benzamide To a stirred solution of 4-[(3,3-dibromo-2-oxo-1H-pyrrolo[2,3-b]pyridin-5-yl)amino]-N-methyl-3-nitro-benzamide (1 g) in a 1:1 mixture of methanol/THF (20 ml) at room temperature was added 10% palladium on charcoal (120 mg). The reaction mixture was hydrogenated at room temperature under an atmosphere of hydrogen. After stirring vigorously for 3 hours, the catalyst was collected by filtration, washing with methanol. The filtrate was then concentrated in vacuo. The crude material was purified by column chromatography ($SiO_2$, petrol ether/ethylacetate 1:1) to afford 3-amino-N-methyl-4-[(2-oxo-1,3-dihydropyrrolo[2,3-b]pyridin-5-yl)amino]benzamide (500 mg, 89%) as a brown solid. MS (ISP): 298.8 ($[M+H]^+$).

d) 2-Isopropyl-N-methyl-1-(2-oxo-1,3-dihydropyrrolo[2,3-b]pyridin-5-yl)benzimidazole-5-carboxamide The title compound was obtained in analogy to example 4 step c using 3-amino-A-methyl-4-[(2-oxo-1,3-dihydropyrrolo[2,3-b]pyridin-5-yl)amino]benzamide in place of 3-amino-A-methyl-4-[(2-oxoindolin-6-yl)amino]benzamide. Brown oil. MS (ISP): 350.3 ($[M+H]^+$).

Example 27

5-(2-Isopropylbenzimidazol-1-yl)-1,3-dihydropyrrolo[2,3-b]pyridin-2-one

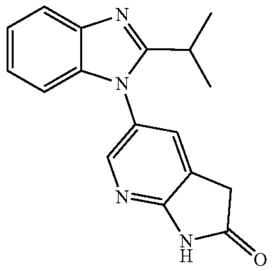 [SMILES: CC(C)c1nc2ccccc2n1-c1cnc2c(c1)CC(=O)N2]

The title compound was obtained in analogy to example 26 using 1-fluoro-2-nitrobenzene (CAS 1493-27-2) in place of 4-fluoro-A-methyl-3-nitrobenzamide for step a. Green solid. MS (ISP): 293.3 ($[M+H]^+$).

Example 28

5-(5-(Piperidin-4-yl)indoline-1-carbonyl)-1,3-dihydro-2H-pyrrolo[2,3-b]pyridin-2-one

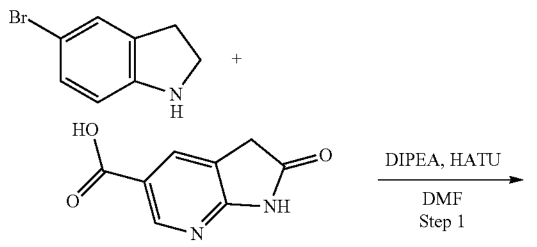

-continued

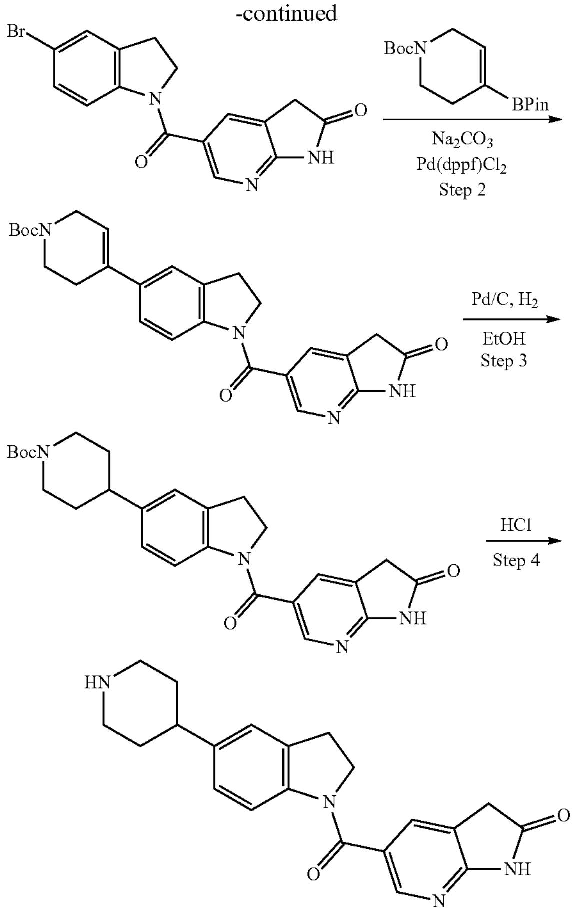

Step 1: 5-(5-Bromoindoline-1-carbonyl)-1,3-dihydropyrrolo[2,3-b]pyridin-2-one

The title compound is obtained in analogy to example 12 using 5-bromoindoline (CAS 22190-33-6) in place of 1-(4-aminopiperidin-1-yl)ethan-1-one and 2-oxo-2,3-dihydro-1H-pyrrolo[2,3-b]pyridine-5-carboxylic acid (CAS 1260665-66-4) instead of 2-oxo-2,3-dihydrobenzo[d]oxazole-6-carboxylic acid.

Step 2: tert-Butyl 4-(1-(2-Oxo-2,3-dihydro-1H-pyrrolo[2,3-b]pyridine-5-carbonyl)indolin-5-yl)-3,6-dihydropyridine-1(2H)-carboxylate 5-(5-bromoindoline-1-carbonyl)-1,3-dihydropyrrolo[2,3-b]pyridin-2-one is dissolved in a dioxane:water mixture (3:1) (0.1M), tert-butyl 4-(4,4,5,5-tetramethyl-1,3,2-dioxaborolan-2-yl)-3,6-dihydropyridine-1(2H)-carboxylate (CAS 286961-14-6, 1.3 equiv.) is added followed by sodium carbonate (2.5 equiv.) and 1,1'-Bis(diphenylphosphino)ferrocene]dichloropalladium(II) (0.1 equiv.). The solution is degassed with nitrogen and heated at 80° C. for 2 hours. The organic supernatant is separated, evaporated under reduced pressure, and the residue is purified by silica gel column chromatography to afford the title compound.

Step 3: tert-butyl 4-(1-(2-oxo-2,3-dihydro-1H-pyrrolo[2,3-b]pyridine-5-carbonyl)indolin-5-yl)piperidine-1-carboxylate tert-Butyl 4-(1-(2-oxo-2,3-dihydro-1H-pyrrolo[2,3-b]pyridine-5-carbonyl)indolin-5-yl)-3,6-dihydropyridine-1

(2H)-carboxylate is dissolved in ethanol (0.1 M), and palladium on charcoal 10% is added to the reaction mixture. The container is sealed and placed under an atmosphere of hydrogen for 24 hours. The reaction mixture is filtered on celite, and the filtrate is evaporated under reduced pressure to afford the title compound.

Step 4: 5-(5-(piperidin-4-yl)indoline-1-carbonyl)-1,3-dihydro-2H-pyrrolo[2,3-b]pyridin-2-one tert-butyl 4-(1-(2-oxo-2,3-dihydro-1H-pyrrolo[2,3-b]pyridine-5-carbonyl)indolin-5-yl)piperidine-1-carboxylate is dissolved in 1,4-dioxane:methanol (1:1), and hydrogen chloride (4 M in 1,4-dioxane) is added. The reaction mixture is stirred for 2 hours at 40° C. and the reaction mixture is evaporated under reduced pressure to afford the title compound.

Example 29

3-(1-(2-Oxo-2,3-dihydro-1H-pyrrolo[2,3-b]pyridine-5-carbonyl)indolin-6-yl)propanoic acid

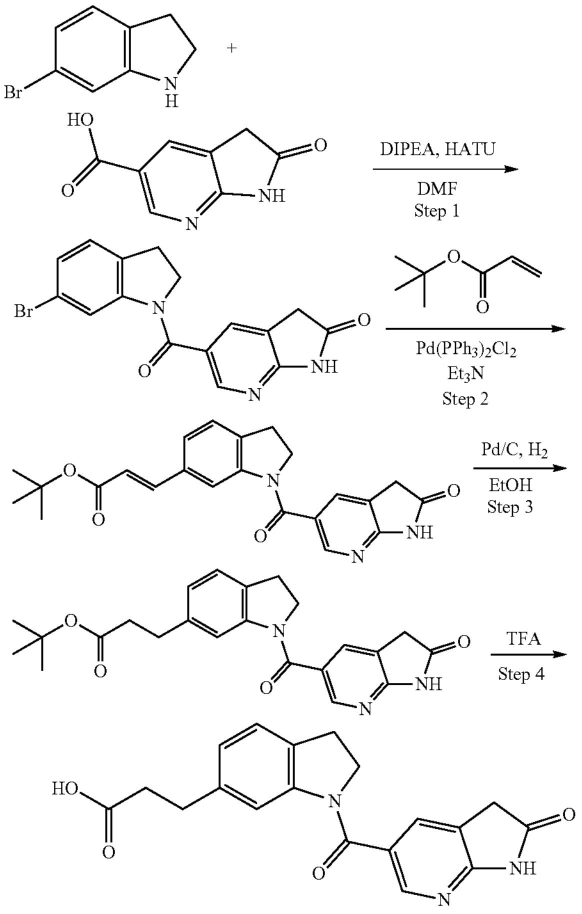

Step 1: 5-(6-bromoindoline-1-carbonyl)-1,3-dihydropyrrolo[2,3-b]pyridin-2-one

The title compound is obtained in analogy to example 12 using 6-bromoindoline (CAS 63839-24-7) in place of 1-(4-aminopiperidin-1-yl)ethan-1-one and 2-oxo-2,3-dihydro-1H-pyrrolo[2,3-b]pyridine-5-carboxylic acid (CAS 1260665-66-4) instead of 2-oxo-2,3-dihydrobenzo[d]oxazole-6-carboxylic acid.

Step 2: tert-butyl (E)-3-(1-(2-oxo-2,3-dihydro-1H-pyrrolo[2,3-b]pyridine-5-carbonyl)indolin-6-yl)acrylate 5-(6-bromoindoline-1-carbonyl)-1,3-dihydropyrrolo[2,3-b]pyridin-2-one is dissolved in N,N-dimethylformamide. Tert-butyl acrylate (1.3 equiv), triethylamine (2.5 equiv.) and bis(triphenylphosphine)palladium(II) dichloride (0.1 equiv.) is added, and the reaction mixture is degassed with nitrogen for 10 minutes. The reaction mixture is heated at 90° C. for 4 hours. The reaction mixture is diluted in ethyl acetate, washed twice with brine, and the organic layer is evaporated under reduced pressure. The crude residue is purified by silica gel column chromatography to afford tert-butyl (E)-3-(1-(2-oxo-2,3-dihydro-1H-pyrrolo[2,3-b]pyridine-5-carbonyl)indolin-6-yl)acrylate.

Step 3: tert-butyl 3-(1-(2-oxo-2,3-dihydro-1H-pyrrolo[2,3-b]pyridine-5-carbonyl)indolin-6-yl)propanoate tert-Butyl (E)-3-(1-(2-oxo-2,3-dihydro-1H-pyrrolo[2,3-b]pyridine-5-carbonyl)indolin-6-yl)acrylate is dissolved in ethanol (0.1 M), and palladium on charcoal 10% is added to the reaction mixture. The container is sealed and placed under an atmosphere of hydrogen for 24 hours. The reaction mixture is filtered on celite, and the filtrate is evaporated under reduced pressure to afford the title compound.

Step 4: 3-(1-(2-oxo-2,3-dihydro-1H-pyrrolo[2,3-b]pyridine-5-carbonyl)indolin-6-yl)propanoic Acid tert-Butyl 3-(1-(2-oxo-2,3-dihydro-1H-pyrrolo[2,3-b]pyridine-5-carbonyl)indolin-6-yl)propanoate is dissolved in dichloromethane (0.1 M), and trifluoracetic acid is added. The reaction mixture is stirred at 35 degrees for 24 hours. The volatiles are evaporated under reduced pressure to afford the title compound.

Example 30

5-(4-((1-(2-hydroxyethyl)-1H-1,2,3-triazol-4-yl)methoxy)indoline-1-carbonyl)-1,3-dihydro-2H-pyrrolo[2,3-b]pyridin-2-one

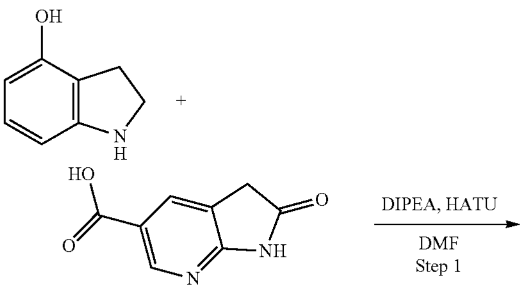

-continued

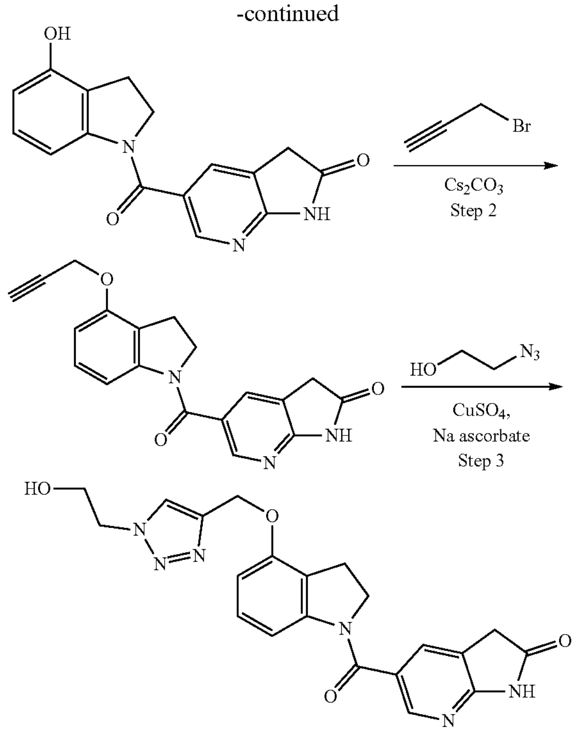

Step 1: 5-(4-hydroxyindoline-1-carbonyl)-1,3-dihydro-2H-pyrrolo[2,3-b]pyridin-2-one The title compound is obtained in analogy to example 12 using indolin-4-ol (CAS 85926-99-4) in place of 1-(4-aminopiperidin-1-yl)ethan-1-one and 2-oxo-2,3-dihydro-1H-pyrrolo[2,3-b]pyridine-5-carboxylic acid (CAS 1260665-66-4) instead of 2-oxo-2,3-dihydrobenzo[d]oxazole-6-carboxylic acid.

Step 2: 5-(4-(prop-2-yn-1-yloxy)indoline-1-carbonyl)-1,3-dihydro-2H-pyrrolo[2,3-b]pyridin-2-one 5-(4-Hydroxyindoline-1-carbonyl)-1,3-dihydro-2H-pyrrolo[2,3-b]pyridin-2-one is dissolved in N,N-dimethylformamide, and cesium carbonate (1.1 equiv.) and propargyl bromide are added. The reaction mixture is stirred at 25° C. for 2 hours. The reaction mixture is partitioned between ethyl acetate and sodium bicarbonate, and the organic layer is evaporated under reduced pressure. The crude residue is purified by silica gel chromatography to afford 5-(4-(prop-2-yn-1-yloxy)indoline-1-carbonyl)-1,3-dihydro-2H-pyrrolo[2,3-b]pyridin-2-one.

Step 3: 5-(4-((1-(2-hydroxyethyl)-1H-1,2,3-triazol-4-yl)methoxy)indoline-1-carbonyl)-1,3-dihydro-2H-pyrrolo[2,3-b]pyridin-2-one 5-(4-(prop-2-yn-1-yloxy)indoline-1-carbonyl)-1,3-dihydro-2H-pyrrolo[2,3-b]pyridin-2-one is dissolved in DMSO (0.1 M), 2-azidoethanol (2.0 equiv., CAS 1517-05-1) is added, the reaction mixture is degassed with nitrogen. Aqueous copper sulfate (1M, 1.0 equiv.) and aqueous sodium ascorbate (2M, 2.0 equiv.) are added dropwise, in sequence, to the reaction mixture. The compound is purified by column chromatography to afford the title compound.

Example 31

2-(2-Oxo-2,3-dihydrobenzo[d]oxazole-6-carbonyl)isoindolin-4-yl Piperidine-4-carboxylate

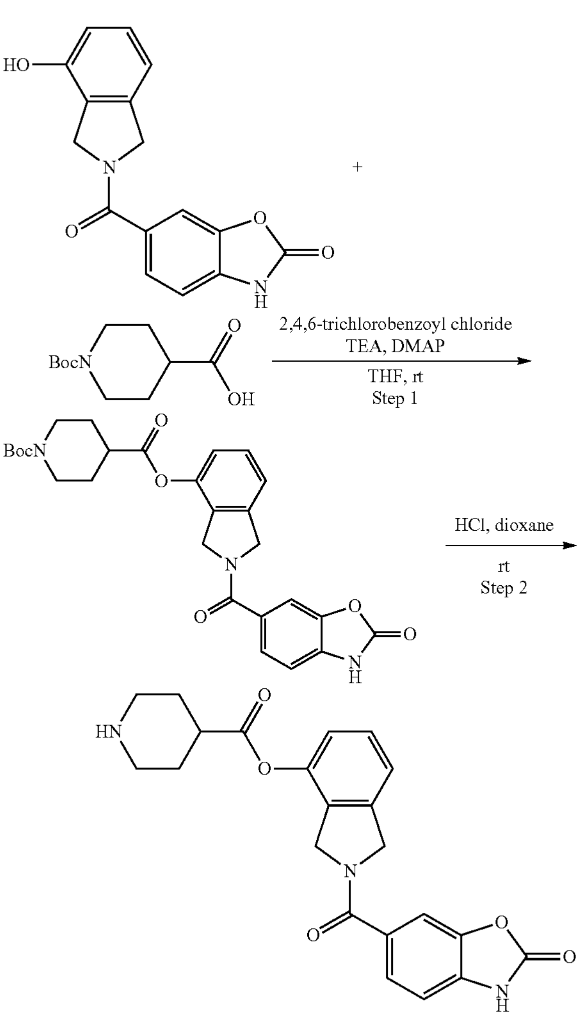

Step 1: 1-(tert-Butyl) 4-(2-(2-Oxo-2,3-dihydrobenzo[d]oxazole-6-carbonyl)isoindolin-4-yl) Piperidine-1,4-dicarboxylate 1-(tert-Butoxycarbonyl)piperidine-4-carboxylic acid (CAS 84358-13-4, 1 equiv.), 2,4,6-trichlorobenzoyl chloride (CAS 4136-95-2, 1 equiv.), and 6-(4-hydroxyisoindoline-2-carbonyl)benzo[6/]oxazol-2(3H)-one (1 equiv.) are dissolved in dry THF (0.1 M). Triethylamine (2 equiv.) is added slowly, followed by DMAP (25 mol %). The reaction mixture is stirred at rt until the reaction is complete and then quenched with 10% hydrochloric acid solution. The solution is extracted twice with ethyl acetate. The combined organic phase is washed twice with saturated sodium bicarbonate solution, dried and purified by flash column chromatography on silica gel to afford the title compound.

Step 2: 2-(2-Oxo-2,3-dihydrobenzo[d]oxazole-6-carbonyl)isoindolin-4-yl Piperidine-4-carboxylate 1-(tert-Butyl) 4-(2-(2-oxo-2,3-dihydrobenzo[d]oxazole-6-carbonyl)isoindolin-4-yl) piperidine-1,4-dicarboxylate (1 equiv.) is dissolved in DCM (0.2 M) and a solution of 4 M HCl in dioxane (0.2 M) is added at rt. The reaction is stirred at rt to completion. The mixture is concentrated and lyophilized to afford the title compound.

Example 32

3-((2-(2-Oxo-2,3-dihydrobenzo[d]oxazole-6-carbonyl)isoindolin-4-yl)oxy)propanoic Acid

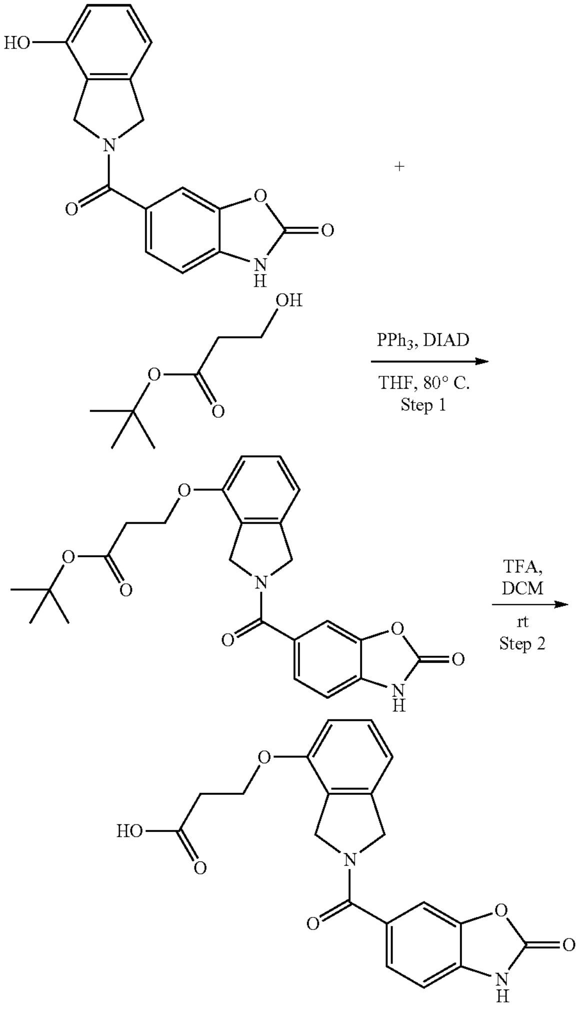

Step 1: tert-Butyl 3-((2-(2-Oxo-2,3-dihydrobenzo[d]oxazole-6-carbonyl)isoindolin-4-yl)oxy)propanoate A solution of diisopropyl azodicarboxylate (1.3 equiv.) in toluene is added drop-wise to a 0° C. solution of 6-(4-hydroxyisoindoline-2-carbonyl)benzo[d]oxazol-2(3H)-one (1 equiv.), tert-butyl 3-hydroxypropanoate (CAS 59854-11-4, 1 equiv.) and $Ph_3P$ (1.3 equiv.) in THF (0.2 M). The reaction mixture is heated at reflux until completion. The reaction mixture is cooled and concentrated, and purified by silica gel flash chromatography to afford the title compound.

Step 2: 3-((2-(2-Oxo-2,3-dihydrobenzo[d]oxazole-6-carbonyl)isoindolin-4-yl)oxy)propanoic Acid tert-Butyl 3-((2-(2-oxo-2,3-dihydrobenzo[d]oxazole-6-carbonyl)isoindolin-4-yl)oxy)propanoate (1 equiv.) is dissolved in DCM (0.2 M), and TFA (0.2 M) is added at it. The reaction is stirred at rt to completion. The mixture is concentrated and lyophilized to afford the title compound.

Example 33

6-(4-Hydroxy-5-((4-(hydroxymethyl)piperidin-1-yl)methyl)isoindoline-2-carbonyl)benzo[d]oxazol-2(3H)-one

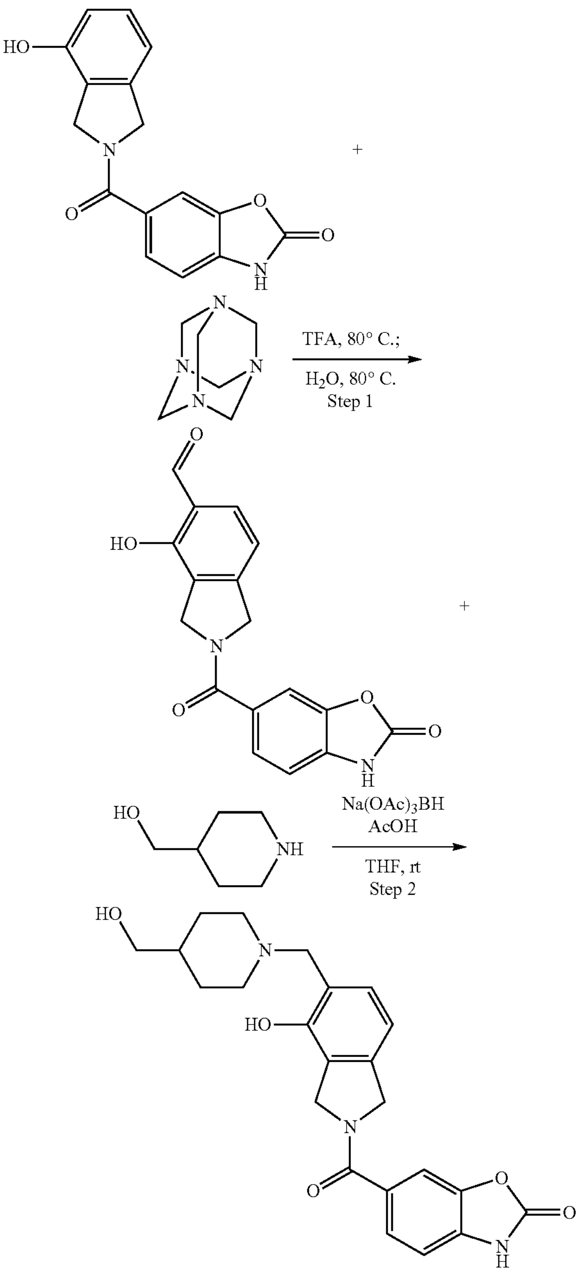

Step 1: 4-Hydroxy-2-(2-oxo-2,3-dihydrobenzo[d]oxazole-6-carbonyl)isoindoline-5-carbaldehyde 6-(4-Hydroxyisoindoline-2-carbonyl)benzo[6/]oxazol-2(3H)-one (1 equiv.) and hexamethylenetetramine (CAS 100-

97-0, 4 equiv.) is dissolved in TFA (0.5 M). The reaction mixture is refluxed using a dean stark system until reaction completion. The mixture is thereafter cooled to room temperature. Water is added, and the reaction is heated to 80° C. for 2 h. After cooling to room temperature, the mixture is filtered, and the precipitate is purified by silica gel flash chromatography to afford the title compound.

Step 2: 6-(4-Hydroxy-5-((4-(hydroxymethyl)piperidin-1-yl)methyl)isoindoline-2-carbonyl)benzo[d]oxazol-2(3H)-one 4-Hydroxy-2-(2-oxo-2,3-dihydrobenzo[d]oxazole-6-carbonyl)isoindoline-5-carbaldehyde (1 equiv.) and 4-Piperidinemethanol (CAS 6457-49-4, 1.1 equiv.) are dissolved in THF (0.4 M). Acetic acid (drops) is added, followed by sodium triacetoxyborohydride (1.3 equiv.). The reaction mixture is stirred at rt until reaction completion. The reaction mixture is partitioned between ethyl acetate and saturated ammonia chloride, and the organic layer is evaporated under reduced pressure. The crude residue is purified by silica gel chromatography to afford the title compound.

Example 34

5-(5-(1-(5-hydroxypentanoyl)piperidin-4-yl)-2-isopropyl-1H-benzo[d]imidazol-1-yl)-1,3-dihydro-2H-pyrrolo[2,3-b]pyridin-2-one

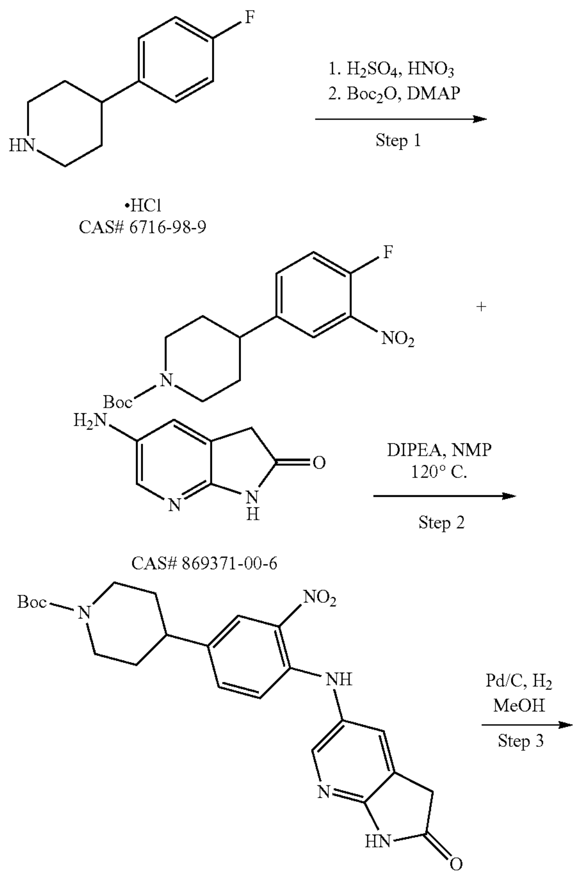

-continued

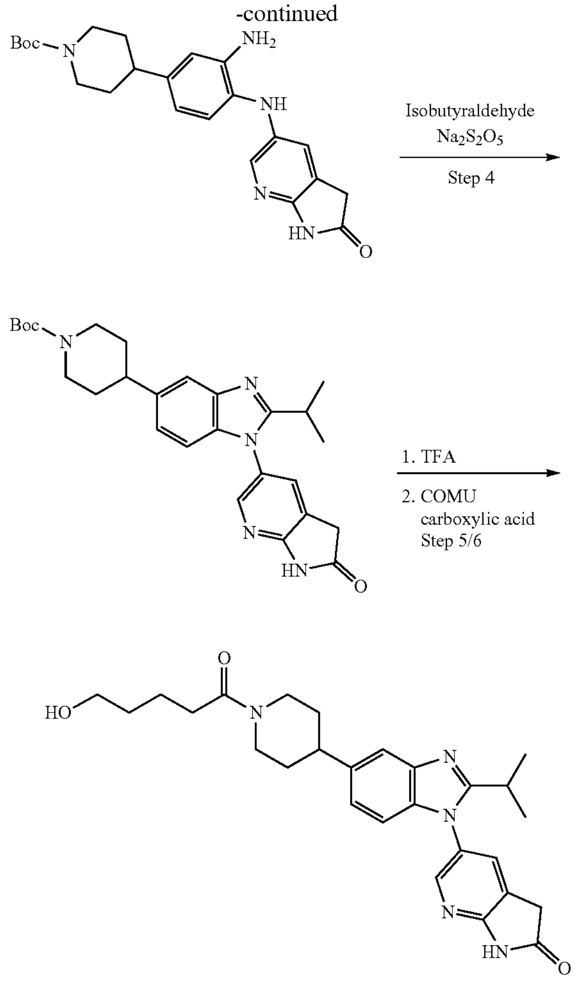

Step 1: tert-Butyl 4-(4-Fluoro-3-nitrophenyl)piperidine-1-carboxylate 4-(4-Fluorophenyl)piperidine hydrochloride (1 equiv.) is dissolved in concentrated sulfuric acid (0.5 M reaction concentration). The mixture is cooled to 0° C., and concentrated nitric acid (1.5 equiv.) is added slowly drop-wise. The solution is slowly warmed to room temperature and then heated to 50° C. The solution is allowed to stir for 24 hours. The mixture is then cooled to room temperature, poured into ice water, and treated with 1M NaOH until basic. The product is then extracted from the solution with ethyl ether (3×). The combined organic layers are washed with brine and dried over sodium sulfate. The solvent is removed under reduced pressure.

The crude material is then dissolved in THF (0.1 M reaction concentration). DMAP (0.1 equiv.) is added followed by Boc anhydride (1 equiv.). The mixture is allowed to stir for two hours. It is then diluted with ethyl acetate and washed with water. The organic layer w is then washed with brine and dried over sodium sulfate before concentrating under reduced pressure. Column chromatography using a gradient of ethyl acetate in hexanes affords tert-butyl 4-(4-fluoro-3-nitrophenyl)piperidine-1-carboxylate.

Step 2: tert-Butyl 4-(3-Nitro-4-((2-oxo-2,3-dihydro-1H-pyrrolo[2,3-b]pyridin-5-yl)amino)phenyl)piperidine-1-carboxylate The title compound is synthesized in analogy to Example 4 using tert-butyl 4-(4-fluoro-3-nitrophenyl)piperidine-1-carboxylate in place of 4-fluoro-A-methyl-3-nitrobenzamide.

Step 3: tert-Butyl 4-(3-Amino-4-((2-oxo-2,3-dihydro-1H-pyrrolo[2,3-b]pyridin-5-yl)amino)phenyl)piperidine-1-carboxylate The title compound is synthesized in analogy to Example 4 using tert-butyl 4-(3-nitro-4-((2-oxo-2,3-dihydro-1H-pyrrolo[2,3-b]pyridin-5-yl)amino)phenyl)piperidine-1-carboxylate in place of N-methyl-3-nitro-4-[(2-oxoindolin-6-yl)amino]benzamide.

Step 4: tert-Butyl 4-(2-Isopropyl-1-(2-oxo-2,3-dihydro-1H-pyrrolo[2,3-b]pyridin-5-yl)-1H-benzo[d]imidazol-5-yl)piperidine-1-carboxylate The title compound is synthesized in analogy to Example 4 using tert-butyl 4-(3-amino-4-((2-oxo-2,3-dihydro-1H-pyrrolo[2,3-b]pyridin-5-yl)amino)phenyl)piperidine-1-carboxylate in place of 3-amino-N-methyl-4-[(2-oxoindolin-6-yl)amino]benzamide.

Step 5: 5-(2-Isopropyl-5-(piperidin-4-yl)-1H-benzo[d]imidazol-1-yl)-1,3-dihydro-2H-pyrrolo[2,3-b]pyridin-2-one Trifluoroacetate tert-Butyl 4-(2-isopropyl-1-(2-oxo-2,3-dihydro-1H-pyrrolo[2,3-b]pyridin-5-yl)-1H-benzo[d]imidazol-5-yl)piperidine-1-carboxylate (1 equiv.) is dissolved in dichloromethane (0.2 M reaction concentration). Trifluoroacetate acid (10 equiv.) is then added, and the mixture is allowed to stir at room temperature for 24 hours. The mixture is then concentrated under reduced pressure to afford the title compound.

Step 6: 5-(5-(1-(5-Hydroxypentanoyl)piperidin-4-yl)-2-isopropyl-1H-benzo[d]imidazol-1-yl)-1,3-dihydro-2H-pyrrolo[2,3-b]pyridin-2-one 5-(2-Isopropyl-5-(piperidin-4-yl)-1H-benzo[d]imidazol-1-yl)-1,3-dihydro-2H-pyrrolo[2,3-b]pyridin-2-one trifluoroacetate (1 equiv.) and 5-hydroxypentanoic acid (1 equiv.) are dissolved in DMF (0.1 M reaction concentration). Hunig's base (3 equiv.) is added followed by COMU (1.1 equiv.). The mixture is allowed to stir at room temperature for 2 hr. The mixture is then diluted with ethyl acetate and water. The organic layer is separated, and the product is extracted from the aqueous layer with ethyl acetate (3×). The combined organic layers are washed with brine and dried over sodium sulfate before concentrating. The crude material is then purified on silica using a gradient of ethyl acetate in hexanes to afford the desired compound.

Example 35

6-(((2-Isopropyl-1-(2-oxo-2,3-dihydro-1H-pyrrolo[2,3-b]pyridin-5-yl)-1H-benzo[d]imidazol-4-yl)methyl)amino)hexanoic Acid

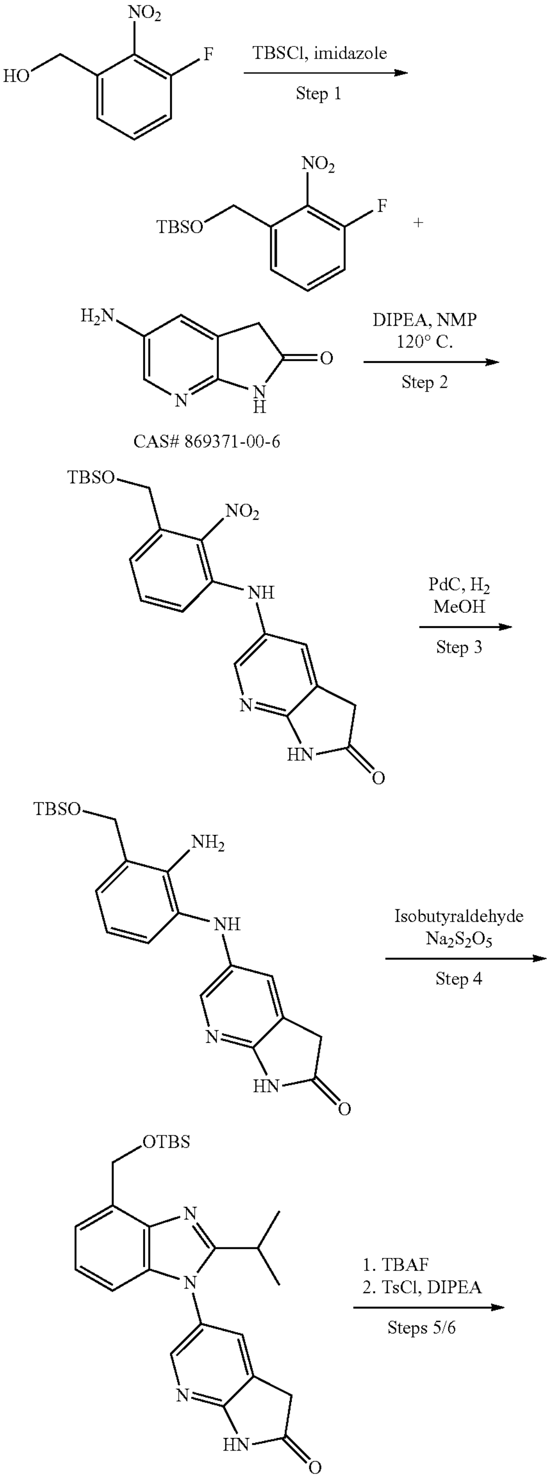

-continued

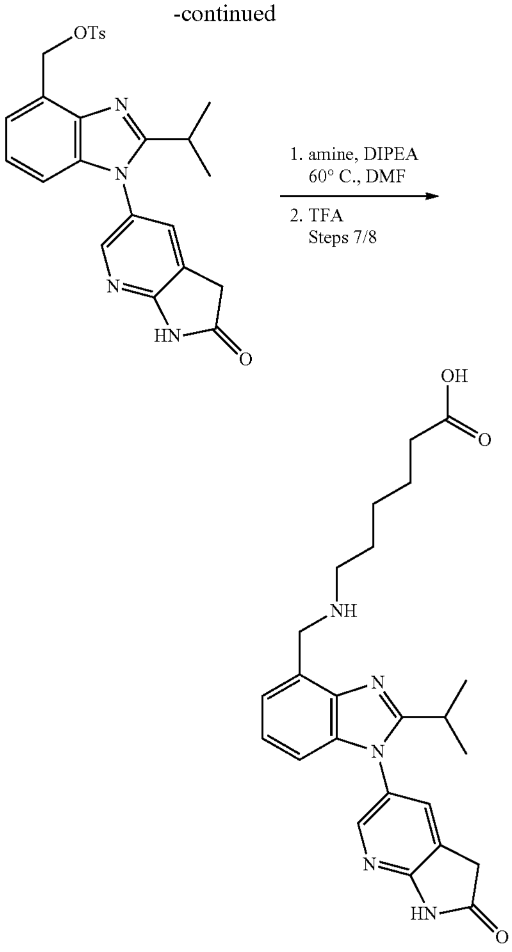

Step 1: tert-Butyl((3-Fluoro-2-nitrobenzyl)oxy)dimethylsilane (3-Fluoro-2-nitrophenyl)methanol (1 equiv.) is dissolved in THF (0.1 M reaction concentration). Imidazole (1.2 equiv.) is added followed by TBSCl (1.1 equiv.). The mixture is allowed to stir for 24 hrs. It is then diluted with ethyl acetate and water. The organic layer is separated, and the product is extracted from the aqueous layer using ethyl acetate (3×). The combined organic layers are washed with brine and dried over sodium sulfate before concentrating. The crude material is then purified on silica using a gradient of ethyl acetate in hexanes to afford the desired compound.

Step 2: 5-((3-(((tert-Butyldimethylsilyl)oxy)methyl)-2-nitrophenyl)amino)-1,3-dihydro-2H-pyrrolo[2,3-b]pyridin-2-one The title compound is synthesized in analogy to Example 4 using tert-butyl((3-fluoro-2-nitrobenzyl)oxy)dimethylsilane in place of 4-fluoro-N-methyl-3-nitrobenzamide.

Step 3: 5-((2-Amino-3-(((tert-butyldimethylsilyl)oxy)methyl)phenyl)amino)-1,3-dihydro-2H-pyrrolo[2,3-b]pyridin-2-one The title compound is synthesized in analogy to Example 4 using 5-((3-(((tert-butyldimethyl silyl)oxy)methyl)-2-nitrophenyl)amino)-1,3-dihydro-2H-pyrrolo[2,3-b]pyridin-2-one in place of N-methyl-3-nitro-4-[(2-oxoindolin-6-yl)amino]benzamide.

Step 4: 5-(4-(((tert-Butyldimethylsilyl)oxy)methyl)-2-isopropyl-1H-benzo[d]imidazol-1-yl)-1,3-dihydro-2H-pyrrolo[2,3-b]pyridin-2-one The title compound is synthesized in analogy to Example 4 using 5-((2-amino-3-(((tert-butyldimethyl silyl)oxy)methyl)phenyl)amino)-1,3-dihydro-2H-pyrrolo[2,3-b]pyridin-2-one in place of 3-amino-N-methyl-4-[(2-oxoindolin-6-yl)amino]benzamide.

Step 5: 5-(4-(Hydroxymethyl)-2-isopropyl-1H-benzo[d]imidazol-1-yl)-1,3-dihydro-2H-pyrrolo[2,3-b]pyridin-2-one 5-(4-(((tert-Butyldimethyl silyl)oxy)methyl)-2-isopropyl-1H-benzo[d]imidazol-1-yl)-1,3-dihydro-2H-pyrrolo[2,3-b]pyridin-2-one (1 equiv.) is dissolved in THF (0.1 M reaction concentration) and cooled to 0° C. TBAF (1 equiv.) is added, and the mixture is allowed to stir for 2 hours. The mixture is then diluted with water. The product is extracted with ethyl acetate (×3). The combined organic layers are then washed with brine and dried over sodium sulfate. The crude material is then purified on silica using a gradient of ethyl acetate in hexanes.

Step 6: (2-Isopropyl-1-(2-oxo-2,3-dihydro-1H-pyrrolo[2,3-b]pyridin-5-yl)-1H-benzo[d]imidazol-4-yl)methyl 4-methylbenzenesulfonate 5-(4-(Hydroxymethyl)-2-isopropyl-1H-benzo[d]imidazol-1-yl)-1,3-dihydro-2H-pyrrolo[2,3-b]pyridin-2-one (1 equiv.) is dissolved in THF (0.1 M reaction concentration). Hunig's base (2 equiv.) is added followed by tosyl chloride. The mixture is allowed to stir for 8 hours. It is then diluted with water. The product is extracted with ethyl acetate (×3). The combined organic layers are then washed with brine and dried over sodium sulfate. The crude material is then purified on silica using a gradient of ethyl acetate in hexanes to afford the desired compound.

Step 7: tert-Butyl 6-(((2-Isopropyl-1-(2-oxo-2,3-dihydro-1H-pyrrolo[2,3-b]pyridin-5-yl)-1H-benzo[d]imidazol-4-yl)methyl)amino)hexanoate (2-Isopropyl-1-(2-oxo-2,3-dihydro-1H-pyrrolo[2,3-b]pyridin-5-yl)-1H-benzo[d]imidazol-4-yl)methyl 4-methylbenzenesulfonate (1 equiv.) is dissolved in DMF (0.2 M reaction concentration). Hunig's base (3 equiv.) is added followed by tert-butyl 6 aminohexanoate (1 equiv.). The mixture is heated to 60° C. for 8 hours. The mixture is then cooled to room temperature and diluted with ethyl acetate and 1.0 M HCl aqueous solution. The organic layer is separated, and the product is extracted from the aqueous layer using ethyl acetate (3×). The combined organic layers are then washed with brine and dried over sodium sulfate. The crude material is then purified on silica using a gradient of methanol in dichloromethane to afford the desired compound.

Step 8: 6-(((2-isopropyl-1-(2-oxo-2,3-dihydro-1H-pyrrolo[2,3-b]pyridin-5-yl)-1H-benzo[d]imidazol-4-yl)methyl)amino)hexanoic acid tert-Butyl 6-(((2-isopropyl-1-(2-oxo-2,3-dihydro-1H-pyrrolo[2,3-b]pyridin-5-yl)-1H-benzo[d]imidazol-4-yl)methyl)

amino)hexanoate (1 equiv.) is dissolved in dichloromethane (0.5 M reaction concentration). Trifluoroacetic acid (10 equiv.) is then added, and the mixture is allowed to stir at room temperature for 24 hours. The solvent is then removed under reduced pressure, and the crude material is purified on silica using a gradient of methanol in dichloromethane to obtain the desired product.

Example 36 tert-Butyl 3-(2-Isopropyl-1-(2-oxo-2,3-dihydro-1H-pyrrolo[2,3-b]pyridin-5-yl)-1H-benzo[d]imidazol-5-yl)propiolate

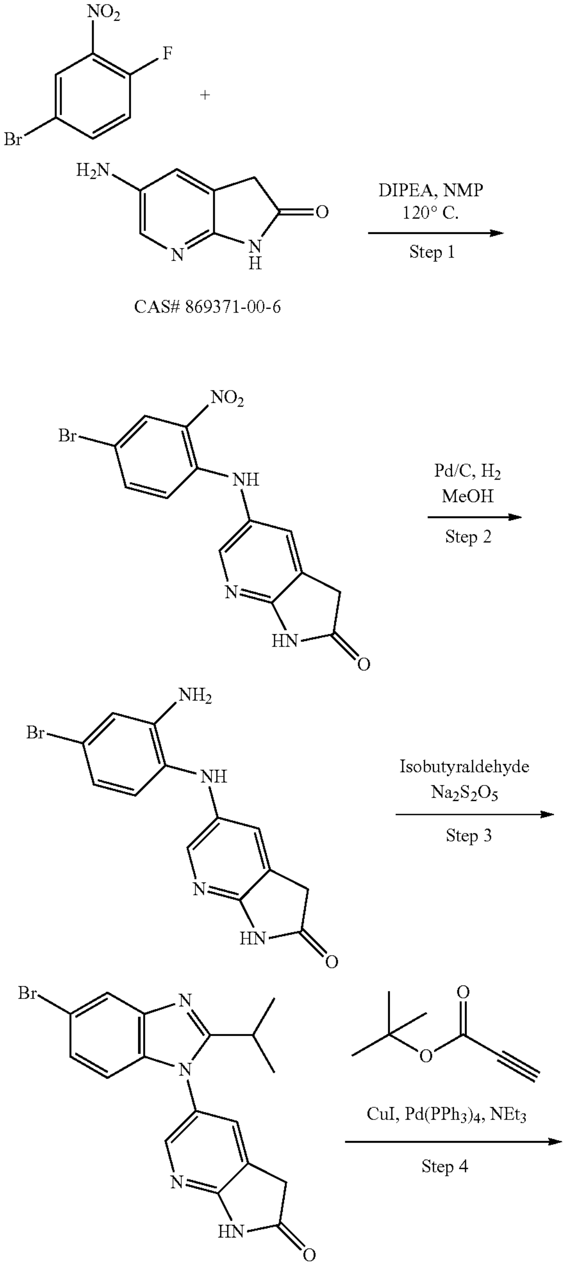

-continued

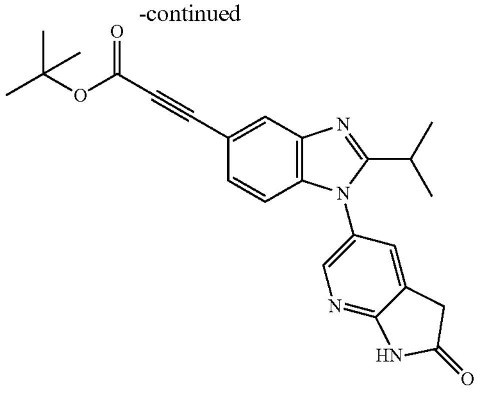

Step 1: 5-((4-Bromo-2-nitrophenyl)amino)-1,3-dihydro-2H-pyrrolo[2,3-b]pyridin-2-one The title compound is synthesized in analogy to Example 4 using 4-bromo-1-fluoro-2-nitrobenzene in place of 4-fluoro-A-methyl-3-nitrobenzamide.

Step 2: 5-((2-amino-4-bromophenyl)amino)-1,3-dihydro-2H-pyrrolo[2,3-b]pyridin-2-one The title compound is synthesized in analogy to Example 4 using 5-((4-bromo-2-nitrophenyl)amino)-1,3-dihydro-2H-pyrrolo[2,3-b]pyridin-2-onein place of N-methyl-3-nitro-4-[(2-oxoindolin-6-yl)amino]benzamide.

Step 3: 5-(5-bromo-2-isopropyl-1H-benzo[d]imidazol-1-yl)-1,3-dihydro-2H-pyrrolo[2,3-b]pyridin-2-one The title compound is synthesized in analogy to Example 4 using 5-((2-amino-4-bromophenyl)amino)-1,3-dihydro-2H-pyrrolo[2,3-b]pyridin-2-one in place of 3-amino-N-methyl-4-[(2-oxoindolin-6-yl)amino]benzamide.

Step 4: tert-butyl 3-(2-isopropyl-1-(2-oxo-2,3-dihydro-1H-pyrrolo[2,3-b]pyridin-5-yl)-1H-benzo[d]imidazol-5-yl)propiolate 5-(5-bromo-2-isopropyl-1H-benzo[d]imidazol-1-yl)-1,3-dihydro-2H-pyrrolo[2,3-b]pyridin-2-one (1 equiv.) and tert-butyl propiolate (1.5 equiv.) are dissolved in DMF (0.2 M reaction concentration). Triethylamine (5 equiv.) is added, and the mixture is degassed for 20 minutes. CuI (0.05 equiv.) is then added followed by $Pd(PPh_3)_4$ (0.1 equiv.). The mixture is degassed a further 10 minutes and then heated to 80° C. The mixture is allowed to stir for 12 hours. It is then cooled to room temperature and diluted with ethyl acetate and water. The organic layer is separated, and the product is extracted from the aqueous layer using ethyl acetate (3×). The combined organic layers are then washed with brine and dried over sodium sulfate. The crude material is then purified on silica using a gradient of methanol in dichloromethane to afford the desired compound.

Pharmacological Tests

The compounds described herein and their pharmaceutically acceptable salts possess valuable pharmacological properties. The compounds were investigated in accordance with the test given hereinafter.

Fluorescence Direct Binding Protocol

Principle

Determination of the affinities of compounds to protein containing one or more tryptophan is measurable by monitoring the fluorescence emission in direct mode. The measurements depending on the protein available amounts are performed either manually in a cuvette on ISS-PC1 photon counting spectrofluorometer or automatically in well plates on a fluorescence plate reader device. Fluorescence titrations are performed at 20° C. in the chosen binding assay buffer by using a defined constant protein concentration against ligand concentration variations. Small aliquots of known ligand concentration solubilized in DMSO were added and the fluorescence, excited at 280 nm, was recorded at 340 nm. The fluorescence intensity was corrected for protein dilution and for the filter effect (Birdsall et al.). The corrected fluorescence intensity was plotted against the ligand concentration and fitted using a four-parameter sigmoidal function, from which the equilibrium dissociation constant Kd was computed using the law of mass action assuming a 1:1 protein-ligand complex (Eftink, 1997).

Process

1) Optimization of measurement parameters to minimize protein consumption and to minimize the dilution effect and the DMSO content
2) Titration measurements of the protein against ligand by at least 12 titration steps to obtain a good s-curve fit
3) Repeat the same titration measurements with the ligand alone to enable correction
4) Check the stability of the protein once by titration against DMSO alone
5) Determination of the molar extinction coefficients of the ligand at 280 and 340 nm with help of an UV-spectrophotometer
6) Use Excel template for the correction of the measured raw data Use GraphPad Prism software for the quadratic binding fit and the $K_D$ evaluation.

TABLE 8

| Protein - buffers, Reference compound: thalidomide, Contergan, Softenon | |
|---|---|
| Protein Batch # | Cereblon_17_13 |
| Construct name | hCereblon(M1-L442)_hDDB1(M1-H1140) |
| Concentration | 2.54 mg/ml |
| MW | 180180 Da |
| Molar extinction coefficient | $\square_{280}$ = 165045 $M^{-1} \cdot cm^{-1}$ |
| Storage buffer | 20 mM MES pH 6.5 200 mM NaCl 1 mM TCEP |
| Assay buffer | 50 mM Hepes 7.4 200 mM NaCl |

TABLE 9

| Settings | |
|---|---|
| Device | ISS-PC1 |
| Excitation wavelength [nm] | 280 |
| Emission wavelength [nm] | 340 |
| Cuvette | Hellma 115F-QS |
| Volume [µL] | 500 |

Protein Preparation

TABLE 10

| Protein preparation | | |
|---|---|---|
| Volume Protein [µL] | Volume buffer [µL] | Protein concentration [M] |
| 1.8 @ 2.54 mg/ml | 498.2 | 5.0E−8 |

TABLE 11

| Titration steps | | | | |
|---|---|---|---|---|
| C Lig [M] | C Aliquot [M] | V Aliquot [µL] | C Prot[M] | Dilution factor |
| 1E−10 | 1.0E−07 | 0.5 | 4.995E−08 | 1.001 |
| 1.1E−09 | 1.0E−06 | 0.5 | 4.990E−08 | 1.002 |
| 3.1E−09 | 1.0E−06 | 1 | 4.980E−08 | 1.004 |
| 5.1E−09 | 1.0E−06 | 1 | 4.970E−08 | 1.006 |
| 1.51E−08 | 1.0E−05 | 0.5 | 4.965E−08 | 1.007 |
| 2.51E−08 | 1.0E−05 | 0.5 | 4.960E−08 | 1.008 |
| 4.51E−08 | 1.0E−05 | 1 | 4.950E−08 | 1.01 |
| 6.51E−08 | 1.0E−05 | 1 | 4.941E−08 | 1.012 |
| 1.651E−07 | 1.0E−04 | 0.5 | 4.936E−08 | 1.013 |
| 3.651E−07 | 1.0E−04 | 1 | 4.926E−08 | 1.015 |
| 5.651E−07 | 1.0E−04 | 1 | 4.916E−08 | 1.017 |
| 7.651E−07 | 1.0E−04 | 1 | 4.907E−08 | 1.019 |
| 9.651E−07 | 1.0E−04 | 1 | 4.897E−08 | 1.021 |
| 1.9651E−06 | 1.0E−03 | 0.5 | 4.892E−08 | 1.022 |
| 2.9651E−06 | 1.0E−03 | 0.5 | 4.888E−08 | 1.023 |
| 1.29651E−05 | 1.0E−02 | 0.5 | 4.883E−08 | 1.024 |
| 2.29651E−05 | 1.0E−02 | 0.5 | 4.878E−08 | 1.025 |
| 4.29651E−05 | 1.0E−02 | 1 | 4.869E−08 | 1.027 |
| 6.29651E−05 | 1.0E−02 | 1 | 4.859E−08 | 1.029 |
| 8.29651E−05 | 1.0E−02 | 1 | 4.850E−08 | 1.031 |

TABLE 12

| affinities of examples to CRBN protein | | |
|---|---|---|
| Ex. | Name | Fluorescence h-Cereblon_DDB1 Mean $K_d$_EQ (µM) |
| 1 | N-(2-oxo-3H-1,3-benzoxazol-6-yl)benzamide | 0.004 |
| 2 | N-(2-oxoindolin-5-yl)furan-2-carboxamide | 0.007 |
| 3 | 2-(2-methylphenoxy)-N-(2-oxo-3H-1,3-benzothiazol-6-yl)acetamide | 0.014 |
| 4 | 2-isopropyl-N-methyl-1-(2-oxoindolin-6-yl)benzimidazole-5-carboxamide | 0.002 |
| 5 | 2-isopropyl-N-methyl-1-(2-oxoindolin-5-yl)benzimidazole-5-carboxamide | 0.003 |
| 6 | 6-(2-aminoanilino)-3H-1,3-benzothiazol-2-one | <0.001 |
| 7 | 6-(2-isopropylbenzimidazol-1-yl)-3H-1,3-benzothiazol-2-one | 0.019 |
| 8 | 6-(2-aminoanilino)-3H-1,3-benzoxazol-2-one | 0.008 |
| 9 | 6-(2-isopropylbenzimidazol-1-yl)-3H-1,3-benzoxazol-2-one | 0.108 |
| 10 | 2-oxo-N-phenylindoline-5-carboxamide | 0.091 |
| 11 | 2-oxo-N-phenyl-3H-1,3-benzoxazole-6-carboxamide | 0.054 |
| 12 | N-(1-acetyl-4-piperidyl)-2-oxo-3H-1,3-benzoxazole-6-carboxamide | 0.006 |
| 13 | 6-(indoline-1-carbonyl)-3H-1,3-benzoxazol-2-one | 0.004 |
| 14 | 6-(2,3-dihydropyrrolo[2,3-b]pyridine-1-carbonyl)-3H-1,3-benzoxazol-2-one | 0.024 |
| 15 | 2-oxo-N-phenyl-3H-1,3-benzothiazole-6-carboxamide | 0.079 |
| 16 | 6-(indoline-1-carbonyl)-3H-1,3-benzothiazol-2-one | 0.028 |
| 17 | 5-(indoline-1-carbonyl)indolin-2-one | 0.015 |
| 18 | 2-oxo-N-phenyl-3H-oxazolo[4,5-b]pyridine-6-carboxamide | 0.024 |

TABLE 12-continued affinities of examples to CRBN protein

| Ex. | Name | Fluorescence h-Cereblon_DDB1 Mean $K_d$_EQ (μM) |
|---|---|---|
| 19 | N-(1-acetyl-4-piperidyl)-2-oxo-3H-oxazolo[4,5-b]pyridine-6-carboxamide | 0.007 |
| 20 | 5-(indoline-1-carbonyl)-1,3-dihydropyrrolo[2,3-b]pyridin-2-one | 0.013 |
| 21 | 3,3-difluoro-5-(2-isopropylbenzimidazol-1-yl)indolin-2-one | <0.001 |
| 22 | 6-(4-hydroxyisoindoline-2-carbonyl)-3H-1,3-benzoxazol-2-one | 0.002 |
| 23 | 6-(4-nitroisoindoline-2-carbonyl)-3H-1,3-benzoxazol-2-one | 0.014 |
| 24 | N-(3,3-difluoro-2-oxo-indolin-5-yl)tetralin-1-carboxamide | 0.028 |
| 25 | N-(3,3-difluoro-2-oxo-indolin-5-yl)benzofuran-3-carboxamide | 0.052 |
| 26 | 2-isopropyl-N-methyl-1-(2-oxo-1,3-dihydropyrrolo[2,3-b]pyridin-5-yl)benzimidazole-5-carboxamide | 0.007 |
| 27 | 5-(2-isopropylbenzimidazol-1-yl)-1,3-dihydropyrrolo[2,3-b]pyridin-2-one | <0.001 |

All publications and patent applications cited in this specification are herein incorporated by reference as if each individual publication or patent application were specifically and individually indicated to be incorporated by reference.

Although the foregoing invention has been described in some detail by way of illustration and example for the purposes of clarity of understanding, it will be readily apparent to one of ordinary skill in the art in light of the teaching of this invention that certain changes and modification may be made thereto without departing from the spirit or scope of the invention as defined in the claims.

What is claimed is:

1. A compound of Formula:

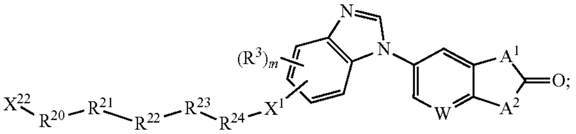

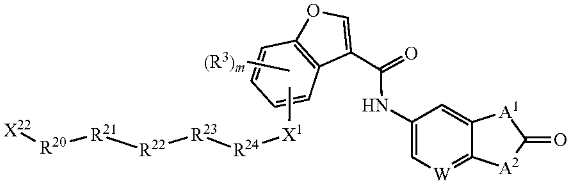

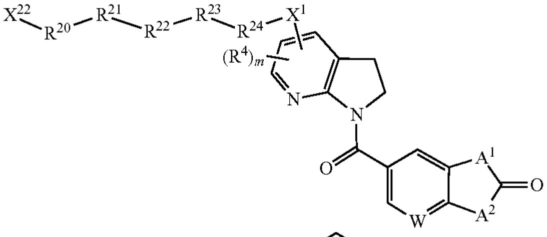

or

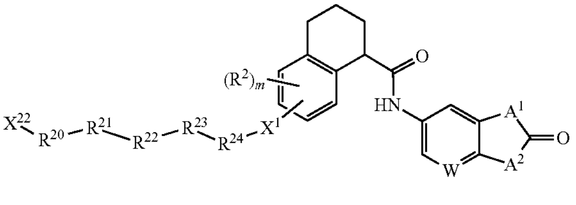

or a pharmaceutically acceptable salt thereof;

wherein:

m is 0, 1, or 2;

$A^1$ is selected from the group consisting of —O—, —S—, —$CH_2$—, —$CF_2$— and —NH—, and $A^2$ is —$CH_2$—; or $A^1$ is selected from the group consisting of —O—, —S—, —$CH_2$—, and —$CF_2$—, and $A^2$ is —NH—;

W is CH or N;

$R^2$ is independently selected at each occurrence from the group consisting of: —$(CH_2)_{0-1}$—($C_{3-7}$cycloalkyl)-aryl substituted by $R^{10}$; —$(CH_2)_{0-1}$—($C_{3-7}$cycloalkyl)-aryl; —$(CH_2)_{0-1}$-aryl substituted by $R^{10}$; —$(CH_2)_{0-1}$-aryl; —$(CH_2)_{0-1}$—$C_{3-7}$cycloalkyl substituted by $R^{10}$; —$(CH_2)_{0-1}$—$C_{3-7}$cycloalkyl; —$(CH_2)_{0-1}$-heteroaryl substituted by $R^9$; —$(CH_2)_{0-1}$-heteroaryl; —C(═O)$C_{1-6}$alkyl; —C(═O)—N($R^7R^8$); —C(═O)O$C_{1-6}$alkyl; —$C_{1-6}$alkoxy; —$C_{1-6}$alkyl; —$CH_2$—O—$(CH_2)_{0-1}$-aryl substituted by $R^{10}$; —$CH_2$—O—$(CH_2)_{0-1}$-aryl; —O—$(CH_2)_{0-1}$-aryl; -halogen; halogen-$C_{1-6}$alkyl; hydroxy-$C_{1-6}$alkyl; —N($R^5R^6$); —$NO_2$; —NH—C(═O)$C_{1-6}$alkyl; and —$SO_2$—N($R^5R^6$);

$R^3$ is independently selected at each occurrence from the group consisting of: —$(CH_2)_{0-1}$—($C_{3-7}$cycloalkyl)-aryl substituted by $R^{10}$; —$(CH_2)_{0-1}$—($C_{3-7}$cycloalkyl)-aryl; —$(CH_2)_{0-1}$-aryl substituted by $R^{10}$; —$(CH_2)_{0-1}$-aryl; —$(CH_2)_{0-1}$—$C_{3-7}$cycloalkyl substituted by $R^{10}$; —$(CH_2)_{0-1}$—$C_{3-7}$-cycloalkyl; —$(CH_2)_{0-1}$-heteroaryl substituted by $R^9$; —$(CH_2)_{0-1}$-heteroaryl; —$(CH_2)_{0-1}$-heterocycloalkyl; —C(═O)$C_{1-6}$alkyl; —$(CH_2)_{0-2}$—C(═O)—N($R^7R^8$); —C(═O)O$C_{1-6}$alkyl; —$C_{1-6}$-alkoxy; —$C_{1-6}$alkyl; —OH; —$NO_2$; —$C_{1-6}$alkyl-N($R^{11}$)—C(═O)—$R^{12}$; —$CH_2$—O—$(CH_2)_{0-1}$-aryl substituted by $R^{10}$; —$CH_2$—O—$(CH_2)_{0-1}$-aryl; —O—$(CH_2)_{0-1}$-aryl; -halogen; halogen-$C_{1-6}$alkyl; hydroxy-$C_{1-6}$alkyl; hydroxy-$C_{1-6}$alkyl-aryl; —N($R^5R^6$); —NH—C(═O)$C_{1-6}$alkyl; and —NH—C(═O)O$C_{1-6}$alkyl;

$R^4$ is independently selected at each occurrence from the group consisting of: —$(CH_2)_{0-1}$—($C_{3-7}$cycloalkyl)-aryl substituted by $R^{10}$; —$(CH_2)_{0-1}$—($C_{3-7}$cycloalkyl)-aryl; —$(CH_2)_{0-1}$-aryl substituted by $R^{10}$; —$(CH_2)_{0-1}$-aryl; —$(CH_2)_{0-1}$—$C_{3-7}$cycloalkyl substituted by $R^{10}$; —$(CH_2)_{0-1}$—$C_{3-7}$-cycloalkyl; —$(CH_2)_{0-1}$-heteroaryl substituted by $R^9$; —$(CH_2)_{0-1}$-heteroaryl; ═O as allowed by valence; —C(═O)$C_{1-6}$alkyl; —C(═O)—N($R^7R^8$); —C(═O)O$C_{1-6}$alkyl; —$C_{1-6}$alkoxy; —$C_{1-6}$alkyl; —$CH_2$—O—$(CH_2)_{0-1}$-aryl substituted by $R^{10}$; —$CH_2$—O—$(CH_2)_{0-1}$-aryl; -halogen; halogen-$C_{1-6}$-alkyl; hydroxy-$C_{1-6}$alkyl; —N($R^5R^6$); and —NH—C(═O)$C_{1-6}$alkyl;

$R^5$ and $R^6$ are independently selected at each occurrence from the group consisting of H, $C_{1-6}$alkyl and phenyl;

or $R^5$ and $R^6$, taken together with the nitrogen to which they are attached, form a heterocycloalkyl ring;

$R^7$ and $R^8$ are independently selected at each occurrence from the group consisting of H and $C_{1-6}$alkyl;

or $R^7$ and $R^8$, taken together with the nitrogen to which they are attached, form a heterocycloalkyl ring;

$R^9$ is independently selected at each occurrence from the group consisting of $C_{1-6}$alkoxy, $C_{1-6}$alkyl, halogen, halogen-$C_{1-6}$alkyl, heteroaryl, and heteroaryl substituted by $C_{1-6}$alkyl or $C_{1-6}$alkoxy;

$R^{10}$ is independently selected at each occurrence from the group consisting of $C_{1-6}$alkoxy, $C_{1-6}$alkyl, $C_{1-6}$alkyl-$C_{1-6}$alkoxy, halogen, and halogen-$C_{1-6}$alkyl;

$R^{11}$ is independently selected at each occurrence from the group consisting of H and $C_{1-6}$alkyl;

$R^{12}$ is independently selected at each occurrence from the group consisting of H, $C_{1-6}$alkyl and $C_{3-7}$cycloalkyl;

$X^1$ is bond, $NR^{34}$, $CH_2$, $CHR^{34}$, $C(R^{34})_2$, O, or S;

$X^{22}$ is halogen, —$NH_2$, —$NHR^{34}$, —$N(R^{34})_2$, hydroxyl, thiol, —$B(OH)_2$, —$Sn(R^{36})_3$, —$Si(R^{36})_3$, —$OS(O)_2$alkyl, —$OS(O)_2$haloalkyl, alkenyl, alkynyl, ethynyl, ethenyl, —C(O)H, —$NR^{34}$C(O)alkene, —$NR^{34}$C(O)alkyne, cyano, —SC(O)alkyl, OC(O)alkyl, heterocycle, —C(O)OH, hydrogen, alkyl, aryl, heteroaryl, or carbocyclic;

$R^{34}$ and $R^{34'}$ are independently selected at each occurrence from the group consisting of hydrogen, $C_1$-$C_6$alkyl $C_1$-$C_6$haloalkyl, $C_2$-$C_6$alkenyl, $C_2$-$C_6$alkynyl, $C_3$-$C_6$cycloalkyl, $C_3$-$C_6$heterocycle, aryl, heteroaryl, —(CO)$R^{36}$, —(CS)$R^{36}$, —(C═NH)$R^{36}$, —(SO)$R^{36}$, and —($SO_2$)$R^{36}$;

$R^{36}$ is independently selected at each occurrence from the group consisting of hydrogen, $C_1$-$C_6$alkyl, $C_1$-$C_6$haloalkyl, $C_2$-$C_6$alkenyl, $C_2$-$C_6$alkynyl, $C_3$-$C_6$cycloalkyl, $C_3$-$C_6$heterocycle, aryl, heteroaryl, hydroxyl, $C_1$-$C_6$alkoxy, thio, $C_1$-$C_6$thioalkyl, —$NH_2$, —NH($C_1$-$C_6$alkyl, $C_3$-$C_7$cycloalkyl, $C_3$-$C_7$heterocycle, aryl, or heteroaryl), and —N(independently $C_1$-$C_6$alkyl, $C_3$-$C_7$cycloalkyl, $C_3$-$C_7$heterocycle, aryl, or heteroaryl)$_2$;

$R^{20}$, $R^{21}$, $R^{22}$, $R^{23}$, and $R^{24}$ are independently selected from the group consisting of covalent bond, alkyl, —C(O)—, —C(O)O—, —OC(O)—, —C(O)alkyl, —C(O)Oalkyl, —$SO_2$—, —S(O)—, —C(S)—, —C(O)NH—, —NHC(O)—, —N(alkyl)C(O)—, —C(O)N(alkyl)-, —O—, —S—, —NH—, —N(alkyl)-, —CH(—O—$R^{26}$)—, —CH(—$NR^{34}R^{34'}$)—, —C(—O—$R^{26}$)alkyl-, —C(—$NR^{34}R^{34'}$)alkyl-, —C($R^{40}R^{40}$)—, -alkyl($R^{27}$)-alkyl($R^{28}$)—, —C($R^{27}R^{28}$)—, —P(O)($OR^{26}$)O—, —P(O)($OR^{26}$)—, —$NR^{34}$C(O)$NR^{34'}$—, alkene, haloalkyl, alkoxy, alkyneheteroarylalkyl, aryl, arylalkyl, heterocycle, heteroaryl, lactic acid, glycolic acid, carbocycle, -(ethylene glycol)$_{1-6}$-, -(lactic-co-glycolic acid)$_{1-6}$-, -(propylene glycol)$_{1-6}$-, —O—$(CH_2)_{1-12}$—O—, —NH—$(CH_2)_{1-12}$—NH—, —NH—$(CH_2)_{1-12}$—O—, —O—$(CH_2)_{1-12}$—NH—, —S—$(CH_2)_{1-12}$—O—, —O—$(CH_2)_{1-12}$—S—, —S—$(CH_2)_{1-12}$—S—, —S—$(CH_2)_{1-12}$—NH—, and —NH—$(CH_2)_{1-12}$—S—;

each of which $R^{20}$, $R^{21}$, $R^{22}$, $R^{23}$, and $R^{24}$ is optionally substituted with one or more substituents selected from $R^{101}$;

wherein at least one of $R^{20}$, $R^{21}$, $R^{22}$, $R^{23}$, and $R^{24}$ is not a bond;

$R^{101}$ is independently selected at each occurrence from the group consisting of hydrogen, alkyl, alkene, alkyne, haloalkyl, alkoxy, hydroxyl, aryl, heteroaryl, heterocycle, arylalkyl, heteroarylalkyl, heterocycloalkyl, aryloxy, heteroaryloxy, CN, —COOalkyl, COOH, $NO_2$, F, Cl, Br, I, $CF_3$, $NH_2$, NHalkyl, and N(alkyl)$_2$;

$R^{26}$ is selected from the group consisting of hydrogen, alkyl, silane, arylalkyl, heteroarylalkyl, alkene, alkyne, aryl, heteroaryl, and heterocyclic;

$R^{27}$ and $R^{28}$ are independently selected from the group consisting of hydrogen, alkyl, amine, or together with the carbon atom to which they are attached, form C(O), C(S), C═$CH_2$, a $C_3$-$C_6$ spirocarbocycle, or a 4-, 5-, or 6-membered spiroheterocycle with 1 or 2 heteroatoms selected from the group consisting of N and O, or form a 1 or 2 carbon bridged ring; and $R^{40}$ is selected at each instance from the group consisting of: hydrogen, alkyl, alkene, alkyne, halogen, hydroxyl, alkoxy, azide, amino, cyano, —NH (alkyl), —N (alkyl)$_2$, —$NHSO_2$(alkyl), —N(alkyl)$SO_2$alkyl, —$NHSO_2$(aryl, heteroaryl or heterocyclic), —N(alkyl)$SO_2$(aryl, heteroaryl or heterocyclic), —$NHSO_2$alkenyl, —N(alkyl)$SO_2$alkenyl, —$NHSO_2$alkynyl, —N(alkyl)$SO_2$alkynyl, haloalkyl, aliphatic, heteroaliphatic, aryl, heteroaryl, heteroalkyl, heterocyclic, and carbocyclic.

2. The compound of claim 1, wherein the compound is:

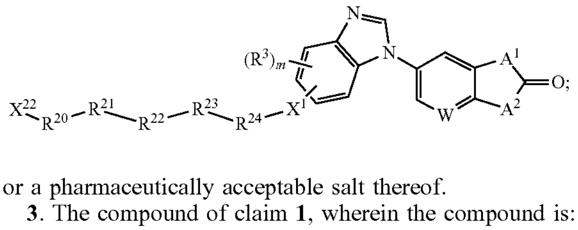

or a pharmaceutically acceptable salt thereof.

3. The compound of claim 1, wherein the compound is:

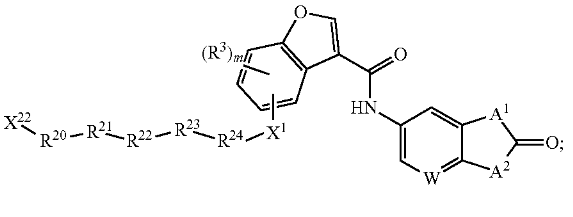

or a pharmaceutically acceptable salt thereof.

4. The compound of claim 1, wherein the compound is:

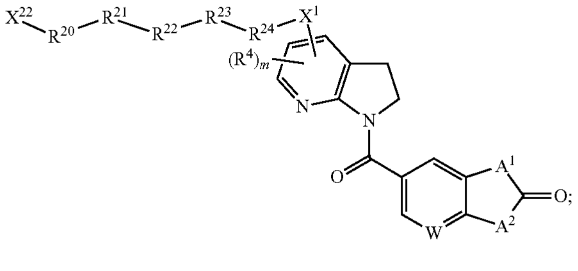

or a pharmaceutically acceptable salt thereof.

5. The compound of claim 1, wherein the compound is:

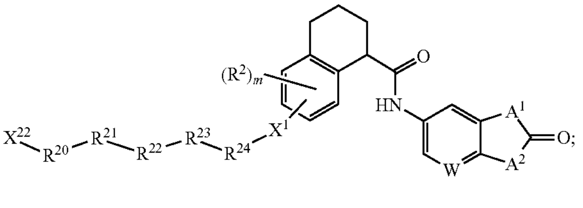

or a pharmaceutically acceptable salt thereof.

6. The compound of claim 1, wherein $A^1$ is selected from the group consisting of —O— and —NH—, and $A^2$ is —$CH_2$—.

7. The compound of claim 1, wherein $A^1$ is selected from the group consisting of —O—, —S—, —$CH_2$—, and —$CF_2$—, and $A^2$ is —NH—.

8. The compound of claim 1, wherein W is CH.

9. The compound of claim 1, wherein W is N.

10. The compound of claim 1, wherein $R^2$ is independently selected at each occurrence from the group consisting of -halogen; halogen-$C_{1-6}$alkyl; hydroxy-$C_{1-6}$alkyl; —$N(R^5R^6)$; —$NO_2$; —NH—C(=O)$C_{1-6}$alkyl; and —$SO_2$—$N(R^5R^6)$.

11. The compound of claim 1, wherein $R^3$ is independently selected at each occurrence from the group consisting of —$(CH_2)_{0-1}$—($C_{3-7}$cycloalkyl)-aryl substituted by $R^{10}$; —$(CH_2)_{0-1}$—($C_{3-7}$cycloalkyl)-aryl; —$(CH_2)_{0-1}$—$C_{3-7}$cycloalkyl substituted by $R^{10}$; —$(CH_2)_{0-1}$—$C_{3-7}$-cycloalkyl; —$(CH_2)_{0-1}$-heteroaryl substituted by $R^9$; and —$(CH_2)_{0-1}$-heterocycloalkyl.

12. The compound of claim 1, wherein $R^4$ is independently selected at each occurrence from the group consisting of —$(CH_2)_{0-1}$—($C_{3-7}$cycloalkyl)-aryl substituted by $R^{10}$; —$(CH_2)_{0-1}$—($C_{3-7}$cycloalkyl)-aryl; —$(CH_2)_{0-1}$—$C_{3-7}$cycloalkyl substituted by $R^{10}$; and —$(CH_2)_{0-1}$—$C_{3-7}$cycloalkyl.

13. The compound of claim 1, wherein $R^5$ and $R^6$ are independently selected at each occurrence from the group consisting of H, $C_{1-6}$alkyl and phenyl.

14. The compound of claim 1, wherein $R^7$ and $R^8$ are independently selected at each occurrence from the group consisting of H and $C_{1-6}$alkyl.

15. The compound of claim 1, wherein $X^1$ is bond or $NR^{34}$.

16. The compound of claim 1, wherein $X^{22}$ is halogen, —$N(R^{34})_2$, hydroxyl, thiol, —$B(OH)_2$, alkynyl, —C(O)H, heterocycle, or —C(O)OH.

17. The compound of claim 1, wherein at least two of $R^{20}$, $R^{21}$, $R^{22}$, $R^{23}$, and $R^{24}$ are not a bond.

18. The compound of claim 1, wherein the compound is selected from the group consisting of:

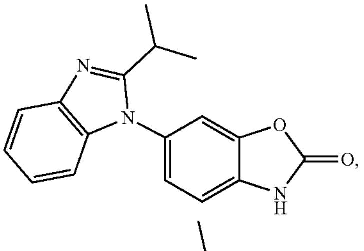

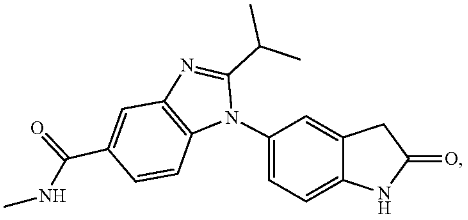

-continued

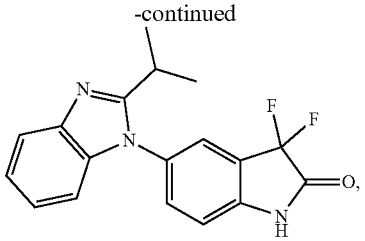

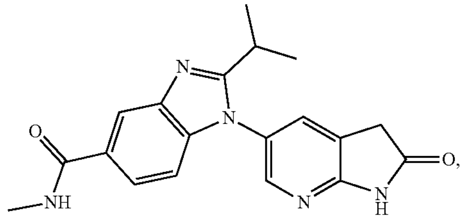

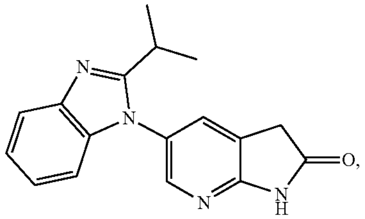

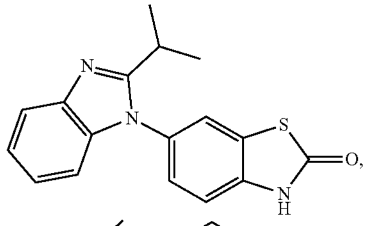

and

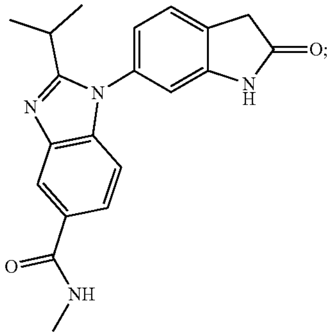

or a pharmaceutically acceptable salt thereof.

19. A pharmaceutical composition comprising a compound of claim 1 and a pharmaceutically acceptable carrier.

20. A method of treating abnormal cellular proliferation in a human subject in need thereof comprising administering an effective amount of a compound of claim 1, or a pharmaceutically acceptable salt thereof.

* * * * *